US012604895B2

(12) United States Patent
Hueter et al.

(10) Patent No.: US 12,604,895 B2
(45) Date of Patent: Apr. 21, 2026

(54) PESTICIDALLY ACTIVE CYCLIC AMINE COMPOUNDS

(71) Applicant: SYNGENTA CROP PROTECTION AG, Basel (CH)

(72) Inventors: Ottmar Franz Hueter, Stein (CH); Caroline Chenel, Basel (CH); Pierre Joseph Marcel Jung, Stein (CH); Elke Maria Hillesheim, Stein (CH); Ruifang Chen, Shanghai (CN); Hua Li, Shanghai (CN); Long Lu, Shanghai (CN)

(73) Assignee: SYNGENTA CROP PROTECTION AG, Basel (CH)

( * ) Notice: Subject to any disclaimer, the term of this patent is extended or adjusted under 35 U.S.C. 154(b) by 812 days.

(21) Appl. No.: 17/799,232

(22) PCT Filed: Feb. 10, 2021

(86) PCT No.: PCT/EP2021/053225

§ 371 (c)(1),
(2) Date: Aug. 11, 2022

(87) PCT Pub. No.: WO2021/160680

PCT Pub. Date: Aug. 19, 2021

(65) Prior Publication Data

US 2023/0146180 A1 May 11, 2023

(30) Foreign Application Priority Data

Feb. 11, 2020 (WO) ................ PCT/CN2020/074744

(51) Int. Cl.

| | |
|---|---|
| ***C07D 205/04*** | (2006.01) |
| ***A01N 25/04*** | (2006.01) |
| ***A01N 43/40*** | (2006.01) |
| ***A01N 43/44*** | (2006.01) |
| ***A01N 43/60*** | (2006.01) |
| ***A01N 43/80*** | (2006.01) |
| ***A01N 43/82*** | (2006.01) |
| ***A01P 7/02*** | (2006.01) |
| ***A01P 7/04*** | (2006.01) |
| ***C07D 211/20*** | (2006.01) |
| ***C07D 213/74*** | (2006.01) |
| ***C07D 413/04*** | (2006.01) |
| ***C07D 417/04*** | (2006.01) |

(52) U.S. Cl.

CPC ............. *A01N 43/82* (2013.01); *A01N 25/04* (2013.01); *A01N 43/40* (2013.01); *A01N 43/44* (2013.01); *A01N 43/60* (2013.01); *A01N 43/80* (2013.01); *A01P 7/02* (2021.08); *A01P 7/04* (2021.08); *C07D 205/04* (2013.01); *C07D 211/20* (2013.01); *C07D 213/74* (2013.01); *C07D 413/04* (2013.01); *C07D 417/04* (2013.01)

(58) Field of Classification Search

CPC .. C07D 205/04; C07D 211/20; C07D 213/74; C07D 413/04; C07D 417/04

See application file for complete search history.

(56) References Cited

U.S. PATENT DOCUMENTS

| | | | | |
|---|---|---|---|---|
| 8,367,679 B2 * | 2/2013 | Ogawa ................. | C07D 403/06 546/256 |
| 2019/0191702 A1 | 6/2019 | Iwata et al. | |
| 2020/0163336 A1 | 5/2020 | Nishio et al. | |
| 2022/0135591 A1 * | 5/2022 | Benz ....................... | A61P 25/28 514/210.16 |

FOREIGN PATENT DOCUMENTS

| | | |
|---|---|---|
| CN | 106316931 A | 1/2017 |
| EP | 2354134 A1 | 8/2011 |
| EP | 3456716 A1 | 3/2019 |
| JP | 2019077618 A | 5/2019 |
| JP | 2019085371 A | 6/2019 |
| WO | 2008074821 A1 | 6/2008 |
| WO | 2008092072 A2 | 7/2008 |
| WO | 2010077624 A1 | 7/2010 |
| WO | 2015032280 A1 | 3/2015 |

(Continued)

OTHER PUBLICATIONS

PubChem CID 46315191, National Center for Biotechnology Information. PubChem Compound Summary for CID 46315191, 2-(Trifluoromethyl)-[1,1'-biphenyl]-4-carboxylic acid. https://pubchem.ncbi.nlm.nih.gov/compound/4-phenyl-3-_trifluoromethyl_benzoic-acid. Accessed Apr. 15, 2025, create date Jul. 21, 2010. (Year: 2010).*

(Continued)

*Primary Examiner* — Laura L Stockton
(74) *Attorney, Agent, or Firm* — BakerHostetler; Toni-Junell Herbert

(57) ABSTRACT

Compounds of formula (I) wherein the substituents are as defined in claim 1, and the agrochemically acceptable salts, stereoisomers, enantiomers, tautomers and N-oxides of those compounds, can be used as insecticides.

(I)

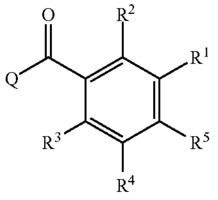

17 Claims, No Drawings

(56) References Cited

FOREIGN PATENT DOCUMENTS

| | | | |
|---|---|---|---|
| WO | 2017195703 | A1 | 11/2017 |
| WO | 2019039429 | A1 | 2/2019 |
| WO | 2019082808 | A1 | 5/2019 |

OTHER PUBLICATIONS

Written Opinion of the International Searching Authority and International Search Report for PCT/EP2021/053225, mailed May 3, 2021.

Zou et al., Design and synthesis of substituted N-(1,3-diphenyl-1H-pyrazol-5-yl)-benzamides as positive allosteric modulators of the metabotropic glutamate receptor subtype 5-Bioorganic Medicinal Chemistry Letters, vol. 21, No. 9, (2011), pp. 2650-2654.

Yonezawa et al., Synthesis of sequentially controlled isomeric, wholly aromatic polyketones composed of 2-trifluoromethylbiphenylene and 2,2-dimethoxybiphenylene units—Reactive Functional Polymer 2002, vol. 52, No. 1. pp. 19-30.

Xu et al., An efficient one-pot two-step three-component process for the systhesis of perfluoroalkylated biphenyls—Tetrahedron 2015, vol. 71, No. 5, pp. 820-825.

Rosenberg, et al. Design synthesis, and in vitro and in vivo evaluation of an 18F-labeled sphingosine 1-phospate receptor 1 (S1P1) Pet tracer, Journal of Medicinal Chemistry, vol. 59, No. 13, Jul. 2016, pp. 6201-6220.

* cited by examiner

PESTICIDALLY ACTIVE CYCLIC AMINE COMPOUNDS

CROSS-REFERENCE TO RELATED APPLICATIONS

This application is a 371 National Stage Application of International Application No. PCT/EP2021/053225 filed Feb. 10, 2021, which claims priority to PCT/CN2020/074744, filed Feb. 11, 2020.

The present invention relates to pesticidally active, in particular insecticidally or acaricidally active cyclic amine compounds, preferably azetidinyl, piperidinyl and piperazinyl aryl carbonyl compounds, having preferably acaricidal activity, to processes for their preparation, to compositions comprising those compounds, and to their use for controlling animal pests, including arthropods and in particular insects or representatives of the order *Acarina.*

WO2015032280, CN106316931, WO2017195703, WO2019039429, WO 2019082808, JP 2019077618, and JP 2019085371 describe certain piperidinyl and piperazinyl pyridinyl carbonyl compounds for use for controlling pests that damage plants.

There have now been found novel pesticidally active azetidinyl, piperidinyl and piperazinyl aryl carbonyl compounds.

The present invention accordingly relates, in a first aspect, to a compound of the formula (I)

(I)

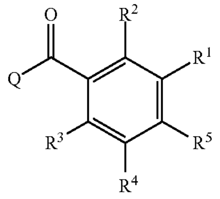

wherein $R^1$ is CN, C(=S)$NH_2$ or $C_1$-$C_6$-haloalkyl;

$R^2$ is H, OH, halogen, $C_1$-$C_6$-alkoxy or $C_1$-$C_6$-haloalkoxy;

$R^3$ is H, halogen, cyano, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_6$-cycloalkyl, $C_3$-$C_6$-halocycloalkyl, $C_1$-$C_6$-alkoxy, or $C_1$-$C_6$-haloalkyoxy;

$R^4$ is H, halogen, cyano, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_6$-cycloalkyl, $C_3$-$C_6$-halocycloalkyl, $C_1$-$C_6$-alkoxy, or $C_1$-$C_6$-haloalkyoxy;

$R^5$ is phenyl, phenyl substituted with 1 to 3 substituents $R^6$, heteroaryl (which is either a 5 or 6 membered monocyclic or a 9 or 10 membered bicyclic), heteroaryl (which is either a 5 or 6 membered monocyclic or a 9 or 10 membered bicyclic) substituted with 1 to 3 substituents $R^7$;

Q is a cyclic amine represented by the formula IIa or a cyclic amine represented by the formula IIb, (IIa)

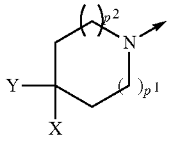

-continued (IIb)

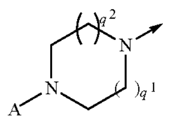

wherein the arrow indicates the connection to the carbonyl group;

$p^1$ is 0, 1 or 2 and indicates the number of methylene groups;

$p^2$ is 0, 1 or 2 and indicates the number of methylene groups;

q is 1 or 2 and indicates the number of methylene groups;

$q^2$ is 1 or 2 and indicates the number of methylene groups;

X is hydrogen, hydroxyl, $C_1$-$C_6$-alkoxy, cyano or halogen;

Y is cyano, $C_1$-$C_6$-alkyl, $C_1$-$C_6$-alkoxy-$C_1$-$C_6$-alkyl, $C_1$-$C_6$-alkylsulfanyl-$C_1$-$C_6$-alkyl, $C_1$-$C_6$-alkylsulfinyl-$C_1$-$C_6$-alkyl, $C_1$-$C_6$-alkylsulfonyl-$C_1$-$C_6$-alkyl, $C_3$-$C_6$-alkenylsulfanyl-$C_1$-$C_6$-alkyl, $C_3$-$C_6$-alkenylsulfinyl-$C_1$-$C_6$-alkyl, $C_3$-$C_6$-alkenylsulfonyl-$C_1$-$C_6$-alkyl, $C_3$-$C_6$-alkynylsulfanyl-$C_1$-$C_6$-alkyl, $C_3$-$C_6$-alkynylsulfinyl-$C_1$-$C_6$-alkyl, $C_3$-$C_6$-alkynylsulfonyl-$C_1$-$C_6$-alkyl, $C_1$-$C_6$-alkoxycarbonyl, $C_1$-$C_6$-alkoxycarbonylamino, $R^aR^b$NC(O), $R^c$C(O)N$R^d$, $R^eSO_2NR^f$, $R^g$O—N═C$R^h$, 4 to 6 membered non-aromatic heterocyclic ring system in which one or two carbons are replaced independently by nitrogen, oxygen, sulfur, or sulfonyl, phenyl, phenyl substituted with 1 to 3 substituents $R^8$, 5 or 6 membered monocyclic heteroaryl, or 5 or 6 membered monocyclic heteroaryl substituted with 1 to 3 substituents $R^9$; or X and Y together form a double bond to a nitrogen which is substituted with a group $R^m$O; A is cyano, $C_1$-$C_6$-cyanoalkyl, $C_2$-$C_6$-cyanoalkenyl, $C_3$-$C_6$-cyanocycloalkyl, $C_1$-$C_6$-haloalkyl, $C_2$-$C_6$-haloalkenyl, $C_3$-$C_6$-halocycloalkyl, $C_1$-$C_6$-alkoxy-$C_1$-$C_6$-alkyl, $C_1$-$C_6$-alkoxycarbonyl, $C_2$-$C_6$-alkenyloxycarbonyl, $C_2$-$C_6$-alkynyloxycarbonyl, $C_1$-$C_6$-alkylsulfanyl-$C_1$-$C_6$-alkyl, $C_1$-$C_6$-alkylsulfinyl-$C_1$-$C_6$-alkyl, $C_1$-$C_6$-alkylsulfonyl-$C_1$-$C_6$-alkyl, $R^iSO_2$, $R^jR^kNSO_2$, phenyl, phenyl substituted with 1 to 3 substituents $R^{10}$, heteroaryl (which is either a 5 or 6 membered monocyclic or a 9 or 10 membered bicyclic), or heteroaryl (which is either a 5 or 6 membered monocyclic or a 9 or 10 membered bicyclic) substituted with 1 to 3 substituents $R^{11}$;

$R^a$ and $R^b$ are independently selected from hydrogen, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_6$-cycloalkyl and $C_3$-$C_6$-halocycloalkyl and $C_1$-$C_6$-alkylsulfonyl;

$R^c$ and $R^d$ are independently selected from hydrogen, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_6$-cycloalkyl and $C_3$-$C_6$-halocycloalkyl;

$R^f$ is hydrogen, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_6$-cycloalkyl or $C_3$-$C_6$-halocycloalkyl;

$R^e$ and $R^i$ are independently selected from $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_6$-cycloalkyl and $C_3$-$C_6$-halocycloalkyl;

$R^g$ and $R^h$ are independently selected from hydrogen, $C_1$-$C_6$-alkyl, $C_1$-$C_6$-haloalkyl, $C_2$-$C_6$-alkenyl, $C_2$-$C_6$- haloalkenyl, $C_2$-$C_6$-alkynyl, $C_2$-$C_6$-haloalkynyl, $C_3$-$C_6$-cycloalkyl and $C_3$-$C_6$-halocycloalkyl;

$R^j$ and $R^k$ are independently selected from hydrogen, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_6$-cycloalkyl and $C_3$-$C_6$-halocycloalkyl;

$R^m$ is hydrogen, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_6$-cycloalkyl or $C_3$-$C_6$-halocycloalkyl; and $R^6$, $R^7$, $R^8$, $R^9$, $R^{10}$, $R^{11}$ are independently selected from halogen, cyano, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_6$-cycloalkyl, $C_3$-$C_6$-halocycloalkyl, $C_1$-$C_6$-alkoxy, $C_1$-$C_6$-haloalkoxy, $C_1$-$C_6$-alkylsulfonyl and $C_1$-$C_6$-haloalkylsulfanyl; or an agrochemically acceptable salt, stereoisomer, enantiomer, tautomer and N-oxide of the compound of formula I.

Compounds of formula (I) which have at least one basic centre can form, for example, acid addition salts, for example with strong inorganic acids such as mineral acids, for example perchloric acid, sulfuric acid, nitric acid, nitrous acid, a phosphorus acid or a hydrohalic acid, with strong organic carboxylic acids, such as $C_1$-$C_4$alkanecarboxylic acids which are unsubstituted or substituted, for example by halogen, for example acetic acid, such as saturated or unsaturated dicarboxylic acids, for example oxalic acid, malonic acid, succinic acid, maleic acid, fumaric acid or phthalic acid, such as hydroxycarboxylic acids, for example ascorbic acid, lactic acid, malic acid, tartaric acid or citric acid, or such as benzoic acid, or with organic sulfonic acids, such as $C_1$-$C_4$alkane- or arylsulfonic acids which are unsubstituted or substituted, for example by halogen, for example methane- or p-toluenesulfonic acid. Compounds of formula (I) which have at least one acidic group can form, for example, salts with bases, for example mineral salts such as alkali metal or alkaline earth metal salts, for example sodium, potassium or magnesium salts, or salts with ammonia or an organic amine, such as morpholine, piperidine, pyrrolidine, a mono-, di- or tri-lower-alkylamine, for example ethyl-, diethyl-, triethyl- or dimethylpropylamine, or a mono-, di- or trihydroxy-lower-alkylamine, for example mono-, di- or triethanolamine.

In each case, the compounds of formula (I) according to the invention are in free form, in oxidized form as a N-oxide or in salt form, e.g. an agronomically usable salt form.

N-oxides are oxidized forms of tertiary amines or oxidized forms of nitrogen containing heteroaromatic compounds. They are described for instance in the book "Heterocyclic N-oxides" by A. Albini and S. Pietra, CRC Press, Boca Raton 1991.

The compounds of formula (I) according to the invention also include hydrates which may be formed during the salt formation.

The term "$C_1$-$C_n$-alkyl" as used herein refers to a saturated straight-chain or branched hydrocarbon radical attached via any of the carbon atoms having 1 to n carbon atoms, for example, any one of the radicals methyl, ethyl, n-propyl, n-butyl, n-pentyl, 2-methylbutyl, 3-methylbutyl, 2,2-dimethylpropyl, 1-ethylpropyl, n-hexyl, n-pentyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, or 1-ethyl-2-methylpropyl.

The term "$C_2$-$C_n$-alkenyl" as used herein refers to a straight or branched alkenyl chain having from two to n carbon atoms and one or two double bonds, for example, ethenyl, prop-I-enyl, but-2-enyl.

The term "$C_2$-$C_n$-alkynyl" as used herein refers to a straight or branched alkynyl chain having from two to n carbon atoms and one triple bond, for example, ethynyl, prop-2-ynyl, but-3-ynyl, The term "$C_3$-$C_n$-cycloalkyl" as used herein refers to 3-n membered cycloalkyl groups such as cyclopropane, cyclobutane, cyclopentane and cyclohexane.

The term "$C_1$-$C_n$-alkoxy" as used herein refers to a straight-chain or branched saturated alkyl radical having 1 to n carbon atoms (as mentioned above) which is attached via an oxygen atom, i.e., for example, any one of the radicals methoxy, ethoxy, n-propoxy, 1-methylethoxy, n-butoxy, 1-methylpropoxy, 2-methylpropoxy or 1,1-dimethylethoxy. The term "halo$C_1$-$C_n$-alkoxy" as used herein refers to a $C_1$-$C_n$-alkoxy radical where one or more hydrogen atoms on the alkyl radical is replaced by the same or different halo atom(s)—examples include trifluoromethoxy, 2-fluoroethoxy, 3-fluoropropoxy, 3,3,3-trifluoropropoxy, 4-chlorobutoxy.

Halogen is generally fluorine, chlorine, bromine or iodine. This also applies, correspondingly, to halogen in combination with other meanings, such as haloalkyl.

The term "$C_1$-$C_n$-haloalkyl" as used herein refers to a straight-chain or branched saturated alkyl radical attached via any of the carbon atoms having 1 to n carbon atoms (as mentioned above), where some or all of the hydrogen atoms in these radicals may be replaced by fluorine, chlorine, bromine and/or iodine, i.e., for example, any one of chloromethyl, dichloromethyl, trichloromethyl, fluoromethyl, difluoromethyl, trifluoromethyl, chlorofluoromethyl, dichlorofluoromethyl, chlorodifluoromethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl or nonafluorobutyl. According a term "$C_1$-$C_2$fluoroalkyl" would refer to a $C_1$-$C_2$alkyl radical which carries 1, 2, 3, 4, or 5 fluorine atoms, for example, any one of difluoromethyl, trifluoromethyl, 1-fluoroethyl, 2-fluoroethyl, 2,2-difluoroethyl, 2,2,2-trifluoroethyl, 1,1,2,2-tetrafluoroethyl or pentafluoroethyl. Similarly, the term "$C_2$-$C_n$-haloalkenyl" or "$C_2$-$C_n$-haloalkynyl" as used herein refers to a $C_2$-$C_n$-alkenyl or $C_2$-$C_n$-alkynyl moiety respectively substituted with one or more halo atoms which may be the same or different. Similarly, the term "$C_3$-$C_n$-halocycloalkyl" as used herein refers to a $C_3$-$C_n$-cycloakyl group substituted with one or more halo atoms which may be the same or different.

The term "$C_1$-$C_n$-cyanoalkyl" as used herein refers to $C_1$-$C_n$-alkyl radical having 1 to n carbon atoms (as mentioned above), where one of the hydrogen atoms in the radical is be replaced by a cyano group: for example, cyanomethyl, 2-cyanoethyl, 2-cyanopropyl, 3-cyanopropyl, 1-(cyanomethyl)-2-ethyl, 1-(methyl)-2-cyanoethyl, 4-cyanobutyl, and the like. Similarly, the term "$C_1$-$C_n$-cyanoalkenyl" or "$C_1$-$C_n$-cyanoalkynyl" refers to a $C_2$-$C_n$-alkenyl or $C_1$-$C_n$-alkynyl moiety respectively substituted with one of the hydrogen atoms in the corresponding moiety being replaced by a cyano group.

The term "$C_1$-$C_n$-alkylsulfanyl-$C_1$-$C_n$-alkyl" as used herein refers to an alkyl radical wherein one of the carbon atoms is replaced by a sulfur atom.

The term "$C_1$-$C_n$-alkylsulfinyl-$C_1$-$C_n$-alkyl" as used herein refers to an alkyl radical wherein one of the carbon atoms is replaced by a S(═O) group.

The term "$C_1$-$C_n$-alkylsulfonyl-$C_1$-$C_n$-alkyl" as used herein refers to an alkyl radical wherein one of the carbon atoms is replaced by a $S(═O)_2$ group.

The term "4 to 6 membered non-aromatic heterocyclic ring system in which one or two carbons is replaced by nitrogen, oxygen, sulfur, or sulfonyl," as used herein refers to a cyclic group where one or two carbon atoms in the ring are replaced independently by nitrogen, oxygen, sulfur, or sulfonyl, and the ring is attached via a carbon, or a nitrogen atom to remainder of the compound. Examples are azetidinyl, oxetanyl, thietanyl, pyrrolidinyl, tetrahydrofuranyl, 2-oxopyrrolidinyl, 2-oxotetrahydrofuranyl, 1,1-dioxo-1,2-thiazolidinyl, 1,3-dioxolanyl, 1,3-dithiolanyl, 2-oxooxazolidinyl, piperidinyl, tetrahydropyranyl, 2-oxopiperidinyl, 1,1-dioxothiazinanyl, 2-oxotetrahydropyranyl, 1,3-dioxolanyl, 1,3-dithianyl, 2-oxo-1,3-oxazinanyl.

The term "phenyl-$C_1$-$C_n$-alkyl" as used herein refers to an alkyl radical substituted with a phenyl ring.

If there is substitution on the phenyl-$C_1$-$C_n$-alkyl group, the substitution is on the phenyl ring.

The term "$C_1$-$C_n$-alkoxy-$C_1$-$C_n$-alkyl" as used herein refers to an alkyl radical substituted with $C_1$-$C_n$-alkoxy group. Examples are methoxymethyl, methoxyethyl, ethoxymethyl and propoxymethyl.

The term "$C_1$-$C_n$-alkoxycarbonyl" as used herein refers to a $C_1$-$C_n$-alkoxy group connected to a carbonyl (C═O) radical, through which the $C_1$-$C_n$-alkoxycarbonyl is attached to the remainder of the compound. Examples are methoxycarbonyl, ethoxycarbonyl, isopropoxycarbonyl and tertiary butyloxycarbonyl.

The term "$C_1$-$C_6$-alkoxycarbonylamino" as used herein refers to a $C_1$-$C_n$-alkoxycarbonyl group connected to an amino (NH) radical, through which the $C_1$-$C_n$-alkoxycarbonylamino is attached to the remainder of the compound. Examples are The term "$C_2$-$C_n$-alkenyloxycarbonyl" as used herein refers to a $C_2$-$C_n$-alkenyl group connected with an oxygen atom to a carbonyl (C═O) radical, and where the attachment to the remainder of the compound is through the carbon atom of the carbonyl. Examples are vinyloxycarbonyl and allyloxycarbonyl.

The term "$C_2$-$C_n$-alkynyloxycarbonyl" as used herein refers to a $C_2$-$C_n$-alkynyl group connected with an oxygen atom to a carbonyl (C═O) radical, and where the attachment to the remainder of the compound is through the carbon atom of the carbonyl. Examples are propargyloxycarbonyl (2-prop-2-ynoxycarbonyl) and 2-pent-3-ynoxycarbonyl, Substituents $R^gO—N═CR^h$ have the general formula below

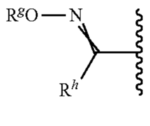

The term "5 or 6 membered monocyclic heteroaryl" as used herein refers to a 5 or 6 membered aromatic ring having 1 to 3 carbon atoms replaced independently by nitrogen, sulfur, or oxygen. Examples are pyridyl, pyridazinyl, pyrimidinyl, pyrazinyl, pyrrolyl, pyrazolyl, imidazolyl, triazolyl (e.g. 1.2.4 triazoyl), furanyl, thiophenyl, oxazolyl, isoxazolyl, oxadiazolyl, thiazolyl, isothiazolyl, and thiadiazolyl. Examples are heteroaryls J-1 to J-35 shown in Scheme A below. Preferred heteroaryl is J-1, J-16, J-18 or, J-20.

The term "9 or 10 membered bicyclic heteroaryl" as used herein refers to a 9 or 10 membered aromatic ring made up of two rings, having 1 to 3 carbon atoms replaced independently by nitrogen, sulfur, or oxygen (the heteroatoms can be in one ring or distributed amongst the two). Examples are purinyl, quinolinyl, cinnolinyl, quinoxalinyl, indolyl, indazolyl, benzimidazolyl, benzothiophenyl and benzothiazolyl.

Scheme A: Heteroaryl J-1 to J-35

J-1

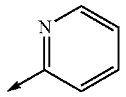

J-2

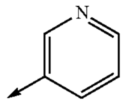

J-3

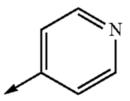

J-4

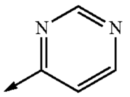

J-5

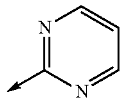

J-6

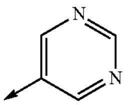

J-7

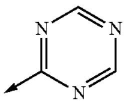

J-8

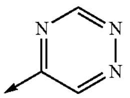

J-9

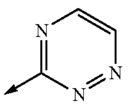

J-10

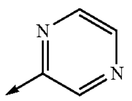

-continued

J-11

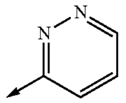

J-12

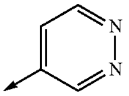

J-13

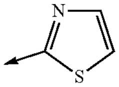

J-14

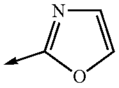

J-15

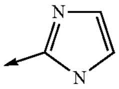

J-16

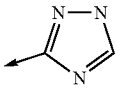

J-17

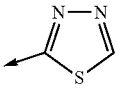

J-18

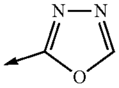

J-19

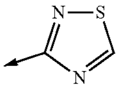

J-20

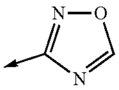

J-21

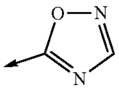

J-22

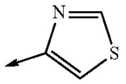

J-23

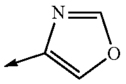

J-24

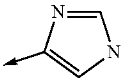

J-25

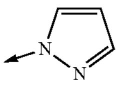

J-26

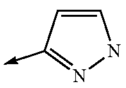

-continued

J-27

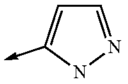

J-28

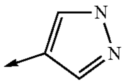

J-29

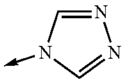

J-30

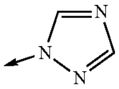

J-31

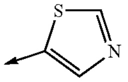

J-32

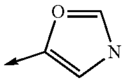

J-33

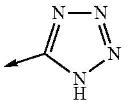

J-34

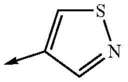

J-35

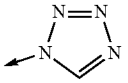

As used herein, the term “controlling” refers to reducing the number of pests, eliminating pests and/or preventing further pest damage such that damage to a plant or to a plant derived product is reduced.

As used herein, the term “pest” refers to insects, and molluscs that are found in agriculture, horticulture, forestry, the storage of products of vegetable origin (such as fruit, grain and timber); and those pests associated with the damage of man-made structures. The term pest encompasses all stages in the life cycle of the pest.

As used herein, the term “effective amount” refers to the amount of the compound, or a salt thereof, which, upon single or multiple applications provides the desired effect.

The staggered line as used herein, for example, in formula IV-aa and IV-ba, represent the point of connection/attachment to the rest of the compound.

An effective amount is readily determined by the skilled person in the art, by the use of known techniques and by observing results obtained under analogous circumstances. In determining the effective amount a number of factors are considered including, but not limited to: the type of plant or derived product to be applied; the pest to be controlled & its lifecycle; the particular compound applied; the type of application; and other relevant circumstances.

Embodiments according to the invention are provided as set out below.

In an embodiment of each aspect of the invention, $R^1$ is

A. CN, $C(=S)NH_2$ or $C_1$-$C_3$-haloalkyl; or

B. CN, $C(=S)NH_2$, difluoromethyl or trifluoromethyl; or

C. CN.

In an embodiment of each aspect of the invention, $R^2$ is

A. hydrogen, halogen, $C_1$-$C_6$-alkoxy or $C_1$-$C_6$-haloalkoxy; or

B. hydrogen, halogen, $C_1$-$C_3$-alkoxy or $C_1$-$C_3$-haloalkoxy; or

C. hydrogen, fluorine, chlorine, methoxy, difluoromethoxy, or trifluoromethoxy; or D. hydrogen.

In an embodiment of each aspect of the invention, $R^3$ is

A. hydrogen, OH, halogen, $C_1$-$C_6$-alkyl, $C_1$-$C_6$-haloalkyl, $C_3$-$C_6$-cycloalkyl, $C_3$-$C_6$-halocycloalkyl, $C_1$-$C_6$-alkoxy or $C_1$-$C_6$-haloalkyloxy; or B. hydrogen, halogen, $C_1$-$C_6$-alkyl, or $C_1$-$C_6$-haloalkyl, $C_1$-$C_6$-alkoxy or $C_1$-$C_6$-haloalkyloxy; or C. hydrogen, halogen, $C_1$-$C_3$-alkyl, $C_1$-$C_3$-haloalkyl, $C_1$-$C_3$-alkoxy or $C_1$-$C_3$-haloalkyloxy; or D. hydrogen, chlorine, fluorine, methyl, ethyl, methoxy, ethoxy, difluoromethyl, trifluoromethyl, or pentafluoroethyl; or E. hydrogen, methyl, ethyl, methoxy, ethoxy, difluoromethyl, trifluoromethyl, or pentafluoroethyl; or F. methyl, methoxy, ethoxy, difluoromethyl or trifluoromethyl.

In an embodiment of each aspect of the invention, $R^4$ is

A. hydrogen, cyano, halogen, $C_1$-$C_3$-alkyl, $C_1$-$C_3$-haloalkyl, $C_3$-$C_3$-cycloalkyl, $C_3$-$C_3$-halocycloalkyl, $C_1$-$C_3$-alkoxy or $C_1$-$C_3$-haloalkyloxy; or B. hydrogen, cyano, or halogen; or C. hydrogen, cyano, fluorine or chlorine; or D. hydrogen or cyano.

In an embodiment of each aspect of the invention, $R^5$ is

A. phenyl, phenyl substituted with 1 to 3 substituents $R^6$, 5 or 6 membered monocyclic heteroaryl or 5 or 6 membered monocyclic heteroaryl substituted with 1 to 3 substituents $R^7$; or B. phenyl or phenyl substituted with 1 to 3 substituents $R^6$; or C. phenyl substituted with 1 to 3 substituents $R^6$.

In an embodiment of each aspect of the invention, Q is

A. a cyclic amine represented by the formula IIa, where both $p^1$ and $p^2$ are both 0 or 1; X is hydrogen, hydroxyl, $C_1$-$C_3$-alkoxy, cyano, or halogen; and Y is cyano, $C_1$-$C_6$-alkoxy-$C_1$-$C_6$-alkyl, $C_1$-$C_6$-alkylsulfanyl-$C_1$-$C_6$-alkyl, $C_1$-$C_6$-alkylsulfinyl-$C_1$-$C_6$-alkyl, $C_1$-$C_6$-alkylsulfonyl-$C_1$-$C_6$-alkyl, $C_3$-$C_6$-alkenylsulfanyl-$C_1$-$C_6$-alkyl, $C_3$-$C_6$-alkenylsulfinyl-$C_1$-$C_6$-alkyl, $C_3$-$C_6$-alkenylsulfonyl-$C_1$-$C_6$-alkyl, $C_3$-$C_6$-alkynylsulfanyl-$C_1$-$C_6$-alkyl, $C_3$-$C_6$-alkynylsulfinyl-$C_1$-$C_6$-alkyl, $C_3$-$C_6$-alkynylsulfonyl-$C_1$-$C_6$-alkyl, $C_1$-$C_6$-alkoxycarbonyl, $C_1$-$C_6$-alkoxycarbonylamino, $R^aR^bNC(O)$, $R^eSO_2NR^f$, $R^gO$—N═$CR^h$, 4 to 6 membered non-aromatic heterocyclic ring system in which one or two carbons are replaced independently by nitrogen or sulfonyl, phenyl, phenyl substituted with 1 to 3 substituents $R^8$, 5 or 6 membered monocyclic heteroaryl, or 5 or 6 membered monocyclic heteroaryl substituted with 1 to 3 substituents $R^9$; or X and Y together form a double bond to a nitrogen which is substituted with a group $R'''O$; or

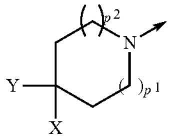

IIa

B. a cyclic amine represented by the formula IIa, where both $p^1$ and $p^2$ are both 0 or 1; X is hydrogen or, hydroxyl; Y is $C_1$-$C_3$-alkylsulfanyl-$C_1$-$C_3$-alkyl, $C_1$-$C_3$-alkylsulfinyl-$C_1$-$C_3$-alkyl, $C_1$-$C_3$-alkylsulfonyl-$C_1$-$C_3$-alkyl, $C_3$-$C_4$-alkenylsulfanyl-$C_1$-$C_3$-alkyl, $C_3$-$C_4$-alkenylsulfinyl-$C_1$-$C_3$-alkyl, $C_3$-$C_4$-alkenylsulfonyl-$C_1$-$C_3$-alkyl, $C_3$-$C_4$-alkynylsulfanyl-$C_1$-$C_3$-alkyl, $C_3$-$C_4$-alkynylsulfinyl-$C_1$-$C_3$-alkyl, $C_3$-$C_4$-alkynylsulfonyl-$C_1$-$C_3$-alkyl, $R^aR^bNC(O)$, $R^eSO_2NR^f$, $R^gO$—N═$CR^h$, 4 to 6 membered non-aromatic heterocyclic ring system in which one or two carbons are replaced independently by nitrogen or sulfonyl, 5 or 6 membered monocyclic heteroaryl, or 5 or 6 membered monocyclic heteroaryl substituted with 1 to 3 substituents $R^9$; or X and Y together form a double bond to a nitrogen which is substituted with a group $R'''O$; or C. a cyclic amine represented by the formula IIa, where both $p^1$ and $p^2$ are both 0 or 1; X is hydrogen or, hydroxyl; Y is $C_1$-$C_3$-alkylsulfanyl-$C_1$-$C_3$-alkyl, $C_1$-$C_3$-alkylsulfinyl-$C_1$-$C_3$-alkyl, $C_1$-$C_3$-alkylsulfonyl-$C_1$-$C_3$-alkyl, $C_3$-$C_4$-alkenylsulfanyl-$C_1$-$C_3$-alkyl, $C_3$-$C_4$-alkenylsulfinyl-$C_1$-$C_3$-alkyl, $C_3$-$C_4$-alkenylsulfonyl-$C_1$-$C_3$-alkyl, $C_3$-$C_4$-alkynylsulfanyl-$C_1$-$C_3$-alkyl, $C_3$-$C_4$-alkynylsulfinyl-$C_1$-$C_3$-alkyl, $C_3$-$C_4$-alkynylsulfonyl-$C_1$-$C_3$-alkyl, $R^aR^bNC(O)$, $R^eSO_2NR^f$, $R^gO$—N═$CR^h$, 4 to 6 membered non-aromatic heterocyclic ring system in which one or two carbons are replaced independently by nitrogen or sulfonyl, 5 or 6 membered monocyclic heteroaryl, or 5 or 6 membered monocyclic heteroaryl selected from J-1 to J-35 substituted with 1 to 3 substituents $R^9$; or X and Y together form a double bond to a nitrogen which is substituted with a group $R'''O$; or D. a cyclic amine represented by the formula IIa, where both $p^1$ and $p^2$ are both 0 or 1; X is hydrogen or, hydroxyl; Y is $C_1$-$C_3$-alkylsulfanyl-methyl, $C_1$-$C_3$-alkylsulfinyl-methyl, $C_1$-$C_3$-alkylsulfonyl-methyl, $C_3$-$C_4$-alkenylsulfanyl-methyl, $C_3$-$C_4$-alkenylsulfinyl-methyl, $C_3$-$C_4$-alkenylsulfonyl-methyl, $C_3$-$C_4$-alkynylsulfanyl-methyl, $C_3$-$C_4$-alkynylsulfinyl-methyl, $C_3$-$C_4$-alkynylsulfonyl-methyl, methanesulfonylamido, ethanesulfonylamido, 1,1-dioxo-1,2-thiazolidin-2-yl, 1,2,4-oxadiazole-3-yl, 2-pyridyl, substituted 2-pyridyl or, substituted 1,2,4-oxadiazole-3-yl, where the substituents for each are 1 to 3 substituents independently selected from chlorine and methyl; or X and Y together form a double bond to a nitrogen which is substituted with methoxy or ethoxy; or E. a cyclic amine represented by the formula IIa, where both $p^1$ and $p^2$ are each 1; X is hydrogen; Y is $C_1$-$C_3$-alkylsulfanyl-methyl, $C_1$-$C_3$-alkylsulfinyl-methyl, $C_1$-$C_3$-alkylsulfonyl-methyl, $C_3$-$C_4$-alkenylsulfanyl-methyl, $C_3$-$C_4$-alkenylsulfinyl-methyl, $C_3$-$C_4$-alkenylsulfonyl-methyl, $C_3$-$C_4$-alkynylsulfanyl-methyl, $C_3$-$C_4$-alkynylsulfinyl-methyl, $C_3$-$C_4$-alkynylsulfonyl-methyl, methanesulfonylamido, ethanesulfonylamido, 1,1-dioxo-1,2-thiazolidin-2-yl, 1,2,4-oxadiazole-3-yl, 2-pyridyl, substituted 2-pyridyl or, substituted 1,2,4- oxadiazole-3-yl, where the substituents for each are 1 to 3 substituents independently selected from chlorine and methyl; or X and Y together form a double bond to a nitrogen which is substituted with methoxy or ethoxy; or F. cyclic amine represented by the formula IIb; where both $q^1$ and $q^2$ are 1; and A is cyano, $C_1$-$C_6$-cyanoalkyl, $C_2$-$C_6$-cyanoalkenyl, $C_3$-$C_6$-cyanocycloalkyl, $C_1$-$C_6$-haloalkyl, $C_2$-$C_6$-haloalkenyl, $C_3$-$C_6$-halocycloalkyl, $C_1$-$C_6$-alkoxy-$C_1$-$C_6$-alkyl, $C_1$-$C_6$-alkoxycarbonyl, $C_2$-$C_6$-alkenyloxycarbonyl, $C_2$-$C_6$-alkynyloxycarbonyl, $C_1$-$C_6$-alkylsulfanyl-$C_1$-$C_6$-alkyl, $C_1$-$C_6$-alkylsulfinyl-$C_1$-$C_6$-alkyl, $R^iSO_2$, $R^jR^kNSO_2$, phenyl, phenyl substituted with 1 to 3 substituents $R^{10}$, heteroaryl (which is either a 5 or 6 membered monocyclic or a 9 or 10 membered bicyclic), or heteroaryl (which is either a 5 or 6 membered monocyclic or a 9 or 10 membered bicyclic) substituted with 1 to 3 substituents $R^{11}$;

IIb

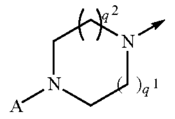

G. cyclic amine represented by the formula IIb; where both $q^1$ and $q^2$ are 1; and A is cyano, $C_1$-$C_3$-cyanoalkyl, $C_2$-$C_4$-cyanoalkenyl, $C_3$-$C_4$-cyanocycloalkyl, $C_1$-$C_3$-haloalkyl, $C_2$-$C_3$-haloalkenyl, $C_3$-$C_4$-halocycloalkyl, $C_1$-$C_3$-alkoxy-$C_1$-$C_3$-alkyl, $C_1$-$C_3$-alkoxycarbonyl, $C_2$-$C_4$-alkenyloxycarbonyl, $C_2$-$C_4$-alkynyloxycarbonyl, $C_1$-$C_3$-alkylsulfanyl-$C_1$-$C_3$-alkyl, $C_1$-$C_3$-alkylsulfinyl-$C_1$-$C_3$-alkyl, $R^iSO_2$, $R^jR^kNSO_2$, phenyl, phenyl substituted with 1 to 3 substituents $R^{10}$, heteroaryl (which is either a 5 or 6 membered monocyclic or a 9 or 10 membered bicyclic), or heteroaryl (which is either a 5 or 6 membered monocyclic or a 9 or 10 membered bicyclic) substituted with 1 to 3 substituents $R^{11}$;

H. cyclic amine represented by the formula IIb; where both $q^1$ and $q^2$ are 1; and A is cyano, $C_1$-$C_3$-cyanoalkyl, $C_1$-$C_3$-haloalkyl, $C_2$-$C_3$-haloalkenyl, $C_1$-$C_3$-alkoxy-$C_1$-$C_3$-alkyl, $C_1$-$C_3$-alkoxycarbonyl, $C_1$-$C_3$-alkylsulfanyl-$C_1$-$C_3$-alkyl, $C_1$-$C_3$-alkylsulfinyl-$C_1$-$C_3$-alkyl, $R^iSO_2$, or 5 or 6 membered monocyclic heteroaryl substituted with 1 to 3 substituents $R^{11}$;

I. cyclic amine represented by the formula IIb; where both $q^1$ and $q^2$ are 1; and A is cyano, $C_1$-$C_3$-cyanoalkyl, $C_1$-$C_3$-haloalkyl, $C_2$-$C_3$-haloalkenyl, $C_1$-$C_3$-alkoxy-$C_1$-$C_3$-alkyl, $C_1$-$C_3$-alkoxycarbonyl, $C_1$-$C_3$-alkylsulfanyl-$C_1$-$C_3$-alkyl, $C_1$-$C_3$-alkylsulfinyl-$C_1$-$C_3$-alkyl, $R^iSO_2$), or 6 membered monocyclic heteroaryl substituted with 1 to 3 substituents independently selected from fluorine and chlorine, or J. cyclic amine represented by the formula IIb; where both $q^1$ and $q^2$ are 1; and A is cyano, cyanomethyl, cyanoethyl, 2,2,2-trifluoroethyl, vinyloxycarbonyl, butyloxycarbonyl, methylsulfanylmethyl, ethylsulfanylethyl, methylsulfanylethyl (i.e $CH_3SCH_2CH_2$), ethylsulfinylethyl, ethylsulfinylmethyl, ethylsulfonylethyl, ethylsulfonylmethyl, methylsulfonylmethyl, 4-chloro-phenyl, or pyridyl substituted with 1 to 3 substituents independently selected from fluorine, chlorine, trifluoromethyl and difluoromethyl; or K. cyclic amine represented by the formula IIb; where both $q^1$ and $q^2$ are 1; and A is cyano, cyanomethyl, cyanoethyl, $CH_3SCH_2CH_2$, or pyridyl substituted with 1 to 3 substituents independently selected from fluorine, chlorine, trifluoromethyl and difluoromethyl.

In an embodiment of each aspect of the invention, X is

A. hydrogen, hydroxyl, $C_1$-$C_3$-alkoxy, cyano or halogen; or

B. hydrogen, hydroxyl, or $C_1$-$C_3$-alkoxy; or

C. hydrogen, or hydroxyl; or

D. hydrogen.

In an embodiment of each aspect of the invention, $R^a$ and $R^b$ are independently selected from A. hydrogen, $C_1$-$C_3$-alkyl, $C_1$-$C_3$-haloalkyl, $C_2$-$C_4$-alkenyl, $C_2$-$C_4$-haloalkenyl, $C_2$-$C_4$-alkynyl, $C_2$-$C_4$-haloalkynyl, $C_3$-$C_4$-cycloalkyl and $C_3$-$C_4$-halocycloalkyl and $C_1$-$C_3$-alkylsulfonyl; or B. hydrogen, $C_1$-$C_3$-alkyl, $C_1$-$C_3$-haloalkyl, $C_3$-$C_4$-cycloalkyl and $C_3$-$C_4$-halocycloalkyl and $C_1$-$C_3$-alkylsulfonyl; or C. hydrogen, $C_1$-$C_3$-alkyl, $C_1$-$C_3$-haloalkyl, or $C_1$-$C_3$-alkylsulfonyl; or D. hydrogen, $C_1$-$C_3$-alkyl, or $C_1$-$C_3$-alkylsulfonyl; or E. hydrogen, methyl, ethyl, methylsulfonyl, or ethylsulfonyl.

In an embodiment of each aspect of the invention, $R^c$ and $R^d$ are independently selected from A. $C_1$-$C_3$-alkyl, $C_1$-$C_3$-haloalkyl, $C_2$-$C_4$-alkenyl, $C_2$-$C_4$-haloalkenyl, $C_2$-$C_4$-alkynyl, $C_2$-$C_4$-haloalkynyl, $C_3$-$C_4$-cycloalkyl and $C_3$-$C_4$-halocycloalkyl; or B. $C_1$-$C_3$-alkyl, $C_1$-$C_3$-haloalkyl, $C_3$-$C_4$-cycloalkyl and $C_3$-$C_4$-halocycloalkyl; or C. $C_1$-$C_3$-alkyl, $C_1$-$C_3$-haloalkyl and $C_3$-$C_4$-halocycloalkyl; or D. $C_1$-$C_3$-alkyl and $C_1$-$C_3$-haloalkyl; or E. methyl, ethyl, difluoromethyl and trifluoromethyl.

In an embodiment of each aspect of the invention, $R^f$ is

A. hydrogen, $C_1$-$C_3$-alkyl, or $C_3$-$C_4$-cycloalkyl; or

B. hydrogen or $C_1$-$C_3$-alkyl; or

C. hydrogen, methyl and ethyl.

In an embodiment of each aspect of the invention, $R^e$ is

A. $C_1$-$C_3$-alkyl, $C_1$-$C_3$-haloalkyl, $C_2$-$C_4$-alkenyl, $C_2$-$C_4$-haloalkenyl, $C_2$-$C_4$-alkynyl, $C_2$-$C_4$-haloalkynyl, $C_3$-$C_4$-cycloalkyl or $C_3$-$C_4$-halocycloalkyl; or B. $C_1$-$C_3$-alkyl, $C_1$-$C_3$-haloalkyl, $C_2$-$C_4$-alkenyl, $C_2$-$C_4$-haloalkenyl, $C_2$-$C_4$-alkynyl, $C_2$-$C_4$-haloalkynyl, $C_3$-$C_4$-cycloalkyl or $C_3$-$C_4$-halocycloalkyl; or C. $C_1$-$C_3$-alkyl or $C_1$-$C_3$-haloalkyl; or D. methyl, ethyl, difluoromethyl or trifluoromethyl.

In an embodiment of each aspect of the invention, $R^i$ is

A. $C_1$-$C_3$-alkyl, $C_1$-$C_3$-haloalkyl, $C_2$-$C_4$-alkenyl, $C_2$-$C_4$-haloalkenyl, $C_2$-$C_4$-alkynyl, $C_2$-$C_4$-haloalkynyl, $C_3$-$C_4$-cycloalkyl or $C_3$-$C_4$-halocycloalkyl; or B. $C_1$-$C_3$-alkyl, $C_1$-$C_3$-haloalkyl, $C_2$-$C_4$-alkenyl, $C_2$-$C_4$-haloalkenyl, $C_2$-$C_4$-alkynyl, $C_2$-$C_4$-haloalkynyl, $C_3$-$C_4$-cycloalkyl or $C_3$-$C_4$-halocycloalkyl; or C. $C_1$-$C_3$-alkyl or $C_1$-$C_3$-haloalkyl; or D. methyl, ethyl, difluoromethyl or trifluoromethyl.

In an embodiment of each aspect of the invention, $R^g$ and $R^h$ are independently selected from A. $C_1$-$C_3$-alkyl, $C_1$-$C_3$-haloalkyl, $C_2$-$C_4$-alkenyl, $C_2$-$C_4$-haloalkenyl, $C_2$-$C_4$-alkynyl, $C_2$-$C_4$-haloalkynyl, $C_3$-$C_4$-cycloalkyl and $C_3$-$C_4$-halocycloalkyl; or B. $C_1$-$C_3$-alkyl, $C_1$-$C_3$-haloalkyl, $C_3$-$C_4$-cycloalkyl and $C_3$-$C_4$-halocycloalkyl; or C. $C_1$-$C_3$-alkyl, $C_1$-$C_3$-haloalkyl and $C_3$-$C_4$-halocycloalkyl; or D. $C_1$-$C_3$-alkyl and $C_1$-$C_3$-haloalkyl; or E. methyl, ethyl, difluoromethyl and trifluoromethyl; or F. methyl and ethyl.

In an embodiment of each aspect of the invention, $R^j$ and $R^k$ are independently selected from A. $C_1$-$C_3$-alkyl, $C_1$-$C_3$-haloalkyl, $C_2$-$C_4$-alkenyl, $C_2$-$C_4$-haloalkenyl, $C_2$-$C_4$-alkynyl, $C_2$-$C_4$-haloalkynyl, $C_3$-$C_4$-cycloalkyl and $C_3$-$C_4$-halocycloalkyl; or B. $C_1$-$C_3$-alkyl, $C_1$-$C_3$-haloalkyl, $C_3$-$C_4$-cycloalkyl and $C_3$-$C_4$-halocycloalkyl; or C. $C_1$-$C_3$-alkyl, $C_1$-$C_3$-haloalkyl and $C_3$-$C_4$-halocycloalkyl; or D. $C_1$-$C_3$-alkyl and $C_1$-$C_3$-haloalkyl; or E. methyl, ethyl, difluoromethyl and trifluoromethyl; or F. methyl and ethyl.

In an embodiment of each aspect of the invention, $R^m$ is

A. $C_1$-$C_4$-alkyl; or

B. methyl, ethyl, or propyl; or

C. methy or ethyl;

In an embodiment of each aspect of the invention, $R^6$ is selected from

A. halogen, cyano, $C_1$-$C_3$-alkyl, $C_1$-$C_3$-haloalkyl, $C_2$-$C_4$-alkenyl, $C_2$-$C_4$-haloalkenyl, $C_2$-$C_4$-alkynyl, $C_2$-$C_4$-haloalkynyl, $C_3$-$C_4$-cycloalkyl, $C_3$-$C_4$-halocycloalkyl, $C_1$-$C_3$-alkoxy; $C_1$-$C_3$-haloalkoxy; $C_1$-$C_3$-alkylsulfonyl and $C_1$-$C_3$-haloalkylsulfanyl; or B. halogen, cyano, $C_1$-$C_3$-alkyl, $C_1$-$C_3$-haloalkyl, $C_3$-$C_4$-cycloalkyl, $C_3$-$C_4$-halocycloalkyl, $C_1$-$C_3$-alkoxy; $C_1$-$C_3$-haloalkoxy; $C_1$-$C_3$-alkylsulfonyl and $C_1$-$C_3$-haloalkylsulfanyl; or C. halogen, cyano, $C_1$-$C_3$-alkyl, $C_1$-$C_3$-haloalkyl, $C_1$-$C_3$-alkoxy; $C_1$-$C_3$-haloalkoxy, $C_1$-$C_3$-alkylsulfonyl and $C_1$-$C_3$-haloalkylsulfanyl; or D. fluorine, chlorine, methyl, ethyl, isopropyl, trifluoromethyl, difluoromethyl, trifluoromethoxy, difluoromethoxy. trifluoromethylsulfanyl and methylsulfonyl.

In an embodiment of each aspect of the invention, $R^7$ is selected from

A. halogen, cyano, $C_1$-$C_3$-alkyl, $C_1$-$C_3$-haloalkyl, $C_2$-$C_4$-alkenyl, $C_2$-$C_4$-haloalkenyl, $C_2$-$C_4$-alkynyl, $C_2$-$C_4$-haloalkynyl, $C_3$-$C_4$-cycloalkyl, $C_3$-$C_4$-halocycloalkyl, $C_1$-$C_3$-alkoxy; $C_1$-$C_3$-haloalkoxy; $C_1$-$C_3$-alkylsulfonyl and $C_1$-$C_3$-haloalkylsulfanyl; or B. halogen, cyano, $C_1$-$C_3$-alkyl, $C_1$-$C_3$-haloalkyl, $C_3$-$C_4$-cycloalkyl, $C_3$-$C_4$-halocycloalkyl, $C_1$-$C_3$-alkoxy; $C_1$-$C_3$-haloalkoxy; $C_1$-$C_3$-alkylsulfonyl and $C_1$-$C_3$-haloalkylsulfanyl; or C. halogen, cyano, $C_1$-$C_3$-alkyl, $C_1$-$C_3$-haloalkyl, $C_3$-$C_4$-cycloalkyl, $C_3$-$C_4$-halocycloalkyl, $C_1$-$C_3$-alkoxy and $C_1$-$C_3$-haloalkoxy; or D. halogen, $C_1$-$C_3$-alkyl, $C_1$-$C_3$-haloalkyl, $C_1$-$C_3$-alkoxy and $C_1$-$C_3$-haloalkoxy; or E. halogen, $C_1$-$C_3$-alkyl, $C_1$-$C_3$-haloalkyl, $C_1$-$C_3$-alkoxy and $C_1$-$C_3$-haloalkoxy; or F. halogen, $C_1$-$C_3$-alkyl and $C_1$-$C_3$-haloalkyl and $C_1$-$C_3$-haloalkoxy; or G. fluorine, chlorine, methyl, ethyl, isopropyl, trifluoromethyl, difluoromethyl, trifluoromethoxy and difluoromethoxy.

In an embodiment of each aspect of the invention, $R^8$ is selected from

A. halogen, cyano, $C_1$-$C_3$-alkyl, $C_1$-$C_3$-haloalkyl, $C_2$-$C_4$-alkenyl, $C_2$-$C_4$-haloalkenyl, $C_2$-$C_4$-alkynyl, $C_2$-$C_4$-haloalkynyl, $C_3$-$C_4$-cycloalkyl, $C_3$-$C_4$-halocycloalkyl, $C_1$-$C_3$-alkoxy; $C_1$-$C_3$-haloalkoxy; $C_1$-$C_3$-alkylsulfonyl and $C_1$-$C_3$-haloalkylsulfanyl; or B. halogen, cyano, $C_1$-$C_3$-alkyl, $C_1$-$C_3$-haloalkyl, $C_3$-$C_4$-cycloalkyl, $C_3$-$C_4$-halocycloalkyl, $C_1$-$C_3$-alkoxy; $C_1$-$C_3$-haloalkoxy; $C_1$-$C_3$-alkylsulfonyl and $C_1$-$C_3$-haloalkylsulfanyl; or C. halogen, cyano, $C_1$-$C_3$-alkyl, $C_1$-$C_3$-haloalkyl, $C_3$-$C_4$-cycloalkyl, $C_3$-$C_4$-halocycloalkyl, $C_1$-$C_3$-alkoxy and $C_1$-$C_3$-haloalkoxy; or D. halogen, $C_1$-$C_3$-alkyl, $C_1$-$C_3$-haloalkyl, $C_1$-$C_3$-alkoxy and $C_1$-$C_3$-haloalkoxy; or E. halogen, $C_1$-$C_3$-alkyl, $C_1$-$C_3$-haloalkyl, $C_1$-$C_3$-alkoxy and $C_1$-$C_3$-haloalkoxy; or F. halogen, $C_1$-$C_3$-alkyl, $C_1$-$C_3$-haloalkyl and $C_1$-$C_3$-haloalkoxy; or G. fluorine, chlorine, methyl, ethyl, isopropyl, trifluoromethyl, difluoromethyl, trifluoromethoxy and difluoromethoxy.

In an embodiment of each aspect of the invention, $R^g$ is selected from

A. halogen, cyano, $C_1$-$C_3$-alkyl, $C_1$-$C_3$-haloalkyl, $C_2$-$C_4$-alkenyl, $C_2$-$C_4$-haloalkenyl, $C_2$-$C_4$-alkynyl, $C_2$-$C_4$-haloalkynyl, $C_3$-$C_4$-cycloalkyl, $C_3$-$C_4$-halocycloalkyl, $C_1$-$C_3$-alkoxy; $C_1$-$C_3$-haloalkoxy; $C_1$-$C_3$-alkylsulfonyl and $C_1$-$C_3$-haloalkylsulfanyl; or B. halogen, cyano, $C_1$-$C_3$-alkyl, $C_1$-$C_3$-haloalkyl, $C_3$-$C_4$-cycloalkyl, $C_3$-$C_4$-halocycloalkyl, $C_1$-$C_3$-alkoxy; $C_1$-$C_3$-haloalkoxy; $C_1$-$C_3$-alkylsulfonyl and $C_1$-$C_3$-haloalkylsulfanyl; or C. halogen, cyano, $C_1$-$C_3$-alkyl, $C_1$-$C_3$-haloalkyl, $C_3$-$C_4$-cycloalkyl, $C_3$-$C_4$-halocycloalkyl, $C_1$-$C_3$-alkoxy and $C_1$-$C_3$-haloalkoxy; or D. halogen, $C_1$-$C_3$-alkyl, $C_1$-$C_3$-haloalkyl, $C_1$-$C_3$-alkoxy and $C_1$-$C_3$-haloalkoxy; or E. halogen, $C_1$-$C_3$-alkyl, $C_1$-$C_3$-haloalkyl, $C_1$-$C_3$-alkoxy and $C_1$-$C_3$-haloalkoxy; or F. halogen, $C_1$-$C_3$-alkyl, $C_1$-$C_3$-haloalkyl and $C_1$-$C_3$-haloalkoxy; or G. fluorine, chlorine, methyl, ethyl, isopropyl, trifluoromethyl, difluoromethyl, trifluoromethoxy and difluoromethoxy; or H. fluorine, chlorine, methyl and ethyl In an embodiment of each aspect of the invention, $R^{10}$ is selected from A. halogen, cyano, $C_1$-$C_3$-alkyl, $C_1$-$C_3$-haloalkyl, $C_2$-$C_4$-alkenyl, $C_2$-$C_4$-haloalkenyl, $C_2$-$C_4$-alkynyl, $C_2$-$C_4$-haloalkynyl, $C_3$-$C_4$-cycloalkyl, $C_3$-$C_4$-halocycloalkyl, $C_1$-$C_3$-alkoxy; $C_1$-$C_3$-haloalkoxy; $C_1$-$C_3$-alkylsulfonyl and $C_1$-$C_3$-haloalkylsulfanyl; or B. halogen, cyano, $C_1$-$C_3$-alkyl, $C_1$-$C_3$-haloalkyl, $C_3$-$C_4$-cycloalkyl, $C_3$-$C_4$-halocycloalkyl, $C_1$-$C_3$-alkoxy; $C_1$-$C_3$-haloalkoxy; $C_1$-$C_3$-alkylsulfonyl and $C_1$-$C_3$-haloalkylsulfanyl; or C. halogen, cyano, $C_1$-$C_3$-alkyl, $C_1$-$C_3$-haloalkyl, $C_3$-$C_4$-cycloalkyl, $C_3$-$C_4$-halocycloalkyl, $C_1$-$C_3$-alkoxy and $C_1$-$C_3$-haloalkoxy; or D. halogen, $C_1$-$C_3$-alkyl, $C_1$-$C_3$-haloalkyl, $C_1$-$C_3$-alkoxy and $C_1$-$C_3$-haloalkoxy; or E. halogen, $C_1$-$C_3$-alkyl, $C_1$-$C_3$-haloalkyl, $C_1$-$C_3$-alkoxy and $C_1$-$C_3$-haloalkoxy; or F. halogen, $C_1$-$C_3$-alkyl, $C_1$-$C_3$-haloalkyl and $C_1$-$C_3$-haloalkoxy; or G. fluorine, chlorine, methyl, ethyl, isopropyl, trifluoromethyl, difluoromethyl, trifluoromethoxy and difluoromethoxy In an embodiment of each aspect of the invention, $R^{11}$ is selected from A. halogen, cyano, $C_1$-$C_3$-alkyl, $C_1$-$C_3$-haloalkyl, $C_2$-$C_4$-alkenyl, $C_2$-$C_4$-haloalkenyl, $C_2$-$C_4$-alkynyl, $C_2$-$C_4$-haloalkynyl, $C_3$-$C_4$-cycloalkyl, $C_3$-$C_4$-halocycloalkyl, $C_1$-$C_3$-alkoxy; $C_1$-$C_3$-haloalkoxy; $C_1$-$C_3$-alkylsulfonyl and $C_1$-$C_3$-haloalkylsulfanyl; or B. halogen, cyano, $C_1$-$C_3$-alkyl, $C_1$-$C_3$-haloalkyl, $C_3$-$C_4$-cycloalkyl, $C_3$-$C_4$-halocycloalkyl, $C_1$-$C_3$-alkoxy; $C_1$-$C_3$-haloalkoxy; $C_1$-$C_3$-alkylsulfonyl and $C_1$-$C_3$-haloalkylsulfanyl; or C. halogen, cyano, $C_1$-$C_3$-alkyl, $C_1$-$C_3$-haloalkyl, $C_3$-$C_4$-cycloalkyl, $C_3$-$C_4$-halocycloalkyl, $C_1$-$C_3$-alkoxy and $C_1$-$C_3$-haloalkoxy; or D. halogen, $C_1$-$C_3$-alkyl, $C_1$-$C_3$-haloalkyl, $C_1$-$C_3$-alkoxy and $C_1$-$C_3$-haloalkoxy; or E. halogen, $C_1$-$C_3$-alkyl, $C_1$-$C_3$-haloalkyl, $C_1$-$C_3$-alkoxy and $C_1$-$C_3$-haloalkoxy; or F. halogen, $C_1$-$C_3$-alkyl, $C_1$-$C_3$-haloalkyl and $C_1$-$C_3$-haloalkoxy; or G. fluorine, chlorine, methyl, ethyl, isopropyl, trifluoromethyl, difluoromethyl, trifluoromethoxy and difluoromethoxy; or H. fluorine, chlorine, methyl, ethyl.

The present invention, accordingly, makes available a compound of formula (I) having the substituents Q, $R^1$, $R^2$, $R^3$, $R^4$ and $R^5$, as defined above in all combinations/each permutation. Accordingly, made available, for example, is a compound of formula (I) with Q being embodiment K (i.e Q is cyclic amine represented by the formula IIb; where both $q^1$ and $q^2$ are 1; and A is cyano, cyanomethyl, cyanoethyl, $CH_3SCH_2CH_2$, or pyridyl substituted with 1 to 3 substituents independently selected from fluorine, chlorine, trifluoromethyl and difluoromethyl); $R^1$ being of the first aspect (i.e. $R^1$ is CN, C(=S)$NH_2$ or $C_1$-$C_6$-haloalkyl); $R^2$ being embodiment D (i.e. $R^2$ is hydrogen); $R^3$ being embodiment A (i.e. $R^3$ is hydrogen, OH, halogen, $C_1$-$C_6$-alkyl, $C_1$-$C_6$-haloalkyl, $C_3$-$C_6$-cycloalkyl, $C_3$-$C_6$-halocycloalkyl, $C_1$-$C_6$-alkoxy, or $C_1$-$C_6$-haloalkyloxy); $R^4$ being embodiment B (i.e. $R^4$ is hydrogen, cyano, or halogen); and $R^5$ being embodiment B (i.e. $R^5$ is phenyl, or phenyl substituted with 1 to 3 substituents $R^6$; with $R^6$ being embodiment C (i.e. $R^6$ is halogen, cyano, $C_1$-$C_3$-alkyl, $C_1$-$C_3$-haloalkyl, $C_1$-$C_3$-alkoxy; $C_1$-$C_3$-haloalkoxy, $C_1$-$C_3$-alkylsulfonyl, or $C_1$-$C_3$-haloalkylsulfanyl)).

The compounds of formula I can be represented by formulae Ia and Ib

Ia

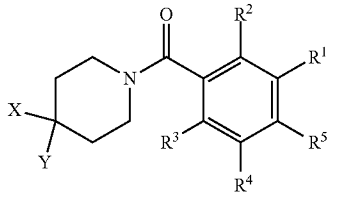

Ib

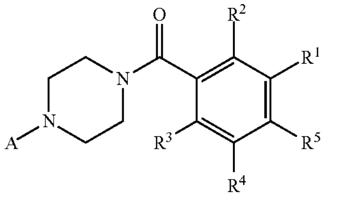

wherein the substituents X, Y, $R^1$, $R^2$, $R^3$, $R^4$ and $R^5$ in formula Ia are as defined for formula I; and the substituents A, $R^1$, $R^2$, $R^3$, $R^4$ and $R^5$ in formula Ib are as defined for formula I.

In an embodiment of each aspect of the invention, the compound of formula (Ia) has as X hydrogen, hydroxyl, $C_1$-$C_6$-alkoxy, cyano or halogen; as Y cyano, $C_1$-$C_6$-alkoxy-$C_1$-$C_6$-alkyl, $C_1$-$C_6$-alkylsulfanyl-$C_1$-$C_6$-alkyl, $C_1$-$C_6$-alkylsulfinyl-$C_1$-$C_6$-alkyl, $C_1$-$C_6$-alkylsulfonyl-$C_1$-$C_6$-alkyl, $C_3$-$C_6$-alkenylsulfanyl-$C_1$-$C_6$-alkyl, $C_3$-$C_6$-alkenylsulfinyl-$C_1$-$C_6$-alkyl, $C_3$-$C_6$-alkenylsulfonyl-$C_1$-$C_6$-alkyl, $C_3$-$C_6$-alkynylsulfanyl-$C_1$-$C_6$-alkyl, $C_3$-$C_6$-alkynylsulfinyl-$C_1$-$C_6$-alkyl, $C_3$-$C_6$-alkynylsulfonyl-$C_1$-$C_6$-alkyl, $C_1$-$C_6$-alkoxycarbonyl, $C_1$-$C_6$-alkoxycarbonylamino, $R^aR^bNC(O)$, $R^eSO_2NR^f$, $R^gO$—N=$CR^h$, 4 to 6 membered non-aromatic heterocyclic ring system in which one or two carbons are replaced independently by nitrogen or sulfonyl, phenyl, phenyl substituted with 1 to 3 substituents $R^8$, 5 or 6 membered monocyclic heteroaryl, or 5 or 6 membered monocyclic heteroaryl substituted with 1 to 3 substituents $R^9$; or X and Y together form a double bond to a nitrogen which is substituted with a group $R^mO$; as $R^1$ CN, C(=S)$NH_2$ or $C_1$-$C_3$-haloalkyl; as $R^2$ hydrogen, halogen, $C_1$-$C_6$-alkoxy, or $C_1$-$C_6$-haloalkoxy; as $R^3$ hydrogen, OH, halogen, $C_1$-$C_6$-alkyl, $C_1$-$C_6$-haloalkyl, $C_3$-$C_6$-cycloalkyl, $C_3$-$C_6$-halocycloalkyl, $C_1$-$C_6$-alkoxy, or $C_1$-$C_6$-haloalkyloxy; as $R^4$ hydrogen, cyano, halogen, $C_1$-$C_3$-alkyl, $C_1$-$C_3$-haloalkyl, $C_3$-$C_3$-cycloalkyl, $C_3$-$C_3$-halocycloalkyl, $C_1$-$C_3$-alkoxy, or $C_1$-$C_3$-haloalkyloxy; and as $R^5$ phenyl, phenyl substituted with 1 to 3 substituents $R^6$, 5 or 6 membered monocyclic heteroaryl, or 5 or 6 membered monocyclic heteroaryl substituted with 1 to 3 substituents $R^7$; wherein $R^a$, $R^b$, $R^e$, $R^f$, $R^g$, $R^h$, $R^m$, $R^6$, $R^7$, $R^8$, $R^9$ are as defined in the first aspect.

In an embodiment of each aspect of the invention, the compound of formula (Ib) has as A cyano, $C_1$-$C_3$-cyanoalkyl, $C_2$-$C_4$-cyanoalkenyl, $C_3$-$C_4$-cyanocycloalkyl, $C_1$-$C_3$-haloalkyl, $C_2$-$C_3$-haloalkenyl, $C_3$-$C_4$-halocycloalkyl, $C_1$-$C_3$-alkoxy-$C_1$-$C_3$-alkyl, $C_1$-$C_3$-alkoxycarbonyl, $C_2$-$C_4$-alkenyloxycarbonyl, $C_2$-$C_4$-alkynyloxycarbonyl, $C_1$-$C_3$-alkylsulfanyl-$C_1$-$C_3$-alkyl, $C_1$-$C_3$-alkylsulfinyl-$C_1$-$C_3$-alkyl, $R^iSO_2$, $R^jR^kNSO_2$, phenyl, phenyl substituted with 1 to 3 substituents $R^{10}$, heteroaryl (which is either a 5 or 6 membered monocyclic or a 9 or 10 membered bicyclic), or heteroaryl (which is either a 5 or 6 membered monocyclic or a 9 or 10 membered bicyclic) substituted with 1 to 3 substituents $R^{11}$; as $R^1$ CN, C(=S)$NH_2$ or $C_1$-$C_3$-haloalkyl; as $R^2$ hydrogen, halogen, $C_1$-$C_6$-alkoxy or $C_1$-$C_6$-haloalkoxy; as $R^3$ hydrogen, OH, halogen, $C_1$-$C_6$-alkyl, $C_1$-$C_6$-haloalkyl, $C_3$-$C_6$-cycloalkyl, $C_3$-$C_6$-halocycloalkyl, $C_1$-$C_6$-alkoxy or $C_1$-$C_6$-haloalkyloxy; as $R^4$ hydrogen, cyano, halogen, $C_1$-$C_3$-alkyl, $C_1$-$C_3$-haloalkyl, $C_3$-$C_3$-cycloalkyl, $C_3$-$C_3$-halocycloalkyl, $C_1$-$C_3$-alkoxy, or $C_1$-$C_3$-haloalkyloxy; and as $R^5$ phenyl, phenyl substituted with 1 to 3 substituents $R^6$, 5 or 6 membered monocyclic heteroaryl, or 5 or 6 membered monocyclic heteroaryl substituted with 1 to 3 substituents $R^7$; wherein $R^i$, $R^j$, $R^k$, $R^6$, $R^7$, $R^{10}$, $R^{11}$ are as defined in the first aspect.

In an embodiment of each aspect of the invention, the compound of formula (Ia) has as X hydrogen; as Y $C_1$-$C_3$-alkylsulfanyl-methyl, $C_1$-$C_3$-alkylsulfinyl-methyl, $C_1$-$C_3$-alkylsulfonyl-methyl, $C_3$-$C_4$-alkenylsulfanyl-methyl, $C_3$-$C_4$-alkenylsulfinyl-methyl, $C_3$-$C_4$-alkenylsulfonyl-methyl, $C_3$-$C_4$-alkynylsulfanyl-methyl, $C_3$-$C_4$-alkynylsulfinyl-methyl, $C_3$-$C_4$-alkynylsulfonyl-methyl, methanesulfonylamido, ethanesulfonylamido, 1,1-dioxo-1,2-thiazolidin-2-yl, 1,2,4-oxadiazole-3-yl, 2-pyridyl, substituted 2-pyridyl or, substituted 1,2,4-oxadiazole-3-yl, where the substituents for each are 1 to 3 substituents independently selected from chlorine and methyl; or X and Y together form a double bond to a nitrogen which is substituted with methoxy or ethoxy;

as $R^1$ CN; as $R^2$ hydrogen; as $R^3$ methyl, methoxy, ethoxy, difluoromethyl, or trifluoromethyl; as $R^4$ hydrogen or cyano; as $R^5$ phenyl substituted with 1 to 3 substituents $R^6$; wherein $R^6$ is fluorine, chlorine, methyl, ethyl, isopropyl, trifluoromethyl, difluoromethyl, trifluoromethoxy, difluoromethoxy. trifluoromethylsulfanyl, or methylsulfonyl.

In an embodiment of each aspect of the invention, the compound of formula (Ib) has as A cyano, cyanomethyl, cyanoethyl, $CH_3SCH_2CH_2$, or pyridyl substituted with 1 to 3 substituents independently selected from fluorine, chlorine, trifluoromethyl and difluoromethyl; as $R^1$ CN; as $R^2$ hydrogen; as $R^3$ methyl, methoxy, ethoxy, difluoromethyl or trifluoromethyl; as $R^4$ hydrogen or cyano; as $R^5$ phenyl substituted with 1 to 3 substituents $R^6$; wherein $R^6$ is fluorine, chlorine, methyl, ethyl, isopropyl, trifluoromethyl, difluoromethyl, trifluoromethoxy, difluoromethoxy. trifluoromethylsulfanyl, or methylsulfonyl.

In a second aspect, the present invention makes available a composition comprising a compound of formula (I) as defined in the first aspect, one or more auxiliaries and diluent, and optionally one or more other active ingredient.

In a third aspect, the present invention makes available a method of combating and controlling insects, acarines, nematodes or molluscs which comprises applying to a pest, to a locus of a pest, or to a plant susceptible to attack by a pest an insecticidally, acaricidally, nematicidally or molluscicidally effective amount of a compound as defined in the first aspect or a composition as defined in the second aspect.

In a fourth aspect, the present invention makes available a method for the protection of plant propagation material from the attack by insects, acarines, nematodes or molluscs, which comprises treating the propagation material or the site, where the propagation material is planted, with an effective amount of a compound of formula (I) as defined in the first aspect or a composition as defined in the second aspect.

In a fifth aspect, the present invention makes available a plant propagation material, such as a seed, comprising, or treated with or adhered thereto, a compound of formula (I) as defined in the first aspect or a composition as defined in the second aspect.

The present invention in a further aspect provides a method of controlling parasites in or on an animal in need thereof comprising administering an effective amount of a compound of the first aspect. The present invention further provides a method of controlling ectoparasites on an animal in need thereof comprising administering an effective amount of a compound of formula (I) as defined om the first aspect. The present invention further provides a method for preventing and/or treating diseases transmitted by ectoparasites comprising administering an effective amount of a compound of formula (I) as defined in the first aspect, to an animal in need thereof.

Compounds of formula (I) can be prepared by those skilled in the art following known methods. More specifically compounds of formulae I, and intermediates therefore can be prepared as described below in the schemes and examples. Certain stereogenic centers have been left unspecified for the clarity and are not intended to limit the teaching of the schemes in any way.

The process according to the invention for preparing compounds of formula (I) is carried out by methods known to those skilled in the art.

The compounds of formula (I) are new and can be prepared by reacting an acid III in which $R^1$, $R^2$, $R^3$, $R^4$ and $R^5$ are as previously defined with an amine IV-a or IV-b in which X, Y, A, $p^1$, $p^2$, $q^1$ and $q^2$ are as previously defined using known amide coupling reagents, such as 1-[bis(dimethylamino)-methylene]-1H-1,2,3-triazolo[4,5-b]pyridinium 3-oxide hexafluorophosphate (HATU) and a base, for example Hunig's base, in a suitable solvent, for example dimethylformamide (DMF) or dimethylacetamide (DMA) according to scheme 1. Piperidines IV-a or piperazines IV-b are commercially available, known from the literature or can be prepared by the person skilled in the art.

Scheme 1

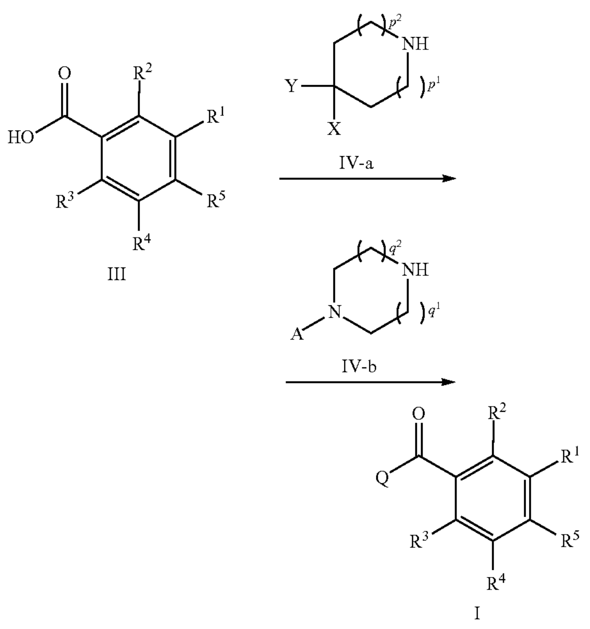

Alternatively the compounds of formula (I) can be prepared by reacting an acid chloride V in which $R^1$, $R^2$, $R^3$, $R^4$ and $R^5$ are as previously defined with an amine IV-a or IV-b in which X, Y, A, $p^1$, $p^2$ $q^1$ and $q^2$ are as previously defined in the presence of a base, for example triethylamine or pyridine, and a suitable solvent, for example dichloromethane (DCM), tetrahydrofuran (THF) or toluene, according to scheme 2.

Scheme 2

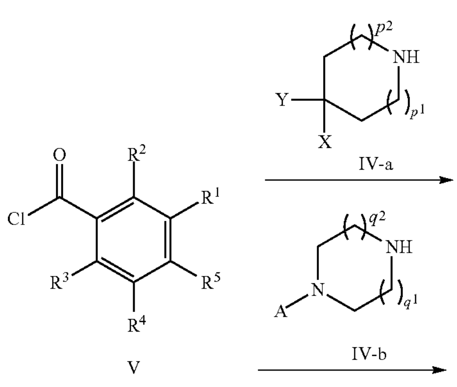

-continued

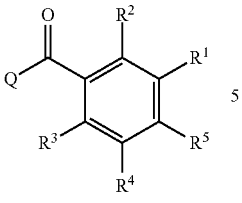

I

The acid chloride V in which $R^1$, $R^2$, $R^3$, $R^4$ and $R^5$ are as previously defined can be prepared from the corresponding acid III in which $R^1$, $R^2$, $R^3$, $R^4$ and $R^5$ are as previously defined by treatment with for example, oxalyl chloride or thionyl chloride in the presence of catalytic quantities of DMF in inert solvents such as DCM or THE at temperatures between 20° C. to 100° C., preferably 25° C. according to scheme 3.

Scheme 3

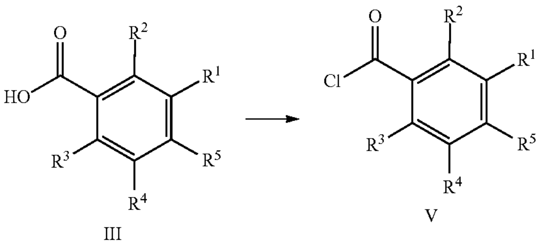

III V

The acid III in which $R^1$, $R^2$, $R^3$, $R^4$ and $R^5$ are as previously defined can be prepared by hydrolysis of the corresponding ester VI in which $R^1$, $R^2$, $R^3$, $R^4$ and $R^5$ are as previously defined and $R^{12}$=$C_1$-$C_6$-alkyl, under basic conditions, for example using an inorganic base such as lithium hydroxide, sodium hydroxide, potassium hydroxide or potassium carbonate in water, methanol, ethanol or THF, according to scheme 4.

Scheme 4

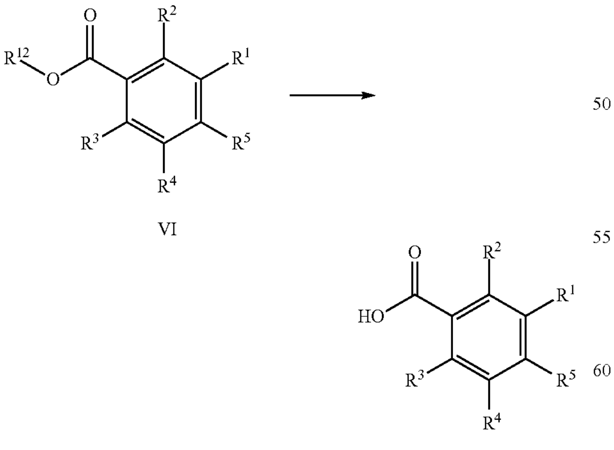

VI III

The ester VI in which $R^1$, $R^2$, $R^3$, $R^4$ and $R^5$ are as previously defined can be prepared by palladium catalyzed cross-coupling reaction of compound VII in which in which $R^1$, $R^2$, $R^3$, $R^4$ are as previously defined and $LG^1$ is a leaving group, for example iodine, bromine, chlorine or a sulfonate, such as trifluoromethanesulfonate with a boronic acid VIII or a stannane reagent IX. Palladium catalyzed cross-coupling reaction are known to the person skilled in the art. These reactions can be performed in various organic or aqueous solvents compatible to these conditions, by temperatures from below 0° C. up to the boiling point of the solvent system and various palladium catalysts, for example tetrakis(triphenylphosphine)palladium(0) or palladium (II) acetate and triphenylphosphine.

Scheme 5

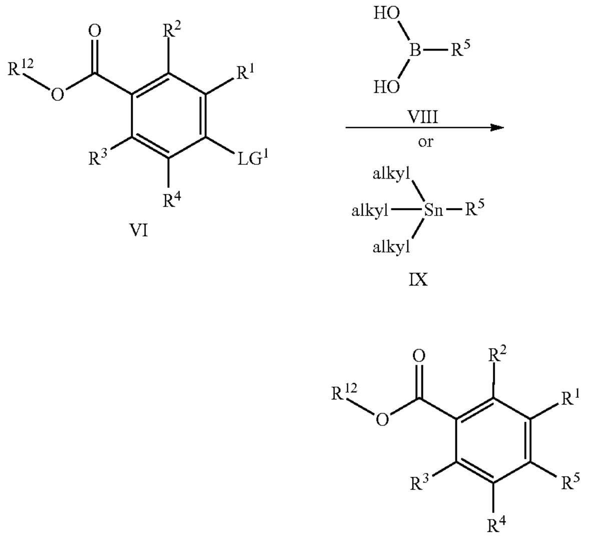

VI VIII or IX VI

The compounds of formula (I) according to the following Tables 1 to 20 can be prepared according to the methods described above. The examples which follow are intended to illustrate the invention and show preferred compounds of formula (I), in the form of a compound of formula (I-a).

(I-a)

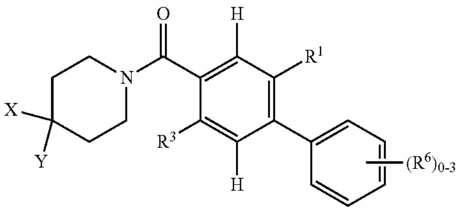

Each of Tables 1 to 20, which follow the Table M below, comprises 864 compounds of the formula (I-a) in which $R^1$, $R^3$ and $R^6$ have the values given in each row in Table M, and Y and X have the values given in the relevant Tables 1 to 20.

Thus compound 1.1 corresponds to a compound of formula (I-a) where $R^1$, $R^3$ and $R^6$ are as defined in row 1 of Table M and where Y and X are as defined in Table 1; compound 14.14 corresponds to a compound of formula (I-a) where $R^1$, $R^3$ and $R^6$ are as defined in row 14 of Table M and where Y and X are as defined in Table 14; and so on.

TABLE M

| Comp. No | $R^1$ | $R^3$ | $R^6$ |
|---|---|---|---|
| M.1. | CN | H | — |
| M.2. | CN | H | 2-F |
| M.3. | CN | H | 3-F |
| M.4. | CN | H | 4-F |
| M.5. | CN | H | 2-Cl |
| M.6. | CN | H | 3-Cl |
| M.7. | CN | H | 4-Cl |
| M.8. | CN | H | 2-Br |
| M.9. | CN | H | 3-Br |
| M.10. | CN | H | 4-Br |
| M.11. | CN | H | 2-$CH_3$ |
| M.12. | CN | H | 3-$CH_3$ |
| M.13. | CN | H | 4-$CH_3$ |
| M.14. | CN | H | 2-$CF_3$ |
| M.15. | CN | H | 3-$CF_3$ |
| M.16. | CN | H | 4-$CF_3$ |
| M.17. | CN | H | 2-$OCF_3$ |
| M.18. | CN | H | 3-$OCF_3$ |
| M.19. | CN | H | 4-$OCF_3$ |
| M.20. | CN | H | 2-$SCF_3$ |
| M.21. | CN | H | 3-$SCF_3$ |
| M.22. | CN | H | 4-$SCF_3$ |
| M.23. | CN | H | 2-CN |
| M.24. | CN | H | 3-CN |
| M.25. | CN | H | 4-CN |
| M.26. | CN | H | 4-$SO_2CH_3$ |
| M.27. | CN | H | 2,3-$F_2$ |
| M.28. | CN | H | 2,4-$F_2$ |
| M.29. | CN | H | 2,5-$F_2$ |
| M.30. | CN | H | 2,6-$F_2$ |
| M.31. | CN | H | 3,4-$F_2$ |
| M.32. | CN | H | 3,5-$F_2$ |
| M.33. | CN | H | 2,4-$Cl_2$ |
| M.34. | CN | H | 2,5-$Cl_2$ |
| M.35. | CN | H | 3,4-$Cl_2$ |
| M.36. | CN | H | 2,3,4-$F_3$ |
| M.37. | CN | H | 2,3,5-$F_3$ |
| M.38. | CN | H | 2,3,6-$F_3$ |
| M.39. | CN | H | 3,4,5-$F_3$ |
| M.40. | CN | H | 2,4,6-$F_3$ |
| M.41. | CN | H | 2-F, 3-Cl |
| M.42. | CN | H | 2-Cl, 4-F |
| M.43. | CN | H | 2-F, 3-$CF_3$ |
| M.44. | CN | H | 2-F, 4-$CF_3$ |
| M.45. | CN | H | 2-F, 5-$CF_3$ |
| M.46. | CN | H | 3-F, 4-$CF_3$ |
| M.47. | CN | H | 3-F, 5-$CF_3$ |
| M.48. | CN | H | 4-F, 3-$CF_3$ |
| M.49. | CN | H | 3,4-$F_2$, 5-$CF_3$ |
| M.50. | CN | H | 2-Cl, 3-$CF_3$ |
| M.51. | CN | H | 2-Cl, 4-$CF_3$ |
| M.52. | CN | H | 2-Cl, 5-$CF_3$ |
| M.53. | CN | H | 3-Cl, 5-$CF_3$ |
| M.54. | CN | H | 4-Cl, 3-$CF_3$ |
| M.55. | CN | $CH_3$ | — |
| M.56. | CN | $CH_3$ | 2-F |
| M.57. | CN | $CH_3$ | 3-F |
| M.58. | CN | $CH_3$ | 4-F |
| M.59. | CN | $CH_3$ | 2-Cl |
| M.60. | CN | $CH_3$ | 3-Cl |
| M.61. | CN | $CH_3$ | 4-Cl |
| M.62. | CN | $CH_3$ | 2-Br |
| M.63. | CN | $CH_3$ | 3-Br |
| M.64. | CN | $CH_3$ | 4-Br |
| M.65. | CN | $CH_3$ | 2-$CH_3$ |
| M.66. | CN | $CH_3$ | 3-$CH_3$ |
| M.67. | CN | $CH_3$ | 4-$CH_3$ |
| M.68. | CN | $CH_3$ | 2-$CF_3$ |
| M.69. | CN | $CH_3$ | 3-$CF_3$ |
| M.70. | CN | $CH_3$ | 4-$CF_3$ |
| M.71. | CN | $CH_3$ | 2-$OCF_3$ |
| M.72. | CN | $CH_3$ | 3-$OCF_3$ |
| M.73. | CN | $CH_3$ | 4-$OCF_3$ |
| M.74. | CN | $CH_3$ | 2-$SCF_3$ |
| M.75. | CN | $CH_3$ | 3-$SCF_3$ |
| M.76. | CN | $CH_3$ | 4-$SCF_3$ |
| M.77. | CN | $CH_3$ | 2-CN |
| M.78. | CN | $CH_3$ | 3-CN |

TABLE M-continued

| Comp. No | $R^1$ | $R^3$ | $R^6$ |
|---|---|---|---|
| M.79. | CN | $CH_3$ | 4-CN |
| M.80. | CN | $CH_3$ | 4-$SO_2CH_3$ |
| M.81. | CN | $CH_3$ | 2,3-$F_2$ |
| M.82. | CN | $CH_3$ | 2,4-$F_2$ |
| M.83. | CN | $CH_3$ | 2,5-$F_2$ |
| M.84. | CN | $CH_3$ | 2,6-$F_2$ |
| M.85. | CN | $CH_3$ | 3,4-$F_2$ |
| M.86. | CN | $CH_3$ | 3,5-$F_2$ |
| M.87. | CN | $CH_3$ | 2,4-$Cl_2$ |
| M.88. | CN | $CH_3$ | 2,5-$Cl_2$ |
| M.89. | CN | $CH_3$ | 3,4-$Cl_2$ |
| M.90. | CN | $CH_3$ | 2,3,4-$F_3$ |
| M.91. | CN | $CH_3$ | 2,3,5-$F_3$ |
| M.92. | CN | $CH_3$ | 2,3,6-$F_3$ |
| M.93. | CN | $CH_3$ | 3,4,5-$F_3$ |
| M.94. | CN | $CH_3$ | 2,4,6-$F_3$ |
| M.95. | CN | $CH_3$ | 2-F, 3-Cl |
| M.96. | CN | $CH_3$ | 2-Cl, 4-F |
| M.97. | CN | $CH_3$ | 2-F, 3-$CF_3$ |
| M.98. | CN | $CH_3$ | 2-F, 4-$CF_3$ |
| M.99. | CN | $CH_3$ | 2-F, 5-$CF_3$ |
| M.100. | CN | $CH_3$ | 3-F, 4-$CF_3$ |
| M.101. | CN | $CH_3$ | 3-F, 5-$CF_3$ |
| M.102. | CN | $CH_3$ | 4-F, 3-$CF_3$ |
| M.103. | CN | $CH_3$ | 3,4-$F_2$, 5-$CF_3$ |
| M.104. | CN | $CH_3$ | 2-Cl, 3-$CF_3$ |
| M.105. | CN | $CH_3$ | 2-Cl, 4-$CF_3$ |
| M.106. | CN | $CH_3$ | 2-Cl, 5-$CF_3$ |
| M.107. | CN | $CH_3$ | 3-Cl, 5-$CF_3$ |
| M.108. | CN | $CH_3$ | 4-Cl, 3-$CF_3$ |
| M.109. | CN | $CH_2CH_3$ | — |
| M.110. | CN | $CH_2CH_3$ | 2-F |
| M.111. | CN | $CH_2CH_3$ | 3-F |
| M.112. | CN | $CH_2CH_3$ | 4-F |
| M.113. | CN | $CH_2CH_3$ | 2-Cl |
| M.114. | CN | $CH_2CH_3$ | 3-Cl |
| M.115. | CN | $CH_2CH_3$ | 4-Cl |
| M.116. | CN | $CH_2CH_3$ | 2-Br |
| M.117. | CN | $CH_2CH_3$ | 3-Br |
| M.118. | CN | $CH_2CH_3$ | 4-Br |
| M.119. | CN | $CH_2CH_3$ | 2-$CH_3$ |
| M.120. | CN | $CH_2CH_3$ | 3-$CH_3$ |
| M.121. | CN | $CH_2CH_3$ | 4-$CH_3$ |
| M.122. | CN | $CH_2CH_3$ | 2-$CF_3$ |
| M.123. | CN | $CH_2CH_3$ | 3-$CF_3$ |
| M.124. | CN | $CH_2CH_3$ | 4-$CF_3$ |
| M.125. | CN | $CH_2CH_3$ | 2-$OCF_3$ |
| M.126. | CN | $CH_2CH_3$ | 3-$OCF_3$ |
| M.127. | CN | $CH_2CH_3$ | 4-$OCF_3$ |
| M.128. | CN | $CH_2CH_3$ | 2-$SCF_3$ |
| M.129. | CN | $CH_2CH_3$ | 3-$SCF_3$ |
| M.130. | CN | $CH_2CH_3$ | 4-$SCF_3$ |
| M.131. | CN | $CH_2CH_3$ | 2-CN |
| M.132. | CN | $CH_2CH_3$ | 3-CN |
| M.133. | CN | $CH_2CH_3$ | 4-CN |
| M.134. | CN | $CH_2CH_3$ | 4-$SO_2CH_3$ |
| M.135. | CN | $CH_2CH_3$ | 2,3-$F_2$ |
| M.136. | CN | $CH_2CH_3$ | 2,4-$F_2$ |
| M.137. | CN | $CH_2CH_3$ | 2,5-$F_2$ |
| M.138. | CN | $CH_2CH_3$ | 2,6-$F_2$ |
| M.139. | CN | $CH_2CH_3$ | 3,4-$F_2$ |
| M.140. | CN | $CH_2CH_3$ | 3,5-$F_2$ |
| M.141. | CN | $CH_2CH_3$ | 2,4-$Cl_2$ |
| M.142. | CN | $CH_2CH_3$ | 2,5-$Cl_2$ |
| M.143. | CN | $CH_2CH_3$ | 3,4-$Cl_2$ |
| M.144. | CN | $CH_2CH_3$ | 2,3,4-$F_3$ |
| M.145. | CN | $CH_2CH_3$ | 2,3,5-$F_3$ |
| M.146. | CN | $CH_2CH_3$ | 2,3,6-$F_3$ |
| M.147. | CN | $CH_2CH_3$ | 3,4,5-$F_3$ |
| M.148. | CN | $CH_2CH_3$ | 2,4,6-$F_3$ |
| M.149. | CN | $CH_2CH_3$ | 2-F, 3-Cl |
| M.150. | CN | $CH_2CH_3$ | 2-Cl, 4-F |
| M.151. | CN | $CH_2CH_3$ | 2-F, 3-$CF_3$ |
| M.152. | CN | $CH_2CH_3$ | 2-F, 4-$CF_3$ |
| M.153. | CN | $CH_2CH_3$ | 2-F, 5-$CF_3$ |
| M.154. | CN | $CH_2CH_3$ | 3-F, 4-$CF_3$ |
| M.155. | CN | $CH_2CH_3$ | 3-F, 5-$CF_3$ |
| M.156. | CN | $CH_2CH_3$ | 4-F, 3-$CF_3$ |

TABLE M-continued

| Comp. No | $R^1$ | $R^3$ | $R^6$ |
|---|---|---|---|
| M.157. | CN | $CH_2CH_3$ | 3,4-$F_2$, 5-$CF_3$ |
| M.158. | CN | $CH_2CH_3$ | 2-Cl, 3-$CF_3$ |
| M.159. | CN | $CH_2CH_3$ | 2-Cl, 4-$CF_3$ |
| M.160. | CN | $CH_2CH_3$ | 2-Cl, 5-$CF_3$ |
| M.161. | CN | $CH_2CH_3$ | 3-Cl, 5-$CF_3$ |
| M.162. | CN | $CH_2CH_3$ | 4-Cl, 3-$CF_3$ |
| M.163. | CN | $CF_3$ | — |
| M.164. | CN | $CF_3$ | 2-F |
| M.165. | CN | $CF_3$ | 3-F |
| M.166. | CN | $CF_3$ | 4-F |
| M.167. | CN | $CF_3$ | 2-Cl |
| M.168. | CN | $CF_3$ | 3-Cl |
| M.169. | CN | $CF_3$ | 4-Cl |
| M.170. | CN | $CF_3$ | 2-Br |
| M.171. | CN | $CF_3$ | 3-Br |
| M.172. | CN | $CF_3$ | 4-Br |
| M.173. | CN | $CF_3$ | 2-$CH_3$ |
| M.174. | CN | $CF_3$ | 3-$CH_3$ |
| M.175. | CN | $CF_3$ | 4-$CH_3$ |
| M.176. | CN | $CF_3$ | 2-$CF_3$ |
| M.177. | CN | $CF_3$ | 3-$CF_3$ |
| M.178. | CN | $CF_3$ | 4-$CF_3$ |
| M.179. | CN | $CF_3$ | 2-$OCF_3$ |
| M.180. | CN | $CF_3$ | 3-$OCF_3$ |
| M.181. | CN | $CF_3$ | 4-$OCF_3$ |
| M.182. | CN | $CF_3$ | 2-$SCF_3$ |
| M.183. | CN | $CF_3$ | 3-$SCF_3$ |
| M.184. | CN | $CF_3$ | 4-$SCF_3$ |
| M.185. | CN | $CF_3$ | 2-CN |
| M.186. | CN | $CF_3$ | 3-CN |
| M.187. | CN | $CF_3$ | 4-CN |
| M.188. | CN | $CF_3$ | 4-$SO_2CH_3$ |
| M.189. | CN | $CF_3$ | 2,3-$F_2$ |
| M.190. | CN | $CF_3$ | 2,4-$F_2$ |
| M.191. | CN | $CF_3$ | 2,5-$F_2$ |
| M.192. | CN | $CF_3$ | 2,6-$F_2$ |
| M.193. | CN | $CF_3$ | 3,4-$F_2$ |
| M.194. | CN | $CF_3$ | 3,5-$F_2$ |
| M.195. | CN | $CF_3$ | 2,4-$Cl_2$ |
| M.196. | CN | $CF_3$ | 2,5-$Cl_2$ |
| M.197. | CN | $CF_3$ | 3,4-$Cl_2$ |
| M.198. | CN | $CF_3$ | 2,3,4-$F_3$ |
| M.199. | CN | $CF_3$ | 2,3,5-$F_3$ |
| M.200. | CN | $CF_3$ | 2,3,6-$F_3$ |
| M.201. | CN | $CF_3$ | 3,4,5-$F_3$ |
| M.202. | CN | $CF_3$ | 2,4,6-$F_3$ |
| M.203. | CN | $CF_3$ | 2-F, 3-Cl |
| M.204. | CN | $CF_3$ | 2-Cl, 4-F |
| M.205. | CN | $CF_3$ | 2-F, 3-$CF_3$ |
| M.206. | CN | $CF_3$ | 2-F, 4-$CF_3$ |
| M.207. | CN | $CF_3$ | 2-F, 5-$CF_3$ |
| M.208. | CN | $CF_3$ | 3-F, 4-$CF_3$ |
| M.209. | CN | $CF_3$ | 3-F, 5-$CF_3$ |
| M.210. | CN | $CF_3$ | 4-F, 3-$CF_3$ |
| M.211. | CN | $CF_3$ | 3,4-$F_2$, 5-$CF_3$ |
| M.212. | CN | $CF_3$ | 2-Cl, 3-$CF_3$ |
| M.213. | CN | $CF_3$ | 2-Cl, 4-$CF_3$ |
| M.214. | CN | $CF_3$ | 2-Cl, 5-$CF_3$ |
| M.215. | CN | $CF_3$ | 3-Cl, 5-$CF_3$ |
| M.216. | CN | $CF_3$ | 4-Cl, 3-$CF_3$ |
| M.217. | CN | $CHF_2$ | — |
| M.218. | CN | $CHF_2$ | 2-F |
| M.219. | CN | $CHF_2$ | 3-F |
| M.220. | CN | $CHF_2$ | 4-F |
| M.221. | CN | $CHF_2$ | 2-Cl |
| M.222. | CN | $CHF_2$ | 3-Cl |
| M.223. | CN | $CHF_2$ | 4-Cl |
| M.224. | CN | $CHF_2$ | 2-Br |
| M.225. | CN | $CHF_2$ | 3-Br |
| M.226. | CN | $CHF_2$ | 4-Br |
| M.227. | CN | $CHF_2$ | 2-$CH_3$ |
| M.228. | CN | $CHF_2$ | 3-$CH_3$ |
| M.229. | CN | $CHF_2$ | 4-$CH_3$ |
| M.230. | CN | $CHF_2$ | 2-$CF_3$ |
| M.231. | CN | $CHF_2$ | 3-$CF_3$ |
| M.232. | CN | $CHF_2$ | 4-$CF_3$ |
| M.233. | CN | $CHF_2$ | 2-$OCF_3$ |
| M.234. | CN | $CHF_2$ | 3-$OCF_3$ |

TABLE M-continued

| Comp. No | $R^1$ | $R^3$ | $R^6$ |
|---|---|---|---|
| M.235. | CN | $CHF_2$ | 4-$OCF_3$ |
| M.236. | CN | $CHF_2$ | 2-$SCF_3$ |
| M.237. | CN | $CHF_2$ | 3-$SCF_3$ |
| M.238. | CN | $CHF_2$ | 4-$SCF_3$ |
| M.239. | CN | $CHF_2$ | 2-CN |
| M.240. | CN | $CHF_2$ | 3-CN |
| M.241. | CN | $CHF_2$ | 4-CN |
| M.242. | CN | $CHF_2$ | 4-$SO_2CH_3$ |
| M.243. | CN | $CHF_2$ | 2,3-$F_2$ |
| M.244. | CN | $CHF_2$ | 2,4-$F_2$ |
| M.245. | CN | $CHF_2$ | 2,5-$F_2$ |
| M.246. | CN | $CHF_2$ | 2,6-$F_2$ |
| M.247. | CN | $CHF_2$ | 3,4-$F_2$ |
| M.248. | CN | $CHF_2$ | 3,5-$F_2$ |
| M.249. | CN | $CHF_2$ | 2,4-$Cl_2$ |
| M.250. | CN | $CHF_2$ | 2,5-$Cl_2$ |
| M.251. | CN | $CHF_2$ | 3,4-$Cl_2$ |
| M.252. | CN | $CHF_2$ | 2,3,4-$F_3$ |
| M.253. | CN | $CHF_2$ | 2,3,5-$F_3$ |
| M.254. | CN | $CHF_2$ | 2,3,6-$F_3$ |
| M.255. | CN | $CHF_2$ | 3,4,5-$F_3$ |
| M.256. | CN | $CHF_2$ | 2,4,6-$F_3$ |
| M.257. | CN | $CHF_2$ | 2-F, 3-Cl |
| M.258. | CN | $CHF_2$ | 2-Cl, 4-F |
| M.259. | CN | $CHF_2$ | 2-F, 3-$CF_3$ |
| M.260. | CN | $CHF_2$ | 2-F, 4-$CF_3$ |
| M.261. | CN | $CHF_2$ | 2-F, 5-$CF_3$ |
| M.262. | CN | $CHF_2$ | 3-F, 4-$CF_3$ |
| M.263. | CN | $CHF_2$ | 3-F, 5-$CF_3$ |
| M.264. | CN | $CHF_2$ | 4-F, 3-$CF_3$ |
| M.265. | CN | $CHF_2$ | 3,4-$F_2$, 5-$CF_3$ |
| M.266. | CN | $CHF_2$ | 2-Cl, 3-$CF_3$ |
| M.267. | CN | $CHF_2$ | 2-Cl, 4-$CF_3$ |
| M.268. | CN | $CHF_2$ | 2-Cl, 5-$CF_3$ |
| M.269. | CN | $CHF_2$ | 3-Cl, 5-$CF_3$ |
| M.270. | CN | $CHF_2$ | 4-Cl, 3-$CF_3$ |
| M.271. | CN | $CF_2CF_3$ | — |
| M.272. | CN | $CF_2CF_3$ | 2-F |
| M.273. | CN | $CF_2CF_3$ | 3-F |
| M.274. | CN | $CF_2CF_3$ | 4-F |
| M.275. | CN | $CF_2CF_3$ | 2-Cl |
| M.276. | CN | $CF_2CF_3$ | 3-Cl |
| M.277. | CN | $CF_2CF_3$ | 4-Cl |
| M.278. | CN | $CF_2CF_3$ | 2-Br |
| M.279. | CN | $CF_2CF_3$ | 3-Br |
| M.280. | CN | $CF_2CF_3$ | 4-Br |
| M.281. | CN | $CF_2CF_3$ | 2-$CH_3$ |
| M.282. | CN | $CF_2CF_3$ | 3-$CH_3$ |
| M.283. | CN | $CF_2CF_3$ | 4-$CH_3$ |
| M.284. | CN | $CF_2CF_3$ | 2-$CF_3$ |
| M.285. | CN | $CF_2CF_3$ | 3-$CF_3$ |
| M.286. | CN | $CF_2CF_3$ | 4-$CF_3$ |
| M.287. | CN | $CF_2CF_3$ | 2-$OCF_3$ |
| M.288. | CN | $CF_2CF_3$ | 3-$OCF_3$ |
| M.289. | CN | $CF_2CF_3$ | 4-$OCF_3$ |
| M.290. | CN | $CF_2CF_3$ | 2-$SCF_3$ |
| M.291. | CN | $CF_2CF_3$ | 3-$SCF_3$ |
| M.292. | CN | $CF_2CF_3$ | 4-$SCF_3$ |
| M.293. | CN | $CF_2CF_3$ | 2-CN |
| M.294. | CN | $CF_2CF_3$ | 3-CN |
| M.295. | CN | $CF_2CF_3$ | 4-CN |
| M.296. | CN | $CF_2CF_3$ | 4-$SO_2CH_3$ |
| M.297. | CN | $CF_2CF_3$ | 2,3-$F_2$ |
| M.298. | CN | $CF_2CF_3$ | 2,4-$F_2$ |
| M.299. | CN | $CF_2CF_3$ | 2,5-$F_2$ |
| M.300. | CN | $CF_2CF_3$ | 2,6-$F_2$ |
| M.301. | CN | $CF_2CF_3$ | 3,4-$F_2$ |
| M.302. | CN | $CF_2CF_3$ | 3,5-$F_2$ |
| M.303. | CN | $CF_2CF_3$ | 2,4-$Cl_2$ |
| M.304. | CN | $CF_2CF_3$ | 2,5-$Cl_2$ |
| M.305. | CN | $CF_2CF_3$ | 3,4-$Cl_2$ |
| M.306. | CN | $CF_2CF_3$ | 2,3,4-$F_3$ |
| M.307. | CN | $CF_2CF_3$ | 2,3,5-$F_3$ |
| M.308. | CN | $CF_2CF_3$ | 2,3,6-$F_3$ |
| M.309. | CN | $CF_2CF_3$ | 3,4,5-$F_3$ |
| M.310. | CN | $CF_2CF_3$ | 2,4,6-$F_3$ |
| M.311. | CN | $CF_2CF_3$ | 2-F, 3-Cl |
| M.312. | CN | $CF_2CF_3$ | 2-Cl, 4-F |

TABLE M-continued

| Comp. No | $R^1$ | $R^3$ | $R^6$ |
|---|---|---|---|
| M.313. | CN | $CF_2CF_3$ | 2-F, 3-$CF_3$ |
| M.314. | CN | $CF_2CF_3$ | 2-F, 4-$CF_3$ |
| M.315. | CN | $CF_2CF_3$ | 2-F, 5-$CF_3$ |
| M.316. | CN | $CF_2CF_3$ | 3-F, 4-$CF_3$ |
| M.317. | CN | $CF_2CF_3$ | 3-F, 5-$CF_3$ |
| M.318. | CN | $CF_2CF_3$ | 4-F, 3-$CF_3$ |
| M.319. | CN | $CF_2CF_3$ | 3,4-$F_2$, 5-$CF_3$ |
| M.320. | CN | $CF_2CF_3$ | 2-Cl, 3-$CF_3$ |
| M.321. | CN | $CF_2CF_3$ | 2-Cl, 4-$CF_3$ |
| M.322. | CN | $CF_2CF_3$ | 2-Cl, 5-$CF_3$ |
| M.323. | CN | $CF_2CF_3$ | 3-Cl, 5-$CF_3$ |
| M.324. | CN | $CF_2CF_3$ | 4-Cl, 3-$CF_3$ |
| M.325. | CN | $OCH_3$ | — |
| M.326. | CN | $OCH_3$ | 2-F |
| M.327. | CN | $OCH_3$ | 3-F |
| M.328. | CN | $OCH_3$ | 4-F |
| M.329. | CN | $OCH_3$ | 2-Cl |
| M.330. | CN | $OCH_3$ | 3-Cl |
| M.331. | CN | $OCH_3$ | 4-Cl |
| M.332. | CN | $OCH_3$ | 2-Br |
| M.333. | CN | $OCH_3$ | 3-Br |
| M.334. | CN | $OCH_3$ | 4-Br |
| M.335. | CN | $OCH_3$ | 2-$CH_3$ |
| M.336. | CN | $OCH_3$ | 3-$CH_3$ |
| M.337. | CN | $OCH_3$ | 4-$CH_3$ |
| M.338. | CN | $OCH_3$ | 2-$CF_3$ |
| M.339. | CN | $OCH_3$ | 3-$CF_3$ |
| M.340. | CN | $OCH_3$ | 4-$CF_3$ |
| M.341. | CN | $OCH_3$ | 2-$OCF_3$ |
| M.342. | CN | $OCH_3$ | 3-$OCF_3$ |
| M.343. | CN | $OCH_3$ | 4-$OCF_3$ |
| M.344. | CN | $OCH_3$ | 2-$SCF_3$ |
| M.345. | CN | $OCH_3$ | 3-$SCF_3$ |
| M.346. | CN | $OCH_3$ | 4-$SCF_3$ |
| M.347. | CN | $OCH_3$ | 2-CN |
| M.348. | CN | $OCH_3$ | 3-CN |
| M.349. | CN | $OCH_3$ | 4-CN |
| M.350. | CN | $OCH_3$ | 4-$SO_2CH_3$ |
| M.351. | CN | $OCH_3$ | 2,3-$F_2$ |
| M.352. | CN | $OCH_3$ | 2,4-$F_2$ |
| M.353. | CN | $OCH_3$ | 2,5-$F_2$ |
| M.354. | CN | $OCH_3$ | 2,6-$F_2$ |
| M.355. | CN | $OCH_3$ | 3,4-$F_2$ |
| M.356. | CN | $OCH_3$ | 3,5-$F_2$ |
| M.357. | CN | $OCH_3$ | 2,4-$Cl_2$ |
| M.358. | CN | $OCH_3$ | 2,5-$Cl_2$ |
| M.359. | CN | $OCH_3$ | 3,4-$Cl_2$ |
| M.360. | CN | $OCH_3$ | 2,3,4-$F_3$ |
| M.361. | CN | $OCH_3$ | 2,3,5-$F_3$ |
| M.362. | CN | $OCH_3$ | 2,3,6-$F_3$ |
| M.363. | CN | $OCH_3$ | 3,4,5-$F_3$ |
| M.364. | CN | $OCH_3$ | 2,4,6-$F_3$ |
| M.365. | CN | $OCH_3$ | 2-F, 3-Cl |
| M.366. | CN | $OCH_3$ | 2-Cl, 4-F |
| M.367. | CN | $OCH_3$ | 2-F, 3-$CF_3$ |
| M.368. | CN | $OCH_3$ | 2-F, 4-$CF_3$ |
| M.369. | CN | $OCH_3$ | 2-F, 5-$CF_3$ |
| M.370. | CN | $OCH_3$ | 3-F, 4-$CF_3$ |
| M.371. | CN | $OCH_3$ | 3-F, 5-$CF_3$ |
| M.372. | CN | $OCH_3$ | 4-F, 3-$CF_3$ |
| M.373. | CN | $OCH_3$ | 3,4-$F_2$, 5-$CF_3$ |
| M.374. | CN | $OCH_3$ | 2-Cl, 3-$CF_3$ |
| M.375. | CN | $OCH_3$ | 2-Cl, 4-$CF_3$ |
| M.376. | CN | $OCH_3$ | 2-Cl, 5-$CF_3$ |
| M.377. | CN | $OCH_3$ | 3-Cl, 5-$CF_3$ |
| M.378. | CN | $OCH_3$ | 4-Cl, 3-$CF_3$ |
| M.379. | CN | $OCH_2CH_3$ | — |
| M.380. | CN | $OCH_2CH_3$ | 2-F |
| M.381. | CN | $OCH_2CH_3$ | 3-F |
| M.382. | CN | $OCH_2CH_3$ | 4-F |
| M.383. | CN | $OCH_2CH_3$ | 2-Cl |
| M.384. | CN | $OCH_2CH_3$ | 3-Cl |
| M.385. | CN | $OCH_2CH_3$ | 4-Cl |
| M.386. | CN | $OCH_2CH_3$ | 2-Br |
| M.387. | CN | $OCH_2CH_3$ | 3-Br |
| M.388. | CN | $OCH_2CH_3$ | 4-Br |
| M.389. | CN | $OCH_2CH_3$ | 2-$CH_3$ |
| M.390. | CN | $OCH_2CH_3$ | 3-$CH_3$ |

TABLE M-continued

| Comp. No | $R^1$ | $R^3$ | $R^6$ |
|---|---|---|---|
| M.391. | CN | $OCH_2CH_3$ | 4-$CH_3$ |
| M.392. | CN | $OCH_2CH_3$ | 2-$CF_3$ |
| M.393. | CN | $OCH_2CH_3$ | 3-$CF_3$ |
| M.394. | CN | $OCH_2CH_3$ | 4-$CF_3$ |
| M.395. | CN | $OCH_2CH_3$ | 2-$OCF_3$ |
| M.396. | CN | $OCH_2CH_3$ | 3-$OCF_3$ |
| M.397. | CN | $OCH_2CH_3$ | 4-$OCF_3$ |
| M.398. | CN | $OCH_2CH_3$ | 2-$SCF_3$ |
| M.399. | CN | $OCH_2CH_3$ | 3-$SCF_3$ |
| M.400. | CN | $OCH_2CH_3$ | 4-$SCF_3$ |
| M.401. | CN | $OCH_2CH_3$ | 2-CN |
| M.402. | CN | $OCH_2CH_3$ | 3-CN |
| M.403. | CN | $OCH_2CH_3$ | 4-CN |
| M.404. | CN | $OCH_2CH_3$ | 4-$SO_2CH_3$ |
| M.405. | CN | $OCH_2CH_3$ | 2,3-$F_2$ |
| M.406. | CN | $OCH_2CH_3$ | 2,4-$F_2$ |
| M.407. | CN | $OCH_2CH_3$ | 2,5-$F_2$ |
| M.408. | CN | $OCH_2CH_3$ | 2,6-$F_2$ |
| M.409. | CN | $OCH_2CH_3$ | 3,4-$F_2$ |
| M.410. | CN | $OCH_2CH_3$ | 3,5-$F_2$ |
| M.411. | CN | $OCH_2CH_3$ | 2,4-$Cl_2$ |
| M.412. | CN | $OCH_2CH_3$ | 2,5-$Cl_2$ |
| M.413. | CN | $OCH_2CH_3$ | 3,4-$Cl_2$ |
| M.414. | CN | $OCH_2CH_3$ | 2,3,4-$F_3$ |
| M.415. | CN | $OCH_2CH_3$ | 2,3,5-$F_3$ |
| M.416. | CN | $OCH_2CH_3$ | 2,3,6-$F_3$ |
| M.417. | CN | $OCH_2CH_3$ | 3,4,5-$F_3$ |
| M.418. | CN | $OCH_2CH_3$ | 2,4,6-$F_3$ |
| M.419. | CN | $OCH_2CH_3$ | 2-F, 3-Cl |
| M.420. | CN | $OCH_2CH_3$ | 2-Cl, 4-F |
| M.421. | CN | $OCH_2CH_3$ | 2-F, 3-$CF_3$ |
| M.422. | CN | $OCH_2CH_3$ | 2-F, 4-$CF_3$ |
| M.423. | CN | $OCH_2CH_3$ | 2-F, 5-$CF_3$ |
| M.424. | CN | $OCH_2CH_3$ | 3-F, 4-$CF_3$ |
| M.425. | CN | $OCH_2CH_3$ | 3-F, 5-$CF_3$ |
| M.426. | CN | $OCH_2CH_3$ | 4-F, 3-$CF_3$ |
| M.427. | CN | $OCH_2CH_3$ | 3,4-$F_2$, 5-$CF_3$ |
| M.428. | CN | $OCH_2CH_3$ | 2-Cl, 3-$CF_3$ |
| M.429. | CN | $OCH_2CH_3$ | 2-Cl, 4-$CF_3$ |
| M.430. | CN | $OCH_2CH_3$ | 2-Cl, 5-$CF_3$ |
| M.431. | CN | $OCH_2CH_3$ | 3-Cl, 5-$CF_3$ |
| M.432. | CN | $OCH_2CH_3$ | 4-Cl, 3-$CF_3$ |
| M.433. | C(=S)$NH_2$ | H | — |
| M.434. | C(=S)$NH_2$ | H | 2-F |
| M.435. | C(=S)$NH_2$ | H | 3-F |
| M.436. | C(=S)$NH_2$ | H | 4-F |
| M.437. | C(=S)$NH_2$ | H | 2-Cl |
| M.438. | C(=S)$NH_2$ | H | 3-Cl |
| M.439. | C(=S)$NH_2$ | H | 4-Cl |
| M.440. | C(=S)$NH_2$ | H | 2-Br |
| M.441. | C(=S)$NH_2$ | H | 3-Br |
| M.442. | C(=S)$NH_2$ | H | 4-Br |
| M.443. | C(=S)$NH_2$ | H | 2-$CH_3$ |
| M.444. | C(=S)$NH_2$ | H | 3-$CH_3$ |
| M.445. | C(=S)$NH_2$ | H | 4-$CH_3$ |
| M.446. | C(=S)$NH_2$ | H | 2-$CF_3$ |
| M.447. | C(=S)$NH_2$ | H | 3-$CF_3$ |
| M.448. | C(=S)$NH_2$ | H | 4-$CF_3$ |
| M.449. | C(=S)$NH_2$ | H | 2-$OCF_3$ |
| M.450. | C(=S)$NH_2$ | H | 3-$OCF_3$ |
| M.451. | C(=S)$NH_2$ | H | 4-$OCF_3$ |
| M.452. | C(=S)$NH_2$ | H | 2-$SCF_3$ |
| M.453. | C(=S)$NH_2$ | H | 3-$SCF_3$ |
| M.454. | C(=S)$NH_2$ | H | 4-$SCF_3$ |
| M.455. | C(=S)$NH_2$ | H | 2-CN |
| M.456. | C(=S)$NH_2$ | H | 3-CN |
| M.457. | C(=S)$NH_2$ | H | 4-CN |
| M.458. | C(=S)$NH_2$ | H | 4-$SO_2CH_3$ |
| M.459. | C(=S)$NH_2$ | H | 2,3-$F_2$ |
| M.460. | C(=S)$NH_2$ | H | 2,4-$F_2$ |
| M.461. | C(=S)$NH_2$ | H | 2,5-$F_2$ |
| M.462. | C(=S)$NH_2$ | H | 2,6-$F_2$ |
| M.463. | C(=S)$NH_2$ | H | 3,4-$F_2$ |
| M.464. | C(=S)$NH_2$ | H | 3,5-$F_2$ |
| M.465. | C(=S)$NH_2$ | H | 2,4-$Cl_2$ |
| M.466. | C(=S)$NH_2$ | H | 2,5-$Cl_2$ |
| M.467. | C(=S)$NH_2$ | H | 3,4-$Cl_2$ |
| M.468. | C(=S)$NH_2$ | H | 2,3,4-$F_3$ |

TABLE M-continued

| Comp. No | $R^1$ | $R^3$ | $R^6$ |
|---|---|---|---|
| M.469. | C(═S)NH$_2$ | H | 2,3,5-F$_3$ |
| M.470. | C(═S)NH$_2$ | H | 2,3,6-F$_3$ |
| M.471. | C(═S)NH$_2$ | H | 3,4,5-F$_3$ |
| M.472. | C(═S)NH$_2$ | H | 2,4,6-F$_3$ |
| M.473. | C(═S)NH$_2$ | H | 2-F, 3-Cl |
| M.474. | C(═S)NH$_2$ | H | 2-Cl, 4-F |
| M.475. | C(═S)NH$_2$ | H | 2-F, 3-CF$_3$ |
| M.476. | C(═S)NH$_2$ | H | 2-F, 4-CF$_3$ |
| M.477. | C(═S)NH$_2$ | H | 2-F, 5-CF$_3$ |
| M.478. | C(═S)NH$_2$ | H | 3-F, 4-CF$_3$ |
| M.479. | C(═S)NH$_2$ | H | 3-F, 5-CF$_3$ |
| M.480. | C(═S)NH$_2$ | H | 4-F, 3-CF$_3$ |
| M.481. | C(═S)NH$_2$ | H | 3,4-F$_2$, 5-CF$_3$ |
| M.482. | C(═S)NH$_2$ | H | 2-Cl, 3-CF$_3$ |
| M.483. | C(═S)NH$_2$ | H | 2-Cl, 4-CF$_3$ |
| M.484. | C(═S)NH$_2$ | H | 2-Cl, 5-CF$_3$ |
| M.485. | C(═S)NH$_2$ | H | 3-Cl, 5-CF$_3$ |
| M.486. | C(═S)NH$_2$ | H | 4-Cl, 3-CF$_3$ |
| M.487. | C(═S)NH$_2$ | CH$_3$ | — |
| M.488. | C(═S)NH$_2$ | CH$_3$ | 2-F |
| M.489. | C(═S)NH$_2$ | CH$_3$ | 3-F |
| M.490. | C(═S)NH$_2$ | CH$_3$ | 4-F |
| M.491. | C(═S)NH$_2$ | CH$_3$ | 2-Cl |
| M.492. | C(═S)NH$_2$ | CH$_3$ | 3-Cl |
| M.493. | C(═S)NH$_2$ | CH$_3$ | 4-Cl |
| M.494. | C(═S)NH$_2$ | CH$_3$ | 2-Br |
| M.495. | C(═S)NH$_2$ | CH$_3$ | 3-Br |
| M.496. | C(═S)NH$_2$ | CH$_3$ | 4-Br |
| M.497. | C(═S)NH$_2$ | CH$_3$ | 2-CH$_3$ |
| M.498. | C(═S)NH$_2$ | CH$_3$ | 3-CH$_3$ |
| M.499. | C(═S)NH$_2$ | CH$_3$ | 4-CH$_3$ |
| M.500. | C(═S)NH$_2$ | CH$_3$ | 2-CF$_3$ |
| M.501. | C(═S)NH$_2$ | CH$_3$ | 3-CF$_3$ |
| M.502. | C(═S)NH$_2$ | CH$_3$ | 4-CF$_3$ |
| M.503. | C(═S)NH$_2$ | CH$_3$ | 2-OCF$_3$ |
| M.504. | C(═S)NH$_2$ | CH$_3$ | 3-OCF$_3$ |
| M.505. | C(═S)NH$_2$ | CH$_3$ | 4-OCF$_3$ |
| M.506. | C(═S)NH$_2$ | CH$_3$ | 2-SCF$_3$ |
| M.507. | C(═S)NH$_2$ | CH$_3$ | 3-SCF$_3$ |
| M.508. | C(═S)NH$_2$ | CH$_3$ | 4-SCF$_3$ |
| M.509. | C(═S)NH$_2$ | CH$_3$ | 2-CN |
| M.510. | C(═S)NH$_2$ | CH$_3$ | 3-CN |
| M.511. | C(═S)NH$_2$ | CH$_3$ | 4-CN |
| M.512. | C(═S)NH$_2$ | CH$_3$ | 4-SO$_2$CH$_3$ |
| M.513. | C(═S)NH$_2$ | CH$_3$ | 2,3-F$_2$ |
| M.514. | C(═S)NH$_2$ | CH$_3$ | 2,4-F$_2$ |
| M.515. | C(═S)NH$_2$ | CH$_3$ | 2,5-F$_2$ |
| M.516. | C(═S)NH$_2$ | CH$_3$ | 2,6-F$_2$ |
| M.517. | C(═S)NH$_2$ | CH$_3$ | 3,4-F$_2$ |
| M.518. | C(═S)NH$_2$ | CH$_3$ | 3,5-F$_2$ |
| M.519. | C(═S)NH$_2$ | CH$_3$ | 2,4-Cl$_2$ |
| M.520. | C(═S)NH$_2$ | CH$_3$ | 2,5-Cl$_2$ |
| M.521. | C(═S)NH$_2$ | CH$_3$ | 3,4-Cl$_2$ |
| M.522. | C(═S)NH$_2$ | CH$_3$ | 2,3,4-F$_3$ |
| M.523. | C(═S)NH$_2$ | CH$_3$ | 2,3,5-F$_3$ |
| M.524. | C(═S)NH$_2$ | CH$_3$ | 2,3,6-F$_3$ |
| M.525. | C(═S)NH$_2$ | CH$_3$ | 3,4,5-F$_3$ |
| M.526. | C(═S)NH$_2$ | CH$_3$ | 2,4,6-F$_3$ |
| M.527. | C(═S)NH$_2$ | CH$_3$ | 2-F, 3-Cl |
| M.528. | C(═S)NH$_2$ | CH$_3$ | 2-Cl, 4-F |
| M.529. | C(═S)NH$_2$ | CH$_3$ | 2-F, 3-CF$_3$ |
| M.530. | C(═S)NH$_2$ | CH$_3$ | 2-F, 4-CF$_3$ |
| M.531. | C(═S)NH$_2$ | CH$_3$ | 2-F, 5-CF$_3$ |
| M.532. | C(═S)NH$_2$ | CH$_3$ | 3-F, 4-CF$_3$ |
| M.533. | C(═S)NH$_2$ | CH$_3$ | 3-F, 5-CF$_3$ |
| M.534. | C(═S)NH$_2$ | CH$_3$ | 4-F, 3-CF$_3$ |
| M.535. | C(═S)NH$_2$ | CH$_3$ | 3,4-F$_2$, 5-CF$_3$ |
| M.536. | C(═S)NH$_2$ | CH$_3$ | 2-Cl, 3-CF$_3$ |
| M.537. | C(═S)NH$_2$ | CH$_3$ | 2-Cl, 4-CF$_3$ |
| M.538. | C(═S)NH$_2$ | CH$_3$ | 2-Cl, 5-CF$_3$ |
| M.539. | C(═S)NH$_2$ | CH$_3$ | 3-Cl, 5-CF$_3$ |
| M.540. | C(═S)NH$_2$ | CH$_3$ | 4-Cl, 3-CF$_3$ |
| M.541. | C(═S)NH$_2$ | CH$_2$CH$_3$ | — |
| M.542. | C(═S)NH$_2$ | CH$_2$CH$_3$ | 2-F |
| M.543. | C(═S)NH$_2$ | CH$_2$CH$_3$ | 3-F |
| M.544. | C(═S)NH$_2$ | CH$_2$CH$_3$ | 4-F |
| M.545. | C(═S)NH$_2$ | CH$_2$CH$_3$ | 2-Cl |
| M.546. | C(═S)NH$_2$ | CH$_2$CH$_3$ | 3-Cl |

TABLE M-continued

| Comp. No | $R^1$ | $R^3$ | $R^6$ |
|---|---|---|---|
| M.547. | C(═S)NH$_2$ | CH$_2$CH$_3$ | 4-Cl |
| M.548. | C(═S)NH$_2$ | CH$_2$CH$_3$ | 2-Br |
| M.549. | C(═S)NH$_2$ | CH$_2$CH$_3$ | 3-Br |
| M.550. | C(═S)NH$_2$ | CH$_2$CH$_3$ | 4-Br |
| M.551. | C(═S)NH$_2$ | CH$_2$CH$_3$ | 2-CH$_3$ |
| M.552. | C(═S)NH$_2$ | CH$_2$CH$_3$ | 3-CH$_3$ |
| M.553. | C(═S)NH$_2$ | CH$_2$CH$_3$ | 4-CH$_3$ |
| M.554. | C(═S)NH$_2$ | CH$_2$CH$_3$ | 2-CF$_3$ |
| M.555. | C(═S)NH$_2$ | CH$_2$CH$_3$ | 3-CF$_3$ |
| M.556. | C(═S)NH$_2$ | CH$_2$CH$_3$ | 4-CF$_3$ |
| M.557. | C(═S)NH$_2$ | CH$_2$CH$_3$ | 2-OCF$_3$ |
| M.558. | C(═S)NH$_2$ | CH$_2$CH$_3$ | 3-OCF$_3$ |
| M.559. | C(═S)NH$_2$ | CH$_2$CH$_3$ | 4-OCF$_3$ |
| M.560. | C(═S)NH$_2$ | CH$_2$CH$_3$ | 2-SCF$_3$ |
| M.561. | C(═S)NH$_2$ | CH$_2$CH$_3$ | 3-SCF$_3$ |
| M.562. | C(═S)NH$_2$ | CH$_2$CH$_3$ | 4-SCF$_3$ |
| M.563. | C(═S)NH$_2$ | CH$_2$CH$_3$ | 2-CN |
| M.564. | C(═S)NH$_2$ | CH$_2$CH$_3$ | 3-CN |
| M.565. | C(═S)NH$_2$ | CH$_2$CH$_3$ | 4-CN |
| M.566. | C(═S)NH$_2$ | CH$_2$CH$_3$ | 4-SO$_2$CH$_3$ |
| M.567. | C(═S)NH$_2$ | CH$_2$CH$_3$ | 2,3-F$_2$ |
| M.568. | C(═S)NH$_2$ | CH$_2$CH$_3$ | 2,4-F$_2$ |
| M.569. | C(═S)NH$_2$ | CH$_2$CH$_3$ | 2,5-F$_2$ |
| M.570. | C(═S)NH$_2$ | CH$_2$CH$_3$ | 2,6-F$_2$ |
| M.571. | C(═S)NH$_2$ | CH$_2$CH$_3$ | 3,4-F$_2$ |
| M.572. | C(═S)NH$_2$ | CH$_2$CH$_3$ | 3,5-F$_2$ |
| M.573. | C(═S)NH$_2$ | CH$_2$CH$_3$ | 2,4-Cl$_2$ |
| M.574. | C(═S)NH$_2$ | CH$_2$CH$_3$ | 2,5-Cl$_2$ |
| M.575. | C(═S)NH$_2$ | CH$_2$CH$_3$ | 3,4-Cl$_2$ |
| M.576. | C(═S)NH$_2$ | CH$_2$CH$_3$ | 2,3,4-F$_3$ |
| M.577. | C(═S)NH$_2$ | CH$_2$CH$_3$ | 2,3,5-F$_3$ |
| M.578. | C(═S)NH$_2$ | CH$_2$CH$_3$ | 2,3,6-F$_3$ |
| M.579. | C(═S)NH$_2$ | CH$_2$CH$_3$ | 3,4,5-F$_3$ |
| M.580. | C(═S)NH$_2$ | CH$_2$CH$_3$ | 2,4,6-F$_3$ |
| M.581. | C(═S)NH$_2$ | CH$_2$CH$_3$ | 2-F, 3-Cl |
| M.582. | C(═S)NH$_2$ | CH$_2$CH$_3$ | 2-Cl, 4-F |
| M.583. | C(═S)NH$_2$ | CH$_2$CH$_3$ | 2-F, 3-CF$_3$ |
| M.584. | C(═S)NH$_2$ | CH$_2$CH$_3$ | 2-F, 4-CF$_3$ |
| M.585. | C(═S)NH$_2$ | CH$_2$CH$_3$ | 2-F, 5-CF$_3$ |
| M.586. | C(═S)NH$_2$ | CH$_2$CH$_3$ | 3-F, 4-CF$_3$ |
| M.587. | C(═S)NH$_2$ | CH$_2$CH$_3$ | 3-F, 5-CF$_3$ |
| M.588. | C(═S)NH$_2$ | CH$_2$CH$_3$ | 4-F, 3-CF$_3$ |
| M.589. | C(═S)NH$_2$ | CH$_2$CH$_3$ | 3,4-F$_2$, 5-CF$_3$ |
| M.590. | C(═S)NH$_2$ | CH$_2$CH$_3$ | 2-Cl, 3-CF$_3$ |
| M.591. | C(═S)NH$_2$ | CH$_2$CH$_3$ | 2-Cl, 4-CF$_3$ |
| M.592. | C(═S)NH$_2$ | CH$_2$CH$_3$ | 2-Cl, 5-CF$_3$ |
| M.593. | C(═S)NH$_2$ | CH$_2$CH$_3$ | 3-Cl, 5-CF$_3$ |
| M.594. | C(═S)NH$_2$ | CH$_2$CH$_3$ | 4-Cl, 3-CF$_3$ |
| M.595. | C(═S)NH$_2$ | CF$_3$ | — |
| M.596. | C(═S)NH$_2$ | CF$_3$ | 2-F |
| M.597. | C(═S)NH$_2$ | CF$_3$ | 3-F |
| M.598. | C(═S)NH$_2$ | CF$_3$ | 4-F |
| M.599. | C(═S)NH$_2$ | CF$_3$ | 2-Cl |
| M.600. | C(═S)NH$_2$ | CF$_3$ | 3-Cl |
| M.601. | C(═S)NH$_2$ | CF$_3$ | 4-Cl |
| M.602. | C(═S)NH$_2$ | CF$_3$ | 2-Br |
| M.603. | C(═S)NH$_2$ | CF$_3$ | 3-Br |
| M.604. | C(═S)NH$_2$ | CF$_3$ | 4-Br |
| M.605. | C(═S)NH$_2$ | CF$_3$ | 2-CH$_3$ |
| M.606. | C(═S)NH$_2$ | CF$_3$ | 3-CH$_3$ |
| M.607. | C(═S)NH$_2$ | CF$_3$ | 4-CH$_3$ |
| M.608. | C(═S)NH$_2$ | CF$_3$ | 2-CF$_3$ |
| M.609. | C(═S)NH$_2$ | CF$_3$ | 3-CF$_3$ |
| M.610. | C(═S)NH$_2$ | CF$_3$ | 4-CF$_3$ |
| M.611. | C(═S)NH$_2$ | CF$_3$ | 2-OCF$_3$ |
| M.612. | C(═S)NH$_2$ | CF$_3$ | 3-OCF$_3$ |
| M.613. | C(═S)NH$_2$ | CF$_3$ | 4-OCF$_3$ |
| M.614. | C(═S)NH$_2$ | CF$_3$ | 2-SCF$_3$ |
| M.615. | C(═S)NH$_2$ | CF$_3$ | 3-SCF$_3$ |
| M.616. | C(═S)NH$_2$ | CF$_3$ | 4-SCF$_3$ |
| M.617. | C(═S)NH$_2$ | CF$_3$ | 2-CN |
| M.618. | C(═S)NH$_2$ | CF$_3$ | 3-CN |
| M.619. | C(═S)NH$_2$ | CF$_3$ | 4-CN |
| M.620. | C(═S)NH$_2$ | CF$_3$ | 4-SO$_2$CH$_3$ |
| M.621. | C(═S)NH$_2$ | CF$_3$ | 2,3-F$_2$ |
| M.622. | C(═S)NH$_2$ | CF$_3$ | 2,4-F$_2$ |
| M.623. | C(═S)NH$_2$ | CF$_3$ | 2,5-F$_2$ |
| M.624. | C(═S)NH$_2$ | CF$_3$ | 2,6-F$_2$ |

TABLE M-continued

| Comp. No | $R^1$ | $R^3$ | $R^6$ |
|---|---|---|---|
| M.625. | C(=S)$NH_2$ | $CF_3$ | 3,4-$F_2$ |
| M.626. | C(=S)$NH_2$ | $CF_3$ | 3,5-$F_2$ |
| M.627. | C(=S)$NH_2$ | $CF_3$ | 2,4-$Cl_2$ |
| M.628. | C(=S)$NH_2$ | $CF_3$ | 2,5-$Cl_2$ |
| M.629. | C(=S)$NH_2$ | $CF_3$ | 3,4-$Cl_2$ |
| M.630. | C(=S)$NH_2$ | $CF_3$ | 2,3,4-$F_3$ |
| M.631. | C(=S)$NH_2$ | $CF_3$ | 2,3,5-$F_3$ |
| M.632. | C(=S)$NH_2$ | $CF_3$ | 2,3,6-$F_3$ |
| M.633. | C(=S)$NH_2$ | $CF_3$ | 3,4,5-$F_3$ |
| M.634. | C(=S)$NH_2$ | $CF_3$ | 2,4,6-$F_3$ |
| M.635. | C(=S)$NH_2$ | $CF_3$ | 2-F, 3-Cl |
| M.636. | C(=S)$NH_2$ | $CF_3$ | 2-Cl, 4-F |
| M.637. | C(=S)$NH_2$ | $CF_3$ | 2-F, 3-$CF_3$ |
| M.638. | C(=S)$NH_2$ | $CF_3$ | 2-F, 4-$CF_3$ |
| M.639. | C(=S)$NH_2$ | $CF_3$ | 2-F, 5-$CF_3$ |
| M.640. | C(=S)$NH_2$ | $CF_3$ | 3-F, 4-$CF_3$ |
| M.641. | C(=S)$NH_2$ | $CF_3$ | 3-F, 5-$CF_3$ |
| M.642. | C(=S)$NH_2$ | $CF_3$ | 4-F, 3-$CF_3$ |
| M.643. | C(=S)$NH_2$ | $CF_3$ | 3,4-$F_2$, 5-$CF_3$ |
| M.644. | C(=S)$NH_2$ | $CF_3$ | 2-Cl, 3-$CF_3$ |
| M.645. | C(=S)$NH_2$ | $CF_3$ | 2-Cl, 4-$CF_3$ |
| M.646. | C(=S)$NH_2$ | $CF_3$ | 2-Cl, 5-$CF_3$ |
| M.647. | C(=S)$NH_2$ | $CF_3$ | 3-Cl, 5-$CF_3$ |
| M.648. | C(=S)$NH_2$ | $CF_3$ | 4-Cl, 3-$CF_3$ |
| M.649. | C(=S)$NH_2$ | $CHF_2$ | — |
| M.650. | C(=S)$NH_2$ | $CHF_2$ | 2-F |
| M.651. | C(=S)$NH_2$ | $CHF_2$ | 3-F |
| M.652. | C(=S)$NH_2$ | $CHF_2$ | 4-F |
| M.653. | C(=S)$NH_2$ | $CHF_2$ | 2-Cl |
| M.654. | C(=S)$NH_2$ | $CHF_2$ | 3-Cl |
| M.655. | C(=S)$NH_2$ | $CHF_2$ | 4-Cl |
| M.656. | C(=S)$NH_2$ | $CHF_2$ | 2-Br |
| M.657. | C(=S)$NH_2$ | $CHF_2$ | 3-Br |
| M.658. | C(=S)$NH_2$ | $CHF_2$ | 4-Br |
| M.659. | C(=S)$NH_2$ | $CHF_2$ | 2-$CH_3$ |
| M.660. | C(=S)$NH_2$ | $CHF_2$ | 3-$CH_3$ |
| M.661. | C(=S)$NH_2$ | $CHF_2$ | 4-$CH_3$ |
| M.662. | C(=S)$NH_2$ | $CHF_2$ | 2-$CF_3$ |
| M.663. | C(=S)$NH_2$ | $CHF_2$ | 3-$CF_3$ |
| M.664. | C(=S)$NH_2$ | $CHF_2$ | 4-$CF_3$ |
| M.665. | C(=S)$NH_2$ | $CHF_2$ | 2-$OCF_3$ |
| M.666. | C(=S)$NH_2$ | $CHF_2$ | 3-$OCF_3$ |
| M.667. | C(=S)$NH_2$ | $CHF_2$ | 4-$OCF_3$ |
| M.668. | C(=S)$NH_2$ | $CHF_2$ | 2-$SCF_3$ |
| M.669. | C(=S)$NH_2$ | $CHF_2$ | 3-$SCF_3$ |
| M.670. | C(=S)$NH_2$ | $CHF_2$ | 4-$SCF_3$ |
| M.671. | C(=S)$NH_2$ | $CHF_2$ | 2-CN |
| M.672. | C(=S)$NH_2$ | $CHF_2$ | 3-CN |
| M.673. | C(=S)$NH_2$ | $CHF_2$ | 4-CN |
| M.674. | C(=S)$NH_2$ | $CHF_2$ | 4-$SO_2CH_3$ |
| M.675. | C(=S)$NH_2$ | $CHF_2$ | 2,3-$F_2$ |
| M.676. | C(=S)$NH_2$ | $CHF_2$ | 2,4-$F_2$ |
| M.677. | C(=S)$NH_2$ | $CHF_2$ | 2,5-$F_2$ |
| M.678. | C(=S)$NH_2$ | $CHF_2$ | 2,6-$F_2$ |
| M.679. | C(=S)$NH_2$ | $CHF_2$ | 3,4-$F_2$ |
| M.680. | C(=S)$NH_2$ | $CHF_2$ | 3,5-$F_2$ |
| M.681. | C(=S)$NH_2$ | $CHF_2$ | 2,4-$Cl_2$ |
| M.682. | C(=S)$NH_2$ | $CHF_2$ | 2,5-$Cl_2$ |
| M.683. | C(=S)$NH_2$ | $CHF_2$ | 3,4-$Cl_2$ |
| M.684. | C(=S)$NH_2$ | $CHF_2$ | 2,3,4-$F_3$ |
| M.685. | C(=S)$NH_2$ | $CHF_2$ | 2,3,5-$F_3$ |
| M.686. | C(=S)$NH_2$ | $CHF_2$ | 2,3,6-$F_3$ |
| M.687. | C(=S)$NH_2$ | $CHF_2$ | 3,4,5-$F_3$ |
| M.688. | C(=S)$NH_2$ | $CHF_2$ | 2,4,6-$F_3$ |
| M.689. | C(=S)$NH_2$ | $CHF_2$ | 2-F, 3-Cl |
| M.690. | C(=S)$NH_2$ | $CHF_2$ | 2-Cl, 4-F |
| M.691. | C(=S)$NH_2$ | $CHF_2$ | 2-F, 3-$CF_3$ |
| M.692. | C(=S)$NH_2$ | $CHF_2$ | 2-F, 4-$CF_3$ |
| M.693. | C(=S)$NH_2$ | $CHF_2$ | 2-F, 5-$CF_3$ |
| M.694. | C(=S)$NH_2$ | $CHF_2$ | 3-F, 4-$CF_3$ |
| M.695. | C(=S)$NH_2$ | $CHF_2$ | 3-F, 5-$CF_3$ |
| M.696. | C(=S)$NH_2$ | $CHF_2$ | 4-F, 3-$CF_3$ |
| M.697. | C(=S)$NH_2$ | $CHF_2$ | 3,4-$F_2$, 5-$CF_3$ |
| M.698. | C(=S)$NH_2$ | $CHF_2$ | 2-Cl, 3-$CF_3$ |
| M.699. | C(=S)$NH_2$ | $CHF_2$ | 2-Cl, 4-$CF_3$ |
| M.700. | C(=S)$NH_2$ | $CHF_2$ | 2-Cl, 5-$CF_3$ |
| M.701. | C(=S)$NH_2$ | $CHF_2$ | 3-Cl, 5-$CF_3$ |
| M.702. | C(=S)$NH_2$ | $CHF_2$ | 4-Cl, 3-$CF_3$ |

TABLE M-continued

| Comp. No | $R^1$ | $R^3$ | $R^6$ |
|---|---|---|---|
| M.703. | C(=S)$NH_2$ | $CF_2CF_3$ | — |
| M.704. | C(=S)$NH_2$ | $CF_2CF_3$ | 2-F |
| M.705. | C(=S)$NH_2$ | $CF_2CF_3$ | 3-F |
| M.706. | C(=S)$NH_2$ | $CF_2CF_3$ | 4-F |
| M.707. | C(=S)$NH_2$ | $CF_2CF_3$ | 2-Cl |
| M.708. | C(=S)$NH_2$ | $CF_2CF_3$ | 3-Cl |
| M.709. | C(=S)$NH_2$ | $CF_2CF_3$ | 4-Cl |
| M.710. | C(=S)$NH_2$ | $CF_2CF_3$ | 2-Br |
| M.711. | C(=S)$NH_2$ | $CF_2CF_3$ | 3-Br |
| M.712. | C(=S)$NH_2$ | $CF_2CF_3$ | 4-Br |
| M.713. | C(=S)$NH_2$ | $CF_2CF_3$ | 2-$CH_3$ |
| M.714. | C(=S)$NH_2$ | $CF_2CF_3$ | 3-$CH_3$ |
| M.715. | C(=S)$NH_2$ | $CF_2CF_3$ | 4-$CH_3$ |
| M.716. | C(=S)$NH_2$ | $CF_2CF_3$ | 2-$CF_3$ |
| M.717. | C(=S)$NH_2$ | $CF_2CF_3$ | 3-$CF_3$ |
| M.718. | C(=S)$NH_2$ | $CF_2CF_3$ | 4-$CF_3$ |
| M.719. | C(=S)$NH_2$ | $CF_2CF_3$ | 2-$OCF_3$ |
| M.720. | C(=S)$NH_2$ | $CF_2CF_3$ | 3-$OCF_3$ |
| M.721. | C(=S)$NH_2$ | $CF_2CF_3$ | 4-$OCF_3$ |
| M.722. | C(=S)$NH_2$ | $CF_2CF_3$ | 2-$SCF_3$ |
| M.723. | C(=S)$NH_2$ | $CF_2CF_3$ | 3-$SCF_3$ |
| M.724. | C(=S)$NH_2$ | $CF_2CF_3$ | 4-$SCF_3$ |
| M.725. | C(=S)$NH_2$ | $CF_2CF_3$ | 2-CN |
| M.726. | C(=S)$NH_2$ | $CF_2CF_3$ | 3-CN |
| M.727. | C(=S)$NH_2$ | $CF_2CF_3$ | 4-CN |
| M.728. | C(=S)$NH_2$ | $CF_2CF_3$ | 4-$SO_2CH_3$ |
| M.729. | C(=S)$NH_2$ | $CF_2CF_3$ | 2,3-$F_2$ |
| M.730. | C(=S)$NH_2$ | $CF_2CF_3$ | 2,4-$F_2$ |
| M.731. | C(=S)$NH_2$ | $CF_2CF_3$ | 2,5-$F_2$ |
| M.732. | C(=S)$NH_2$ | $CF_2CF_3$ | 2,6-$F_2$ |
| M.733. | C(=S)$NH_2$ | $CF_2CF_3$ | 3,4-$F_2$ |
| M.734. | C(=S)$NH_2$ | $CF_2CF_3$ | 3,5-$F_2$ |
| M.735. | C(=S)$NH_2$ | $CF_2CF_3$ | 2,4-$Cl_2$ |
| M.736. | C(=S)$NH_2$ | $CF_2CF_3$ | 2,5-$Cl_2$ |
| M.737. | C(=S)$NH_2$ | $CF_2CF_3$ | 3,4-$Cl_2$ |
| M.738. | C(=S)$NH_2$ | $CF_2CF_3$ | 2,3,4-$F_3$ |
| M.739. | C(=S)$NH_2$ | $CF_2CF_3$ | 2,3,5-$F_3$ |
| M.740. | C(=S)$NH_2$ | $CF_2CF_3$ | 2,3,6-$F_3$ |
| M.741. | C(=S)$NH_2$ | $CF_2CF_3$ | 3,4,5-$F_3$ |
| M.742. | C(=S)$NH_2$ | $CF_2CF_3$ | 2,4,6-$F_3$ |
| M.743. | C(=S)$NH_2$ | $CF_2CF_3$ | 2-F, 3-Cl |
| M.744. | C(=S)$NH_2$ | $CF_2CF_3$ | 2-Cl, 4-F |
| M.745. | C(=S)$NH_2$ | $CF_2CF_3$ | 2-F, 3-$CF_3$ |
| M.746. | C(=S)$NH_2$ | $CF_2CF_3$ | 2-F, 4-$CF_3$ |
| M.747. | C(=S)$NH_2$ | $CF_2CF_3$ | 2-F, 5-$CF_3$ |
| M.748. | C(=S)$NH_2$ | $CF_2CF_3$ | 3-F, 4-$CF_3$ |
| M.749. | C(=S)$NH_2$ | $CF_2CF_3$ | 3-F, 5-$CF_3$ |
| M.750. | C(=S)$NH_2$ | $CF_2CF_3$ | 4-F, 3-$CF_3$ |
| M.751. | C(=S)$NH_2$ | $CF_2CF_3$ | 3,4-$F_2$, 5-$CF_3$ |
| M.752. | C(=S)$NH_2$ | $CF_2CF_3$ | 2-Cl, 3-$CF_3$ |
| M.753. | C(=S)$NH_2$ | $CF_2CF_3$ | 2-Cl, 4-$CF_3$ |
| M.754. | C(=S)$NH_2$ | $CF_2CF_3$ | 2-Cl, 5-$CF_3$ |
| M.755. | C(=S)$NH_2$ | $CF_2CF_3$ | 3-Cl, 5-$CF_3$ |
| M.756. | C(=S)$NH_2$ | $CF_2CF_3$ | 4-Cl, 3-$CF_3$ |
| M.757. | C(=S)$NH_2$ | $OCH_3$ | — |
| M.758. | C(=S)$NH_2$ | $OCH_3$ | 2-F |
| M.759. | C(=S)$NH_2$ | $OCH_3$ | 3-F |
| M.760. | C(=S)$NH_2$ | $OCH_3$ | 4-F |
| M.761. | C(=S)$NH_2$ | $OCH_3$ | 2-Cl |
| M.762. | C(=S)$NH_2$ | $OCH_3$ | 3-Cl |
| M.763. | C(=S)$NH_2$ | $OCH_3$ | 4-Cl |
| M.764. | C(=S)$NH_2$ | $OCH_3$ | 2-Br |
| M.765. | C(=S)$NH_2$ | $OCH_3$ | 3-Br |
| M.766. | C(=S)$NH_2$ | $OCH_3$ | 4-Br |
| M.767. | C(=S)$NH_2$ | $OCH_3$ | 2-$CH_3$ |
| M.768. | C(=S)$NH_2$ | $OCH_3$ | 3-$CH_3$ |
| M.769. | C(=S)$NH_2$ | $OCH_3$ | 4-$CH_3$ |
| M.770. | C(=S)$NH_2$ | $OCH_3$ | 2-$CF_3$ |
| M.771. | C(=S)$NH_2$ | $OCH_3$ | 3-$CF_3$ |
| M.772. | C(=S)$NH_2$ | $OCH_3$ | 4-$CF_3$ |
| M.773. | C(=S)$NH_2$ | $OCH_3$ | 2-$OCF_3$ |
| M.774. | C(=S)$NH_2$ | $OCH_3$ | 3-$OCF_3$ |
| M.775. | C(=S)$NH_2$ | $OCH_3$ | 4-$OCF_3$ |
| M.776. | C(=S)$NH_2$ | $OCH_3$ | 2-$SCF_3$ |
| M.777. | C(=S)$NH_2$ | $OCH_3$ | 3-$SCF_3$ |
| M.778. | C(=S)$NH_2$ | $OCH_3$ | 4-$SCF_3$ |
| M.779. | C(=S)$NH_2$ | $OCH_3$ | 2-CN |
| M.780. | C(=S)$NH_2$ | $OCH_3$ | 3-CN |

TABLE M-continued

| Comp. No | $R^1$ | $R^3$ | $R^6$ |
|---|---|---|---|
| M.781. | $C(=S)NH_2$ | $OCH_3$ | 4-CN |
| M.782. | $C(=S)NH_2$ | $OCH_3$ | 4-$SO_2CH_3$ |
| M.783. | $C(=S)NH_2$ | $OCH_3$ | 2,3-$F_2$ |
| M.784. | $C(=S)NH_2$ | $OCH_3$ | 2,4-$F_2$ |
| M.785. | $C(=S)NH_2$ | $OCH_3$ | 2,5-$F_2$ |
| M.786. | $C(=S)NH_2$ | $OCH_3$ | 2,6-$F_2$ |
| M.787. | $C(=S)NH_2$ | $OCH_3$ | 3,4-$F_2$ |
| M.788. | $C(=S)NH_2$ | $OCH_3$ | 3,5-$F_2$ |
| M.789. | $C(=S)NH_2$ | $OCH_3$ | 2,4-$Cl_2$ |
| M.790. | $C(=S)NH_2$ | $OCH_3$ | 2,5-$Cl_2$ |
| M.791. | $C(=S)NH_2$ | $OCH_3$ | 3,4-$Cl_2$ |
| M.792. | $C(=S)NH_2$ | $OCH_3$ | 2,3,4-$F_3$ |
| M.793. | $C(=S)NH_2$ | $OCH_3$ | 2,3,5-$F_3$ |
| M.794. | $C(=S)NH_2$ | $OCH_3$ | 2,3,6-$F_3$ |
| M.795. | $C(=S)NH_2$ | $OCH_3$ | 3,4,5-$F_3$ |
| M.796. | $C(=S)NH_2$ | $OCH_3$ | 2,4,6-$F_3$ |
| M.797. | $C(=S)NH_2$ | $OCH_3$ | 2-F, 3-Cl |
| M.798. | $C(=S)NH_2$ | $OCH_3$ | 2-Cl, 4-F |
| M.799. | $C(=S)NH_2$ | $OCH_3$ | 2-F, 3-$CF_3$ |
| M.800. | $C(=S)NH_2$ | $OCH_3$ | 2-F, 4-$CF_3$ |
| M.801. | $C(=S)NH_2$ | $OCH_3$ | 2-F, 5-$CF_3$ |
| M.802. | $C(=S)NH_2$ | $OCH_3$ | 3-F, 4-$CF_3$ |
| M.803. | $C(=S)NH_2$ | $OCH_3$ | 3-F, 5-$CF_3$ |
| M.804. | $C(=S)NH_2$ | $OCH_3$ | 4-F, 3-$CF_3$ |
| M.805. | $C(=S)NH_2$ | $OCH_3$ | 3,4-$F_2$, 5-$CF_3$ |
| M.806. | $C(=S)NH_2$ | $OCH_3$ | 2-Cl, 3-$CF_3$ |
| M.807. | $C(=S)NH_2$ | $OCH_3$ | 2-Cl, 4-$CF_3$ |
| M.808. | $C(=S)NH_2$ | $OCH_3$ | 2-Cl, 5-$CF_3$ |
| M.809. | $C(=S)NH_2$ | $OCH_3$ | 3-Cl, 5-$CF_3$ |
| M.810. | $C(=S)NH_2$ | $OCH_3$ | 4-Cl, 3-$CF_3$ |
| M.811. | $C(=S)NH_2$ | $OCH_2CH_3$ | — |
| M.812. | $C(=S)NH_2$ | $OCH_2CH_3$ | 2-F |
| M.813. | $C(=S)NH_2$ | $OCH_2CH_3$ | 3-F |
| M.814. | $C(=S)NH_2$ | $OCH_2CH_3$ | 4-F |
| M.815. | $C(=S)NH_2$ | $OCH_2CH_3$ | 2-Cl |
| M.816. | $C(=S)NH_2$ | $OCH_2CH_3$ | 3-Cl |
| M.817. | $C(=S)NH_2$ | $OCH_2CH_3$ | 4-Cl |
| M.818. | $C(=S)NH_2$ | $OCH_2CH_3$ | 2-Br |
| M.819. | $C(=S)NH_2$ | $OCH_2CH_3$ | 3-Br |
| M.820. | $C(=S)NH_2$ | $OCH_2CH_3$ | 4-Br |
| M.821. | $C(=S)NH_2$ | $OCH_2CH_3$ | 2-$CH_3$ |
| M.822. | $C(=S)NH_2$ | $OCH_2CH_3$ | 3-$CH_3$ |
| M.823. | $C(=S)NH_2$ | $OCH_2CH_3$ | 4-$CH_3$ |
| M.824. | $C(=S)NH_2$ | $OCH_2CH_3$ | 2-$CF_3$ |
| M.825. | $C(=S)NH_2$ | $OCH_2CH_3$ | 3-$CF_3$ |
| M.826. | $C(=S)NH_2$ | $OCH_2CH_3$ | 4-$CF_3$ |
| M.827. | $C(=S)NH_2$ | $OCH_2CH_3$ | 2-$OCF_3$ |
| M.828. | $C(=S)NH_2$ | $OCH_2CH_3$ | 3-$OCF_3$ |
| M.829. | $C(=S)NH_2$ | $OCH_2CH_3$ | 4-$OCF_3$ |
| M.830. | $C(=S)NH_2$ | $OCH_2CH_3$ | 2-$SCF_3$ |
| M.831. | $C(=S)NH_2$ | $OCH_2CH_3$ | 3-$SCF_3$ |
| M.832. | $C(=S)NH_2$ | $OCH_2CH_3$ | 4-$SCF_3$ |
| M.833. | $C(=S)NH_2$ | $OCH_2CH_3$ | 2-CN |
| M.834. | $C(=S)NH_2$ | $OCH_2CH_3$ | 3-CN |
| M.835. | $C(=S)NH_2$ | $OCH_2CH_3$ | 4-CN |
| M.836. | $C(=S)NH_2$ | $OCH_2CH_3$ | 4-$SO_2CH_3$ |
| M.837. | $C(=S)NH_2$ | $OCH_2CH_3$ | 2,3-$F_2$ |
| M.838. | $C(=S)NH_2$ | $OCH_2CH_3$ | 2,4-$F_2$ |
| M.839. | $C(=S)NH_2$ | $OCH_2CH_3$ | 2,5-$F_2$ |
| M.840. | $C(=S)NH_2$ | $OCH_2CH_3$ | 2,6-$F_2$ |
| M.841. | $C(=S)NH_2$ | $OCH_2CH_3$ | 3,4-$F_2$ |
| M.842. | $C(=S)NH_2$ | $OCH_2CH_3$ | 3,5-$F_2$ |
| M.843. | $C(=S)NH_2$ | $OCH_2CH_3$ | 2,4-$Cl_2$ |
| M.844. | $C(=S)NH_2$ | $OCH_2CH_3$ | 2,5-$Cl_2$ |
| M.845. | $C(=S)NH_2$ | $OCH_2CH_3$ | 3,4-$Cl_2$ |
| M.846. | $C(=S)NH_2$ | $OCH_2CH_3$ | 2,3,4-$F_3$ |
| M.847. | $C(=S)NH_2$ | $OCH_2CH_3$ | 2,3,5-$F_3$ |
| M.848. | $C(=S)NH_2$ | $OCH_2CH_3$ | 2,3,6-$F_3$ |
| M.849. | $C(=S)NH_2$ | $OCH_2CH_3$ | 3,4,5-$F_3$ |
| M.850. | $C(=S)NH_2$ | $OCH_2CH_3$ | 2,4,6-$F_3$ |
| M.851. | $C(=S)NH_2$ | $OCH_2CH_3$ | 2-F, 3-Cl |
| M.852. | $C(=S)NH_2$ | $OCH_2CH_3$ | 2-Cl, 4-F |
| M.853. | $C(=S)NH_2$ | $OCH_2CH_3$ | 2-F, 3-$CF_3$ |
| M.854. | $C(=S)NH_2$ | $OCH_2CH_3$ | 2-F, 4-$CF_3$ |
| M.855. | $C(=S)NH_2$ | $OCH_2CH_3$ | 2-F, 5-$CF_3$ |
| M.856. | $C(=S)NH_2$ | $OCH_2CH_3$ | 3-F, 4-$CF_3$ |
| M.857. | $C(=S)NH_2$ | $OCH_2CH_3$ | 3-F, 5-$CF_3$ |
| M.858. | $C(=S)NH_2$ | $OCH_2CH_3$ | 4-F, 3-$CF_3$ |

TABLE M-continued

| Comp. No | $R^1$ | $R^3$ | $R^6$ |
|---|---|---|---|
| M.859. | $C(=S)NH_2$ | $OCH_2CH_3$ | 3,4-$F_2$, 5-$CF_3$ |
| M.860. | $C(=S)NH_2$ | $OCH_2CH_3$ | 2-Cl, 3-$CF_3$ |
| M.861. | $C(=S)NH_2$ | $OCH_2CH_3$ | 2-Cl, 4-$CF_3$ |
| M.862. | $C(=S)NH_2$ | $OCH_2CH_3$ | 2-Cl, 5-$CF_3$ |
| M.863. | $C(=S)NH_2$ | $OCH_2CH_3$ | 3-Cl, 5-$CF_3$ |
| M.864. | $C(=S)NH_2$ | $OCH_2CH_3$ | 4-Cl, 3-$CF_3$ |

Table 1: This table discloses the 864 compounds 1.1 to 1.864 of the formula (I-a), wherein Y is 5-methyl-1,2,4-oxadiazole-3-yl, X is hydrogen and $R^1$, $R^3$, and $R^6$ are as defined in Table M. For example, compound No. 1.1 has the following structure:

(1.1)

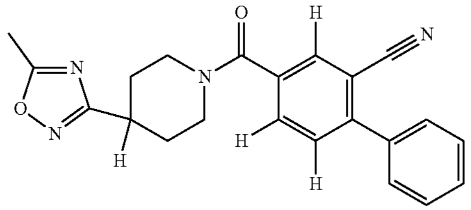

Table 2: This table discloses the 864 compounds 2.1 to 2.864 of the formula (I-a), wherein Y is 1-methyl-1,2,4-triazole-3-yl, X is hydrogen and $R^1$, $R^3$, and $R^6$ are as defined in Table M.

Table 3: This table discloses the 864 compounds 3.1 to 3.864 of the formula (I-a), wherein Y is 3,5-dichloropyridine-2-yl, X is hydrogen and $R^1$, $R^3$, and $R^6$ are as defined in Table M.

Table 4: This table discloses the 864 compounds 4.1 to 4.864 of the formula (I-a), wherein Y is 3-chloro-5-(trifluoromethyl)pyridine-2-yl, X is hydrogen and $R^1$, $R^3$ and $R^6$ are as defined in Table M.

Table 5: This table discloses the 864 compounds 5.1 to 5.864 of the formula (I-a), wherein Y is phenyl, X is hydrogen and $R^1$, $R^3$ and $R^6$ are as defined in Table M.

Table 6: This table discloses the 864 compounds 6.1 to 6.864 of the formula (I-a), wherein Y is phenyl, X is hydroxy and $R^1$, $R^3$ and $R^6$ are as defined in Table M.

Table 7: This table discloses the 864 compounds 7.1 to 7.864 of the formula (I-a), wherein Y is 4-chloro-phenyl-1-yl, X is hydrogen and $R^1$, $R^3$ and $R^6$ are as defined in Table M.

Table 8: This table discloses the 864 compounds 8.1 to 8.864 of the formula (I-a), wherein Y is 4-chloro-phenyl-1-yl, X is hydroxyl and $R^1$, $R^3$ and $R^6$ are as defined in Table M.

Table 9: This table discloses the 864 compounds 9.1 to 9.864 of the formula (I-a), wherein Y is methylsulfanylmethyl, X is hydrogen and $R^1$, $R^3$ and $R^6$ are as defined in Table M.

Table 10: This table discloses the 864 compounds 10.1 to 10.864 of the formula (I-a), wherein Y is methylsulfinylmethyl, X is hydrogen and $R^1$, $R^3$ and $R^6$ are as defined in Table M.

Table 11: This table discloses the 84 compounds 11.1 to 11.864 of the formula (I-a), wherein Y is methylsulfonylmethyl, X is hydrogen and $R^1$, $R^3$ and $R^6$ are as defined in Table M.

Table 12: This table discloses the 864 compounds 12.1 to 12.864 of the formula (I-a), wherein Y is ethylsulfanylmethyl, X is hydrogen and $R^1$, $R^3$ and $R^6$ are as defined in Table M.

Table 13: This table discloses the 864 compounds 13.1 to 13.864 of the formula (I-a), wherein Y is ethylsulfinylmethyl, X is hydrogen and $R^1$, $R^3$ and $R^6$ are as defined in Table M.

Table 14: This table discloses the 864 compounds 14.1 to 14.864 of the formula (I-a), wherein Y is ethylsulfonylmethyl, X is hydrogen and $R^1$, $R^3$ and $R^6$ are as defined in Table M.

Table 15: This table discloses the 864 compounds 15.1 to 15.864 of the formula (I-a), wherein Y is 1,1-dioxo-1,2-thiazolidin-2-yl, X is hydrogen and $R^1$, $R^3$ and $R^6$ are as defined in Table M.

Table 16: This table discloses the 864 compounds 16.1 to 16.864 of the formula (I-a), wherein Y is (E)-methoxyiminomethyl, X is hydrogen and $R^1$, $R^3$ and $R^6$ are as defined in Table M.

Table 17: This table discloses the 864 compounds 17.1 to 17.864 of the formula (I-a), wherein Y is (E)-ethoxyiminomethyl, X is hydrogen and $R^1$, $R^3$ and $R^6$ are as defined in Table M.

Table 18: This table discloses the 864 compounds 18.1 to 18.864 of the formula (I-a), wherein Y is N,N-dimethylcarboxamide, X is hydrogen and $R^1$, $R^3$ and $R^6$ are as defined in Table M.

Table 19: This table discloses the 864 compounds 19.1 to 19.864 of the formula (I-a), wherein Y is methanesulfonamido, X is hydrogen and $R^1$, $R^3$ and $R^6$ are as defined in Table M.

Table 20: This table discloses the 864 compounds 20.1 to 20.864 of the formula (I-a), wherein Y is cyano, X is hydrogen and $R^1$, $R^3$ and $R^6$ are as defined in Table M.

Specific examples of compounds of the present invention are represented by the formula (I-b) in the following Tables 21 to 35:

(I-b)

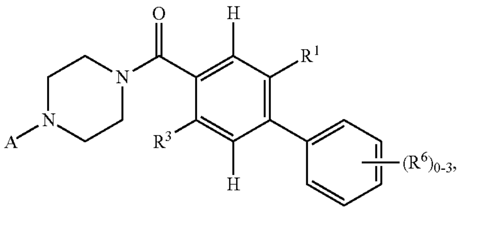

wherein $R^1$, $R^3$ and Rr are as defined above in table M.

Each of Tables 21 to 35 below, comprises 864 compounds of the formula (I-b) in which $R^1$, $R^3$ and $R^6$ have the values given in each row in Table M, and A has the values given in the relevant Tables 21 to 35. Thus compound 21.1 corresponds to a compound of formula (I-b) where $R^1$, $R^3$ and $R^6$ are as defined in row 1 of Table M and where A is as defined in Table 21; compound 30.14 corresponds to a compound of formula (I-b) where $R^1$, $R^3$ and $R^6$ are as defined in row 14 of Table M and where A is as defined in Table 30; and so on.

Table 21: This table discloses the 864 compounds 21.1 to 21.864 of the formula (I-b), wherein A is 3,5-dichloropyridine-2-yl, and $R^1$, $R^3$ and $R^6$ are as defined in Table M. For example, compound No. 1.1 has the following structure:

(21.1)

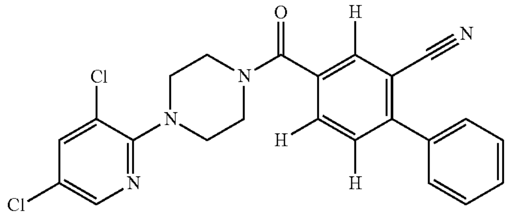

Table 22: This table discloses the 864 compounds 22.1 to 22.864 of the formula (I-b), wherein A is 3-chloro-5-(trifluoromethyl)pyridine-2-yl, and $R^1$, $R^3$ and $R^6$ are as defined in Table M.

Table 23: This table discloses the 864 compounds 23.1 to 23.864 of the formula (I-b), wherein A is 3-chloro-pyridine-2-yl, and $R^1$, $R^3$ and $R^6$ are as defined in Table M.

Table 24: This table discloses the 864 compounds 24.1 to 24 864 of the formula (I-b), wherein A is cyano, and $R^1$, $R^3$ and $R^6$ are as defined in Table M.

Table 25: This table discloses the 864 compounds 25.1 to 25.864 of the formula (I-b), wherein A is cyanomethyl and $R^1$, $R^3$ and $R^6$ are as defined in Table M.

Table 26: This table discloses the 864 compounds 26.1 to 6.864 of the formula (I-b), wherein A is cyanoethyl, and $R^1$, $R^3$ and $R^6$ are as defined in Table M.

Table 27: This table discloses the 864 compounds 27.1 to 27.864 of the formula (I-b), wherein A is 2,2,2-trifluoroethyl, and $R^1$, $R^3$ and $R^6$ are as defined in Table M.

Table 28: This table discloses the 864 compounds 28.1 to 28.864 of the formula (I-b), wherein A is vinyloxycarbonyl, and $R^1$, $R^3$ and $R^6$ are as defined in Table M.

Table 29: This table discloses the 864 compounds 29.1 to 29.864 of the formula (I-b), wherein A is tert.butyloxycarbonyl and $R^1$, $R^3$ and $R^6$ are as defined in Table M.

Table 30: This table discloses the 864 compounds 30.1 to 30.864 of the formula (I-b), wherein A is 4-fluoro-phenyl, and $R^1$, $R^3$ and $R^6$ are as defined in Table M.

Table 31: This table discloses the 84 compounds 31.1 to 31.864 of the formula (I-b), wherein A is 4-chloro-phenyl, and $R^1$, $R^3$ and $R^6$ are as defined in Table M.

Table 32: This table discloses the 864 compounds 32.1 to 32.864 of the formula (I-b), wherein A is 2,4-dichlorophenyl, and $R^1$, $R^3$ and $R^6$ are as defined in Table M.

Table 33: This table discloses the 864 compounds 33.1 to 33.864 of the formula (I-b), wherein A is ethylsulfanylethyl, and $R^1$, $R^3$ and $R^6$ are as defined in Table M.

Table 34: This table discloses the 864 compounds 34.1 to 34.864 of the formula (I-b), wherein A is ethylsulfinylethyl, and $R^1$, $R^3$ and $R^6$ are as defined in Table M.

Table 35: This table discloses the 864 compounds 35.1 to 35.864 of the formula (I-b), wherein A is ethylsulfonylethyl, and $R^1$, $R^3$ and $R^6$ are as defined in Table M.

Also made available are certain intermediate compounds of formulae III, V, VI, some of which are novel.

Accordingly, made available herein are:

compounds of formulae III-a

III-a

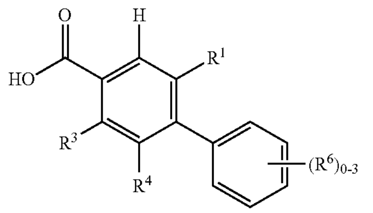

wherein $R^1$, $R^3$ and $R^6$ are defined in each row of Table M and $R^4$ is hydrogen or $R^1$, $R^3$ and $R^6$ are defined in each row of Table M and $R^4$ is cyano;

compounds of V-a

V-a

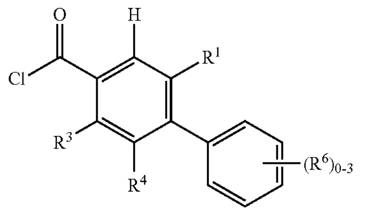

wherein $R^1$, $R^3$ and $R^6$ are defined in each row of Table M and $R^4$ is hydrogen or $R^1$, $R^3$ and $R^6$ are defined in each row of Table M and $R^4$ is cyano;

compounds of VI-a

VI-a

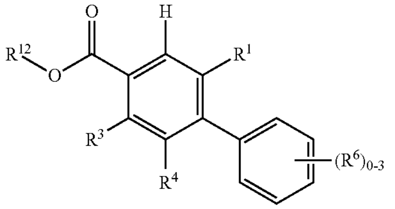

wherein $R^1$, $R^3$ and $R^6$ are defined in each row of Table M, $R^4$ is hydrogen and $R^{12}$ is selected from methyl, ethyl, propyl, iso-propyl, butyl, iso-butyl and tert-butyl. or $R^1$, $R^3$ and $R^6$ are defined in each row of Table M, $R^4$ is cyano and $R^{12}$ is selected from methyl, ethyl, propyl, iso-propyl, butyl, iso-butyl and tert-butyl;

compounds of formula IV-Aa

IV-aa

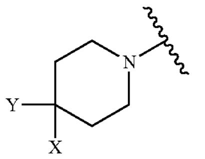

wherein X and Y are as defined in any one of Tables 1 to 20; and compounds of formula IV-ba IV-b

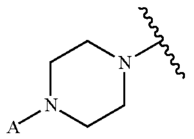

Wherein A is as defined in any one of Tables 21 to 35.

In further aspect, the present invention accordingly makes available compounds of formulae III, V and VI, wherein in each case, $R^1$, $R^2$, $R^3$, $R^4$ and $R^5$ are as defined for formula I in the first aspect, and $R^{12}$ for formula VI, is $C_1$-$C_6$-alkyl. Furthermore, the corresponding embodiments for $R^1$, $R^2$, $R^3$, $R^4$ and $R^5$ illustrated for formula I also apply to the compounds of formulae III, V and VI. $R^{12}$, for formula VI, is preferably methyl, ethyl, or propyl; more preferably methyl.

The compounds of formula (I) according to the invention are preventively and/or curatively valuable active ingredients in the field of pest control, even at low rates of application, which have a very favorable biocidal spectrum and are well tolerated by warm-blooded species, fish and plants. The active ingredients according to the invention act against all or individual developmental stages of normally sensitive, but also resistant, animal pests, such as insects or representatives of the order *Acarina*. The insecticidal or acaricidal activity of the active ingredients according to the invention can manifest itself directly, i. e. in destruction of the pests, which takes place either immediately or only after some time has elapsed, for example during ecdysis, or indirectly, for example in a reduced oviposition and/or hatching rate.

Examples of the above mentioned animal pests are:

from the order *Acarina*, for example, *Acalitus* spp, *Aculus* spp, *Acaricalus* spp, *Aceria* spp, *Acarus siro, Amblyomma* spp., *Argas* spp., *Boophilus* spp., *Brevipalpus* spp., *Bryobia* spp, *Calipitrimerus* spp., *Chorioptes* spp., *Dermanyssus gallinae, Dermatophagoides* spp, *Eotetranychus* spp, *Eriophyes* spp., *Hemitarsonemus* spp, *Hyalomma* spp., *Ixodes* spp., *Olygonychus* spp, *Ornithodoros* spp., *Polyphagotarsone latus, Panonychus* spp., *Phyllocoptruta oleivora, Phytonemus* spp, *Polyphagotarsonemus* spp, *Psoroptes* spp., *Rhipicephalus* spp., *Rhizoglyphus* spp., *Sarcoptes* spp., *Steneotarsonemus* spp, *Tarsonemus* spp. and *Tetranychus* spp.;

from the order *Anoplura*, for example,

*Haematopinus* spp., *Linognathus* spp., *Pediculus* spp., *Pemphigus* spp. and *Phylloxera* spp.;

from the order *Coleoptera*, for example,

*Agriotes* spp., *Amphimallon majale, Anomala orientalis, Anthonomus* spp., *Aphodius* spp, *Astylus atromaculatus, Ataenius* spp, *Atomaria linearis, Chaetocnema tibialis, Cerotoma* spp, *Conoderus* spp, *Cosmopolites* spp., *Cotinis nitida, Curculio* spp., *Cyclocephala* spp, *Dermestes* spp., *Diabrotica* spp., *Diloboderus abderus, Epilachna* spp., *Eremnus* spp., *Heteronychus arator, Hypothenemus hampei, Lagria vilosa, Leptinotarsa decemlineata, Lissorhoptrus* spp., *Liogenys* spp, *Maecolaspis* spp, *Maladera castanea, Megascelis* spp, *Melighetes aeneus, Melolontha* spp., *Myochrous armatus, Orycaephilus* spp., *Otiorhynchus* spp., *Phyllophaga* spp, *Phlyctinus* spp., *Popillia* spp., *Psylliodes* spp., *Rhyssomatus aubtilis, Rhizopertha* spp., *Scarabeidae, Sitophilus* spp., *Sitotroga* spp., *Somaticus* spp,

*Sphenophorus* spp, *Sternechus subsignatus, Tenebrio* spp., *Tribolium* spp. and *Trogoderma* spp.;

from the order *Diptera*, for example, *Aedes* spp., *Anopheles* spp, *Antherigona soccata, Bactrocea oleae, Bibio hortulanus, Bradysia* spp, *Calliphora erythrocephala, Ceratitis* spp., *Chrysomyia* spp., *Culex* spp., *Cuterebra* spp., *Dacus* spp., *Delia* spp, *Drosophila melanogaster, Fannia* spp., *Gastrophilus* spp., *Geomyza tripunctata, Glossina* spp., *Hypoderma* spp., *Hyppobosca* spp., *Liriomyza* spp., *Lucilia* spp., *Melanagromyza* spp., *Musca* spp., *Oestrus* spp., *Orseolia* spp., *Oscinella frit, Pegomyia hyoscyami, Phorbia* spp., *Rhagoletis* spp, *Rivelia quadrifasciata, Scatella* spp, *Sciara* spp., *Stomoxys* spp., *Tabanus* spp., *Tannia* spp. and *Tipula* spp.;

from the order *Hemiptera*, for example,

*Acanthocoris scabrator, Acrosternum* spp, *Adelphocoris lineolatus, Aleurodes* spp., *Amblypelta nitida, Bathycoelia thalassina, Blissus* spp, *Cimex* spp., *Clavigralla tomentosicollis, Creontiades* spp, *Distantiella theobroma, Dichelops furcatus, Dysdercus* spp., *Edessa* spp, *Euchistus* spp., *Eurydema pulchrum, Eurygaster* spp., *Halyomorpha halys, Horcias nobilellus, Leptocorisa* spp., *Lygus* spp, *Margarodes* spp, *Murgantia histrionic, Neomegalotomus* spp, *Nesidiocoris tenuis, Nezara* spp., *Nysius simulans, Oebalus insularis, Piesma* spp., *Piezodorus* spp, *Rhodnius* spp., *Sahlbergella singularis, Scaptocoris castanea, Scotinophara* spp., *Thyanta* spp, *Triatoma* spp., *Vatiga illudens; Acyrthosium pisum, Adalges* spp, *Agalliana ensigera, Agonoscena targionii, Aleurodicus* spp, *Aleurocanthus* spp, *Aleurolobus barodensis, Aleurothrixus floccosus, Aleyrodes brassicae, Amarasca biguttula, Amritodus atkinsoni, Aonidiella* spp., *Aphididae, Aphis* spp., *Aspidiotus* spp., *Aulacorthum solani, Bactericera cockerelli, Bemisia* spp, *Brachycaudus* spp, *Brevicoryne brassicae, Cacopsylla* spp, *Cavariella aegopodii* Scop., *Ceroplaster* spp., *Chrysomphalus aonidium, Chrysomphalus dictyospermi, Cicadella* spp, *Cofana spectra, Cryptomyzus* spp, *Cicadulina* spp, *Coccus hesperidum, Dalbulus maidis, Dialeurodes* spp, *Diaphorina citri, Diuraphis noxia, Dysaphis* spp, *Empoasca* spp., *Eriosoma larigerum, Erythroneura* spp., *Gascardia* spp., *Glycaspis brimblecombei, Hyadaphis pseudobrassicae, Hyalopterus* spp, *Hyperomyzus pallidus, Idioscopus clypealis, Jacobiasca lybica, Laodelphax* spp., *Lecanium corni, Lepidosaphes* spp., *Lopaphis erysimi, Lyogenys maidis, Macrosiphum* spp., *Mahanarva* spp, *Metcalfa pruinosa, Metopolophium dirhodum, Myndus crudus, Myzus* spp., *Neotoxoptera* sp, *Nephotettix* spp., *Nilaparvata* spp., *Nippolachnus piri* Mats, *Odonaspis ruthae, Oregma lanigera Zehnter, Parabemisia myricae, Paratrioza cockerelli, Parlatoria* spp., *Pemphigus* spp., *Peregrinus maidis, Perkinsiella* spp, *Phorodon humuli, Phylloxera* spp, *Planococcus* spp., *Pseudaulacaspis* spp., *Pseudococcus* spp., *Pseudatomoscelis seriatus, Psylla* spp., *Pulvinaria aethiopica, Quadraspidiotus* spp., *Quesada gigas, Recilia dorsalis, Rhopalosiphum* spp., *Saissetia* spp., *Scaphoideus* spp., *Schizaphis* spp., *Sitobion* spp., *Sogatella furcifera, Spissistilus festinus, Tarophagus Proserpina, Toxoptera* spp, *Trialeurodes* spp, *Tridiscus sporoboli, Trionymus* spp, *Trioza erytreae, Unaspis citri, Zygina flammigera, Zyginidia scutellaris;* from the order Hymenoptera, for example,

*Acromyrmex, Arge* spp, *Atta* spp., *Cephus* spp., *Diprion* spp., *Diprionidae, Gilpinia polytoma, Hoplocampa* spp., *Lasius* spp., *Monomorium pharaonis, Neodiprion* spp., *Pogonomyrmex* spp, *Slenopsis invicta, Solenopsis* spp. and *Vespa* spp.;

from the order *Isoptera*, for example,

*Coptotermes* spp, *Cornitermes cumulans, Incisitermes* spp, *Macrotermes* spp, *Mastotermes* spp, *Microtermes* spp, *Reticulitermes* spp.; *Solenopsis geminate* from the order *Lepidoptera*, for example,

*Acleris* spp., *Adoxophyes* spp., *Aegeria* spp., *Agrotis* spp., *Alabama argillaceae, Amylois* spp., *Anticarsia gemmatalis, Archips* spp., *Argyresthia* spp, *Argyrotaenia* spp., *Autographa* spp., *Bucculatrix thurberiella, Busseola fusca, Cadra cautella, Carposina nipponensis, Chilo* spp., *Choristoneura* spp., *Chrysoteuchia topiaria, Clysia ambiguella, Cnaphalocrocis* spp., *Cnephasia* spp., *Cochylis* spp., *Coleophora* spp., *Colias lesbia, Cosmophila flava, Crambus* spp, *Crocidolomia binotalis, Cryptophlebia leucotreta, Cydalima perspectalis, Cydia* spp., *Diaphania perspectalis, Diatraea* spp., *Diparopsis castanea, Earias* spp., *Elasmopalpus lignosellus, Eldana saccharina, Ephestia* spp., *Epinotia* spp, *Estigmene acrea, Etiella zinckinella, Eucosma* spp., *Eupoecilia ambiguella, Euproctis* spp., *Euxoa* spp., *Feltia jaculiferia, Grapholita* spp., *Hedya nubiferana, Heliothis* spp., *Hellula undalis, Herpetogramma* spp, *Hyphantria cunea, Keiferia lycopersicella, Lasmopalpus lignosellus, Leucoptera scitella, Lithocollethis* spp., *Lobesia botrana, Loxostege bifidalis, Lymantria* spp., *Lyonetia* spp., *Malacosoma* spp., *Mamestra brassicae, Manduca sexta, Mythimna* spp, *Noctua* spp, *Operophtera* spp., *Orniodes indica, Ostrinia nubilalis, Pammene* spp., *Pandemis* spp., *Panolis flammea, Papaipema nebris, Pectinophora gossypiela, Perileucoptera coffeella, Pseudaletia unipuncta, Phthorimaea operculella, Pieris rapae, Pieris* spp., *Plutella xylostella, Prays* spp., *Pseudoplusia* spp, *Rachiplusia nu, Richia albicosta, Scirpophaga* spp., *Sesamia* spp., *Sparganothis* spp., *Spodoptera* spp., *Sylepta* derogate, *Synanthedon* spp., *Thaumetopoea* spp., *Tortrix* spp., *Trichoplusia ni, Tuta absoluta* and *Yponomeuta* spp.;

from the order *Mallophaga*, for example,

*Damalinea* spp. and *Trichodectes* spp.;

from the order Orthoptera, for example,

*Blatta* spp., *Blattella* spp., *Gryllotalpa* spp., *Leucophaea maderae, Locusta* spp., *Neocurtilla hexadactyla, Periplaneta* spp., *Scapteriscus* spp and *Schistocerca* spp.;

from the order Psocoptera, for example,

*Liposcelis* spp.;

from the order *Siphonaptera*, for example,

*Ceratophyllus* spp., *Ctenocephalides* spp. and *Xenopsylla cheopis;* from the order Thysanoptera, for example,

*Calliothrips phaseoli, Frankliniella* spp., *Heliothrips* spp, *Hercinothrips* spp., *Parthenothrips* spp, *Scirtothrips aurantii, Sericothrips variabilis, Taeniothrips* spp., *Thrips* spp;

from the order Thysanura, for example, *Lepisma saccharina.*

In a further aspect, the invention may also relate to a method of controlling damage to plant and parts thereof by plant parasitic nematodes (Endoparasitic-, Semiendoparasitic- and Ectoparasitic nematodes), especially plant parasitic nematodes such as root knot nematodes, *Meloidogyne hapla, Meloidogyne incognita, Meloidogyne javanica, Meloidogyne arenaria* and other *Meloidogyne* species; cyst-forming nematodes, *Globodera rostochiensis* and other *Globodera* species; *Heterodera avenae, Heterodera glycines,*

*Heterodera schachtii, Heterodera trifolii* and other *Heterodera* species; Seed gall nematodes, *Anguina* species; Stem and foliar nematodes, *Aphelenchoides* species; Sting nematodes, *Belonolaimus longicaudatus* and other *Belonolaimus* species; Pine nematodes, *Bursaphelenchus xylophilus* and other *Bursaphelenchus* species; Ring nematodes, *Criconema* species, *Criconemella* species, *Criconemoides* species, *Mesocriconema* species; Stem and bulb nematodes, *Ditylenchus destructor, Ditylenchus dipsaci* and other *Ditylenchus* species; Awl nematodes, *Dolichodorus* species; Spiral nematodes, *Heliocotylenchus multicinctus* and other *Helicotylenchus* species; Sheath and sheathoid nematodes, *Hemicycliophora* species and *Hemicriconemoides* species; *Hirshmanniella* species; Lance nematodes, *Hoploaimus* species; false rootknot nematodes, *Nacobbus* species; Needle nematodes, *Longidorus elongatus* and other *Longidorus* species; Pin nematodes, *Pratylenchus* species; Lesion nematodes, *Pratylenchus neglectus, Pratylenchus penetrans, Pratylenchus curvitatus, Pratylenchus goodeyi* and other *Pratylenchus* species; Burrowing nematodes, *Radopholus similis* and other *Radopholus* species; Reniform nematodes, *Rotylenchus robustus, Rotylenchus reniformis* and other *Rotylenchus* species; *Scutellonema* species; Stubby root nematodes, *Trichodorus primitivus* and other *Trichodorus* species, *Paratrichodorus* species; Stunt nematodes, *Tylenchorhynchus claytoni, Tylenchorhynchus dubius* and other *Tylenchorhynchus* species; Citrus nematodes, *Tylenchulus* species; Dagger nematodes, *Xiphinema* species; and other plant parasitic nematode species, such as *Subanguina* spp., *Hypsoperine* spp., *Macroposthonia* spp., *Melinius* spp., *Punctodera* spp. and *Quinisulcius* spp.

The compounds of the invention may also have activity against the molluscs. Examples of which include, for example, *Ampullariidae; Arion* (*A. ater, A. circumscriptus, A. hortensis, A. rufus*); *Bradybaenidae* (*Bradybaena fruticum*); *Cepaea* (*C. hortensis, C. Nemoralis*); *ochlodina; Deroceras* (*D. agrestis, D. empiricorum, D. laeve, D. reticulatum*); *Discus* (*D. rotundatus*); *Euomphalia; Galba* (*G. trunculata*); *Helicelia* (*H. itala, H. obvia*); *Helicidae Helicigona arbustorum*); *Helicodiscus; Helix* (*H. aperta*); *Limax* (*L. cinereoniger, L. flavus, L. marginatus, L. maximus, L. tenellus*); *Lymnaea; Milax* (*M. gagates, M. marginatus, M. sowerbyi*); *Opeas; Pomacea* (*P. canaticulata*); *Vallonia* and *Zanitoides*.

The active ingredients according to the invention can be used for controlling, i. e. containing or destroying, pests of the abovementioned type which occur in particular on plants, especially on useful plants and ornamentals in agriculture, in horticulture and in forests, or on organs, such as fruits, flowers, foliage, stalks, tubers or roots, of such plants, and in some cases even plant organs which are formed at a later point in time remain protected against these pests.

Suitable target crops are, in particular, cereals, such as wheat, barley, rye, oats, rice, maize or sorghum; beet, such as sugar or fodder beet; fruit, for example pomaceous fruit, stone fruit or soft fruit, such as apples, pears, plums, peaches, almonds, cherries or berries, for example strawberries, raspberries or blackberries; leguminous crops, such as beans, lentils, peas or soya; oil crops, such as oilseed rape, mustard, poppies, olives, sunflowers, coconut, castor, cocoa or ground nuts; cucurbits, such as pumpkins, cucumbers or melons; fibre plants, such as cotton, flax, hemp orjute; citrus fruit, such as oranges, lemons, grapefruit or tangerines; vegetables, such as spinach, lettuce, asparagus, cabbages, carrots, onions, tomatoes, potatoes or bell peppers; Lauraceae, such as avocado, Cinnamonium or camphor; and also tobacco, nuts, coffee, eggplants, sugarcane, tea, pepper, grapevines, hops, the plantain family and latex plants.

In a particular embodiment, a compound of the formula (I) controls mites, rust mites and spider mites in crops, tress and plants selected from vegetables (especially tomatoes and cucurbits), citrus, pome fruits, stone fruit, tree nuts, cotton, tropical crops, avocados, ornamentals, beans, soybean, strawberry and grapes.

The compositions and/or methods of the present invention may be also used on any ornamental and/or vegetable crops, including flowers, shrubs, broad-leaved trees and evergreens.

For example the invention may be used on any of the following ornamental species: *Ageratum* spp., *Alonsoa* spp., *Anemone* spp., *Anisodontea capsenisis, Anthemis* spp., *Antirrhinum* spp., *Aster* spp., *Begonia* spp. (e.g. *B. elatior, B. semperflorens, B. tubereux*), *Bougainvillea* spp., *Brachycome* spp., *Brassica* spp. (ornamental), *Calceolaria* spp., *Capsicum annuum, Catharanthus roseus, Canna* spp., *Centaurea* spp., *Chrysanthemum* spp., *Cineraria* spp. (*C. maritime*), *Coreopsis* spp., *Crassula coccinea, Cuphea ignea, Dahlia* spp., *Delphinium* spp., *Dicentra spectabilis, Dorotheantus* spp., *Eustoma grandiflorum, Forsythia* spp., *Fuchsia* spp., *Geranium gnaphalium, Gerbera* spp., *Gomphrena globosa, Heliotropium* spp., *Helianthus* spp., *Hibiscus* spp., *Hortensia* spp., *Hydrangea* spp., *Hypoestes phyllostachya, Impatiens* spp. (I. *Walleriana*), *Iresines* spp., *Kalanchoe* spp., *Lantana camara, Lavatera trimestris, Leonotis leonurus, Lilium* spp., *Mesembryanthemum* spp., *Mimulus* spp., *Monarda* spp., *Nemesia* spp., *Tagetes* spp., *Dianthus* spp. (carnation), *Canna* spp., *Oxalis* spp., *Bellis* spp., *Pelargonium* spp. (*P. peltatum, P. Zonale*), *Viola* spp. (pansy), *Petunia* spp., *Phlox* spp., *Plecthranthus* spp., *Poinsettia* spp., *Parthenocissus* spp. (*P. quinquefolia, P. tricuspidata*), *Primula* spp., *Ranunculus* spp., *Rhododendron* spp., *Rosa* spp. (rose), *Rudbeckia* spp., *Saintpaulia* spp., *Salvia* spp., *Scaevola aemola, Schizanthus wisetonensis, Sedum* spp., *Solanum* spp., *Surfinia* spp., *Tagetes* spp., *Nicotinia* spp., *Verbena* spp., *Zinnia* spp. and other bedding plants.

For example the invention may be used on any of the following vegetable species: *Allium* spp. (*A. sativum, A. cepa, A. oschaninii, A. Porrum, A. ascalonicum, A. fistulosum*), *Anthriscus cerefolium, Apium graveolus, Asparagus officinalis, Beta vulgarus, Brassica* spp. (*B. Oleracea, B. Pekinensis, B. rapa*), *Capsicum annuum, Cicer arietinum, Cichorium endivia, Cichorum* spp. (*C. intybus, C. endivia*), *Citrillus lanatus, Cucumis* spp. (*C. sativus, C. melo*), *Cucurbita* spp. (*C. pepo, C. maxima*), *Cyanara* spp. (*C. scolymus, C. cardunculus*), *Daucus carota, Foeniculum vulgare, Hypericum* spp., *Lactuca sativa, Lycopersicon* spp. (*L. esculentum, L. lycopersicum*), *Mentha* spp., *Ocimum basilicum, Petroselinum crispum, Phaseolus* spp. (*P. vulgaris, P. coccineus*), *Pisum sativum, Raphanus sativus, Rheum rhaponticum, Rosemarinus* spp., *Salvia* spp., *Scorzonera hispanica, Solanum melongena, Spinacea oleracea, Valerianella* spp. (*V. locusta, V. eriocarpa*) and *Vicia faba*.

Preferred ornamental species include African violet, *Begonia, Dahlia, Gerbera, Hydrangea, Verbena, Rosa, Kalanchoe, Poinsettia, Aster, Centaurea, Coreopsis, Delphinium, Monarda, Phlox, Rudbeckia, Sedum, Petunia, Viola, Impatiens, Geranium, Chrysanthemum, Ranunculus, Fuchsia, Salvia, Hortensia*, rosemary, sage, St. Johnswort, mint, sweet pepper, tomato and cucumber.

The active ingredients according to the invention are especially suitable for controlling *Aphis craccivora, Diabrotica balteata, Heliothis virescens, Myzus persicae, Plutella xylostella* and *Spodoptera littoralis* in cotton, vegetable, maize, rice and soya crops. The active ingredients according to the invention are further especially suitable for controlling *Mamestra* (preferably in vegetables), *Cydia pomonella* (preferably in apples), *Empoasca* (preferably in vegetables, vineyards), *Leptinotarsa* (preferably in potatos) and *Chilo supressalis* (preferably in rice).

The compounds of formula (I) are particularly suitable for control of mites, spider mites and rust mites, for example, *Acarapis* spp; *Acarapis woodi; Acarus siro; Acarus* spp; *Aceria sheldoni; Aculops pelekassi; Aculops* spp; *Aculus schlechtendali; Aculus* spp; *Amblyseius fallacis; Brevipalpus* spp; *Brevipalpus phoenicis; Bryobia praetiosa; Bryobia rubrioculus; Caloglyphus* spp; *Cheyletiella blakei; Cheyletiella* spp; *Cheyletiella yasguri; Chorioptes bovis; Chorioptes* spp; *Cytodites* spp; *Demodex bovis; Demodex caballi; Demodex canis; Demodex caprae; Demodex equi; Demodex ovis; Demodex* spp; *Demodex suis; Dermanyssus gallinae; Dermanyssus* spp; *Eotetranychus* spp; *Eotetranychus willamettei; Epitrimerus pyri; Eriophyes ribis; Eriophyes* spp; *Eriophyes vitis; Eutetranychus* spp; *Halotydeus destructor; Hemitarsonemus* spp; *Knemidocoptes* spp; *Laminosioptes* spp; *Listrophorus* spp; *Myobia* spp; *Neoschongastia xerothermobia; Neotrombicula autumnalis; Neotrombicula desaleri; Notoedres cati; Notoedres* spp; *Oligonychus coffeae; Oligonychus ilicis; Oligonychus* spp; *Ornithocheyletia* spp; *Ornithonyssus bursa; Ornithonyssus* spp; *Ornithonyssus sylviarum; Otodectes cynotis; Otodectes* spp; *Panonychus citri; Panonychus* spp; *Panonychus ulmi; Phyllocoptruta oleivora; Phyllocoptruta* spp.; *Phytoseiulus* spp.; *Pneumonyssoides caninum; Polyphagotarsonemus latus; Polyphagotarsonemus* spp; *Psorergates ovis; Psorergates* spp; *Psoroptes cuniculi; Psoroptes equi; Psoroptes ovis; Psoroptes* spp; *Pterolichus* spp; *Raillietia* spp; *Rhizoglyphus* spp; *Sarcoptes bovis; Sarcoptes canis; Sarcoptes caprae; Sarcoptes equi; Sarcoptes ovis; Sarcoptes rupicaprae; Sarcoptes* spp; *Sarcoptes suis; Steneotarsonemus spinki; Steneotarsonemus* spp; *Sternostoma* spp; *Tarsonemus* spp; *Tetranychus cinnabarinus; Tetranychus kanzawai; Tetranychus* spp; *Tetranychus urticae; Trombicula akamushi; Trombicula* spp; *Typhlodromus occidentalis; Tyrophagus* spp; *Varroa jacobsoni; Varroa* spp; *Vasates lycopersici*; and *Zetzellia mali.*

In an embodiment, a compound of formula (I) are especially suitable for controlling one or more of: *Aceria sheldoni; Aculus lycopersici; Aculus pelekassi; Aculus schlechtendali; Brevipalpus phoenicis; Brevipalpus* spp.; *Bryobia rubrioculus; Eotetranychus carpini; Eotetranychus* spp.; *Epitrimerus pyri; Eriophyes piri; Eriophyes* spp.; *Eriophyes vitis; Eutetranychus africanus; Eutetranychus orientalis; Oligonychus pratensis; Panonychus citri; Panonychus ulmi; Phyllocoptes vitis; Phyllocoptruta oleivora; Polyphagotarsonemus latus; Tetranychus cinnabarinus; Tetranychus kanzawai; Tetranychus* spp.; and *Tetranychus urticae.*

In a further embodiment, a compound of formula (I) are more especially suitable for controlling one or more of: *Aceria sheldoni; Aculus pelekassi; Brevipalpus phoenicis; Brevipalpus* spp.; *Eriophyes piri; Eriophyes vitis; Eutetranychus africanus; Eutetranychus orientalis; Oligonychus pratensis; Panonychus ulmi; Phyllocoptes vitis; Phyllocoptruta oleivora; Polyphagotarsonemus latus; Tetranychus cinnabarinus; Tetranychus kanzawai; Tetranychus* spp.; and *Tetranychus urticae.*

The term "crops" is to be understood as including also crop plants which have been so transformed by the use of recombinant DNA techniques that they are capable of synthesising one or more selectively acting toxins, such as are known, for example, from toxin-producing bacteria, especially those of the genus *Bacillus.*

Toxins that can be expressed by such transgenic plants include, for example, insecticidal proteins, for example insecticidal proteins from *Bacillus cereus* or *Bacillus popilliae*; or insecticidal proteins from *Bacillus thuringiensis*, such as δ-endotoxins, e.g. Cry1Ab, Cry1Ac, Cry1F, Cry1 Fa2, Cry2Ab, Cry3A, Cry3Bb1 or Cry9C, or vegetative insecticidal proteins (Vip), e.g. Vip1, Vip2, Vip3 or Vip3A; or insecticidal proteins of bacteria colonising nematodes, for example *Photorhabdus* spp. or *Xenorhabdus* spp., such as *Photorhabdus luminescens, Xenorhabdus nematophilus*; toxins produced by animals, such as scorpion toxins, arachnid toxins, wasp toxins and other insect-specific neurotoxins; toxins produced by fungi, such as Streptomycetes toxins, plant lectins, such as pea lectins, barley lectins or snowdrop lectins; agglutinins; proteinase inhibitors, such as trypsin inhibitors, serine protease inhibitors, patatin, cystatin, papain inhibitors; ribosome-inactivating proteins (RIP), such as ricin, maize-RIP, abrin, luffin, saporin or bryodin; steroid metabolism enzymes, such as 3-hydroxysteroidoxidase, ecdysteroid-UDP-glycosyl-transferase, cholesterol oxidases, ecdysone inhibitors, HMG-COA-reductase, ion channel blockers, such as blockers of sodium or calcium channels, juvenile hormone esterase, diuretic hormone receptors, stilbene synthase, bibenzyl synthase, chitinases and glucanases.

In the context of the present invention there are to be understood by δ-endotoxins, for example Cry1Ab, Cry1Ac, Cry1F, Cry1Fa2, Cry2Ab, Cry3A, Cry3Bb1 or Cry9C, or vegetative insecticidal proteins (Vip), for example Vip1, Vip2, Vip3 or Vip3A, expressly also hybrid toxins, truncated toxins and modified toxins. Hybrid toxins are produced recombinantly by a new combination of different domains of those proteins (see, for example, WO 02/15701). Truncated toxins, for example a truncated Cry1Ab, are known. In the case of modified toxins, one or more amino acids of the naturally occurring toxin are replaced. In such amino acid replacements, preferably non-naturally present protease recognition sequences are inserted into the toxin, such as, for example, in the case of Cry3A055, a cathepsin-G-recognition sequence is inserted into a Cry3A toxin (see WO 03/018810).

Examples of such toxins or transgenic plants capable of synthesising such toxins are disclosed, for example, in EP-A-0 374 753, WO 93/07278, WO 95/34656, EP-A-0 427 529, EP-A-451 878 and WO 03/052073.

The processes for the preparation of such transgenic plants are generally known to the person skilled in the art and are described, for example, in the publications mentioned above. Cry1-type deoxyribonucleic acids and their preparation are known, for example, from WO 95/34656, EP-A-0 367 474, EP-A-0 401 979 and WO 90/13651.

The toxin contained in the transgenic plants imparts to the plants tolerance to harmful insects. Such insects can occur in any taxonomic group of insects, but are especially commonly found in the beetles (*Coleoptera*), two-winged insects (*Diptera*) and moths (*Lepidoptera*).

Transgenic plants containing one or more genes that code for an insecticidal resistance and express one or more toxins are known and some of them are commercially available. Examples of such plants are: YieldGard® (maize variety that expresses a Cry1Ab toxin); YieldGard Rootworm® (maize variety that expresses a Cry3Bb1 toxin); YieldGard Plus® (maize variety that expresses a Cry1Ab and a Cry3Bb1 toxin); Starlink® (maize variety that expresses a Cry9C toxin); Herculex I® (maize variety that expresses a Cry1 Fa2 toxin and the enzyme phosphinothricine N-acetyltransferase (PAT) to achieve tolerance to the herbicide glufosinate ammonium); NuCOTN 33B® (cotton variety that expresses a Cry1Ac toxin); Bollgard I® (cotton variety that expresses a Cry1Ac toxin); Bollgard II® (cotton variety that expresses a Cry1Ac and a Cry2Ab toxin); VipCot® (cotton variety that expresses a Vip3A and a Cry1Ab toxin); NewLeaf® (potato variety that expresses a Cry3A toxin); NatureGard®, Agrisure® GT Advantage (GA21 glyphosate-tolerant trait), Agrisure® CB Advantage (Bt11 corn borer (CB) trait) and Protecta®.

Further examples of such transgenic crops are:

1. Bt11 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a truncated Cry1Ab toxin. Bt11 maize also transgenically expresses the enzyme PAT to achieve tolerance to the herbicide glufosinate ammonium.

2. Bt176 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a Cry1Ab toxin. Bt176 maize also transgenically expresses the enzyme PAT to achieve tolerance to the herbicide glufosinate ammonium.

3. MIR604 Maize from Syngenta Seeds SAS, Chemin de l'Hobit 27, F-31 790 St. Sauveur, France, registration number C/FR/96/05/10. Maize which has been rendered insect-resistant by transgenic expression of a modified Cry3A toxin. This toxin is Cry3A055 modified by insertion of a cathepsin-G-protease recognition sequence. The preparation of such transgenic maize plants is described in WO 03/018810.

4. MON 863 Maize from Monsanto Europe S.A. 270-272 Avenue de Tervuren, B-1150 Brussels, Belgium, registration number C/DE/02/9. MON 863 expresses a Cry3Bb1 toxin and has resistance to certain *Coleoptera* insects.

5. IPC 531 Cotton from Monsanto Europe S.A. 270-272 Avenue de Tervuren, B-1150 Brussels, Belgium, registration number C/ES/96/02.

6. 1507 Maize from Pioneer Overseas Corporation, Avenue Tedesco, 7 B-1160 Brussels, Belgium, registration number C/NL/00/10. Genetically modified maize for the expression of the protein Cry1F for achieving resistance to certain *Lepidoptera* insects and of the PAT protein for achieving tolerance to the herbicide glufosinate ammonium.

7. NK603×MON 810 Maize from Monsanto Europe S.A. 270-272 Avenue de Tervuren, B-1150 Brussels, Belgium, registration number C/GB/02/M3/03. Consists of conventionally bred hybrid maize varieties by crossing the genetically modified varieties NK603 and MON 810. NK603×MON 810 Maize transgenically expresses the protein CP4 EPSPS, obtained from *Agrobacterium* sp. strain CP4, which imparts tolerance to the herbicide Roundup® (contains glyphosate) and also a Cry1Ab toxin obtained from *Bacillus thuringiensis* subsp. *kurstaki* which brings about tolerance to certain *Lepidoptera*, include the European corn borer.

Transgenic crops of insect-resistant plants are also described in BATS (Zentrum für Biosicherheit und Nachhaltigkeit, Zentrum BATS, Clarastrasse 13, 4058 Basel, Switzerland) Report 2003, (http://bats.ch).

The term "crops" is to be understood as including also crop plants which have been so transformed by the use of recombinant DNA techniques that they are capable of synthesising antipathogenic substances having a selective action, such as, for example, the so-called "pathogenesis-related proteins" (PRPs, see e.g. EP-A-0 392 225). Examples of such antipathogenic substances and transgenic plants capable of synthesising such antipathogenic substances are known, for example, from EP-A-0 392 225, WO 95/33818 and EP-A-0 353 191. The methods of producing such transgenic plants are generally known to the person skilled in the art and are described, for example, in the publications mentioned above.

Crops may also be modified for enhanced resistance to fungal (for example *Fusarium, Anthracnose*, or *Phytophthora*), bacterial (for example *Pseudomonas*) or viral (for example potato leafroll virus, tomato spotted wilt virus, cucumber mosaic virus) pathogens.

Crops also include those that have enhanced resistance to nematodes, such as the soybean cyst nematode.

Crops that are tolerance to abiotic stress include those that have enhanced tolerance to drought, high salt, high temperature, chill, frost, or light radiation, for example through expression of NF-YB or other proteins known in the art.

Antipathogenic substances which can be expressed by such transgenic plants include, for example, ion channel blockers, such as blockers for sodium and calcium channels, for example the viral KP1, KP4 or KP6 toxins; stilbene synthases; bibenzyl synthases; chitinases; glucanases; the so-called "pathogenesis-related proteins" (PRPs; see e.g. EP-A-0 392 225); antipathogenic substances produced by microorganisms, for example peptide antibiotics or heterocyclic antibiotics (see e.g. WO 95/33818) or protein or polypeptide factors involved in plant pathogen defence (so-called "plant disease resistance genes", as described in WO 03/000906).

Further areas of use of the compositions according to the invention are the protection of stored goods and store rooms and the protection of raw materials, such as wood, textiles, floor coverings or buildings and also in the hygiene sector, especially the protection of humans, domestic animals and productive livestock against pests of the mentioned type.

The present invention provides a compound of the first aspect for use in therapy. The present invention provides a compound of the first aspect, for use in controlling parasites in or on an animal. The present invention further provides a compound of the first aspect, for use in controlling ectoparasites on an animal. The present invention further provides a compound of the first aspect, for use in preventing and/or treating diseases transmitted by ectoparasites.

The present invention provides the use of a compound of the first aspect, for the manufacture of a medicament for controlling parasites in or on an animal. The present invention further provides the use of a compound of the first aspect, for the manufacture of a medicament for controlling ectoparasites on an animal. The present invention further provides the use of a compound of the first aspect, for the manufacture of a medicament for preventing and/or treating diseases transmitted by ectoparasites.

The present invention provides the use of a compound of the first aspect, in controlling parasites in or on an animal. The present invention further provides the use of a compound of the first aspect, in controlling ectoparasites on an animal.

The term "controlling" when used in context of parasites in or on an animal refers to reducing the number of pests or parasites, eliminating pests or parasites and/or preventing further pest or parasite infestation.

The term "treating" when used used in context of parasites in or on an animal refers to restraining, slowing, stopping or reversing the progression or severity of an existing symptom or disease. The term "preventing" when used used in context of parasites in or on an animal refers to the avoidance of a symptom or disease developing in the animal.

The term "animal" when used used in context of parasites in or on an animal may refer to a mammal and a non-mammal, such as a bird or fish. In the case of a mammal, it may be a human or non-human mammal. Non-human mammals include, but are not limited to, livestock animals and companion animals. Livestock animals include, but are not limited to, cattle, camellids, pigs, sheep, goats and horses. Companion animals include, but are not limited to, dogs, cats and rabbits.

A "parasite" is a pest which lives in or on the host animal and benefits by deriving nutrients at the host animal's expense. An "endoparasite" is a parasite which lives in the host animal. An "ectoparasite" is a parasite which lives on the host animal. Ectoparasites include, but are not limited to, *acari*, insects and crustaceans (e.g. sea lice). The *Acari* (or *Acarina*) sub-class comprises ticks and mites. Ticks include, but are not limited to, members of the following genera: *Rhipicaphalus*, for example, *Rhipicaphalus* (*Boophilus*) *microplus* and *Rhipicephalus sanguineus; Amblyomrna; Dermacentor; Haemaphysalis; Hyalomma; Ixodes; Rhipicentor; Margaropus; Argas; Otobius*; and *Ornithodoros*. Mites include, but are not limited to, members of the following genera: *Chorioptes*, for example *Chorioptes bovis; Psoroptes*, for example *Psoroptes ovis; Cheyletiella; Dermanyssus*; for example *Dermanyssus gallinae; Ortnithonyssus; Demodex*, for example *Demodex canis; Sarcoptes*, for example *Sarcoptes scabiei*; and *Psorergates*. Insects include, but are not limited to, members of the orders: *Siphonaptera, Diptera, Phthiraptera, Lepidoptera, Coleoptera* and *Homoptera*. Members of the *Siphonaptera* order include, but are not limited to, *Ctenocephalides felis* and *Ctenocephatides canis*. Members of the *Diptera* order include, but are not limited to, *Musca* spp.; bot fly, for example *Gasterophilus intestinalis* and *Oestrus ovis*; biting flies; horse flies, for example *Haematopota* spp. and *Tabunus* spp.; *haematobia*, for example *haematobia irritans; Stomoxys; Lucilia*; midges; and mosquitoes. Members of the *Phthiraptera* class include, but are not limited to, blood sucking lice and chewing lice, for example *Bovicola Ovis* and *Bovicola Bovis.*

The term "effective amount" when used used in context of parasites in or on an animal refers to the amount or dose of the compound of the invention, or a salt thereof, which, upon single or multiple dose administration to the animal, provides the desired effect in or on the animal. The effective amount can be readily determined by the attending diagnostician, as one skilled in the art, by the use of known techniques and by observing results obtained under analogous circumstances. In determining the effective amount a number of factors are considered by the attending diagnostician, including, but not limited to: the species of mammal; its size, age and general health; the parasite to be controlled and the degree of infestation; the specific disease or disorder involved; the degree of or involvement or the severity of the disease or disorder; the response of the individual; the particular compound administered; the mode of administration; the bioavailability characteristics of the preparation administered; the dose regimen selected; the use of concomitant medication; and other relevant circumstances.

The compounds of the invention may be administered to the animal by any route which has the desired effect including, but not limited to topically, orally, parenterally and subcutaneously. Topical administration is preferred. Formulations suitable for topical administration include, for example, solutions, emulsions and suspensions and may take the form of a pour-on, spot-on, spray-on, spray race or dip. In the alternative, the compounds of the invention may be administered by means of an ear tag or collar.

Salt forms of the compounds of the invention include both pharmaceutically acceptable salts and veterinary acceptable salts, which can be different to agrochemically acceptable salts. Pharmaceutically and veterinary acceptable salts and common methodology for preparing them are well known in the art. See, for example, Gould, P. L., "Salt selection for basic drugs", International Journal of Pharmaceutics, 33: 201-217 (1986); Bastin, R. J., et al. "Salt Selection and Optimization Procedures for Pharmaceutical New Chemical Entities", Organic Process Research and Development, 4: 427-435 (2000); and Berge, S. M., et al., "Pharmaceutical Salts", Journal of Pharmaceutical Sciences, 66: 1-19, (1977). One skilled in the art of synthesis will appreciate that the compounds of the invention are readily converted to and may be isolated as a salt, such as a hydrochloride salt, using techniques and conditions well known to one of ordinary skill in the art. In addition, one skilled in the art of synthesis will appreciate that the compounds of the invention are readily converted to and may be isolated as the corresponding free base from the corresponding salt.

The present invention also provides a method for controlling pests (such as mosquitoes and other disease vectors; see also http://www.who.int/malaria/vector_control/irs/en/). In one embodiment, the method for controlling pests comprises applying the compositions of the invention to the target pests, to their locus or to a surface or substrate by brushing, rolling, spraying, spreading or dipping. By way of example, an IRS (indoor residual spraying) application of a surface such as a wall, ceiling or floor surface is contemplated by the method of the invention. In another embodiment, it is contemplated to apply such compositions to a substrate such as non-woven or a fabric material in the form of (or which can be used in the manufacture of) netting, clothing, bedding, curtains and tents.

In one embodiment, the method for controlling such pests comprises applying a pesticidally effective amount of the compositions of the invention to the target pests, to their locus, or to a surface or substrate so as to provide effective residual pesticidal activity on the surface or substrate. Such application may be made by brushing, rolling, spraying, spreading or dipping the pesticidal composition of the invention. By way of example, an IRS application of a surface such as a wall, ceiling or floor surface is contemplated by the method of the invention so as to provide effective residual pesticidal activity on the surface. In another embodiment, it is contemplated to apply such compositions for residual control of pests on a substrate such as a fabric material in the form of (or which can be used in the manufacture of) netting, clothing, bedding, curtains and tents.

Substrates including non-woven, fabrics or netting to be treated may be made of natural fibres such as cotton, raffia, jute, flax, sisal, hessian, or wool, or synthetic fibres such as polyamide, polyester, polypropylene, polyacrylonitrile or the like. The polyesters are particularly suitable. The methods of textile treatment are known, e.g. WO 2008/151984, WO 2003/034823, U.S. Pat. No. 5,631,072, WO 2005/64072, WO2006/128870, EP 1724392, WO 2005113886 or WO 2007/090739.

Further areas of use of the compositions according to the invention are the field of tree injection/trunk treatment for all ornamental trees as well all sort of fruit and nut trees.

In the field of tree injection/trunk treatment, the compounds according to the present invention are especially suitable against wood-boring insects from the order *Lepidoptera* as mentioned above and from the order *Coleoptera*, especially against woodborers listed in the following tables A and B:

TABLE A

Examples of exotic woodborers of economic importance.

| Family | Species | Host or Crop Infested |
|---|---|---|
| Buprestidae | *Agrilus planipennis* | Ash |
| Cerambycidae | *Anoplura glabripennis* | Hardwoods |
| Scolytidae | *Xylosandrus crassiusculus* | Hardwoods |
| | *X. mutilatus* | Hardwoods |
| | *Tomicus piniperda* | Conifers |

TABLE B

Examples of native woodborers of economic importance.

| Family | Species | Host or Crop Infested |
|---|---|---|
| Buprestidae | *Agrilus anxius* | Birch |
| | *Agrilus politus* | Willow, Maple |
| | *Agrilus sayi* | Bayberry, Sweetfern |
| | *Agrilus vittaticolllis* | Apple, Pear, Cranberry, Serviceberry, Hawthorn |
| | *Chrysobothris femorata* | Apple, Apricot, Beech, Boxelder, Cherry, Chestnut, Currant, Elm, Hawthorn, Hackberry, Hickory, Horsechestnut, Linden, Maple, Mountain-ash, Oak, Pecan, Pear, Peach, Persimmon, Plum, Poplar, Quince, Redbud, Serviceberry, Sycamore, Walnut, Willow |
| | *Texania campestris* | Basswood, Beech, Maple, Oak, Sycamore, Willow, Yellow-poplar |
| Cerambycidae | *Goes pulverulentus* | Beech, Elm, Nuttall, Willow, Black oak, Cherrybark oak, Water oak, Sycamore |
| | *Goes tigrinus* | Oak |
| | *Neoclytus acuminatus* | Ash, Hickory, Oak, Walnut, Birch, Beech, Maple, Eastern hophornbeam, Dogwood, Persimmon, Redbud, Holly, Hackberry, Black locust, Honeylocust, Yellow-poplar, Chestnut, Osage-orange, Sassafras, Lilac, Mountain-mahogany, Pear, Cherry, Plum, Peach, Apple, Elm, Basswood, Sweetgum |
| | *Neoptychodes trilineatus* | Fig, Alder, Mulberry, Willow, Netleaf hackberry |
| | *Oberea ocellata* | Sumac, Apple, Peach, Plum, Pear, Currant, Blackberry |
| | *Oberea tripunctata* | Dogwood, Viburnum, Elm, Sourwood, Blueberry, Rhododendron, Azalea, Laurel, Poplar, Willow, Mulberry |
| | *Oncideres cingulata* | Hickory, Pecan, Persimmon, Elm, Sourwood, Basswood, Honeylocust, Dogwood, Eucalyptus, Oak, Hackberry, Maple, Fruit trees |
| | *Saperda calcarata* | Poplar |
| | *Strophiona nitens* | Chestnut, Oak, Hickory, Walnut, Beech, Maple |

TABLE B-continued

Examples of native woodborers of economic importance.

| Family | Species | Host or Crop Infested |
|---|---|---|
| Scolytidae | *Corthylus columbianus* | Maple, Oak, Yellow-poplar, Beech, Boxelder, Sycamore, Birch, Basswood, Chestnut, Elm |
| | *Dendroctonus frontalis* | Pine |
| | *Dryocoetes betulae* | Birch, Sweetgum, Wild cherry, Beech, Pear |
| | *Monarthrum fasciatum* | Oak, Maple, Birch, Chestnut, Sweetgum, Blackgum, Poplar, Hickory, Mimosa, Apple, Peach, Pine |
| | *Phloeotribus liminaris* | Peach, Cherry, Plum, Black cherry, Elm, Mulberry, Mountain-ash |
| | *Pseudopityophthorus pruinosus* | Oak, American beech, Black cherry, Chickasaw plum, Chestnut, Maple, Hickory, Hornbeam, Hophornbeam |
| Sesiidae | *Paranthrene simulans* | Oak, American chestnut |
| | *Sannina uroceriformis* | Persimmon |
| | *Synanthedon exitiosa* | Peach, Plum, Nectarine, Cherry, Apricot, Almond, Black cherry |
| | *Synanthedon pictipes* | Peach, Plum, Cherry, Beach, Black Cherry |
| | *Synanthedon rubrofascia* | Tupelo |
| | *Synanthedon scitula* | Dogwood, Pecan, Hickory, Oak, Chestnut, Beech, Birch, Black cherry, Elm, Mountain-ash, Viburnum, Willow, Apple, Loquat, Ninebark, Bayberry |
| | *Vitacea polistiformis* | Grape |

The present invention may be also used to control any insect pests that may be present in turfgrass, including for example beetles, caterpillars, fire ants, ground pearls, millipedes, sow bugs, mites, mole crickets, scales, mealybugs, ticks, spittlebugs, southern chinch bugs and white grubs. The present invention may be used to control insect pests at various stages of their life cycle, including eggs, larvae, nymphs and adults.

In particular, the present invention may be used to control insect pests that feed on the roots of turfgrass including white grubs (such as *Cyclocephala* spp. (e.g. masked chafer, *C. lurida*), *Rhizotrogus* spp. (e.g. European chafer, *R. majalis*), *Cotinus* spp. (e.g. Green June beetle, *C. nitida*), *Popillia* spp. (e.g. Japanese beetle, *P. japonica*), *Phyllophaga* spp. (e.g. May/June beetle), *Ataenius* spp. (e.g. Black turfgrass *ataenius, A. spretulus*), *Maladera* spp. (e.g. Asiatic garden beetle, *M. castanea*) and *Tomarus* spp.), ground pearls (*Margarodes* spp.), mole crickets (tawny, southern and short-winged; *Scapteriscus* spp., *Gryllotalpa africana*) and leatherjackets (European crane fly, *Tipula* spp.).

The present invention may also be used to control insect pests of turfgrass that are thatch dwelling, including armyworms (such as fall armyworm *Spodoptera frugiperda* and common armyworm *Pseudaletia unipuncta*), cutworms, billbugs (*Sphenophorus* spp., such as *S. venatus verstitus* and *S. parvulus*) and sod webworms (such as *Crambus* spp. and the tropical sod webworm, *Herpetogramma phaeopteralis*).

The present invention may also be used to control insect pests of turfgrass that live above the ground and feed on the turfgrass leaves, including chinch bugs (such as southern chinch bugs, *Blissus insularis*), Bermudagrass mite (*Eriophyes cynodoniensis*), rhodesgrass mealybug (*Antonina graminis*), two-lined spittlebug (*Propsapia bicincta*), leafhoppers, cutworms (Noctuidae family), and greenbugs.

The present invention may also be used to control other pests of turfgrass such as red imported fire ants (*Solenopsis invicta*) that create ant mounds in turf.

In the hygiene sector, the compositions according to the invention are active against ectoparasites such as hard ticks, soft ticks, mange mites, harvest mites, flies (biting and licking), parasitic fly larvae, lice, hair lice, bird lice and fleas.

Examples of such parasites are:

Of the order *Anoplurida: Haematopinus* spp., *Linognathus* spp., *Pediculus* spp. and *Phtirus* spp., *Solenopotes* spp.

Of the order *Mallophagida: Trimenopon* spp., *Menopon* spp., *Trinoton* spp., *Bovicola* spp., *Werneckiella* spp., *Lepikentron* spp., *Damalina* spp., *Trichodectes* spp. and *Felicola* spp.

Of the order *Diptera* and the suborders Nematocerina and Brachycerina, for example *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp. and *Melophagus* spp.

Of the order *Siphonapterida*, for example *Pulex* spp., *Ctenocephalides* spp., *Xenopsylla* spp., *Ceratophyllus* spp.

Of the order *Heteropterida*, for example *Cimex* spp., *Triatoma* spp., *Rhodnius* spp., *Panstrongylus* spp.

Of the order *Blattarida*, for example *Blatta orientalis, Periplaneta americana, Blattelagermanica* and *Supella* spp.

Of the subclass Acaria (Acarida) and the orders Meta- and Meso-*stigmata*, for example *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp. and *Varroa* spp.

Of the orders *Actinedida* (*Prostigmata*) and *Acaridida* (*Astigmata*), for example *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp.

The compositions according to the invention are also suitable for protecting against insect infestation in the case of materials such as wood, textiles, plastics, adhesives, glues, paints, paper and card, leather, floor coverings and buildings.

The compositions according to the invention can be used, for example, against the following pests: beetles such as *Hylotrupes bajulus, Chlorophorus pilosis, Anobium punctatum, Xestobium rufovillosum, Ptilinuspecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthesrugicollis, Xyleborus* spec., *Tryptodendron* spec., *Apate monachus, Bostrychus capucins, Heterobostrychus brunneus, Sinoxylon* spec. and *Dinoderus minutus* and also hymenopterans such as *Sirexjuvencus, Urocerus gigas, Urocerus gigas taignus and Urocerus augur*; termites such as *Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis* and *Coptotermes formosanus*; and bristletails such as *Lepisma saccharina*. The compounds of formulae I and I'a, or salts thereof, are especially suitable for controlling one or more pests selected from the family: Noctuidae, Plutellidae, Chrysomelidae, Thripidae, Pentatomidae, Tortricidae, Delphacidae, Aphididae, Noctuidae, Crambidae, Meloidogynidae and Heteroderidae. In a preferred embodiment of each aspect, a compound TX (where the abbreviation "TX" means "one compound selected from the compounds defined in Tables 1 to 35 and Tables P1 to P8) controls one or more of pests selected from the family: Noctuidae, Plutellidae, Chrysomelidae, Thripidae, Pentatomidae, Tortricidae, Delphacidae, Aphididae, Noctuidae, Crambidae, Meloidogynidae and Heteroderidae.

The compounds of formulae I and I'a, or salts thereof, are especially suitable for controlling one or more of pests selected from the genus: *Spodoptera* spp, *Plutella* spp, *Frankliniella* spp, *Thrips* spp, *Euschistus* spp, *Cydia* spp, *Nilaparvata* spp, *Myzus* spp, *Aphis* spp, *Diabrotica* spp, *Rhopalosiphum* spp, *Pseudoplusia* spp and *Chilo* spp. In a preferred embodiment of each aspect, a compound TX (where the abbreviation "TX" means "one compound selected from the compounds defined in Tables 1 to 35 and Tables P1 to P8) controls one or more of pests selected from the genus: *Spodoptera* spp, *Plutella* spp, *Frankliniella* spp, *Thrips* spp, *Euschistus* spp, *Cydia* spp, *Nilaparvata* spp, *Myzus* spp, *Aphis* spp, *Diabrotica* spp, *Rhopalosiphum* spp, *Pseudoplusia* spp and *Chilo* spp.

The compounds of formulae I and I'a, or salts thereof, are especially suitable for controlling one or more of *Spodoptera littoralis, Plutella xylostella, Frankliniella occidentalis, Thrips tabaci, Euschistus heros, Cydia pomonella, Nilaparvata lugens, Myzus persicae, Chrysodeixis includens, Aphis craccivora, Diabrotica balteata, Rhopalosiphum padi* and *Chilo suppressalis.*

In a preferred embodiment of each aspect, a compound TX (where the abbreviation "TX" means "one compound selected from the compounds defined in Tables 1 to 35 and Tables P1 to P8) controls one or more of *Spodoptera littoralis, Plutella xylostella, Frankliniella occidentalis, Thrips tabaci, Euschistus heros, Cydia pomonella, Nilaparvata lugens, Myzus persicae, Chrysodeixis includens, Aphis craccivora, Diabrotica balteata, Rhopalosiphum Padia* and *Chilo Suppressalis*, such as *Spodoptera littoralis*+TX, *Plutella xylostella*+TX; *Frankliniella occidentalis*+TX, *Thrips tabaci*+TX, *Euschistus heros*+TX, *Cydia pomonella*+TX, *Nilaparvata lugens*+TX, *Myzus persicae*+TX, *Chrysodeixis includens*+TX, *Aphis craccivora*+TX, *Diabrotica balteata*+TX, *Rhopalosiphum Padi*+TX and *Chilo suppressalis*+TX.

In an embodiment, of each aspect, one compound from Tables 1 to 35 and Tables P1 to P8 is suitable for controlling *Spodoptera littoralis, Plutella xylostella, Frankliniella occidentalis, Thrips tabaci, Euschistus heros, Cydia pomonella, Nilaparvata lugens, Myzus persicae, Chrysodeixis includens, Aphis craccivora, Diabrotica balteata, Rhopalosiphum Padia* and *Chilo Suppressalis* in cotton, vegetable, maize, cereal, rice and soya crops.

In an embodiment, one compound from Tables 1 to 35 and Table P1 to P8 is suitable for controlling *Mamestra* (preferably in vegetables), *Cydia pomonella* (preferably in apples), *Empoasca* (preferably in vegetables, vineyards), *Leptinotarsa* (preferably in potatos) and *Chilo supressalis* (preferably in rice).

Compounds according to the invention may possess any number of benefits including, inter alia, advantageous levels of biological activity for protecting plants against insects or superior properties for use as agrochemical active ingredients (for example, greater biological activity, an advantageous spectrum of activity, an increased safety profile (against non-target organisms above and below ground (such as fish, birds and bees), improved physico-chemical properties, or increased biodegradability). In particular, it has been surprisingly found that certain compounds of formula (I) may show an advantageous safety profile with respect to non-target arthropods, in particular pollinators such as honey bees, solitary bees and bumble bees. Most particularly, *Apis mellifera.*

The compounds according to the invention can be used as pesticidal agents in unmodified form, but they are generally formulated into compositions in various ways using formulation adjuvants, such as carriers, solvents and surface-active substances. The formulations can be in various physical forms, e.g. in the form of dusting powders, gels, wettable powders, water-dispersible granules, water-dispersible tablets, effervescent pellets, emulsifiable concentrates, microemulsifiable concentrates, oil-in-water emulsions, oil-flowables, aqueous dispersions, oily dispersions, suspo-emulsions, capsule suspensions, emulsifiable granules, soluble liquids, water-soluble concentrates (with water or a water-miscible organic solvent as carrier), impregnated polymer films or in other forms known e.g. from the Manual on Development and Use of FAO and WHO Specifications for Pesticides, United Nations, First Edition, Second Revision (2010). Such formulations can either be used directly or diluted prior to use. The dilutions can be made, for example, with water, liquid fertilisers, micronutrients, biological organisms, oil or solvents.

The formulations can be prepared e.g. by mixing the active ingredient with the formulation adjuvants in order to obtain compositions in the form of finely divided solids, granules, solutions, dispersions or emulsions. The active ingredients can also be formulated with other adjuvants, such as finely divided solids, mineral oils, oils of vegetable or animal origin, modified oils of vegetable or animal origin, organic solvents, water, surface-active substances or combinations thereof.

The active ingredients can also be contained in very fine microcapsules. Microcapsules contain the active ingredients in a porous carrier. This enables the active ingredients to be released into the environment in controlled amounts (e.g. slow-release). Microcapsules usually have a diameter of from 0.1 to 500 microns. They contain active ingredients in an amount of about from 25 to 95% by weight of the capsule weight. The active ingredients can be in the form of a monolithic solid, in the form of fine particles in solid or liquid dispersion or in the form of a suitable solution. The encapsulating membranes can comprise, for example, natural or synthetic rubbers, cellulose, styrene/butadiene copolymers, polyacrylonitrile, polyacrylate, polyesters, polyamides, polyureas, polyurethane or chemically modified polymers and starch xanthates or other polymers that are known to the person skilled in the art. Alternatively, very fine microcapsules can be formed in which the active ingredient is contained in the form of finely divided particles in a solid matrix of base substance, but the microcapsules are not themselves encapsulated.

The formulation adjuvants that are suitable for the preparation of the compositions according to the invention are known per se. As liquid carriers there may be used: water, toluene, xylene, petroleum ether, vegetable oils, acetone, methyl ethyl ketone, cyclohexanone, acid anhydrides, acetonitrile, acetophenone, amyl acetate, 2-butanone, butylene carbonate, chlorobenzene, cyclohexane, cyclohexanol, alkyl esters of acetic acid, diacetone alcohol, 1,2-dichloropropane, diethanolamine, p-diethylbenzene, diethylene glycol, diethylene glycol abietate, diethylene glycol butyl ether, diethylene glycol ethyl ether, diethylene glycol methyl ether, N,N-dimethylformamide, dimethyl sulfoxide, 1,4-dioxane, dipropylene glycol, dipropylene glycol methyl ether, dipropylene glycol dibenzoate, diproxitol, alkylpyrrolidone, ethyl acetate, 2-ethylhexanol, ethylene carbonate, 1,1,1-trichloroethane, 2-heptanone, alpha-pinene, d-limonene, ethyl lactate, ethylene glycol, ethylene glycol butyl ether, ethylene glycol methyl ether, gamma-butyrolactone, glycerol, glycerol acetate, glycerol diacetate, glycerol triacetate, hexadecane, hexylene glycol, isoamyl acetate, isobornyl acetate, isooctane, isophorone, isopropylbenzene, isopropyl myristate, lactic acid, laurylamine, mesityl oxide, methoxypropanol, methyl isoamyl ketone, methyl isobutyl ketone, methyl laurate, methyl *octanoate*, methyl oleate, methylene chloride, m-xylene, n-hexane, n-octylamine, octadecanoic acid, octylamine acetate, oleic acid, oleylamine, o-xylene, phenol, polyethylene glycol, propionic acid, propyl lactate, propylene carbonate, propylene glycol, propylene glycol methyl ether, p-xylene, toluene, triethyl phosphate, triethylene glycol, xylenesulfonic acid, paraffin, mineral oil, trichloroethylene, perchloroethylene, ethyl acetate, amyl acetate, butyl acetate, propylene glycol methyl ether, diethylene glycol methyl ether, methanol, ethanol, isopropanol and alcohols of higher molecular weight, such as amyl alcohol, tetrahydrofurfuryl alcohol, hexanol, octanol, ethylene glycol, propylene glycol, glycerol, N-methyl-2-pyrrolidone and the like.

Suitable solid carriers are, for example, talc, titanium dioxide, pyrophyllite clay, silica, attapulgite clay, kieselguhr, limestone, calcium carbonate, bentonite, calcium montmorillonite, cottonseed husks, wheat flour, soybean flour, pumice, wood flour, ground walnut shells, lignin and similar substances.

A large number of surface-active substances can advantageously be used in both solid and liquid formulations, especially in those formulations which can be diluted with a carrier prior to use. Surface-active substances may be anionic, cationic, non-ionic or polymeric and they can be used as emulsifiers, wetting agents or suspending agents or for other purposes. Typical surface-active substances include, for example, salts of alkyl sulfates, such as diethanolammonium lauryl sulfate; salts of alkylarylsulfonates, such as calcium dodecylbenzenesulfonate; alkylphenol/alkylene oxide addition products, such as nonylphenol ethoxylate; alcohol/alkylene oxide addition products, such as tridecylalcohol ethoxylate; soaps, such as sodium stearate; salts of alkylnaphthalenesulfonates, such as sodium dibutylnaphthalenesulfonate; dialkyl esters of sulfosuccinate salts, such as sodium di(2-ethylhexyl)sulfosuccinate; sorbitol esters, such as sorbitol oleate; quaternary amines, such as lauryltrimethylammonium chloride, polyethylene glycol esters of fatty acids, such as polyethylene glycol stearate; block copolymers of ethylene oxide and propylene oxide; and salts of mono- and di-alkylphosphate esters; and also further substances described e.g. in McCutcheon's Detergents and Emulsifiers Annual, MC Publishing Corp., Ridgewood New Jersey (1981).

Further adjuvants that can be used in pesticidal formulations include crystallisation inhibitors, viscosity modifiers, suspending agents, dyes, anti-oxidants, foaming agents, light absorbers, mixing auxiliaries, antifoams, complexing agents, neutralising or pH-modifying substances and buffers, corrosion inhibitors, fragrances, wetting agents, take-up enhancers, micronutrients, plasticisers, glidants, lubricants, dispersants, thickeners, antifreezes, microbicides, and liquid and solid fertilisers.

The compositions according to the invention can include an additive comprising an oil of vegetable or animal origin, a mineral oil, alkyl esters of such oils or mixtures of such oils and oil derivatives. The amount of oil additive in the composition according to the invention is generally from 0.01 to 10%, based on the mixture to be applied. For example, the oil additive can be added to a spray tank in the desired concentration after a spray mixture has been prepared. Preferred oil additives comprise mineral oils or an oil of vegetable origin, for example rapeseed oil, olive oil or sunflower oil, emulsified vegetable oil, alkyl esters of oils of vegetable origin, for example the methyl derivatives, or an oil of animal origin, such as fish oil or beef tallow. Preferred oil additives comprise alkyl esters of $C_8$-$C_{22}$ fatty acids, especially the methyl derivatives of $C_{12}$-$C_{18}$ fatty acids, for example the methyl esters of lauric acid, palmitic acid and oleic acid (methyl laurate, methyl palmitate and methyl oleate, respectively). Many oil derivatives are known from the Compendium of Herbicide Adjuvants, $10^{th}$ Edition, Southern Illinois University, 2010.

The inventive compositions generally comprise from 0.1 to 99% by weight, especially from 0.1 to 95% by weight, of compounds of the present invention and from 1 to 99.9% by weight of a formulation adjuvant which preferably includes from 0 to 25% by weight of a surface-active substance. Whereas commercial products may preferably be formulated as concentrates, the end user will normally employ dilute formulations.

The rates of application vary within wide limits and depend on the nature of the soil, the method of application, the crop plant, the pest to be controlled, the prevailing climatic conditions, and other factors governed by the method of application, such as the time of application and the target crop. As a general guideline compounds may be applied at a rate of from 1 to 2000 I/ha, especially from 10 to 1000 I/ha.

Preferred formulations can have the following compositions (weight %):

Emulsifiable Concentrates:
- active ingredient: 1 to 95%, preferably 60 to 90%
- surface-active agent: 1 to 30%, preferably 5 to 20%
- liquid carrier: 1 to 80%, preferably 1 to 35%

Dusts:
- active ingredient: 0.1 to 10%, preferably 0.1 to 5%
- solid carrier: 99.9 to 90%, preferably 99.9 to 99%

Suspension Concentrates:
- active ingredient: 5 to 75%, preferably 10 to 50%
- water: 94 to 24%, preferably 88 to 30%
- surface-active agent: 1 to 40%, preferably 2 to 30%

Wettable Powders:
- active ingredient: 0.5 to 90%, preferably 1 to 80%
- surface-active agent: 0.5 to 20%, preferably 1 to 15%
- solid carrier: 5 to 95%, preferably 15 to 90%

Granules:
- active ingredient: 0.1 to 30%, preferably 0.1 to 15%
- solid carrier: 99.5 to 70%, preferably 97 to 85%

The following Examples further illustrate, but do not limit, the invention.

| Wettable powders | a) | b) | c) |
|---|---|---|---|
| active ingredients | 25% | 50% | 75% |
| sodium lignosulfonate | 5% | 5% | — |
| sodium lauryl sulfate | 3% | — | 5% |
| sodium diisobutylnaphthalenesulfonate | — | 6% | 10% |

-continued

| Wettable powders | a) | b) | c) |
|---|---|---|---|
| phenol polyethylene glycol ether (7-8 mol of ethylene oxide) | — | 2% | — |
| highly dispersed silicic acid | 5% | 10% | 10% |
| Kaolin | 62% | 27% | — |

The combination is thoroughly mixed with the adjuvants and the mixture is thoroughly ground in a suitable mill, affording wettable powders that can be diluted with water to give suspensions of the desired concentration.

| Powders for dry seed treatment | a) | b) | c) |
|---|---|---|---|
| active ingredients | 25% | 50% | 75% |
| light mineral oil | 5% | 5% | 5% |
| highly dispersed silicic acid | 5% | 5% | — |
| Kaolin | 65% | 40% | — |
| Talcum | — | | 20% |

The combination is thoroughly mixed with the adjuvants and the mixture is thoroughly ground in a suitable mill, affording powders that can be used directly for seed treatment.

| Emulsifiable concentrate | |
|---|---|
| active ingredients | 10% |
| octylphenol polyethylene glycol ether (4-5 mol of ethylene oxide) | 3% |
| calcium dodecylbenzenesulfonate | 3% |
| castor oil polyglycol ether (35 mol of ethylene oxide) | 4% |
| Cyclohexanone | 30% |
| xylene mixture | 50% |

Emulsions of any required dilution, which can be used in plant protection, can be obtained from this concentrate by dilution with water.

| Dusts | a) | b) | c) |
|---|---|---|---|
| Active ingredients | 5% | 6% | 4% |
| Talcum | 95% | — | — |
| Kaolin | — | 94% | — |
| mineral filler | — | — | 96% |

Ready-for-use dusts are obtained by mixing the combination with the carrier and grinding the mixture in a suitable mill. Such powders can also be used for dry dressings for seed.

| Extruder granules | |
|---|---|
| Active ingredients | 15% |
| sodium lignosulfonate | 2% |
| carboxymethylcellulose | 1% |
| Kaolin | 82% |

The combination is mixed and ground with the adjuvants, and the mixture is moistened with water. The mixture is extruded and then dried in a stream of air.

| Coated granules | |
|---|---|
| Active ingredients | 8% |
| polyethylene glycol (mol. wt. 200) | 3% |
| Kaolin | 89% |

The finely ground combination is uniformly applied, in a mixer, to the kaolin moistened with polyethylene glycol. Non-dusty coated granules are obtained in this manner.

Suspension Concentrate

| | |
|---|---|
| active ingredients | 40% |
| propylene glycol | 10% |
| nonylphenol polyethylene glycol ether (15 mol of ethylene oxide) | 6% |
| Sodium lignosulfonate | 10% |
| carboxymethylcellulose | 1% |
| silicone oil (in the form of a 75% emulsion in water) | 1% |
| Water | 32% |

The finely ground combination is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

Flowable Concentrate for Seed Treatment

| | |
|---|---|
| active ingredients | 40% |
| propylene glycol | 5% |
| copolymer butanol PO/EO | 2% |
| Tristyrenephenole with 10-20 moles EO | 2% |
| 1,2-benzisothiazolin-3-one (in the form of a 20% solution in water) | 0.5% |
| monoazo-pigment calcium salt | 5% |
| Silicone oil (in the form of a 75% emulsion in water) | 0.2% |
| Water | 45.3% |

The finely ground combination is intimately mixed with adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

Slow Release Capsule Suspension 28 parts of the combination are mixed with 2 parts of an aromatic solvent and 7 parts of toluene diisocyanate/polymethylene-polyphenylisocyanate-mixture (8:1). This mixture is emulsified in a mixture of 1.2 parts of polyvinylalcohol, 0.05 parts of a defoamer and 51.6 parts of water until the desired particle size is achieved. To this emulsion a mixture of 2.8 parts 1,6-diaminohexane in 5.3 parts of water is added. The mixture is agitated until the polymerization reaction is completed. The obtained capsule suspension is stabilized by adding 0.25 parts of a thickener and 3 parts of a dispersing agent. The capsule suspension formulation contains 28% of the active ingredients. The medium capsule diameter is 8-15 microns. The resulting formulation is applied to seeds as an aqueous suspension in an apparatus suitable for that purpose.

Formulation types include an emulsion concentrate (EC), a suspension concentrate (SC), a suspo-emulsion (SE), a capsule suspension (CS), a water dispersible granule (WG), an emulsifiable granule (EG), an emulsion, water in oil (EO), an emulsion, oil in water (EW), a micro-emulsion (ME), an oil dispersion (OD), an oil miscible flowable (OF), an oil miscible liquid (OL), a soluble concentrate (SL), an ultra-low volume suspension (SU), an ultra-low volume liquid (UL), a technical concentrate (TK), a dispersible concentrate (DC), a wettable powder (WP), a soluble granule (SG) or any technically feasible formulation in combination with agriculturally acceptable adjuvants.

PREPARATORY EXAMPLES

Lcms Methods:

Method 1:

Spectra were recorded on a ZQ Mass Spectrometer from Waters (Single quadrupole mass spectrometer); Instrument Parameter: Ionisation method: Electrospray Polarity: positive (negative) ions; Capillary (kV) 3.00, Cone (V) 30.00, Extractor (V) 2.00, Gas Temperature (° C.) 350, Drying Gas Flow (mL/min) 9.8, Neb press 45 psig, Mass range: 90 to 1000 Da.

LC: HP 1100 HPLC from Agilent: solvent degasser, quaternary pump (ZCQ)/binary pump (ZDQ), heated column compartment and diode-array detector. Column: porpshell 120 $C_{18}$, 2.7 m particle size, 120 Angström, 4.6×50 mm; Temp: 30° C. DAD Wavelength range (nm): 190 to 400 Solvent Gradient: A=water+n 0.1% HCOOH. B=Acetonitrile+0.8% HCOOH

| Time (min) | A % | B % | Flow (ml/min) |
|---|---|---|---|
| 0.00 | 85.0 | 15.0 | 0.6 |
| 4.00 | 5.00 | 95.00 | 0.6 |
| 10.00 | 5.00 | 95.00 | 0.6 |

Method 2:

Spectra were recorded on a ACQUITY Mass Spectrometer from Waters Corporations (SQD or SQDII Single quadrupole mass spectrometer) equipped with an electrospray source (Polarity: positive or negative ions, Capillary: 3.0 kV, Cone: 30V, Extractor: 3.00 V, Source Temperature: 150° C., Desolvation Temperature: 400° C., Cone Gas Flow: 60 L/hr, Desolvation Gas Flow: 700 L/hr, Mass range: 140 to 800 Da) and an ACQUITY UPLC from Waters Corporations with solvent degasser, binary pump, heated column compartment and diode-array detector. Column: Waters UPLC HSS T3, 1.8 μm, 30×2.1 mm, Temp: 60° C., DAD Wavelength range (nm): 210 to 400, Solvent Gradient: A=Water/Methanol 9:1+0.1% formic acid, B=Acetonitrile+0.1% formic acid, gradient: 0-100% B in 2.5 min; Flow (ml/min) 0.75.

Method 3:

Spectra were recorded on a Mass Spectrometer from Waters (SQD, SQDII Single quadrupole mass spectrometer) equipped with an electrospray source (Polarity: positive and negative ions, Capillary: 3.00 kV, Cone range: 30 V, Extractor: 2.00 V, Source Temperature: 150° C., Desolvation Temperature: 350° C., Cone Gas Flow: 50 l/h, Desolvation Gas Flow: 650 l/h, Mass range: 100 to 900 Da) and an Acquity UPLC from Waters: Binary pump, heated column compartment, diode-array detector and ELSD detector. Column: Waters UPLC HSS T3, 1.8 m, 30×2.1 mm, Temp: 60° C., DAD Wavelength range (nm): 210 to 500, Solvent Gradient: A=water+5% MeOH+0.05% HCOOH, B=Acetonitrile+0.05% HCOOH, gradient: 10-100% B in 1.2 min; Flow (ml/min) 0.85.

The following abbreviations are used in the experimental description below: s=singlet, d=doublet, t=triplet, q=quartet, m=multiplet, RT=retention time, min=minutes.

Example P1: 5-[4-(5-methyl-1,2,4-oxadiazol-3-yl) Piperidine-1-carbonyl]-4-(trifluoromethyl)-2-[4-(trifluoromethyl)phenyl]benzonitrile (Compound P1.1)

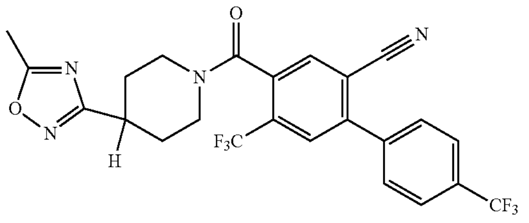 [SMILES: Cc1nc(C2CCN(C(=O)c3cc(C#N)c(-c4ccc(C(F)(F)F)cc4)cc3C(F)(F)F)CC2)no1]

Step 1: Methyl 4-hydroxy-5-iodo-2-(trifluoromethyl)benzoate

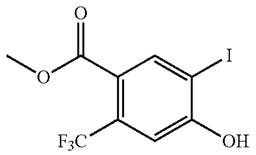

Methyl 4-hydroxy-2-(trifluoromethyl)benzoate (10.5 g, 47.7 mmol), iodine (18.0 g, 70.9 mmol) and potassium carbonate (13.2 g, 95.5 mmol) were added to THE (150 mL). The reaction mixture was heated under reflux for 16 hours. Then sodium thiosulfate solution was added. The mixture was extracted with ethyl acetate, and the organic phase was washed three times with brine. The solvent was evaporated and the residue was purified by chromatography (petroleum ether: ethyl acetate=5:1) to give a white solid (6.90 g, 41.8%). $^1$H-NMR [ppm] in DMSO-d6: 11.75 (s, 1H), 8.23 (s, 1H), 7.23 (s, 1H), 3.81 (s, 3H). LC-MS (method 1): RT=4.34 min; $[M-H]^-$=344.9.

Step 2: Methyl 5-cyano-4-hydroxy-2-(trifluoromethyl)benzoate

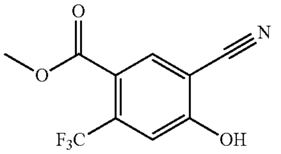 [SMILES: COC(=O)c1cc(C#N)c(O)cc1C(F)(F)F]

Methyl 4-hydroxy-5-iodo-2-methyl-benzoate (2.50 g, 8.56 mmol) and copper (I) cyanide (1.94 g, 21.7 mmol) were stirred in 1-methylpyrrolidin-2-one (20 mL) at 110° C. for 12 hours. The mixture was poured into water and extracted with ethyl acetate (50 mL), dried over $Na_2SO_4$, filtered and concentrated under vacuum. The crude product was purified by column chromatography on silica gel (ethyl acetate/petroleum ether=1/5) to give a white solid (1.30 g, 73.4%). $^1$H-NMR [ppm] in DMSO-d6: 12.75 (bs, 1H), 8.23 (s, 1H), 7.40 (s, 1H), 3.83 (s, 3H). LC-MS (method 1): RT=3.88 min; [M-H]-=244.

Step 3: Methyl 5-cyano-2-(trifluoromethyl)-4-(trifluoromethylsulfonyloxy)benzoate

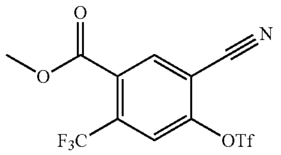 [SMILES: COC(=O)c1cc(C#N)c(OS(=O)(=O)C(F)(F)F)cc1C(F)(F)F]

Into the reaction vessel was added methyl 5-cyano-4-hydroxy-2-(trifluoromethyl)benzoate (1.00 g, 4.08 mmol), dichloromethane (20 mL), and pyridine (0.968 g, 12.2 mmol), The reaction mixture was cooled to 0° C. and triflic anhydride (2.88 g, 10.2 mmol). The reaction mixture was allowed to warm to room temperature, stirred at room temperature for 30 minutes, cooled to 0° C. Dichloromethane (30 mL) and water (50 mL) were added. The organic phase was collected, dried over $Na_2SO_4$, concentrated under reduced pressure, and subjected to silica gel chromatography purification (ethyl acetate/petroleum ether=1:10) to give colorless oil (1.38 g, 90.0%). $^1$H-NMR [ppm] in DMSO-d6: 8.70 (s, 1H), 8.46 (s, 1H), 3.92 (s, 3H).

Step 4: Methyl 5-cyano-2-(trifluoromethyl)-4-[4-(trifluoromethyl)phenyl]benzoate

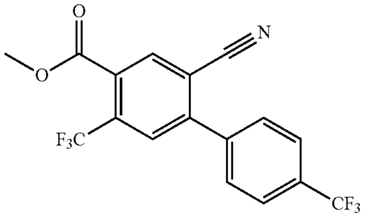 [SMILES: COC(=O)c1cc(C#N)c(-c2ccc(C(F)(F)F)cc2)cc1C(F)(F)F]

A mixture of methyl 5-cyano-2-(trifluoromethyl)-4-(trifluoromethylsulfonyloxy)benzoate (1.75 g, 4.64 mmol), [4-(trifluoromethyl)phenyl]boronic acid (1.76 g, 9.28 mmol), tetrakis(triphenylphosphine)-palladium(0) (0.536 g, 0.464 mmol), potassium carbonate (1.6 g, 11.6 mmol) in 1,4-dioxane (30.0 mL) was stirred at 110° C. under nitrogen atmosphere for 16 hours. The reaction mixture was poured into water and extracted with ethyl acetate three times. The combined organic layers were dried over Na2$SO_4$, filtered and concentrated under vacuum. The crude product was purified by column chromatography on silica gel to give a white solid (1.50 g, 86.6%). $^1$H-NMR [ppm] in DMSO-d6: 8.53 (s, 1H), 8.17 (s, 1H), 7.90-8.10 (m, 4H), 3.93 (s, 3H).

Step 5: 5-Cyano-2-(trifluoromethyl)-4-[4-(trifluoromethyl)phenyl]benzoate

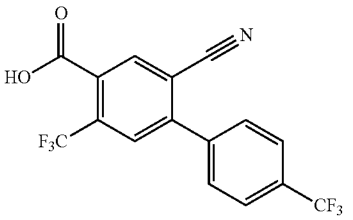 [SMILES: N#Cc1cc(C(=O)O)c(C(F)(F)F)cc1-c1ccc(C(F)(F)F)cc1]

Sodium hydroxide (0.643 g, 16.1 mmol) in water (5 mL) was added dropwise to a solution of methyl 5-cyano-2-(trifluoromethyl)-4-[4-(trifluoromethyl)phenyl]benzoate (2.00 g, 5.36 mmol) in methanol (10 mL) and water (5 mL). Tetrahydrofuran (10 mL) was added after 5 minutes. The mixture was stirred at room temperature for 2 hours. The reaction mixture was poured into aqueous hydrochloric acid and extracted with ethyl acetate (50 mL), dried over $Na_2SO_4$, filtered and concentrated under vacuum to give white solid (1.40 g, 72.7%). $^1$H-NMR [ppm] in DMSO-d6: 8.46 (s, 1H), 8.11 (s, 1H), 7.90-8.10 (m, 4H). This material was used for next step.

Step 6: 5-[4-(5-Methyl-1,2,4-oxadiazol-3-yl)piperidine-1-carbonyl]-4-(trifluoromethyl)-2-[4-(trifluoromethyl)phenyl]benzonitrile (Compound P1.1)

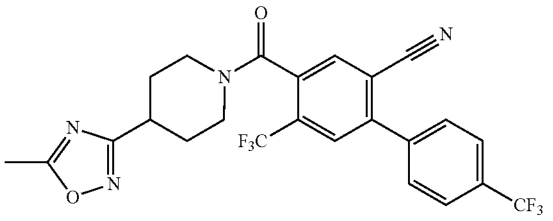 [SMILES: Cc1nc(C2CCN(C(=O)c3cc(C#N)c(-c4ccc(C(F)(F)F)cc4)cc3C(F)(F)F)CC2)no1]

To a solution of 5-cyano-2-(trifluoromethyl)-4-[4-(trifluoromethyl)phenyl]benzoic acid (200 mg, 0.557 mmol) in dichloromethane (10.0 mL) was added the hydrochloride salt of 5-methyl-3-(4-piperidyl)-1,2,4-oxadiazole (126 mg, 0.618 mmol, 1.11 eq) which was synthesized as described in Nippon Soda patent application WO 2017195703. Subsequently HATU (234 mg, 0.615 mmol, 1.11 eq) and diisopropyl-ethyl-amine (216 mg, 1.68 mmol, 3.01 eq) were added. The reaction mixture was stirred at room temperature for 21 hours and then poured into an aqueous $NaHCO_3$ solution. The mixture was extracted three times with ethyl acetate. The water layer was acidified with 2N hydrochloric acid and extracted three times with ethyl acetate. The combined organic layers were washed with brine, dried over $Na_2SO_4$, filtered and concentrated under reduced pressure. The residue was purified via chromatography (ethyl acetate/petroleum ether=1:2) to give 205 mg (yield: 72%) of 5-[4-(5-methyl-1,2,4-oxadiazol-3-yl)piperidine-1-carbonyl]-4-(trifluoromethyl)-2-[4-(trifluoromethyl)phenyl]benzonitrile as a white solid. $^1$H-NMR [ppm] in $CDCl_3$: 7.85 (d, 2H), 7.82-7.74 (m, 2H), 7.70 (d, 2H), 4.64 (s, 1H), 3.49 (d, 1H), 3.31-3.02 (m, 3H), 2.59 (d, 3H), 2.19 (d, 1H), 2.06-1.79 (m, 3H). 7.74-7.88 (m, 4H), 7.70 (d, 2H), 4.60 (t, 1H), 3.50 (t, 1H), 3.02-3.40 (m, 3H), 2.57 (d, 3H), 2.10-2.25 (m, 1H), 1.79-2.06 (m, 3H). LC-MS (method 1): RT=4.80 min; $[M+H]^+$=509.

Example P2: 5-[4-(3,5-Dichloro-2-pyridyl)piperazine-1-carbonyl]-4-(trifluoromethyl)-2-[4-(trifluoromethyl)phenyl]benzonitrile (Compound P2.1)

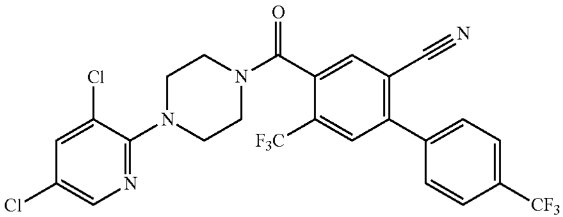 [SMILES: N#Cc1cc(C(=O)N2CCN(c3ncc(Cl)cc3Cl)CC2)c(C(F)(F)F)cc1-c1ccc(C(F)(F)F)cc1]

To a solution of 5-cyano-2-(trifluoromethyl)-4-[4-(trifluoromethyl)phenyl]benzoic acid (158 mg, 0.44 mmol) in DMF (5 mL) was added 4-(3,5-dichloro-2-pyridyl)piperazine (108 mg, 0.463 mmol), HATU (201 mg, 0.528 mmol) and diisopropylethylamine (227 mg, 1.76 mmol). The reaction mixture was stirred at room temperature for 16 hours. Then the mixture was poured into water and extracted with ethyl acetate three times. The combined organic layer were washed two times with water and once with brine, dried over $Na_2SO_4$ and the solvent was removed. The crude product was purified by chromatography on silica gel (ethyl acetate/petroleum ether=1:1) to give the product (187 mg, 74%) as a white solid. $^1$H-NMR [ppm] in $CDCl_3$: 8.16 (s, 1H), 7.88 (s, 1H), 7.76-7.85 (m, 3H), 7.71 (d, 2H), 7.70 (s, 1H), 3.85-4.10 (m, 2H), 3.25-3.53 (m, 6H). LC-MS (method 1): RT=5.51 min; $[M+H]^+$=574.

Example P3: 5-[4-(3,5-Dichloro-2-pyridyl)piperazine-1-carbonyl]-4-(trifluoromethyl)-2-[4-(trifluoromethyl)phenyl]benzenecarbothioamide (Compound P8.1)

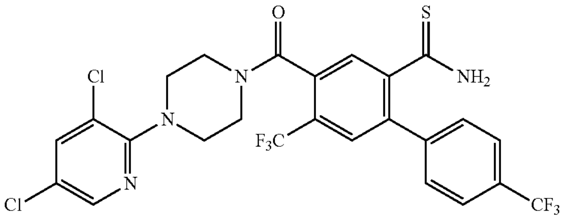 [SMILES: NC(=S)c1cc(C(=O)N2CCN(c3ncc(Cl)cc3Cl)CC2)c(C(F)(F)F)cc1-c1ccc(C(F)(F)F)cc1]

To a solution of 5-[4-(3,5-dichloro-2-pyridyl)piperazine-1-carbonyl]-4-(trifluoromethyl)-2-[4-(trifluoromethyl)phenyl]benzonitrile (0.134 g, 0.234 mmol) in DMF (2.3 mL) was added magnesium dichloride (0.062 g, 0.304 mmol, 1.3 eq). The mixture was stirred for 1 hour at room temperature. Then sodium hydrosulfide (0.05 g, 0.888 mmol, 3.8 eq) was added and stirring was continued for 1 hour at room temperature. The reaction mixture was treated with saturated aqueous $NHCl_4$ solution and then extracted three times with ethyl acetate. The organic phase was dried over Na2$SO_4$ and the solvent was removes solvent under reduced pressure. The residue was purified by chromatography to give the desired product (130 mg, 91%) as a white foam. $^1$H-NMR [ppm] in $CDCl_3$: 8.18 (s, 1H), 7.62-7.80 (m, 7H), 7.01 (bs, 1H), 6.97 (bs, 1H), 3.85-4.10 (m, 2H), 3.25-3.60 (m, 6H). LC-MS (method 2): RT=1.25 min; $[M+H]^+$=607.

Example P4: 5-[4-(3,5-Dichloro-2-pyridyl)piperazine-1-carbonyl]-4-ethoxy-2-[4-(trifluoromethyl)-phenyl]-benzonitrile (Compound P2.5)

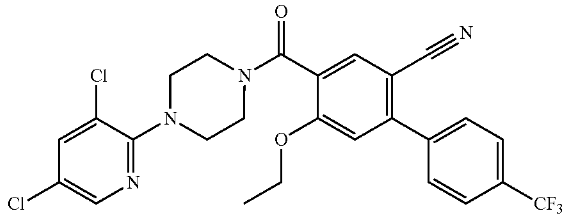 [SMILES: CCOc1cc(-c2ccc(C(F)(F)F)cc2)c(C#N)cc1C(=O)N1CCN(c2ncc(Cl)cc2Cl)CC1]

Step 1: Ethyl 4-amino-5-cyano-2-hydroxy-benzoate

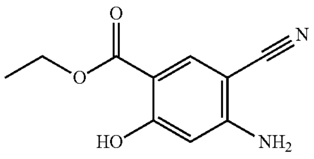

To a solution of sodium ethoxide (1.1 eq.) in ethanol (20% w/w) was added slowly propanedinitrile (1.32 g, 20 mmol, 1 eq) at 4° C. and the mixture was stirred for 15 minutes. Then a solution ethyl (2E)-2-(ethoxymethylene)-3-oxo-butanoate (3.72 g, 20 mmol) in ethanol (50 mL) was added under ice cooling. The reaction mixture was heated to reflux for 1 hour. After cooling the reaction mixture was diluted with ethyl acetate and water. The phases were separated and the aqueous phase was extracted three times with ethyl acetate. The combined organic layer was washed two times with water and once with brine, dried over $Na_2SO_4$ and the solvent was removed. 2.45 g (59% yield) of ethyl 4-amino-5-cyano-2-hydroxy-benzoate were obtained as a white solid. $^1$H NMR [ppm] in DMSO: 10.98 (s, 1H), 7.89 (s, 1H), 6.79 (s, 2H), 6.20 (s, 1H), 4.28 (q, 2H), 1.30 (t, 3H). LC-MS (method 1): RT=3.98 min; $[M+H]^+$=207.

Step 2: Ethyl 5-cyano-2-hydroxy-4-iodo-benzoate

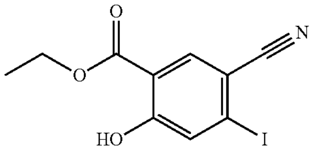

To a solution of boron trifluoride diethyl etherate (568 mg, 4 mmol) in THE (5 mL) was added a solution of ethyl 4-amino-5-cyano-2-hydroxy-benzoate (412 mg, 4 mmol) in THE (5 mL) at 0° C. Then the mixture was cooled to −10° C., tert-butyl nitrite (268 mg, 2.6 mmol) was added and the reaction mixture was stirred at −10° C. for 0.5 hours. Then sodium iodide (390 mg, 2.6 mmol) in acetone (10 mL) was added and the mixture was stirred at room temperature for 1.5 hours. The reaction mixture was diluted with ethyl acetate and water. The phases were separated, and the aqueous phase was extracted three times with ethyl acetate. The combined organic layer was washed two times with water and once with brine, dried over $Na_2SO_4$ and the solvent was removed. The crude product was purified by chromatography on silica gel (ethyl acetate/petroleum ether=1:2) to afford the product (599 mg, 94.5%) as a white solid. $^1$H NMR [ppm] in DMSO-d6: 11.36 (s, 1H), 8.07 (s, 1H), 7.63 (s, 1H), 4.32 (q, 2H), 1.32 (t, 3H). LC-MS (method 1): RT=4.76 min; $[M+H]^+$=318.

Step 3: Ethyl 5-cyano-2-ethoxy-4-iodo-benzoate

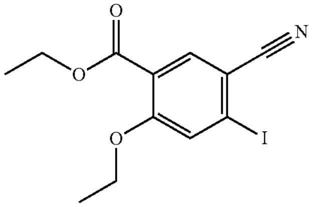 [SMILES: CCOC(=O)c1cc(C#N)c(I)cc1OCC]

To a solution of ethyl 5-cyano-2-hydroxy-4-iodo-benzoate (1.17 g, 3.7 mmol) in acetone (50 mL) was added iodoethane (867 mg, 5.56 mmol) and potassium carbonate (767 mg, 5.56 mmol). The mixture was stirred and heated to reflux for 5 hours. After cooling, the reaction mixture was diluted with ethyl acetate and water. The phases were separated and the aqueous phase was extracted three times with ethyl acetate. The combined organic layer was washed two times with water and once with brine, dried over $Na_2SO_4$ and the solvent was removed. The crude product was purified by chromatography on silica gel (ethyl acetate/petroleum ether=1:5) to afford the product (372 mg, 29%) as a white solid. $^1$H NMR [ppm] in $CDCl_3$: 7.99 (s, 1H), 7.45 (s, 1H), 4.35 (q, 2H), 4.16 (q, 2H), 1.49 (t, 3H), 1.38 (t, 3H). LC-MS (method 1): RT=4.683 min; $[M+H]^+$=346.

Step 4: Ethyl 5-cyano-2-ethoxy-6-[4-(trifluoromethyl)phenyl]pyridine-3-carboxylate

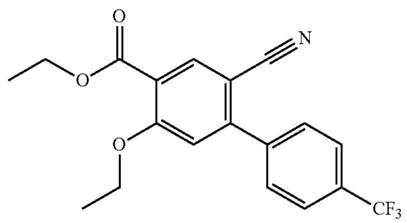 [SMILES: CCOC(=O)c1cc(C#N)c(-c2ccc(C(F)(F)F)cc2)cc1OCC]

A mixture of ethyl 5-cyano-2-ethoxy-6-iodo-pyridine-3-carboxylate (370 mg, 1.07 mmol), 1-[4-(trifluoromethyl) phenyl]boronic acid (408 mg, 2.14 mmol), $Pd(PPh_3)_4$ (247 mg, 0.21 mmol) and potassium carbonate (443 mg, 3.21 mmol) in 1,4-dioxane (20.0 mL) was stirred under nitrogen at 90° C. for 16 hours. Then the mixture was poured into water and extracted with ethyl acetate three times. The combined organic layer was washed two times with water and once with brine, dried over $Na_2SO_4$ and the solvent was removed. The crude product was purified by chromatography on silica gel (ethyl acetate/petroleum ether=1:5) to give the product (380 mg, 97.5%) as a white solid. $^1$H NMR [ppm] in $CDCl_3$: 8.22 (s, 1H), 7.77 (d, 2H), 7.68 (d, 2H), 7.01 (s, 1H), 4.40 (q, 2H), 4.22 (q, 2H), 1.52 (t, 3H), 1.41 (t, 3H). LC-MS (method 1): RT=3.615 min; $[M+H]^+$=364.

Step 5: 5-Cyano-2-ethoxy-4-[4-(trifluoromethyl) phenyl]benzoic Acid

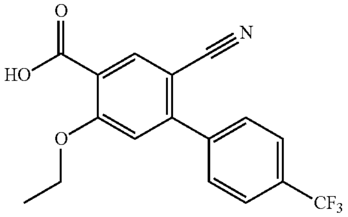 [SMILES: CCOc1cc(-c2ccc(C(F)(F)F)cc2)c(C#N)cc1C(=O)O]

Ethyl 5-cyano-2-ethoxy-4-[4-(trifluoromethyl)phenyl] benzoate (1.3 g, 3.58 mmol) was dissolved in tetrahydrofuran (10 mL) and potassium hydroxide (429 mg, 10.7 mmol, 3.0 eq.) dissolved in water (2 mL) was added. The reaction mixture was stirred at room temperature for 16 hours. Then the reaction mixture was diluted with ethyl acetate and 2 N hydrochloric acid. The mixture was extracted three times with ethyl acetate. The combined organic layer was washed two times with water and once with brine, dried over $Na_2SO_4$ and the solvent was removed to give the crude product (1.2 g, 100%) as a white solid witch was used directly for the next step.

Step 6: 5-[4-(3,5-Dichloro-2-pyridyl)piperazine-1-carbonyl]-4-ethoxy-2-[4-(trifluoromethyl)-phenyl]-benzonitrile (Compound P2.5)

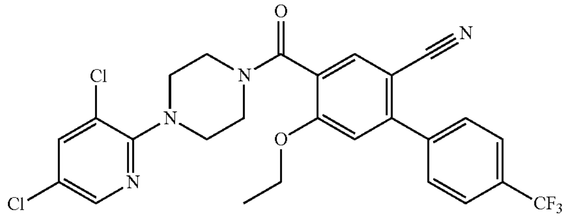 [SMILES: CCOc1cc(-c2ccc(C(F)(F)F)cc2)c(C#N)cc1C(=O)N1CCN(c2ncc(Cl)cc2Cl)CC1]

To a solution of 5-cyano-2-ethoxy-4-[4-(trifluoromethyl) phenyl]benzoic acid (121 mg, 0.36 mmol) in DMF (5 mL) was added 1-(3,5-dichloro-2-pyridyl)piperazine (99 mg, 0.43 mmol), HATU (163 mg, 0.43 mmol) and diisopropylethylamine (139 mg, 1.08 mmol). The reaction mixture was stirred at room temperature for 16 hours. Then the mixture was poured into water and extracted with ethyl acetate three times. The combined organic layer was washed two times with water and once with brine, dried over $Na_2SO_4$ and the solvent was removed. The crude product was purified by chromatography on silica gel (ethyl acetate/petroleum ether=1/1) to give the product (140 mg, 71%) as a white solid. $^1$H NMR [ppm] in $CDCl_3$: 8.16 (d, 1H), 7.74 (d, 2H), 7.71 (s, 1H), 7.64-7.68 (m, 3H), 6.97 (s, 1H), 4.15-4.25 (m, 2H), 3.80-4.20 (m, 2H), 1.48 (t, 3H). LC-MS (method 1): RT=5.627 min; $[M+H]^+$=550.

Example P5: 4-Ethoxy-5-[4-(ethylsulfanylmethyl) piperidine-1-carbonyl]-2-[4-(trifluoromethyl)phenyl]-benzonitrile (Compound P1.46)

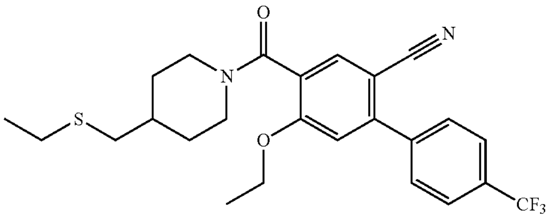 [SMILES: CCOc1cc(-c2ccc(C(F)(F)F)cc2)c(C#N)cc1C(=O)N1CCC(CSCC)CC1]

To a solution of 5-cyano-2-ethoxy-4-[4-(trifluoromethyl) phenyl]benzoic acid (140 mg, 0.42 mmol) in DMF (5 mL) was added 4-(ethylsulfanylmethyl)piperidine hydrochloride (117 mg, 0.598 mmol), HATU (190 mg, 0.5 mmol) and diisopropylethylamine (163 mg, 1.62 mmol). The reaction mixture was stirred at room temperature for 16 hours. Then the mixture was poured into water and extracted with ethyl acetate three times. The combined organic layer was washed two times with water and once with brine, dried over $Na_2SO_4$ and the solvent was removed. The crude product was purified by chromatography on silica gel (ethyl acetate/petroleum ether=1:1) to give the product (127 mg, 64%) as a white solid. $^1$H NMR [ppm] in $CDCl_3$: 7.76 (d, 2H), 7.60-7.70 (m, 3H), 6.94 (d, 1H), 4.78 (t, 1H), 4.09-4.25 (m, 2H), 3.49 (d, 1H), 2.90-3.10 (m, 1H), 2.79 (q, 1H), 2.42-2.59 (m, 4H), 1.90-2.05 (m, 1H), 1.69-1.85 (m, 2H), 1.40-1.51 (m, 3H), 1.20-1.30 (m, 5H). LC-MS (method 1): RT=5.32 min; $[M+H]^+$=477.

Example P6: 4-Ethoxy-5-[4-(ethylsulfanylmethyl) piperidine-1-carbonyl]-2-[4-(trifluoromethyl)phenyl]-benzonitrile (Compound P3.7)

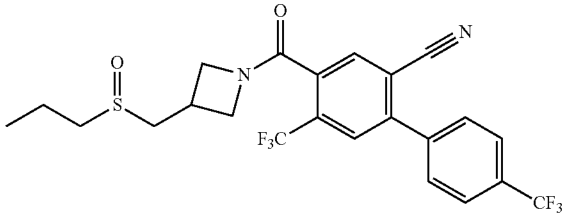 [SMILES: CCCS(=O)CC1CN(C(=O)c2cc(C#N)c(-c3ccc(C(F)(F)F)cc3)cc2C(F)(F)F)C1]

Step 1: tert-Butyl 3-(acetylsulfanylmethyl)azetidine-1-carboxylate

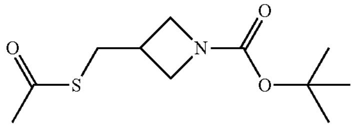 [SMILES: CC(=O)SCC1CN(C(=O)OC(C)(C)C)C1]

Acetyl sulfanyl sodium (85.0%, 0.462 g, 4.00 mmol) was added to the tert-butyl 3-(bromomethyl)-azetidine-1-carboxylate (0.500 g, 2.00 mmol) in acetone (10.0 mL) at room temperature and the mixture was stirred at room temperature for 16 hours. Then the mixture was poured into dilute hydrochloric acid and extracted with ethyl acetate three times. The combined organic layers were dried over $Na_2SO_4$, filtered and concentrated under vacuum. The crude product was purified by column chromatography on silica gel (petroleum ether/ethyl acetate=20:1) to afford 315 mg (yield: 64%) tert-butyl 3-(acetylsulfanylmethyl)-azetidine-1-carboxylate. $^1H$ NMR [ppm] in $CDCl_3$: 3.98 (t, 2H), 3.56 (dd, 2H), 3.09 (d, 2H), 2.62-2.78 (m, 1H), 2.34 (s, 3H), 1.42 (d, 9H). LC-MS (method 1): RT=4.25 min; $[M+Na]^+$=268.

Step 2: tert-Butyl 3-(sulfanylmethyl)azetidine-1-carboxylate

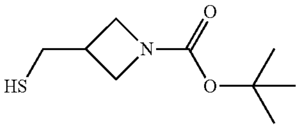

Sodium borohydride (0.308 g, 8.15 mmol) was added to tert-butyl 3-(acetylsulfanylmethyl)azetidine-1-carboxylate (1.00 g, 4.08 mmol) in methanol (10.0 mL) and stirred for 16 hours at room temperature. Then the mixture was poured into dilute hydrochloric acid and extracted with ethyl acetate three times. The combined organic layers were dried over $Na_2SO_4$, filtered and concentrated under vacuum. The crude product was purified by column chromatography on silica gel (petroleum ether/ethyl acetate=20:1) to afford 528 mg (yield: 64%) tert-butyl 3-(sulfanylmethyl)azetidine-1-carboxylate. $^1H$ NMR [ppm] in $CDCl_3$: 4.02 (t, 2H), 3.60 (dd, 2H), 2.73 (t, 2H), 2.61-2.65 (m, 1H), 1.43 (s, 9H), 1.30 (t, 1H). LC-MS (method 1): RT=4.11 min; $[M+Na]^+$=226.

Step 3: tert-Butyl 3-(propylsulfanylmethyl)azetidine-1-carboxylate

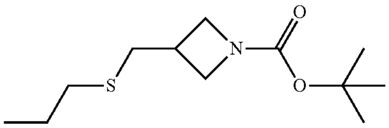 [SMILES: CCCSCC1CN(C(=O)OC(C)(C)C)C1]

1-Iodopropane (0.627 g, 3.69 mmol) was added to tert-butyl 3-(sulfanylmethyl)azetidine-1-carboxylate (500 mg, 2.46 mmol) and $K_2CO_3$ (1.02 g, 7.38 mmol) in acetone (10.0 mL) and the reaction mixture was stirred for 16 hours at room temperature. Then the mixture was poured into dilute hydrochloric acid and extracted with ethyl acetate three times. The combined organic layers were dried over $Na_2SO_4$, filtered and concentrated under vacuum. The crude product was purified by column chromatography on silica gel (petroleum ether/ethyl acetate=20:1) to afford 331 mg (yield: 52%) of tert-butyl 3-(propylsulfanylmethyl)azetidine-1-carboxylate. $^1H$ NMR [ppm] in $CDCl_3$: 4.02 (t, 2H), 3.60 (dd, 2H), 2.60-2.75 (m, 3H), 2.47 (t, 2H), 1.54-1.63 (m, 2H), 1.43 (s, 9H), 0.98 (t, 3H).

Step 4: Trifluoroacetic acid salt of 3-(propylsulfanylmethyl)azetidine

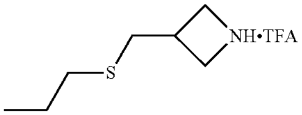

tert-Butyl 3-(propylsulfanylmethyl)azetidine-1-carboxylate (500 mg, 2.04 mmol) and 2,2,2-trifluoroacetic acid (0.929 g, 8.15 mmol) in dichloromethane (15.0 mL) was stirred at room temperature for 16 hours. The reaction mixture was concentrated under vacuum and used for the next step. $^1H$ NMR [ppm] in DMSO-d6: 4.17 (s, 2H), 3.90 (s, 2H), 3.13 (t, 1H), 2.78 (d, 2H), 2.48 (t, 2H), 1.64-1.52 (m, 2H), 0.98 (t, 3H).

Step 5: 5-[3-(propylsulfanylmethyl)azetidine-1-carbonyl]-4-(trifluoromethyl)-2-[4-(trifluoromethyl)-phenyl]benzonitrile

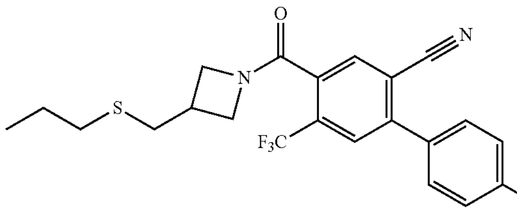

To a solution of 5-cyano-2-(trifluoromethyl)-4-[4-(trifluoromethyl)phenyl]benzoic acid (150 mg, 0.418 mmol) in DMF (5 mL) was added the trifluoroacetic acid salt of 3-(propylsulfanylmethyl)azetidine (162 mg, 0.626 mmol, 1.5 eq). Subsequently HATU (238 mg, 0.626 mmol, 1.5 eq.) and diisopropylethylamine (162 mg, 1.25 mmol, 3.00 eq.) were added. The reaction mixture was stirred at room temperature for 16 hours and then poured into an aqueous $NaHCO_3$ solution. The mixture was extracted three times with ethyl acetate. The water layer was acidified with 2N hydrochloric acid and extracted three times with ethyl acetate. The combined organic layers were washed with brine, dried over $Na_2SO_4$, filtered and concentrated under reduced pressure. The residue was purified via chromatography (petroleum ether/ethyl acetate=1:1) to afford 121 mg (yield: 60%) of 5-[3-(propylsulfanylmethyl)azetidine-1-carbonyl]-4-(trifluoromethyl)-2-[4-(trifluoromethyl)phenyl]-benzonitrile were obtained as a colorless gum. $^1H$-NMR [ppm] in $CDCl_3$): 7.85 (s, 1H), 7.77-7.83 (m, 3H), 7.69 (d, 2H), 4.33 (t, 1H), 4.05 (t, 1H), 3.92 (dd, 1H), 3.66 (dd, 1H), 2.65-2.99 (m, 3H), 2.40-2.60 (m, 2H), 1.55-1-70 (m, 2H), 0.98 (t, 3H). LC-MS (method 1): RT=5.38 min; $[M+H]^+$=487.

Step 6: 5-[3-(Propylsulfinylmethyl)azetidine-1-carbonyl]-4-(trifluoromethyl)-2-[4-(trifluoromethyl) phenyl]-benzonitrile (Compound P3.7)

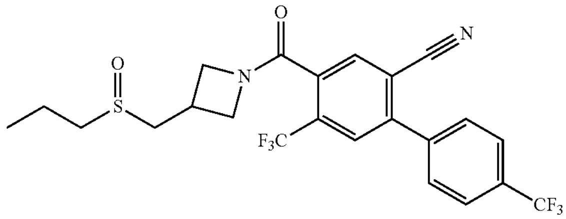 [SMILES: CCCS(=O)CC1CN(C(=O)c2cc(C#N)c(-c3ccc(C(F)(F)F)cc3)cc2C(F)(F)F)C1]

3-Chloro-perbenzoic acid (0.034 g, 0.197 mmol, 0.8 eq) was added to 5-[3-(propylsulfanylmethyl)-azetidine-1-carbonyl]-4-(trifluoromethyl)-2-[4-(trifluoromethyl)phenyl] benzonitrile (120 mg, 0.247 mmol) in dichloromethane (20 mL) and stirred for 2 hours at room temperature. Then the mixture was poured into a saturated solution of $NaHCO_3$ and $Na_2SO_3$ in water and extracted with ethyl acetate three times. The combined organic layers were dried over $Na_2SO_4$, filtered and concentrated under vacuum. The crude product was purified by column chromatography on silica gel (ethyl acetate/petroleum ether=1:2) to give 41 mg (yield: 33%) of 5-[3-(propylsulfinylmethyl)azetidine-1-carbonyl]-4-(trifluoromethyl)-2-[4-(trifluoromethyl)phenyl]benzonitrile as a colorless gum. $^1$H-NMR [ppm] in DMSO-d6): 8.32 (s, 1H), 8.09 (s, 1H), 7.88-7.96 (m, 4H), 4.24 (t, 1H), 4.05-4.15 (m, 1H), 3.68-3.97 (m, 1H), 3.82 (dd, 1H), 2.96-3.20 (m, 3H), 2.60-2.75 (m, 2H), 1.53-1.71 (m, 2H), 0.98 (t, 3H). LC-MS (method 1): RT=4.36 min; $[M+H]^+$=503.

Example P7: 4-Methyl-5-[4-(5-methyl-1,2,4-oxadiazol-3-yl)piperazine-1-carbonyl]-2-[4-(trifluoromethyl)phenyl]benzene-1,3-dicarbonitrile (Compound P6.1)

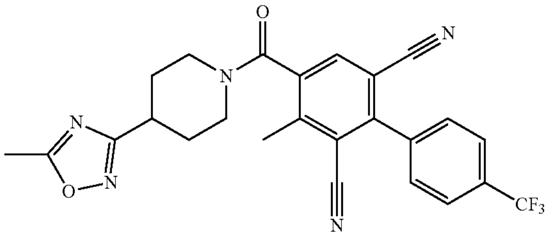

Step 1: Ethyl 4-amino-3,5-dicyano-2-methyl-benzoate

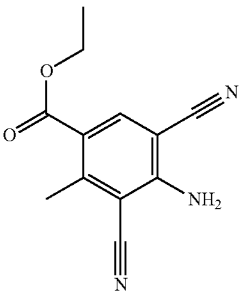 [SMILES: CCOC(=O)c1cc(C#N)c(N)c(C#N)c1C]

A solution of ethyl acetoacetate (1.3 mL, 0.01 mmol) in methanol was cooled to 0° C., then treated with aqueous formaldehyde (1 mL). The reaction mixture was stirred for 3 hours and then a solution of malononitrile (1.2 g, 0.2 mmol) in methanol (30 mL) was added gradually with stirring over a period of 1 hour after which time a morpholine solution (0.8 mL, 0.1 mmol) in methanol (20 mL) was added to the mixture. This mixture was cooled with ice for 3 hours, then allowed to stand at room temperature for 48 hours. The solid was filtered off and washed with a small amount of methanol to give the target compound (1.8 g, 78%). $^1$H-NMR [ppm] in $CDCl_3$: 8.02 (s, 1H), 7.17 (s, 2H), 4.26 (q, 2H), 2.65 (s, 3H), 1.35 (t, 3H). MS (ESI) $[M+H]^+$=230.0.

Step 2: Ethyl 3,5-dicyano-4-iodo-2-methyl-benzoate

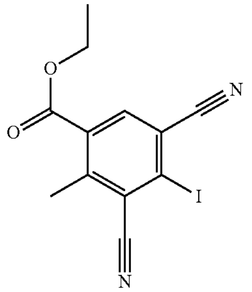 [SMILES: CCOC(=O)c1cc(C#N)c(I)c(C#N)c1C]

Ethyl 4-amino-3,5-dicyano-2-methyl-benzoate (1.90 g, 8.3 mmol) was suspended in $H_2SO_4$ (40 mL, 50%), cooled to −5° C. and stirred for 1 hour. A solution of sodium nitrite (0.86 g, 12.5 mmol) in water (5 mL) was added slowly, and the mixture stirred for 30 minutes at 0° C. The yellow slurry was then slowly added to an ice-cooled solution of potassium iodide (13.8 g, 83 mmol) in water (230 mL). The ice bath was then removed, and the foamy suspension was stirred for 2 hours at room temperature. Dichloromethane (100 mL) was added, followed by a saturated $Na_2S_2O_3$ solution. The organic layer was separated, and the aqueous layer was extracted with dichloromethane. The combined dichloromethane layer was dried over $Na_2SO_4$, the solvent was evaporated to yield ethyl 3,5-dicyano-4-iodo-2-methylbenzoate. (0.8 g, 28%). $^1$H-NMR [ppm] in $CDCl_3$: 8.27 (s, 1H), 4.20 (q, 2H), 2.50 (s, 3H), 1.42 (t, 3H). MS (ESI) $[M+H]^+$=341.1.

Step 3: Ethyl 3,5-dicyano-2-methyl-4-[4-(trifluoromethyl)phenyl]benzoate

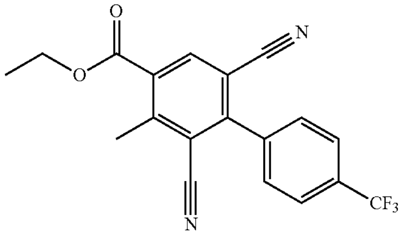 [SMILES: CCOC(=O)c1cc(C#N)c(-c2ccc(C(F)(F)F)cc2)c(C#N)c1C]

The mixture of ethyl 3,5-dicyano-4-iodo-2-methyl-benzoate (0.74 g, 2.18 mmol), [4-(trifluoromethyl)phenyl]boronic acid (0.62 g, 3.26 mmol), sodium carbonate (0.46 g, 4.33 mmol) and tetrakis(triphenylphosphine)palladium(0) (0.25 g, 0.218 mmol) in toluene (20 mL)/water (6 mL) was stirred at 80° C. overnight. The reaction mixture was cooled to room temperature and extracted with ethyl acetate. The organic layer was separated, washed with brine (20 mL), dried over magnesium sulfate and concentrated in vacuum. Purification through column chromatography (ethyl acetate/petroleum ether=2:1) gave the target compound (0.7 g, 90%). $^1$H-NMR [ppm] in $CDCl_3$: 8.45 (s, 1H), 7.84 (d, 2H), 7.64 (d, 2H), 4.46 (q, 2H), 2.97 (s, 3H), 1.45 (t, 3H). MS (ESI) $[M+H]^+$=359.3.

Step 4: 3,5-dicyano-2-methyl-4-[4-(trifluoromethyl)phenyl]benzoic Acid

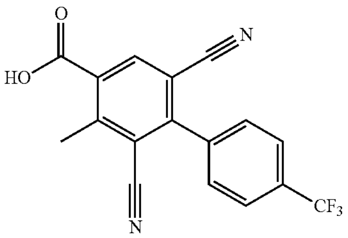 [SMILES: Cc1c(C(=O)O)cc(C#N)c(-c2ccc(C(F)(F)F)cc2)c1C#N]

A solution of ethyl 3,5-dicyano-2-methyl-4-[4-(trifluoromethyl)phenyl]benzoate (0.56 g, 1.56 mmol) in methanol (10 mL), sodium hydroxide (75 mg, 1.88 mmol) was added. The mixture was stirred at room temperature for 2 hours. Then the pH was adjusted to 2-3 by addition of hydrochloric acid and the mixture was extracted with ethyl acetate. The organic layer was separated, washed with brine, dried over magnesium sulfate and concentrated in vacuum to give the product (0.5 g, 97%). $^1$H-NMR [ppm] in DMSO-d6: 8.57 (s, 1H), 8.02 (d, 2H), 7.87 (d, 2H), 2.83 (s, 3H). MS (ESI) $[M+H]^+$=331.3.

Step 5: 4-Methyl-5-[4-(5-methyl-1,2,4-oxadiazol-3-yl)piperazine-1-carbonyl]-2-[4-(trifluoromethyl)-phenyl]benzene-1,3-dicarbonitrile (Compound P6.1)

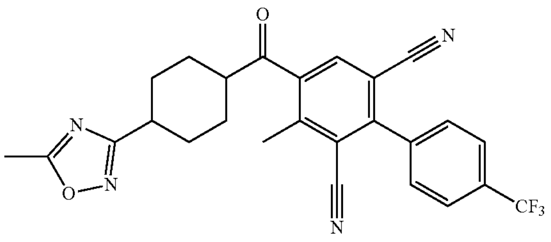 [SMILES: Cc1nc(C2CCC(C(=O)c3cc(C#N)c(-c4ccc(C(F)(F)F)cc4)c(C#N)c3C)CC2)no1]

A mixture of 3,5-dicyano-2-methyl-4-[4-(trifluoromethyl)phenyl]benzoic acid (250 mg, 0.757 mmol), 5-methyl-3-(4-piperidyl)-1,2,4-oxadiazole (127 mg, 0.757 mmol) which was synthesized as described in Nippon Soda patent application WO 2017195703, diisopropylethylamine (294 mg, 2.27 mmol) and HATU (431 mg, 1.14 mol) in dichloromethane (10 mL) was stirred at room temperature for 4 hours. The mixture was poured into water (50 mL) and the mixture extracted three times with ethyl acetate (50 mL each), the combined organic phases were dried over $Na_2SO_4$ and concentrated. The material was purified by chromatography (ethyl acetate/petroleum ether=1:2) to give the title compound as solid (230 mg, 63%). $^1$H-NMR [ppm] in $CDCl_3$: 7.84 (d, 2H), 7.76, 7.79 (2s, 1H), 7.63 (d, 2H), 4.63 (t, 1H), 3.53 (d, 1H), 3.10-3.30 (m, 3H), 2.64, 2.59 (2s, 3H), 2.58 (s, 3H), 1.75-2.25 (m, 4H). MS (ESI) $[M+H]^+$=480.2.

The compounds in Tables P1, P2, P3, P4, P5, P6, P7 and P8 were prepared as described in the examples above or similar methodology.

Table P1: Compounds of Formula (I-c)

(I-c)

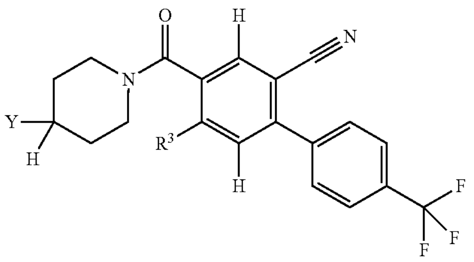

The compounds in Table P1 can be prepared as described in the examples above or similar methodology. The following abbreviations are used in the table below: RT=retention time, min=minutes m.p.=melting point or melting range.

TABLE P1

| Comp. No | Y | $R^3$ | $[M + H]^+$ | LC-MS RT (min) | Method | m.p. [° C.] |
|---|---|---|---|---|---|---|
| P1.1 | 5-methyl-1,2,4-oxadiazole-3-yl | $CF_3$ | 509 | 4.80 | 1 | 91-92 |
| P1.2 | $CH_2SCH_2CH_3$ | $CF_3$ | 501 | 5.47 | 1 | 118-120 |
| P1.3 | $CH_2S(=O)CH_2CH_3$ | $CF_3$ | 517 | 4.34 | 1 | 85-88 |
| P1.4 | $CH_2SO_2CH_2CH_3$ | $CF_3$ | 533 | 4.63 | 1 | 87-89 |
| P1.5 | 1,1-dioxo-1,2-thiazolidin-2-yl | $CF_3$ | 546 | 4.61 | 1 | 92-94 |

TABLE P1-continued

| Comp. No | Y | $R^3$ | $[M + H]^+$ | LC-MS RT (min) | Method | m.p. [° C.] |
|---|---|---|---|---|---|---|
| P1.6 | 5-methyl-1,2,4-oxadiazole-3-yl | $CH_3$ | 455 | 4.56 | 1 | 90-92 |
| P1.7 | $CH_2SCH_2CH_3$ | $CH_3$ | 447 | 5.24 | 1 | 95-97 |
| P1.8 | 1,1-dioxo-1,2-thiazolidin-2-yl | $CH_3$ | 492 | 4.36 | 1 | 208-210 |
| P1.9 | 5-methyl-1,2,4-oxadiazole-3-yl | H | 441 | 4.45 | 1 | |
| P1.10 | $CH_2SCH_2CH_3$ | H | 433 | 5.16 | 1 | 96-98 |
| P1.11 | 1,1-dioxo-1,2-thiazolidin-2-yl | H | 478 | 4.26 | 1 | 92-94 |
| P1.12 | $CH_2SCH_3$ | $CF_3$ | 487 | 5.30 | 1 | 148-150 |
| P1.13 | $CH_2S({=}O)CH_3$ | $CF_3$ | 503 | 4.24 | 1 | 98-100 |
| P1.14 | $CH_2SO_2CH_3$ | $CF_3$ | 519 | 4.55 | 1 | 186-188 |
| P1.15 | $CH_2SCH_2CH{=}CH_2$ | $CF_3$ | 513 | 5.53 | 1 | 110-112 |
| P1.16 | $CH_2S({=}O)CH_2CH{=}CH_2$ | $CF_3$ | 529 | 4.47 | 1 | |
| P1.17 | $CH_2SO_2CH_2CH{=}CH_2$ | $CF_3$ | 545 | 4.75 | 1 | 96-98 |
| P1.18 | $CH_2SCH_2CHCH$ | $CF_3$ | 511 | 5.25 | 1 | |
| P1.19 | $CH_2S({=}O)CH_2CHCH$ | $CF_3$ | 527 | 4.46 | 1 | |
| P1.20 | $CH_2SO_2CH_2CHCH$ | $CF_3$ | 543 | 4.73 | 1 | |
| P1.21 | $CH_2SCH_2CH_2CH_3$ | $CF_3$ | 515 | 5.68 | 1 | 112-114 |
| P1.22 | $CH_2S({=}O)CH_2CH_2CH_3$ | $CF_3$ | 531 | 4.54 | 1 | 91-93 |
| P1.23 | $CH_2SO_2CH_2CH_2CH_3$ | $CF_3$ | 547 | 4.63 | 1 | 93-95 |
| P1.24 | $CH_2SCH_3$ | $CH_3$ | 433 | 5.11 | 1 | 120-122 |
| P1.25 | $CH_2S({=}O)CH_3$ | $CH_3$ | 449 | 3.99 | 1 | 167-169 |
| P1.26 | $CH_2SO_2CH_3$ | $CH_3$ | 465 | 5.11 | 1 | 161-163 |
| P1.27 | $CH_2SCH_2CH{=}CH_2$ | $CH_3$ | 459 | 5.37 | 1 | 100-102 |
| P1.28 | $CH_2S({=}O)CH_2CH{=}CH_2$ | $CH_3$ | 475 | 4.25 | 1 | |
| P1.29 | $CH_2SO_2CH_2CH{=}CH_2$ | $CH_3$ | 491 | 4.56 | 1 | 90-92 |
| P1.30 | $CH_2SCH_2CHCH$ | $CH_3$ | 457 | 5.10 | 1 | |
| P1.31 | $CH_2S({=}O)CH_2CHCH$ | $CH_3$ | 473 | 4.25 | 1 | 63-65 |
| P1.32 | $CH_2SO_2CH_2CHCH$ | $CH_3$ | 489 | 4.53 | 1 | |
| P1.33 | $CH_2SCH_2CH_2CH_3$ | $CH_3$ | 461 | 5.56 | 1 | 118-120 |
| P1.34 | $CH_2S({=}O)CH_2CH_2CH_3$ | $CH_3$ | 477 | 4.26 | 1 | |
| P1.35 | $CH_2SO_2CH_2CH_2CH_3$ | $CH_3$ | 493 | 4.60 | 1 | 99-101 |
| P1.36 | (E)-N-methoxy-imino-methyl | $CF_3$ | 484 | 5.04 | 1 | 130-132 |
| P1.37 | (E)-N-ethoxy-imino-methyl | $CF_3$ | 498 | 5.22 | 1 | 115-117 |
| P1.38 | methylsulfonyl-carbamoyl | $CF_3$ | | | 1 | 188-190 |
| P1.39 | dimethylcarbamoyl | $CF_3$ | 498 | 4.47 | 1 | 143-145 |
| P1.40 | ethyl(methyl)carbamoyl | $CF_3$ | | | 1 | |
| P1.41 | methanesulfonamido | $CF_3$ | 520 | 4.48 | 1 | 215-217 |
| P1.42 | ethanesulfonamido | $CF_3$ | 534 | 4.60 | 1 | 224-226 |
| P1.43 | 5-methyl-1,2,4-oxadiazole-3-yl | $OCH_3$ | 471 | 4.47 | 1 | |
| P1.44 | $CH_2SCH_2CH_3$ | $OCH_3$ | 463 | 5.14 | 1 | 162-164 |
| P1.45 | 5-methyl-1,2,4-oxadiazole-3-yl | $OCH_2CH_3$ | 485 | 4.66 | 1 | |
| P1.46 | $CH_2SCH_2CH_3$ | $OCH_2CH_3$ | 477 | 5.32 | 1 | 68-70 |
| P1.47 | ethoxycarbonyl | $CF_3$ | 499 | 5.09 | 1 | |
| P1.48 | tert-butoxy-carbonylamino | $CF_3$ | | 5.11 | 1 | 168-170 |
| P1.49 | trifluoromethyl-sulfonylamino | $CF_3$ | 538 | 4.66 | 1 | 215-217 |
| P1.50 | 1-methyl-1,2,4-triazol-3-yl | $CF_3$ | 508 | 4.36 | 1 | |
| P1.51 | phenyl | $CF_3$ | 503 | 5.51 | 1 | 154-156 |
| P1.52 | ethoxymethyl | $CF_3$ | 485 | 5.23 | 1 | 110-112 |
| P1.53 | cyano | $CF_3$ | 452 | 5.25 | 1 | 102-104 |

Table P2: Compounds of Formula (I-d)

(I-d)

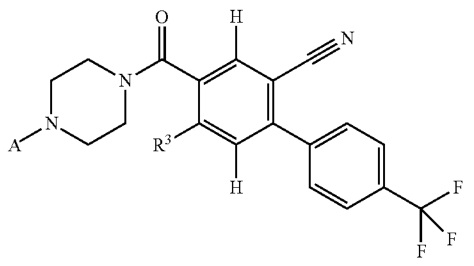

The compounds in Table P2 can be prepared as described in the examples above or similar methodology. The following abbreviations are used in the table below: RT=retention time, min=minutes, m.p.=melting point.

TABLE P2

| Comp. No | A | $R^3$ | $[M + H]^+$ | LC-MS RT (min) | Method | m.p. [° C.] |
|---|---|---|---|---|---|---|
| P2.1 | 3,5-dichloro-2-pyridyl | $CF_3$ | 573 | 5.69 | 1 | 79-80 |
| P2.2 | 3,5-dichloro-2-pyridyl | $CH_3$ | 519 | 5.55 | 1 | 135-137 |
| P2.3 | 3,5-dichloro-2-pyridyl | H | 505 | 5.43 | 1 | 160-162 |
| P2.4 | 3,5-dichloro-2-pyridyl | $OCH_3$ | 536 | 5.45 | 1 | 222-224 |
| P2.5 | 3,5-dichloro-2-pyridyl | $OCH_2CH_3$ | 549 | 5.63 | 1 | 97-99 |
| P2.6 | cyano | $CF_3$ | 453 | 1.03 | 2 | 152-155 |
| P2.7 | $CH_2CN$ | $CF_3$ | 467 | 4.63 | 2 | 138-140 |
| P2.8 | $CH_2CH_2CN$ | $CF_3$ | 481 | 4.27 | 1 | 140-142 |
| P2.9 | 2,2,2-trifluoroethyl | $CF_3$ | 510 | 1.17 | 2 | 142-144 |
| P2.10 | 3,3-dichloroallyl | $CF_3$ | 536 | 4.52 | 1 | 148-150 |
| P2.11 | $CH_2CH_2SCH_3$ | $CF_3$ | 502 | 3.95 | 1 | 114-116 |
| P2.12 | $CH_2CH_2S(=O)CH_3$ | $CF_3$ | 518 | 3.71 | 1 | 94-96 |
| P2.13 | methylsulfonyl | $CF_3$ | 506 | 4.64 | 1 | 200-202 |
| P2.14 | trifluoromethyl-sulfonyl | $CF_3$ | 560 | 5.21 | 1 | 217-219 |
| P2.15 | tert-butoxy-carbonyl | $CF_3$ | n/a | 1.19 | 2 | 159-161 |
| P2.16 | trifluoromethyl-carbonyl | $CF_3$ | 524 | 4.97 | 1 | 193-195 |
| P2.17 | methoxyethyl | $CF_3$ | 486 | 3.81 | 1 | |

Table P3: Compounds of Formula (I-e)

(I-e)

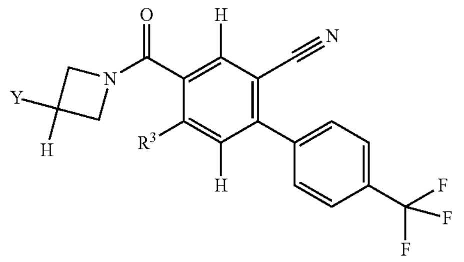

The compounds in Table P3 can be prepared as described in the examples above or similar methodology. The following abbreviations are used in the table below: RT=retention time, min=minutes; m.p.=melting point.

TABLE P3

| Comp. No | Y | $R^3$ | $[M + H]^+$ | LC-MS RT (min) | Method | m.p. [° C.] |
|---|---|---|---|---|---|---|
| P3.1 | $CH_2SCH_3$ | $CF_3$ | 459 | 5.01 | 1 | 120-122 |
| P3.2 | $CH_2S(=O)CH_3$ | $CF_3$ | 475 | 4.07 | 1 | 142-144 |
| P3.3 | $CH_2SO_2CH_3$ | $CF_3$ | 491 | 4.39 | 1 | 167-169 |
| P3.4 | $CH_2SCH_2CH_3$ | $CF_3$ | 473 | 5.78 | 1 | 97-99 |
| P3.5 | $CH_2S(=O)CH_2CH_3$ | $CF_3$ | 489 | 4.20 | 1 | 75-77 |
| P3.6 | $CH_2SO_2CH_2CH_3$ | $CF_3$ | 505 | 4.50 | 1 | 150-152 |
| P3.7 | $CH_2S(=O)CH_2CH_2CH_3$ | $CF_3$ | 503 | 4.36 | 1 | |
| P3.8 | $CH_2SO_2CH_2CH_2CH_3$ | $CF_3$ | 519 | 4.66 | 1 | 80-82 |
| P3.9 | $CH_2SCH_2CH_2CH_3$ | $CF_3$ | 487 | 5.38 | 1 | |

Table P4: Compounds of Formula (I-e)

(I-e)

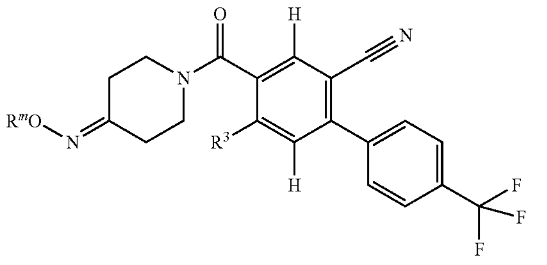

The compounds in Table P2 can be prepared as described in the examples above or similar methodology. The following abbreviations are used in the table below: RT=retention time, min=minutes, m.p.=melting point.

TABLE P4

| Comp. No | R''' | $R^3$ | $[M + H]^+$ | LC-MS RT (min) | Method | m.p. [° C.] |
|---|---|---|---|---|---|---|
| P4.1 | methyl | $CF_3$ | 470 | 4.93 | 1 | 136-138 |
| P4.2 | ethyl | $CF_3$ | 484 | 5.11 | 1 | 118-120 |

Table P5: Compounds of Formula (I-q)

(I-g)

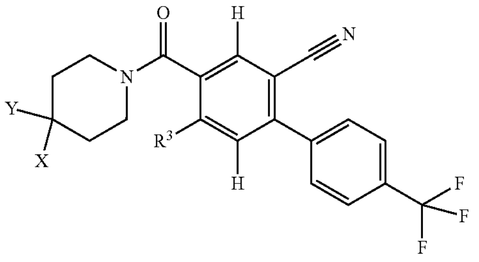

The compound in Table P5 can be prepared as described in the examples above or similar methodology. The following abbreviations are used in the table below: RT=retention time, min=minutes; m.p.=melting point.

TABLE P5

| Comp. No | Y | X | $R^3$ | $[M + H]^+$ | LC-MS RT (min) | Method | m.p. [° C.] |
|---|---|---|---|---|---|---|---|
| P5.1 | phenyl | OH | $CF_3$ | 519 | 4.4 | 1 | 221-223 |
| P5.2 | 4-Cl-phenyl | OH | $CF_3$ | 553 | 5.2 | 1 | 250-251 |
| P5.3 | 4-Cl-phenyl | $OCH_3$ | $CF_3$ | 567 | 1.29 | 2 | 103-105 |

Table P6: Compounds of Formula (I-h)

(I-h)

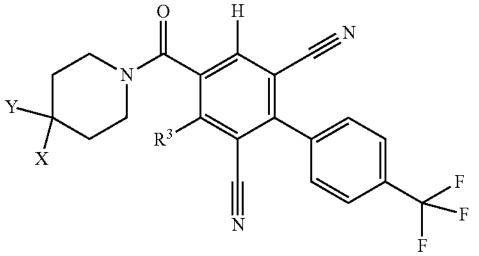

The compound in Table P6 can be prepared as described in the examples above or similar methodology. The following abbreviations are used in the table below: RT=retention time, min=minutes; m.p.=melting point.

TABLE P6

| Comp. No | Y | $R^3$ | $[M + H]^+$ | LC-MS RT (min) | Method | m.p. [° C.] |
|---|---|---|---|---|---|---|
| P6.1 | 5-methyl-1,2,4-oxadiazole-3-yl | $CH_3$ | 480 | 4.46 | 1 | 118-120 |

Table P7: Compounds of Formula (I-i)

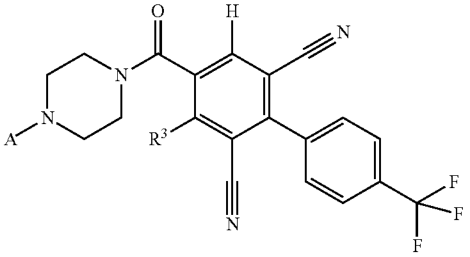

(I-i)

The compound in Table P7 can be prepared as described in the examples above or similar methodology. The following abbreviations are used in the table below: RT=retention time, min=minutes; m.p.=melting point.

TABLE P7

| Comp. No | A | $R^3$ | $[M + H]^+$ | LC-MS RT (min) | Method | m.p. [° C.] |
|---|---|---|---|---|---|---|
| P7.1 | 3,5-dichloro-2-pyridyl | $CH_3$ | 544 | 5.31 | 1 | 185-187 |

Table P8: Compounds of Formula (I-j)

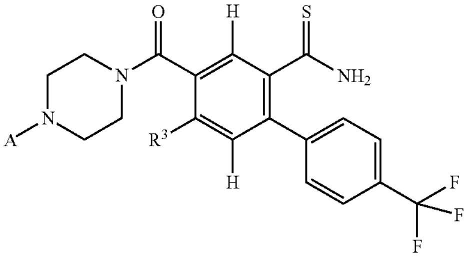

(I-j)

The compound in Table P8 can be prepared as described in the examples above or similar methodology. The following abbreviations are used in the table below: RT=retention time, min=minutes; m.p.=melting point.

TABLE P8

| Comp. No | A | $R^3$ | $[M + H]^+$ | LC-MS RT (min) | Method | m.p. [° C.] |
|---|---|---|---|---|---|---|
| P8.1 | 3,5-dichloro-2-pyridyl | $CF_3$ | 607 | 1.25 | 2 | |

The intermediates in Table U1 are new and useful for the synthesis of some compounds of the general structure I. They can be prepared as described in the examples above or similar methodology. The following abbreviations are used in the table below: s=singlet, d=doublet, t=triplet, q=quartet, m=multiplet.

TABLE U1

| Comp. No | Structure | $^1$H-NMR: δ in [ppm] |
|---|---|---|
| U1.1 | 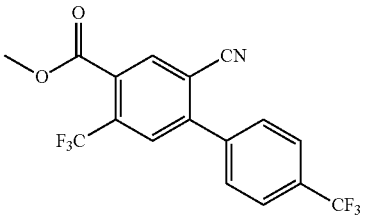 [SMILES: COC(=O)c1cc(C#N)c(-c2ccc(C(F)(F)F)cc2)cc1C(F)(F)F] | In DMSO-d6: 8.53 (s, 1H), 8.17 (s, 1H), 7.9-8.1 (m, 4H), 3.93 (s, 3H). |
| U1.2 | 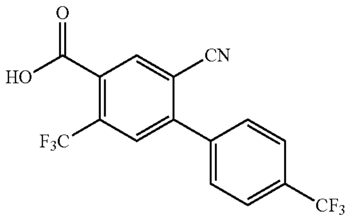 [SMILES: N#Cc1cc(C(=O)O)c(C(F)(F)F)cc1-c1ccc(C(F)(F)F)cc1] | In DMSO-d6: 8.46 (s, 1H), 8.11 (s, 1H), 7.8-8.0 (m, 4H). |

TABLE U1-continued
| Comp. No | Structure | $^1$H-NMR: δ in [ppm] |
|---|---|---|
| U1.3 | 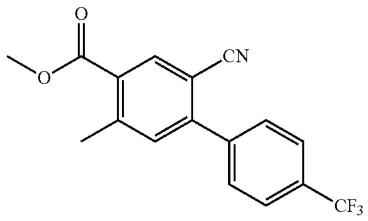 [SMILES: COC(=O)c1cc(C#N)c(-c2ccc(C(F)(F)F)cc2)cc1C] | In DMSO-d6: 8.33 (s, 1H) , 7.94 (d, 2H), 7.86 (d, 2H), 7.71 (s, 1H), 3.33 (s, 3H), 2.65 (s, 3H). |
| U1.4 | 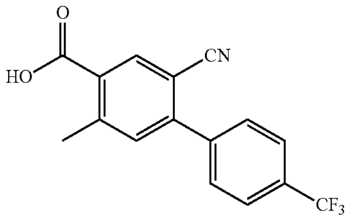 [SMILES: Cc1cc(-c2ccc(C(F)(F)F)cc2)c(C#N)cc1C(=O)O] | In DMSO-d6: 8.31 (s, 1H), 7.94 (d, 2H), 7.86 (d, 2H), 7.78 (s, 1H), 2.66 (s, 3H). |
| U1.5 | 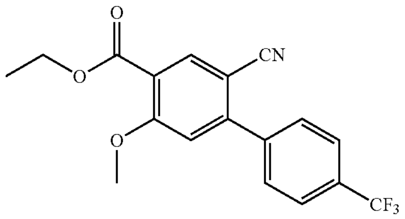 [SMILES: CCOC(=O)c1cc(C#N)c(-c2ccc(C(F)(F)F)cc2)cc1OC] | In DMSO-d6: 8.20 (s, 1H), 7.95 (d, 2H), 7.89 (d, 2H), 7.40 (s, 1H), 4.30 (q, 2H), 3.99 (s, 3H), 1.30 (dd, 3H). |
| U1.6 | 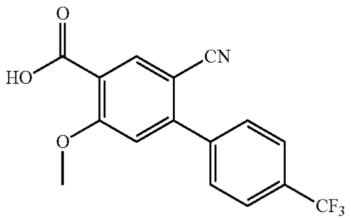 [SMILES: COc1cc(-c2ccc(C(F)(F)F)cc2)c(C#N)cc1C(=O)O] | In $CDCl_3$: 8.58 (s, 1H), 7.81 (d, 2H), 7.70 (d, 2H), 7.14 (s, 1H), 4.18 (s, 3H). |
| U1.7 | 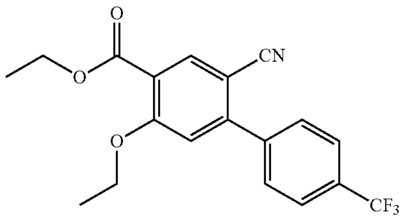 [SMILES: CCOC(=O)c1cc(C#N)c(-c2ccc(C(F)(F)F)cc2)cc1OCC] | In $CDCl_3$: 8.22 (s, 1H), 7.77 (d, 2H), 7.68 (d, 2H), 7.01 (s, 1H), 4.40 (q, 2H), 4.22 (q, 2H), 1.52 (t, 3H), 1.41 (t, 3H). |
| U1.8 | 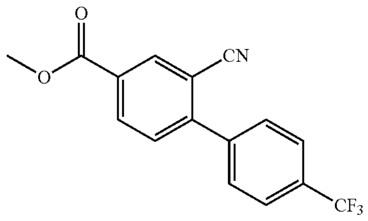 [SMILES: COC(=O)c1ccc(-c2ccc(C(F)(F)F)cc2)c(C#N)c1] | In DMSO-d6: 8.44 (s, 1H), 8.30 (d, 1H), 7.93 (d, 2H), 7.79-7.90 (m, 3H), 3.91 (s, 3H). |
| U1.9 | 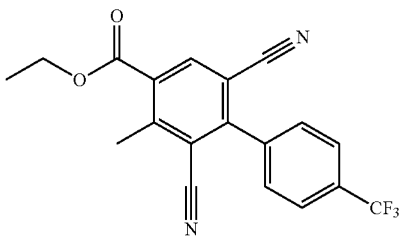 [SMILES: CCOC(=O)c1cc(C#N)c(-c2ccc(C(F)(F)F)cc2)c(C#N)c1C] | In $CDCl_3$: 8.45 (s, 1H), 7.84 (d, 2H), 7.64 (d, 2H), 4.46 (q, 2H), 2.97 (s, 3H), 1.45 (t, 3H). |

TABLE U1-continued

| Comp. No | Structure | $^1$H-NMR: δ in [ppm] |
|---|---|---|
| U1.10 | 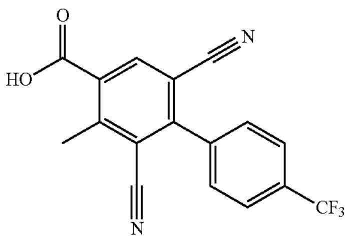 [SMILES: Cc1c(C(=O)O)cc(C#N)c(-c2ccc(C(F)(F)F)cc2)c1C#N] | In DMSO-d6: 8.57 (s, 1H), 8.02 (d, 2H), 7.87 (d, 2H), 2.83 (s, 3H). |

The activity of the compositions according to the invention can be broadened considerably, and adapted to prevailing circumstances, by adding other insecticidally, acaricidally and/or fungicidally active ingredients. The mixtures of the compounds of formula (I) with other insecticidally, acaricidally and/or fungicidally active ingredients may also have further surprising advantages which can also be described, in a wider sense, as synergistic activity. For example, better tolerance by plants, reduced phytotoxicity, insects can be controlled in their different development stages or better behaviour during their production, for example during grinding or mixing, during their storage or during their use.

Suitable additions to active ingredients here are, for example, representatives of the following classes of active ingredients: organophosphorus compounds, nitrophenol derivatives, thioureas, juvenile hormones, formamidines, benzophenone derivatives, ureas, pyrrole derivatives, carbamates, pyrethroids, chlorinated hydrocarbons, acylureas, pyridylmethyleneamino derivatives, macrolides, neonicotinoids and *Bacillus thuringiensis* preparations.

The following mixtures of a compound of formula (I) with an active substances are preferred (the abbreviation "TX" means "one compound selected from the compounds defined in Tables 1 to 35 and Tables P1 to P8):

an adjuvant selected from the group of substances consisting of petroleum oils (alternative name) (628)+TX, an insect control active substance selected from Abamectin+TX, Acequinocyl+TX, Acetamiprid+TX, Acetoprole+TX, Acrinathrin+TX, Acynonapyr+TX, Afidopyropen+TX, Afoxolaner+TX, Alanycarb+TX, Allethrin+TX, Alpha-Cypermethrin+TX, Alphamethrin+TX, Amidoflumet+TX, Aminocarb+TX, Azocyclotin+TX, Bensultap+TX, Benzoximate+TX, Benzpyrimoxan+TX, Betacyfluthrin+TX, Beta-cypermethrin+TX, Bifenazate+TX, Bifenthrin+TX, Binapacryl+TX, Bioallethrin+TX, Bioallethrin S)-cyclopentylisomer+TX, Bioresmethrin+TX, Bistrifluron+TX, Broflanilide+TX, Brofluthrinate+TX, Bromophos-ethyl+TX, Buprofezine+TX, Butocarboxim+TX, Cadusafos+TX, Carbaryl+TX, Carbosulfan+TX, Cartap+TX, CAS number: 1632218-00-8+TX, CAS number: 1808115-49-2+TX, CAS number: 2032403-97-5+TX, CAS number: 2044701-44-0+TX, CAS number: 2128706-05-6+TX, CAS number: 2246757-58-2 (or 2249718-27-0)+TX, CAS number: 907187-07-9+TX, Chlorantraniliprole+TX, Chlordane+TX, Chlorfenapyr+TX, Chloroprallethrin+TX, Chromafenozide+TX, Clenpirin+TX, Cloethocarb+TX, Clothianidin+TX, 2-chlorophenyl N-methylcarbamate (CPMC)+TX, Cyanofenphos+TX, Cyantraniliprole+TX, Cyclaniliprole+TX, Cyclobutrifluram+TX, Cycloprothrin+TX, Cycloxaprid+TX, Cycloxaprid+TX, Cyenopyrafen+TX, Cyetpyrafen+TX, Cyflumetofen+TX, Cyfluthrin+TX, Cyhalodiamide+TX, Cyhalothrin+TX, Cypermethrin+TX, Cyphenothrin+TX, Cyproflanilide+TX, Cyromazine+TX, Deltamethrin+TX, Diafenthiuron+TX, Dialifos+TX, Dibrom+TX, Dicloromezotiaz+TX, Diflovidazine+TX, Diflubenzuron+TX, dimpropyridaz+TX, Dinactin+TX, Dinocap+TX, Dinotefuran+TX, Dioxabenzofos+TX, Emamectin (or Emamectin Benzoate)+TX, Empenthrin+TX, Epsilon-momfluorothrin+TX, Epsilon-metofluthrin+TX, Esfenvalerate+TX, Ethion+TX, Ethiprole+TX, Etofenprox+TX, Etoxazole+TX, Famphur+TX, Fenazaquin+TX, Fenfluthrin+TX, Fenitrothion+TX, Fenobucarb+TX, Fenothiocarb+TX, Fenoxycarb+TX, Fenpropathrin+TX, Fenpyroxymate+TX, Fensulfothion+TX, Fenthion+TX, Fentinacetate+TX, Fenvalerate+TX, Fipronil+TX, Flometoquin+TX, Flonicamid+TX, Fluacrypyrim+TX, Fluazaindolizine+TX, Fluazuron+TX, Flubendiamide+TX, Flubenzimine+TX, Flucitrinate+TX, Flucycloxuron+TX, Flucythrinate+TX, Fluensulfone+TX, Flufenerim+TX, Flufenprox+TX, Flufiprole+TX, Fluhexafon+TX, Flumethrin+TX, Fluopyram+TX, Flupentiofenox+TX, Flupyradifurone+TX, Flupyrimin+TX, Fluralaner+TX, Fluvalinate+TX, Fluxametamide+TX, Fosthiazate+TX, Gamma-Cyhalothrin+TX, Gossyplure™+TX, Guadipyr+TX, Halofenozide+TX, Halofenozide+TX, Halfenprox+TX, Heptafluthrin+TX, Hexythiazox+TX, Hydramethylnon+TX, Imicyafos+TX, Imidacloprid+TX, Imiprothrin+TX, Indoxacarb+TX, Iodomethane+TX, Iprodione+TX, Isocycloseram+TX, Isothioate+TX, Ivermectin+TX, Kappa-bifenthrin+TX, Kappa-tefluthrin+TX, Lambda-Cyhalothrin+TX, Lepimectin+TX, Lufenuron+TX, Metaflumizone+TX, Metaldehyde+TX, Metam+TX, Methomyl+TX, Methoxyfenozide+TX, Metofluthrin+TX, Metolcarb+TX, Mexacarbate+TX, Milbemectin+TX, Momfluorothrin+TX, Niclosamide+TX, Nicofluprole+TX; Nitenpyram+TX, Nithiazine+TX, Omethoate+TX, Oxamyl+TX, Oxazosulfyl+TX, Parathion-ethyl+TX, Permethrin+TX, Phenothrin+TX, Phosphocarb+TX, Piperonylbutoxide+TX, Pirimicarb+TX, Pirimiphos-ethyl+TX, Pirimiphos-methyl+TX, Polyhedrosis virus+TX, Prallethrin+TX, Profenofos+TX, Profenofos+TX, Profluthrin+TX, Propargite+TX, Propetamphos+TX, Propoxur+TX, Prothiophos+TX, Protrifenbute+TX, Pyflubumide+TX, Pymetrozine+TX, Pyraclofos+TX, Pyrafluprole+TX, Pyridaben+TX, Pyridalyl+TX, Pyrifluquinazon+TX, Pyrimidifen+TX, Pyriminostrobin+TX, Pyriprole+TX, Pyriproxyfen+TX, Resmethrin+TX, Sarolaner+TX, Selamectin+TX, Silafluofen+TX, Spinetoram+TX, Spinosad+TX, Spirodiclofen+TX, Spiromesifen+TX, Spiropidion+TX, Spirotetramat+TX, Sulfoxaflor+TX, Tebufenozide+TX, Tebufenpyrad+TX, Tebupirimiphos+TX, Tefluthrin+TX, Temephos+TX, Tetrachlorantraniliprole+TX, Tetradiphon+TX, Tetramethrin+TX, Tetramethylfluthrin+TX, Tetranactin+TX, Tetraniliprole+TX, Theta-cypermethrin+TX, Thiacloprid+TX, Thiamethoxam+TX, Thiocyclam+TX, Thiodicarb+TX, Thiofanox+TX, Thiometon+TX, Thiosultap+TX, Tioxazafen+TX, Tolfenpyrad+TX, Toxaphene+TX, Tralomethrin+TX, Transfluthrin+TX, Triazamate+TX, Triazophos+TX, Trichlorfon+TX, Trichloronate+TX, Trichlorphon+TX, Triflumezopyrim+TX, Tyclopyrazoflor+TX, Zeta-Cypermethrin+TX, Extract of seaweed and fermentation product derived from melasse+TX, Extract of seaweed and fermentation product derived from melasse comprising urea+TX, amino acids+TX, potassium and molybdenum and EDTA-chelated manganese+TX, Extract of seaweed and fermented plant products+TX, Extract of seaweed and fermented plant products comprising phytohormones+TX, vitamins+TX, EDTA-chelated copper+TX, zinc+TX and iron+TX, Azadirachtin+TX, *Bacillus aizawai*+TX, *Bacillus chitinosporus* AQ746 (NRRL Accession No B-21 618)+TX, *Bacillus firmus*+TX, *Bacillus kurstaki*+TX, *Bacillus mycoides* AQ726 (NRRL Accession No. B-21664)+TX, *Bacillus pumilus* (NRRL Accession No B-30087)+TX, *Bacillus pumilus* AQ717 (NRRL Accession No. B-21662)+TX, *Bacillus* sp. AQ178 (ATCC Accession No. 53522)+TX, *Bacillus* sp. AQ175 (ATCC Accession No. 55608)+TX, *Bacillus* sp. AQ177 (ATCC Accession No. 55609)+TX, *Bacillus subtilis* unspecified+TX, *Bacillus subtilis* AQ153 (ATCC Accession No. 55614)+TX, *Bacillus subtilis* AQ30002 (NRRL Accession No. B-50421)+TX, *Bacillus subtilis* AQ30004 (NRRL Accession No. B-50455)+TX, *Bacillus subtilis* AQ713 (NRRL Accession No. B-21661)+TX, *Bacillus subtilis* AQ743 (NRRL Accession No. B-21665)+TX, *Bacillus thuringiensis* AQ52 (NRRL Accession No. B-21619)+TX, *Bacillus thuringiensis* BD #32 (NRRL Accession No B-21530)+TX, *Bacillus thuringiensis* subspec. *kurstaki* BMP 123+TX, *Beauveria bassiana*+TX, D-limonene+TX, *Granulovirus*+TX, Harpin+TX, *Helicoverpa armigera* Nucleopolyhedrovirus+TX, *Helicoverpa zea* Nucleopolyhedrovirus+TX, *Heliothis virescens* Nucleopolyhedrovirus+TX, *Heliothis punctigera* Nucleopolyhedrovirus+TX, *Metarhizium* spp.+TX, *Muscodor albus* 620 (NRRL Accession No. 30547)+TX, *Muscodor roseus* A3-5 (NRRL Accession No. 30548)+TX, Neem tree based products+TX, *Paecilomyces fumosoroseus*+TX, *Paecilomyces lilacinus*+TX, *Pasteuria nishizawae*+TX, *Pasteuria penetrans*+TX, *Pasteuria ramosa*+TX, *Pasteuria thornei*+TX, *Pasteuria usgae*+TX, P-cymene+TX, *Plutella xylostella* Granulosis virus+TX, *Plutella xylostella* Nucleopolyhedrovirus+TX, Polyhedrosis virus+TX, *pyrethrum*+TX, QRD 420 (a terpenoid blend)+TX, QRD 452 (a terpenoid blend)+TX, QRD 460 (a terpenoid blend)+TX, *Quillaja saponaria*+TX, *Rhodococcus globerulus* AQ719 (NRRL Accession No B-21663)+TX, *Spodoptera frugiperda* Nucleopolyhedrovirus+TX, *Streptomyces galbus* (NRRL Accession No. 30232)+TX, *Streptomyces* sp. (NRRL Accession No. B-30145)+TX, Terpenoid blend+TX and *Verticillium* spp.;

an algicide selected from the group of substances consisting of bethoxazin [CCN]+TX, copper dioctanoate (IUPAC name) (170)+TX, copper sulfate (172)+TX, cybutryne [CCN]+TX, dichlone (1052)+TX, dichlorophen (232)+TX, endothal (295)+TX, fentin (347)+TX, hydrated lime [CCN]+TX, nabam (566)+TX, quinoclamine (714)+TX, quinonamid (1379)+TX, simazine (730)+TX, triphenyltin acetate (IUPAC name) (347) and triphenyltin hydroxide (IUPAC name) (347)+TX;

an anthelmintic selected from the group of substances consisting of abamectin (1)+TX, crufomate (1011)+TX, Cyclobutrifluram+TX, doramectin (alternative name) [CCN]+TX, emamectin (291)+TX, emamectin benzoate (291)+TX, eprinomectin (alternative name) [CCN]+TX, ivermectin (alternative name) [CCN]+TX, milbemycin oxime (alternative name) [CCN]+TX, moxidectin (alternative name) [CCN]+TX, piperazine [CCN]+TX, selamectin (alternative name) [CCN]+TX, spinosad (737) and thiophanate (1435)+TX;

an avicide selected from the group of substances consisting of chloralose (127)+TX, endrin (1122)+TX, fenthion (346)+TX, pyridin-4-amine (IUPAC name) (23) and strychnine (745)+TX; a bactericide selected from the group of substances consisting of 1-hydroxy-1H-pyridine-2-thione (IUPAC name) (1222)+TX, 4-(quinoxalin-2-ylamino)benzenesulfonamide (IUPAC name) (748)+TX, 8-hydroxyquinoline sulfate (446)+TX, bronopol (97)+TX, copper dioctanoate (IUPAC name) (170)+TX, copper hydroxide (IUPAC name) (169)+TX, cresol [CCN]+TX, dichlorophen (232)+TX, dipyrithione (1105)+TX, dodicin (1112)+TX, fenaminosulf (1144)+TX, formaldehyde (404)+TX, hydrargaphen (alternative name) [CCN]+TX, kasugamycin (483)+TX, kasugamycin hydrochloride hydrate (483)+TX, nickel bis(dimethyldithiocarbamate) (IUPAC name) (1308)+TX, nitrapyrin (580)+TX, octhilinone (590)+TX, oxolinic acid (606)+TX, oxytetracycline (611)+TX, potassium hydroxyquinoline sulfate (446)+TX, probenazole (658)+TX, streptomycin (744)+TX, streptomycin sesquisulfate (744)+TX, tecloftalam (766)+TX, and thiomersal (alternative name) [CCN]+TX;

a biological agent selected from the group of substances consisting of *Adoxophyes orana* GV (alternative name) (12)+TX, *Agrobacterium radiobacter* (alternative name) (13)+TX, *Amblyseius* spp. (alternative name) (19)+TX, *Anagrapha falcifera* NPV (alternative name) (28)+TX, *Anagrus atomus* (alternative name) (29)+TX, *Aphelinus abdominalis* (alternative name) (33)+TX, *Aphidius colemani* (alternative name) (34)+TX, *Aphidoletes aphidimyza* (alternative name) (35)+TX, *Autographa californica* NPV (alternative name) (38)+TX, *Bacillus firmus* (alternative name) (48)+TX, *Bacillus sphaericus* Neide (scientific name) (49)+TX, *Bacillus thuringiensis* Berliner (scientific name) (51)+TX, *Bacillus thuringiensis* subsp. *aizawai* (scientific name) (51)+TX, *Bacillus thuringiensis* subsp. *israelensis* (scientific name) (51)+TX, *Bacillus thuringiensis* subsp. *japonensis* (scientific name) (51)+TX, *Bacillus thuringiensis* subsp. *kurstaki* (scientific name) (51)+TX, *Bacillus thuringiensis* subsp. *tenebrionis* (scientific name) (51)+TX, *Beauveria bassiana* (alternative name) (53)+TX, *Beauveria brongniartii* (alternative name) (54)+TX, *Chrysoperla carnea* (alternative name) (151)+TX, *Cryptolaemus montrouzieri* (alternative name) (178)+TX, *Cydia pomonella* GV (alternative name) (191)+TX, *Dacnusa sibirica* (alternative name) (212)+TX, *Diglyphus isaea* (alternative name) (254)+TX, *Encarsia formosa* (scientific name) (293)+TX, *Eretmocerus eremicus* (alternative name) (300)+TX, *Helicoverpa zea* NPV (alternative name) (431)+TX, *Heterorhabditis bacteriophora* and *H. megidis* (alternative name) (433)+TX, *Hippodamia convergens* (alternative name) (442)+TX, *Leptomastix dactylopii* (alternative name) (488)+TX, *Macrolophus caliginosus* (alternative name) (491)+TX, *Mamestra brassicae* NPV (alternative name) (494)+TX, *Metaphycus helvolus* (alternative name) (522)+TX, *Metarhizium anisopliae* var. *acridum* (scientific name) (523)+TX, *Metarhizium anisopliae* var. *anisopliae* (scientific name) (523)+TX, *Neodiprion sertifer* NPV and *N. lecontei* NPV (alternative name) (575)+TX, *Orius* spp. (alternative name) (596)+TX, *Paecilomyces fumosoroseus* (alternative name) (613)+TX, *Phytoseiulus persimilis* (alternative name) (644)+TX, *Spodoptera exigua* multicapsid nuclear polyhedrosis virus (scientific name) (741)+TX, *Steinernema bibionis* (alternative name) (742)+TX, *Steinernema carpocapsae* (alternative name) (742)+TX, *Steinernema feltiae* (alternative name) (742)+TX, *Steinernema glaseri* (alternative name) (742)+TX, *Steinernema riobrave* (alternative name) (742)+TX, *Steinernema riobravis* (alternative name) (742)+TX, *Steinernema scapterisci* (alternative name) (742)+TX, *Steinernema* spp. (alternative name) (742)+TX, *Trichogramma* spp. (alternative name) (826)+TX, *Typhlodromus occidentalis* (alternative name) (844) and *Verticillium lecanii* (alternative name) (848)+TX;

a soil sterilant selected from the group of substances consisting of iodomethane (IUPAC name) (542) and methyl bromide (537)+TX;

a chemosterilant selected from the group of substances consisting of apholate [CCN]+TX, bisazir (alternative name) [CCN]+TX, busulfan (alternative name) [CCN]+TX, diflubenzuron (250)+TX, dimatif (alternative name) [CCN]+TX, hemel [CCN]+TX, hempa [CCN]+TX, metepa [CCN]+TX, methiotepa [CCN]+TX, methyl apholate [CCN]+TX, morzid [CCN]+TX, penfluron (alternative name) [CCN]+TX, tepa [CCN]+TX, thiohempa (alternative name) [CCN]+TX, thiotepa (alternative name) [CCN]+TX, tretamine (alternative name) [CCN] and uredepa (alternative name) [CCN]+TX;

an insect pheromone selected from the group of substances consisting of (E)-dec-5-en-1-yl acetate with (E)-dec-5-en-1-ol (IUPAC name) (222)+TX, (E)-tridec-4-en-1-yl acetate (IUPAC name) (829)+TX, (E)-6-methylhept-2-en-4-ol (IUPAC name) (541)+TX, (E,Z)-tetradeca-4,10-dien-1-yl acetate (IUPAC name) (779)+TX, (Z)-dodec-7-en-1-yl acetate (IUPAC name) (285)+TX, (Z)-hexadec-11-enal (IUPAC name) (436)+TX, (Z)-hexadec-11-en-1-yl acetate (IUPAC name) (437)+TX, (Z)-hexadec-13-en-11-yn-1-yl acetate (IUPAC name) (438)+TX, (Z)-icos-13-en-10-one (IUPAC name) (448)+TX, (Z)-tetradec-7-en-1-al (IUPAC name) (782)+TX, (Z)-tetradec-9-en-1-ol (IUPAC name) (783)+TX, (Z)-tetradec-9-en-1-yl acetate (IUPAC name) (784)+TX, (7E,9Z)-dodeca-7,9-dien-1-yl acetate (IUPAC name) (283)+TX, (9Z,11E)-tetradeca-9,11-dien-1-yl acetate (IUPAC name) (780)+TX, (9Z,12E)-tetradeca-9,12-dien-1-yl acetate (IUPAC name) (781)+TX, 14-methyloctadec-1-ene (IUPAC name) (545)+TX, 4-methylnonan-5-ol with 4-methylnonan-5-one (IUPAC name) (544)+TX, alpha-multistriatin (alternative name) [CCN]+TX, brevicomin (alternative name) [CCN]+TX, codlelure (alternative name) [CCN]+TX, codlemone (alternative name) (167)+TX, cuelure (alternative name) (179)+TX, disparlure (277)+TX, dodec-8-en-1-yl acetate (IUPAC name) (286)+TX, dodec-9-en-1-yl acetate (IUPAC name) (287)+TX, dodeca-8+TX, 10-dien-1-yl acetate (IUPAC name) (284)+TX, dominicalure (alternative name) [CCN]+TX, ethyl 4-methyloctanoate (IUPAC name) (317)+TX, eugenol (alternative name) [CCN]+TX, frontalin (alternative name) [CCN]+TX, gossyplure (alternative name) (420)+TX, grandlure (421)+TX, grandlure I (alternative name) (421)+TX, grandlure II (alternative name) (421)+TX, grandlure III (alternative name) (421)+TX, grandlure IV (alternative name) (421)+TX, hexalure [CCN]+TX, ipsdienol (alternative name) [CCN]+TX, ipsenol (alternative name) [CCN]+TX, japonilure (alternative name) (481)+TX, lineatin (alternative name) [CCN]+TX, litlure (alternative name) [CCN]+TX, looplure (alternative name) [CCN]+TX, medlure [CCN]+TX, megatomoic acid (alternative name) [CCN]+TX, methyl eugenol (alternative name) (540)+TX, muscalure (563)+TX, octadeca-2,13-dien-1-yl acetate (IUPAC name) (588)+TX, octadeca-3,13-dien-1-yl acetate (IUPAC name) (589)+TX, orfralure (alternative name) [CCN]+TX, oryctalure (alternative name) (317)+TX, ostramone (alternative name) [CCN]+TX, siglure [CCN]+TX, sordidin (alternative name) (736)+TX, sulcatol (alternative name) [CCN]+TX, tetradec-11-en-1-yl acetate (IUPAC name) (785)+TX, trimedlure (839)+TX, trimedlure A (alternative name) (839)+TX, trimedlure $B_1$ (alternative name) (839)+TX, trimedlure $B_2$ (alternative name) (839)+TX, trimedlure C (alternative name) (839) and trunc-call (alternative name) [CCN]+TX;

an insect repellent selected from the group of substances consisting of 2-(octylthio)ethanol (IUPAC name) (591)+TX, butopyronoxyl (933)+TX, butoxy(polypropylene glycol) (936)+TX, dibutyl adipate (IUPAC name) (1046)+TX, dibutyl phthalate (1047)+TX, dibutyl succinate (IUPAC name) (1048)+TX, diethyltoluamide [CCN]+TX, dimethyl carbate [CCN]+TX, dimethyl phthalate [CCN]+TX, ethyl hexanediol (1137)+TX, hexamide [CCN]+TX, methoquin-butyl (1276)+TX, methylneodecanamide [CCN]+TX, oxamate [CCN] and picaridin [CCN]+TX; a molluscicide selected from the group of substances consisting of bis(tributyltin) oxide (IUPAC name) (913)+TX, bromoacetamide [CCN]+TX, calcium arsenate [CCN]+TX, cloethocarb (999)+TX, copper acetoarsenite [CCN]+TX, copper sulfate (172)+TX, fentin (347)+TX, ferric phosphate (IUPAC name) (352)+TX, metaldehyde (518)+TX, methiocarb (530)+TX, niclosamide (576)+TX, niclosamide-olamine (576)+TX, pentachlorophenol (623)+TX, sodium pentachlorophenoxide (623)+TX, tazimcarb (1412)+TX, thiodicarb (799)+TX, tributyltin oxide (913)+TX, trifenmorph (1454)+TX, trimethacarb (840)+TX, triphenyltin acetate (IUPAC name) (347) and triphenyltin hydroxide (IUPAC name) (347)+TX, pyriprole [394730-71-3]+TX;

a nematicide selected from the group of substances consisting of AKD-3088 (compound code)+TX, 1,2-dibromo-3-chloropropane (IUPAC/Chemical Abstracts name) (1045)+TX, 1,2-dichloropropane (IUPAC/Chemical Abstracts name) (1062)+TX, 1,2-dichloropropane with 1,3-dichloropropene (IUPAC name) (1063)+TX, 1,3-dichloropropene (233)+TX, 3,4-dichlorotetrahydrothiophene 1,1-dioxide (IUPAC/Chemical Abstracts name) (1065)+TX, 3-(4-chlorophenyl)-5-methylrhodanine (IUPAC name) (980)+TX, 5-methyl-6-thioxo-1,3,5-thiadiazinan-3-ylacetic acid (IUPAC name) (1286)+TX, 6-isopentenylaminopurine (alternative name) (210)+TX, abamectin (1)+TX, acetoprole [CCN]+TX, alanycarb (15)+TX, aldicarb (16)+TX, aldoxycarb (863)+TX, AZ 60541 (compound code)+TX, benclothiaz [CCN]+TX, benomyl (62)+TX, butylpyridaben (alternative name)+TX, cadusafos (109)+TX, carbofuran (118)+TX, carbon disulfide (945)+TX, carbosulfan (119)+TX, chloropicrin (141)+TX, chlorpyrifos (145)+TX, cloethocarb (999)+TX, Cyclobutrifluram+TX, cytokinins (alternative name) (210)+TX, dazomet (216)+TX, DBCP (1045)+TX, DCIP (218)+TX, diamidafos (1044)+TX, dichlofenthion (1051)+TX, dicliphos (alternative name)+TX, dimethoate (262)+TX, doramectin (alternative name) [CCN]+TX, emamectin (291)+TX, emamectin benzoate (291)+TX, eprinomectin (alternative name) [CCN]+TX, ethoprophos (312)+TX, ethylene dibromide (316)+TX, fenamiphos (326)+TX, fenpyrad (alternative name)+TX, fensulfothion (1158)+TX, fosthiazate (408)+TX, fosthietan (1196)+TX, furfural (alternative name) [CCN]+TX, GY-81 (development code) (423)+TX, heterophos [CCN]+TX, iodomethane (IUPAC name) (542)+TX, isamidofos (1230)+TX, isazofos (1231)+TX, ivermectin (alternative name) [CCN]+TX, kinetin (alternative name) (210)+TX, mecarphon (1258)+TX, metam (519)+TX, metam-potassium (alternative name) (519)+TX, metam-sodium (519)+TX, methyl bromide (537)+TX, methyl isothiocyanate (543)+TX, milbemycin oxime (alternative name) [CCN]+TX, moxidectin (alternative name) [CCN]+TX, *Myrothecium verrucaria* composition (alternative name) (565)+TX, NC-184 (compound code)+TX, oxamyl (602)+TX, phorate (636)+TX, phosphamidon (639)+TX, phosphocarb [CCN]+TX, sebufos (alternative name)+TX, selamectin (alternative name) [CCN]+TX, spinosad (737)+TX, terbam (alternative name)+TX, terbufos (773)+TX, tetrachlorothiophene (IUPAC/Chemical Abstracts name) (1422)+TX, thiafenox (alternative name)+TX, thionazin (1434)+TX, triazophos (820)+TX, triazuron (alternative name)+TX, xylenols [CCN]+TX, YI-5302 (compound code) and zeatin (alternative name) (210)+TX, fluensulfone [318290-98-1]+TX, fluopyram+TX;

a nitrification inhibitor selected from the group of substances consisting of potassium ethylxanthate [CCN] and nitrapyrin (580)+TX;

a plant activator selected from the group of substances consisting of acibenzolar (6)+TX, acibenzolar-S-methyl (6)+TX, probenazole (658) and *Reynoutria sachalinensis* extract (alternative name) (720)+TX;

a rodenticide selected from the group of substances consisting of 2-isovalerylindan-1,3-dione (IUPAC name) (1246)+TX, 4-(quinoxalin-2-ylamino)benzenesulfonamide (IUPAC name) (748)+TX, alpha-chlorohydrin [CCN]+TX, aluminium phosphide (640)+TX, antu (880)+TX, arsenous oxide (882)+TX, barium carbonate (891)+TX, bisthiosemi (912)+TX, brodifacoum (89)+TX, bromadiolone (including alpha-bromadiolone)+TX, bromethalin (92)+TX, calcium cyanide (444)+TX, chloralose (127)+TX, chlorophacinone (140)+TX, cholecalciferol (alternative name) (850)+TX, coumachlor (1004)+TX, coumafuryl (1005)+TX, coumatetralyl (175)+TX, crimidine (1009)+TX, difenacoum (246)+TX, difethialone (249)+TX, diphacinone (273)+TX, ergocalciferol (301)+TX, flocoumafen (357)+TX, fluoroacetamide (379)+TX, flupropadine (1183)+TX, flupropadine hydrochloride (1183)+TX, gamma-HCH (430)+TX, HCH (430)+TX, hydrogen cyanide (444)+TX, iodomethane (IUPAC name) (542)+TX, lindane (430)+TX, magnesium phosphide (IUPAC name) (640)+TX, methyl bromide (537)+TX, norbormide (1318)+TX, phosacetim (1336)+TX, phosphine (IUPAC name) (640)+TX, phosphorus [CCN]+TX, pindone (1341)+TX, potassium arsenite [CCN]+TX, pyrinuron (1371)+TX, scilliroside (1390)+TX, sodium arsenite [CCN]+TX, sodium cyanide (444)+TX, sodium fluoroacetate (735)+TX, strychnine (745)+TX, thallium sulfate [CCN]+TX, warfarin (851) and zinc phosphide (640)+TX; a synergist selected from the group of substances consisting of 2-(2-butoxyethoxy)ethyl piperonylate (IUPAC name) (934)+TX, 5-(1,3-benzodioxol-5-yl)-3-hexylcyclohex-2-enone (IUPAC name) (903)+TX, farnesol with nerolidol (alternative name) (324)+TX, MB-599 (development code) (498)+TX, MGK 264 (development code) (296)+TX, piperonyl butoxide (649)+TX, piprotal (1343)+TX, propyl isomer (1358)+TX, $S_{421}$ (development code) (724)+TX, sesamex (1393)+TX, sesasmolin (1394) and sulfoxide (1406)+TX;

an animal repellent selected from the group of substances consisting of anthraquinone (32)+TX, chloralose (127)+TX, copper naphthenate [CCN]+TX, copper oxychloride (171)+TX, diazinon (227)+TX, dicyclopentadiene (chemical name) (1069)+TX, guazatine (422)+TX, guazatine acetates (422)+TX, methiocarb (530)+TX, pyridin-4-amine (IUPAC name) (23)+TX, thiram (804)+TX, trimethacarb (840)+TX, zinc naphthenate [CCN] and ziram (856)+TX; a virucide selected from the group of substances consisting of imanin (alternative name) [CCN] and ribavirin (alternative name) [CCN]+TX;

a wound protectant selected from the group of substances consisting of mercuric oxide (512)+TX, octhilinone (590) and thiophanate-methyl (802)+TX;

a biologically active substance selected from 1,1-bis(4-chloro-phenyl)-2-ethoxyethanol+TX, 2,4-dichlorophenyl benzenesulfonate+TX, 2-fluoro-N-methyl-N-1-naphthylacetamide+TX, 4-chlorophenyl phenyl sulfone+TX, acetoprole+TX, aldoxycarb+TX, amidithion+TX, amidothioate+TX, amiton+TX, amiton hydrogen oxalate+TX, amitraz+TX, aramite+TX, arsenous oxide+TX, azobenzene+TX, azothoate+TX, benomyl+TX, benoxa-fos+TX, benzyl benzoate+TX, bixafen+TX, brofenvalerate+TX, bromo-cyclen+TX, bromophos+TX, bromopropylate+TX, buprofezin+TX, butocarboxim+TX, butoxycarboxim+TX, butylpyridaben+TX, calcium polysulfide+TX, camphechlor+TX, carbanolate+TX, carbophenothion+TX, cymiazole+TX, chino-methionat+TX, chlorbenside+TX, chlordimeform+TX, chlordimeform hydrochloride+TX, chlorfenethol+TX, chlorfenson+TX, chlorfensulfide+TX, chlorobenzilate+TX, chloromebuform+TX, chloromethiuron+TX, chloropropylate+TX, chlorthiophos+TX, cinerin I+TX, cinerin II+TX, cinerins+TX, closantel+TX, coumaphos+

TX, crotamiton+TX, crotoxyphos+TX, cufraneb+TX, cyanthoate+TX, DCPM+TX, DDT+TX, demephion+TX, demephion-O+TX, demephion-S+TX, demeton-methyl+TX, demeton-O+TX, demeton-O-methyl+TX, demeton-S+TX, demeton-S-methyl+TX, demeton-S-methylsulfon+TX, dichlofluanid+TX, dichlorvos+TX, dicliphos+TX, dienochlor+TX, dimefox+TX, dinex+TX, dinex-diclexine+TX, dinocap-4+TX, dinocap-6+TX, dinocton+TX, dino-penton+TX, dinosulfon+TX, dinoterbon+TX, dioxathion+TX, diphenyl sulfone+TX, disulfiram+TX, DNOC+TX, dofenapyn+TX, doramectin+TX, endothion+TX, eprinomectin+TX, ethoate-methyl+TX, etrimfos+TX, fenazaflor+TX, fenbutatin oxide+TX, fenothiocarb+TX, fenpyrad+TX, fen-pyroximate+TX, fenpyrazamine+TX, fenson+TX, fentrifanil+TX, flubenzimine+TX, flucycloxuron+TX, fluenetil+TX, fluorbenside+TX, FMC 1137+TX, formetanate+TX, formetanate hydrochloride+TX, formparanate+TX, gamma-HCH+TX, glyodin+TX, halfenprox+TX, hexadecyl cyclopropanecarboxylate+TX, isocarbophos+TX, jasmolin I+TX, jasmolin II+TX, jodfenphos+TX, lindane+TX, malonoben+TX, mecarbam+TX, mephosfolan+TX, mesulfen+TX, methacrifos+TX, methyl bromide+TX, metolcarb+TX, mexacarbate+TX, milbemycin oxime+TX, mipafox+TX, monocrotophos+TX, morphothion+TX, moxidectin+TX, naled+TX, 4-chloro-2-(2-chloro-2-methyl-propyl)-5-[(6-iodo-3-pyridyl)methoxy]pyridazin-3-one+TX, nifluridide+TX, nikkomycins+TX, nitrilacarb+TX, nitrilacarb 1:1 zinc chloride complex+TX, omethoate+TX, oxydeprofos+TX, oxydisulfoton+TX, pp'-DDT+TX, parathion+TX, permethrin+TX, phenkapton+TX, phosalone+TX, phosfolan+TX, phosphamidon+TX, polychloroterpenes+TX, polynactins+TX, proclonol+TX, promacyl+TX, propoxur+TX, prothidathion+TX, prothoate+TX, pyrethrin I+TX, pyrethrin II+TX, pyrethrins+TX, pyridaphenthion+TX, pyrimitate+TX, quinalphos+TX, quintiofos+TX, R-1492+TX, phosglycin+TX, rotenone+TX, schradan+TX, sebufos+TX, selamectin+TX, sophamide+TX, SSI-121+TX, sulfiram+TX, sulfluramid+TX, sulfotep+TX, sulfur+TX, diflovidazin+TX, tau-fluvalinate+TX, TEPP+TX, terbam+TX, tetradifon+TX, tetrasul+TX, thiafenox+TX, thiocarboxime+TX, thiofanox+TX, thiometon+TX, thioquinox+TX, thuringiensin+TX, triamiphos+TX, triarathene+TX, triazophos+TX, triazuron+TX, trifenofos+TX, trinactin+TX, vamidothion+TX, vaniliprole+TX, bethoxazin+TX, copper dioctanoate+TX, copper sulfate+TX, cybutryne+TX, dichlone+TX, dichlorophen+TX, endothal+TX, fentin+TX, hydrated lime+TX, nabam+TX, quinoclamine+TX, quinonamid+TX, simazine+TX, triphenyltin acetate+TX, triphenyltin hydroxide+TX, crufomate+TX, piperazine+TX, thiophanate+TX, chloralose+TX, fenthion+TX, pyridin-4-amine+TX, strychnine+TX, 1-hydroxy-1H-pyridine-2-thione+TX, 4-(quinoxalin-2-ylamino)benzenesulfonamide+TX, 8-hydroxyquinoline sulfate+TX, bronopol+TX, copper hydroxide+TX, cresol+TX, dipyrithione+TX, dodicin+TX, fenaminosulf+TX, formaldehyde+TX, hydrargaphen+TX, kasugamycin+TX, kasugamycin hydrochloride hydrate+TX, nickel bis (dimethyldithiocarbamate)+TX, nitrapyrin+TX, octhilinone+TX, oxolinic acid+TX, oxytetracycline+TX, potassium hydroxyquinoline sulfate+TX, probenazole+TX, streptomycin+TX, streptomycin sesquisulfate+TX, tecloftalam+TX, thiomersal+TX, *Adoxophyes orana* GV+TX, *Agrobacterium radiobacter*+TX, *Amblyseius* spp.+TX, *Anagrapha falcifera* NPV+TX, *Anagrus atomus*+TX, *Aphelinus abdominalis*+TX, *Aphidius colemani*+TX, *Aphidoletes aphidimyza*+TX, *Autographa californica* NPV+TX, *Bacillus sphaericus* Neide+TX, *Beauveria brongniartii*+TX, *Chrysoperla carnea*+TX, *Cryptolaemus montrouzieri*+TX, *Cydia pomonella* GV+TX, *Dacnusa sibirica*+TX, *Diglyphus isaea*+TX, *Encarsia formosa*+TX, *Eretmocerus eremicus*+TX, *Heterorhabditis bacteriophora* and *H. megidis*+TX, *Hippodamia convergens*+TX, *Leptomastix dactylopii*+TX, *Macrolophus caliginosus*+TX, *Mamestra brassicae* NPV+TX, *Metaphycus helvolus*+TX, *Metarhizium anisopliae* var. *acridum*+TX, *Metarhizium anisopliae* var. *anisopliae*+TX, *Neodiprion sertifer* NPV and *N. lecontei* NPV+TX, *Orius* spp.+TX, *Paecilomyces fumosoroseus*+TX, *Phytoseiulus persimilis*+TX, *Steinernema bibionis*+TX, *Steinernema carpocapsae*+TX, *Steinernema feltiae*+TX, *Steinernema glaseri*+TX, *Steinernema riobrave*+TX, *Steinernema riobravis*+TX, *Steinernema scapterisci*+TX, *Steinernema* spp.+TX, *Trichogramma* spp.+TX, *Typhlodromus occidentalis*+TX, *Verticillium lecanii*+TX, apholate+TX, bisazir+TX, busulfan+TX, dimatif+TX, hemel+TX, hempa+TX, metepa+TX, methiotepa+TX, methyl apholate+TX, morzid+TX, penfluron+TX, tepa+TX, thiohempa+TX, thiotepa+TX, tretamine+TX, uredepa+TX, (E)-dec-5-en-1-yl acetate with (E)-dec-5-en-1-ol+TX, (E)-tridec-4-en-1-yl acetate+TX, (E)-6-methylhept-2-en-4-ol+TX, (E,Z)-tetradeca-4,10-dien-1-yl acetate+TX, (Z)-dodec-7-en-1-yl acetate+TX, (Z)-hexadec-11-enal+TX, (Z)-hexadec-11-en-1-yl acetate+TX, (Z)-hexadec-13-en-11-yn-1-yl acetate+TX, (Z)-icos-13-en-10-one+TX, (Z)-tetradec-7-en-1-al+TX, (Z)-tetradec-9-en-1-ol+TX, (Z)-tetradec-9-en-1-yl acetate+TX, (7E,9Z)-dodeca-7,9-dien-1-yl acetate+TX, (9Z,11E)-tetradeca-9,11-dien-1-yl acetate+TX, (9Z,12E)-tetradeca-9,12-dien-1-yl acetate+TX, 14-methyloctadec-1-ene+TX, 4-methylnonan-5-ol with 4-methylnonan-5-one+TX, alpha-multistriatin+TX, brevicomin+TX, codlelure+TX, codlemone+TX, cuelure+TX, disparlure+TX, dodec-8-en-1-yl acetate+TX, dodec-9-en-1-yl acetate+TX, dodeca-8+TX, 10-dien-1-yl acetate+TX, dominicalure+TX, ethyl 4-methyloctanoate+TX, eugenol+TX, frontalin+TX, grandlure+TX, grandlure I+TX, grandlure II+TX, grandlure III+TX, grandlure IV+TX, hexalure+TX, ipsdienol+TX, ipsenol+TX, japonilure+TX, lineatin+TX, litlure+TX, looplure+TX, medlure+TX, megatomoic acid+TX, methyl eugenol+TX, muscalure+TX, octadeca-2,13-dien-1-yl acetate+TX, octadeca-3,13-dien-1-yl acetate+TX, orfralure+TX, oryctalure+TX, ostramone+TX, siglure+TX, sordidin+TX, sulcatol+TX, tetradec-11-en-1-yl acetate+TX, trimedlure+TX, trimedlure A+TX, trimedlure $B_1$+TX, trimedlure $B_2$+TX, trimedlure C+TX, trunc-call+TX, 2-(octylthio)-ethanol+TX, butopyronoxyl+TX, butoxy(polypropylene glycol)+TX, dibutyl adipate+TX, dibutyl phthalate+TX, dibutyl succinate+TX, diethyltoluamide+TX, dimethyl carbate+TX, dimethyl phthalate+TX, ethyl hexanediol+TX, hexamide+TX, methoquin-butyl+TX, methylneodecanamide+TX, oxamate+TX, picaridin+TX, 1-dichloro-1-nitroethane+TX, 1,1-dichloro-2,2-bis(4-ethylphenyl)-ethane+TX, 1,2-dichloropropane with 1,3-dichloropropene+TX, 1-bromo-2-chloroethane+TX, 2,2,2-trichloro-1-(3,4-dichlorophenyl)ethyl acetate+TX, 2,2-dichlorovinyl 2-ethylsulfinylethyl methyl phosphate+TX, 2-(1,3-dithiolan-2-yl)phenyl dimethylcarbamate+TX, 2-(2-butoxyethoxy)ethyl thiocyanate+TX, 2-(4,5-dimethyl-1,3-dioxolan-2-yl)phenyl methylcarbamate+TX, 2-(4-chloro-3,5-xylyloxy)ethanol+TX, 2-chlorovinyl diethyl phosphate+TX, 2-imidazolidone+TX, 2-isovalerylindan-1,3-dione+TX, 2-methyl(prop-2-ynyl)aminophenyl methylcarbamate+TX, 2-thiocyanatoethyl laurate+TX, 3-bromo-1-chloroprop-1-ene+TX, 3-methyl-1-phenylpyrazol-5-yl dimethyl-carbamate+TX, 4-methyl(prop-2-ynyl)amino-3,5-xylyl methylcarbamate+TX, 5,5-dimethyl-3-oxocyclohex-1-enyl dimethylcarbamate+TX, acethion+TX, acrylonitrile+TX, aldrin+TX, allosamidin+TX, allyxycarb+TX, alpha-ecdysone+TX, aluminium phosphide+TX, aminocarb+TX, anabasine+TX, athidathion+TX, azamethiphos+TX, *Bacillus thuringiensis* delta endotoxins+TX, barium hexafluorosilicate+TX, barium polysulfide+TX, barthrin+TX, Bayer 22/190+TX, Bayer 22408+TX, beta-cyfluthrin+TX, beta-cypermethrin+TX, bioethanomethrin+TX, biopermethrin+TX, bis(2-chloroethyl) ether+TX, borax+TX, bromfenvinfos+TX, bromo-DDT+TX, bufencarb+TX, butacarb+TX, butathiofos+TX, butonate+TX, calcium arsenate+TX, calcium cyanide+TX, carbon disulfide+TX, carbon tetrachloride+TX, cartap hydrochloride+TX, cevadine+TX, chlorbicyclen+TX, chlordane+TX, chlordecone+TX, chloroform+TX, chloropicrin+TX, chlorphoxim+TX, chlorprazophos+TX, cis-resmethrin+TX, cismethrin+TX, clocythrin+TX, copper acetoarsenite+TX, copper arsenate+TX, copper oleate+TX, coumithoate+TX, cryolite+TX, CS 708+TX, cyanofenphos+TX, cyanophos+TX, cyclethrin+TX, cythioate+TX, d-tetramethrin+TX, DAEP+TX, dazomet+TX, decarbofuran+TX, diamidafos+TX, dicapthon+TX, dichlofenthion+TX, dicresyl+TX, dicyclanil+TX, dieldrin+TX, diethyl 5-methylpyrazol-3-yl phosphate+TX, dilor+TX, dimefluthrin+TX, dimetan+TX, dimethrin+TX, dimethylvinphos+TX, dimetilan+TX, dinoprop+TX, dinosam+TX, dinoseb+TX, diofenolan+TX, dioxabenzofos+TX, dithicrofos+TX, DSP+TX, ecdysterone+TX, El 1642+TX, EMPC+TX, EPBP+TX, etaphos+TX, ethiofencarb+TX, ethyl formate+TX, ethylene dibromide+TX, ethylene dichloride+TX, ethylene oxide+TX, EXD+TX, fenchlorphos+TX, fenethacarb+TX, fenitrothion+TX, fenoxacrim+TX, fenpirithrin+TX, fensulfothion+TX, fenthion-ethyl+TX, flucofuron+TX, fosmethilan+TX, fospirate+TX, fosthietan+TX, furathiocarb+TX, furethrin+TX, guazatine+TX, guazatine acetates+TX, sodium tetrathiocarbonate+TX, halfenprox+TX, HCH+TX, HEOD+TX, heptachlor+TX, heterophos+TX, HHDN+TX, hydrogen cyanide+TX, hyquincarb+TX, IPSP+TX, isazofos+TX, isobenzan+TX, isodrin+TX, isofenphos+TX, isolane+TX, isoprothiolane+TX, isoxathion+TX, juvenile hormone I+TX, juvenile hormone II+TX, juvenile hormone III+TX, kelevan+TX, kinoprene+TX, lead arsenate+TX, leptophos+TX, lirimfos+TX, lythidathion+TX, m-cumenyl methylcarbamate+TX, magnesium phosphide+TX, mazidox+TX, mecarphon+TX, menazon+TX, mercurous chloride+TX, mesulfenfos+TX, metam+TX, metam-potassium+TX, metam-sodium+TX, methanesulfonyl fluoride+TX, methocrotophos+TX, methoprene+TX, methothrin+TX, methoxychlor+TX, methyl isothiocyanate+TX, methylchloroform+TX, methylene chloride+TX, metoxadiazone+TX, mirex+TX, naftalofos+TX, naphthalene+TX, NC-170+TX, nicotine+TX, nicotine sulfate+TX, nithiazine+TX, nornicotine+TX, 0-5-dichloro-4-iodophenyl O-ethyl ethylphosphonothioate+TX, O,O-diethyl 0-4-methyl-2-oxo-2H-chromen-7-yl phosphorothioate+TX, O,O-diethyl 0-6-methyl-2-propylpyrimidin-4-yl phosphorothioate+TX, O,O,O',O'-tetrapropyl dithiopyrophosphate+TX, oleic acid+TX, para-dichlorobenzene+TX, parathion-methyl+TX, pentachlorophenol+TX, pentachlorophenyl laurate+TX, PH 60-38+TX, phenkapton+TX, phosnichlor+TX, phosphine+TX, phoxim-methyl+TX, pirimetaphos+TX, polychlorodicyclopentadiene isomers+TX, potassium arsenite+TX, potassium thiocyanate+TX, precocene I+TX, precocene II+TX, precocene III+TX, primidophos+TX, profluthrin+TX, promecarb+TX, prothiofos+TX, pyrazophos+TX, pyresmethrin+TX, quassia+TX, quinalphos-methyl+TX, quinothion+TX, rafoxanide+TX, resmethrin+TX, rotenone+TX, kadethrin+TX, ryania+TX, ryanodine+TX, sabadilla)+TX, schradan+TX, sebufos+TX, SI-0009+TX, thiapronil+TX, sodium arsenite+TX, sodium cyanide+TX, sodium fluoride+TX, sodium hexafluorosilicate+TX, sodium pentachlorophenoxide+TX, sodium selenate+TX, sodium thiocyanate+TX, sulcofuron+TX, sulcofuron-sodium+TX, sulfuryl fluoride+TX, sulprofos+TX, tar oils+TX, tazimcarb+TX, TDE+TX, tebupirimfos+TX, temephos+TX, terallethrin+TX, tetrachloroethane+TX, thicrofos+TX, thiocyclam+TX, thiocyclam hydrogen oxalate+TX, thionazin+TX, thiosultap+TX, thiosultap-sodium+TX, tralomethrin+TX, transpermethrin+TX, triazamate+TX, trichlormetaphos-3+TX, trichloronat+TX, trimethacarb+TX, tolprocarb+TX, triclopyricarb+TX, triprene+TX, veratridine+TX, veratrine+TX, XMC+TX, zetamethrin+TX, zinc phosphide+TX, zolaprofos+TX and meperfluthrin+TX, tetramethylfluthrin+TX, bis(tributyltin) oxide+TX, bromoacetamide+TX, ferric phosphate+TX, niclosamide-olamine+TX, tributyltin oxide+TX, pyrimorph+TX, trifenmorph+TX, 1,2-dibromo-3-chloropropane+TX, 1,3-dichloropropene+TX, 3,4-dichlorotetrahydrothiophene 1,1-dioxide+TX, 3-(4-chlorophenyl)-5-methylrhodanine+TX, 5-methyl-6-thioxo-1,3,5-thiadiazinan-3-ylacetic acid+TX, 6-isopentenylaminopurine+TX, 2-fluoro-N-(3-methoxyphenyl)-9H-purin-6-amine+TX, benclothiaz+TX, cytokinins+TX, DCIP+TX, furfural+TX, isamidofos+TX, kinetin+TX, *Myrothecium verrucaria* composition+TX, tetrachlorothiophene+TX, xylenols+TX, zeatin+TX, potassium ethylxanthate+TX, acibenzolar+TX, acibenzolar-S-methyl+TX, *Reynoutria sachalinensis* extract+TX, alpha-chlorohydrin+TX, antu+TX, barium carbonate+TX, bisthiosemi+TX, brodifacoum+TX, bromadiolone+TX, bromethalin+TX, chlorophacinone+TX, cholecalciferol+TX, coumachlor+TX, coumafuryl+TX, coumatetralyl+TX, crimidine+TX, difenacoum+TX, difethialone+TX, diphacinone+TX, ergocalciferol+TX, flocoumafen+TX, fluoroacetamide+TX, flupropadine+TX, flupropadine hydrochloride+TX, norbormide+TX, phosacetim+TX, phosphorus+TX, pindone+TX, pyrinuron+TX, scilliroside+TX, -sodium fluoroacetate+TX, thallium sulfate+TX, warfarin+TX, -2-(2-butoxyethoxy)ethyl piperonylate+TX, 5-(1,3-benzodioxol-5-yl)-3-hexylcyclohex-2-enone+TX, farnesol with nerolidol+TX, verbutin+TX, MGK 264+TX, piperonyl butoxide+TX, piprotal+TX, propyl isomer+TX, S421+TX, sesamex+TX, sesasmolin+TX, sulfoxide+TX, anthraquinone+TX, copper naphthenate+TX, copper oxychloride+TX, dicyclopentadiene+TX, thiram+TX, zinc naphthenate+TX, ziram+TX, imanin+TX, ribavirin+TX, chloroinconazide+TX, mercuric oxide+TX, thiophanate-methyl+TX, azaconazole+TX, bitertanol+TX, bromuconazole+TX, cyproconazole+TX, difenoconazole+TX, diniconazole-+TX, epoxiconazole+TX, fenbuconazole+TX, fluquinconazole+TX, flusilazole+TX, flutriafol+TX, furametpyr+TX, hexaconazole+TX, imazalil-+TX, imiben-conazole+TX, ipconazole+TX, metconazole+TX, myclobutanil+TX, paclobutrazole+TX, pefurazoate+TX, penconazole+TX, prothioconazole+TX, pyrifenox+TX, prochloraz+TX, propiconazole+TX, pyrisoxazole+TX, -simeconazole+TX, tebucon-azole+TX, tetraconazole+TX, triadimefon+TX, triadimenol+TX, triflumizole+TX, triticonazole+TX, ancymidol+TX, fenarimol+TX, nuarimol+TX, bupirimate+TX, dimethirimol+TX, ethirimol+TX, dodemorph+TX, fenpropidin+TX, fenpropimorph+TX, spiroxamine+TX, tridemorph+TX, cyprodinil+TX, mepanipyrim+TX, pyrimethanil+TX, fenpiclonil+TX, fludioxonil+TX, benalaxyl+TX, furalaxyl+TX, -metalaxyl-+TX, Rmetalaxyl+TX, ofurace+TX, oxadixyl+TX, carbendazim+TX, debacarb+TX, fuberidazole-+TX, thiabendazole+TX, chlozolinate+TX, dichlozoline+TX, myclozoline-+TX, procymidone+TX, vinclozoline+TX, boscalid+TX, carboxin+TX, fenfuram+TX, flutolanil+TX, mepronil+TX, oxycarboxin+TX, penthiopyrad+TX, thifluzamide+TX, dodine+TX, iminoctadine+TX, azoxystrobin+TX, dimoxystrobin+TX, enestroburin+TX, fenaminstrobin+TX, flufenoxystrobin+TX, fluoxastrobin+TX, kresoxim-methyl+TX, metominostrobin+TX, trifloxystrobin+TX, orysastrobin+TX, picoxystrobin+TX, pyraclostrobin+TX, pyrametostrobin+TX, pyraoxystrobin+TX, ferbam+TX, mancozeb+TX, maneb+TX, metiram+TX, propineb+TX, zineb+TX, captafol+TX, captan+TX, fluoroimide+TX, folpet+TX, tolylfluanid+TX, bordeaux mixture+TX, copper oxide+TX, mancopper+TX, oxine-copper+TX, nitrothal-isopropyl+TX, edifenphos+TX, iprobenphos+TX, phosdiphen+TX, tolclofos-methyl+TX, anilazine+TX, benthiavalicarb+TX, blasticidin-S+TX, chloroneb-+TX, chloro-thalonil+TX, cyflufenamid+TX, cymoxanil+TX, cyclobutrifluram+TX, diclocymet+TX, diclomezine-+TX, dicloran+TX, diethofencarb+TX, dimethomorph-+TX, flumorph+TX, dithianon+TX, ethaboxam+TX, etridiazole+TX, famoxadone+TX, fenamidone+TX, fenoxanil+TX, ferimzone+TX, fluazinam+TX, fluopicolide+TX, flusulfamide+TX, fluxapyroxad+TX,-fenhexamid+TX, fosetyl-aluminium-+TX, hymexazol+TX, iprovalicarb+TX, cyazofamid+TX, methasulfocarb+TX, metrafenone+TX, pencycuron+TX, phthalide+TX, polyoxins+TX, propamocarb+TX, pyribencarb+TX, proquinazid+TX, pyroquilon+TX, pyriofenone+TX, quinoxyfen+TX, quintozene+TX, tiadinil+TX, triazoxide+TX, tricyclazole+TX, triforine+TX, validamycin+TX, valifenalate+TX, zoxamide+TX, mandipropamid+TX, flubeneteram+TX, isopyrazam+TX, sedaxane+TX, benzovindiflupyr+TX, pydiflumetofen+TX, 3-difluoromethyl-1-methyl-1H-pyrazole-4-carboxylic acid (3',4',5'-trifluoro-biphenyl-2-yl)-amide+TX, isoflucypram+TX, isotianil+TX, dipymetitrone+TX, 6-ethyl-5,7-dioxo-pyrrolo[4,5][1,4]dithiino[1,2-c]isothiazole-3-carbonitrile+TX, 2-(difluoromethyl)-N-[3-ethyl-1,1-dimethyl-indan-4-yl] pyridine-3-carboxamide+TX, 4-(2,6-difluorophenyl)-6-methyl-5-phenyl-pyridazine-3-carbonitrile+TX, (R)-3-(difluoromethyl)-1-methyl-N-[1,1,3-trimethylindan-4-yl]pyrazole-4-carboxamide+TX, 4-(2-bromo-4-fluoro-phenyl)-N-(2-chloro-6-fluoro-phenyl)-2,5-dimethyl-pyrazol-3-amine+TX, 4-(2-bromo-4-fluorophenyl)-N-(2-chloro-6-fluorophenyl)-1,3-dimethyl-1H-pyrazol-5-amine+TX, fluindapyr+TX, coumethoxystrobin (jiaxiangjunzhi)+TX, Ivbenmixianan+TX, dichlobentiazox+TX, mandestrobin+TX, 3-(4,4-difluoro-3,4-dihydro-3,3-dimethylisoquinolin-1-yl)quinolone+TX, 2-[2-fluoro-6-[(8-fluoro-2-methyl-3-quinolyl)oxy]phenyl]propan-2-ol+TX, oxathiapiprolin+TX, tert-butyl N-[6-[[[(1-methyltetrazol-5-yl)-phenyl-methylene]amino]oxymethyl]-2-pyridyl]carbamate+TX, pyraziflumid+TX, inpyrfluxam+TX, trolprocarb+TX, mefentrifluconazole+TX, ipfentrifluconazole+TX, 2-(difluoromethyl)-N-[(3R)-3-ethyl-1,1-dimethyl-indan-4-yl]pyridine-3-carboxamide+TX, N'-(2,5-dimethyl-4-phenoxy-phenyl)-N-ethyl-N-methyl-formamidine+TX, N'-[4-(4,5-dichlorothiazol-2-yl)oxy-2,5-dimethyl-phenyl]-N-ethyl-N-methyl-formamidine+TX, [2-[3-[2-[1-[2-[3,5-bis(difluoromethyl)pyrazol-1-yl]acetyl]-4-piperidyl] thiazol-4-yl]-4,5-dihydroisoxazol-5-yl]-3-chloro-phenyl]methanesulfonate+TX, but-3-ynyl N-[6-[[(Z)-[(1-methyltetrazol-5-yl)-phenyl-methylene]amino] oxymethyl]-2-pyridyl]carbamate+TX, methyl N-[[5-[4-(2,4-dimethylphenyl)triazol-2-yl]-2-methyl-phenyl] methyl]carbamate+TX, 3-chloro-6-methyl-5-phenyl-4-(2,4,6-trifluorophenyl)pyridazine+TX, pyridachlometyl+TX, 3-(difluoromethyl)-1-methyl-N-[1,1,3-trimethylindan-4-yl]pyrazole-4-carboxamide+TX, 1-[2-[[1-(4-chlorophenyl)pyrazol-3-yl]oxymethyl]-3-methyl-phenyl]-4-methyl-tetrazol-5-one+TX, 1-methyl-4-[3-methyl-2-[[2-methyl-4-(3,4,5-trimethylpyrazol-1-yl)phenoxy]methyl]phenyl]tetrazol-5-one+TX, aminopyrifen+TX, ametoctradin+TX, amisulbrom+TX, penflufen+TX, (Z,2E)-5-[1-(4-chlorophenyl)pyrazol-3-yl]oxy-2-methoxyimino-N,3-dimethyl-pent-3-enamide+TX, florylpicoxamid+TX, fenpicoxamid+TX, tebufloquin+TX, ipflufenoquin+TX, quinofumelin+TX, isofetamid+TX, N-[2-[2,4-dichloro-phenoxy]phenyl]-3-(difluoromethyl)-1-methyl-pyrazole-4-carboxamide+TX, N-[2-[2-chloro-4-(trifluoromethyl)phenoxy]phenyl]-3-(difluoromethyl)-1-methyl-pyrazole-4-carboxamide+TX, benzothiostrobin+TX, phenamacril+TX, 5-amino-1,3,4-thiadiazole-2-thiol zinc salt (2:1)+TX, fluopyram+TX, flutianil+TX, fluopimomide+TX, pyrapropoyne+TX, picarbutrazox+TX, 2-(difluoromethyl)-N-(3-ethyl-1,1-dimethyl-indan-4-yl)pyridine-3-carboxamide+TX, 2-(difluoromethyl)-N-((3R)-1, 1, 3-trimethylindan-4-yl) pyridine-3-carboxamide+TX, 4-[[6-[2-(2,4-difluorophenyl)-1,1-difluoro-2-hydroxy-3-(1,2,4-triazol-1-yl)propyl]-3-pyridyl]oxy]benzonitrile+TX, metyltetraprole+TX, 2-(difluoromethyl)-N-((3R)-1, 1, 3-trimethylindan-4-yl) pyridine-3-carboxamide+TX, α-(1, 1-dimethylethyl)-α-[4'-(trifluoromethoxy) [1, 1'-biphenyl]-4-yl]-5-pyrimidinemethanol+TX, fluoxapiprolin+TX, enoxastrobin+TX, 4-[[6-[2-(2,4-difluorophenyl)-1,1-difluoro-2-hydroxy-3-(1,2,4-triazol-1-yl)propyl]-3-pyridyl]oxy]benzonitrile+TX, 4-[[6-[2-(2,4-difluorophenyl)-1,1-difluoro-2-hydroxy-3-(5-sulfanyl-1,2,4-triazol-1-yl)propyl]-3-pyridyl]oxy] benzonitrile+TX, 4-[[6-[2-(2,4-difluorophenyl)-1,1-difluoro-2-hydroxy-3-(5-thioxo-4H-1,2,4-triazol-1-yl) propyl]-3-pyridyl]oxy]benzonitrile+TX, trinexapac+TX, coumoxystrobin+TX, zhongshengmycin+TX, thiodiazole copper+TX, zinc thiazole+TX, amectotractin+TX, iprodione+TX, N-octyl-N'-[2-(octylamino) ethyl]ethane-1,2-diamine+TX; N'-[5-bromo-2-methyl-6-[(1S)-1-methyl-2-propoxy-ethoxy]-3-pyridyl]-N-ethyl-N-methyl-formamidine+TX, N'-[5-bromo-2-methyl-6-[(1R)-1-methyl-2-propoxy-ethoxy]-3-pyridyl]-N-ethyl-N-methyl-formamidine+TX, N'-[5-bromo-2-methyl-6-(1-methyl-2-propoxy-ethoxy)-3-pyridyl]-N-ethyl-N-methyl-formamidine+TX, N'-[5-chloro-2-methyl-6-(1-methyl-2-propoxy-ethoxy)-3-pyridyl]-N-ethyl-N-methyl-formamidine+TX, N'-[5-bromo-2-methyl-6-(1-methyl-2-propoxy-ethoxy)-3-pyridyl]-N-isopropyl-N-methyl-formamidine+TX (these compounds may be prepared from the methods described in WO2015/155075); N'-[5-bromo-2-methyl-6-(2-propoxypropoxy)-3-pyridyl]-N-ethyl-N-methyl-formamidine+TX (this compound may be prepared from the methods described in IPCOM000249876D); N-isopropyl-N'-[5-methoxy-2-methyl-4-(2,2,2-trifluoro-1-hydroxy-1-phenyl-ethyl) phenyl]-N-methyl-formamidine+TX, N'-[4-(1-cyclopropyl-2,2,2-trifluoro-1-hydroxy-ethyl)-5-methoxy-2-methyl-phenyl]-N-isopropyl-N-methyl-formamidine+TX (these compounds may be prepared from the methods described in WO2018/228896); N-ethyl-N'-[5-methoxy-2-methyl-4-[(2-trifluoromethyl)oxetan-2-yl]phenyl]-N-methyl-formamidine+TX, N-ethyl-N'-[5-methoxy-2-methyl-4-[(2-trifluoromethyl) tetrahydrofuran-2-yl]phenyl]-N-methyl-formamidine+TX (these compounds may be prepared from the methods described in WO2019/110427); N-[(1R)-1-benzyl-3-chloro-1-methyl-but-3-enyl]-8-fluoro-quinoline-3-carboxamide+TX, N-[(1S)-1-benzyl-3-chloro-1-methyl-but-3-enyl]-8-fluoro-quinoline-3-carboxamide+TX, N-[(1R)-1-benzyl-3,3,3-trifluoro-1-methyl-propyl]-8-fluoro-quinoline-3-carboxamide+TX, N-[(1S)-1-benzyl-3,3,3-trifluoro-1-methyl-propyl]-8-fluoro-quinoline-3-carboxamide+TX, N-[(1R)-1-benzyl-1,3-dimethyl-butyl]-7,8-difluoro-quinoline-3-carboxamide+TX, N-[(1S)-1-benzyl-1,3-dimethyl-butyl]-7,8-difluoro-quinoline-3-carboxamide+TX, 8-fluoro-N-[(1R)-1-[(3-fluorophenyl)methyl]-1,3-dimethyl-butyl]quinoline-3-carboxamide+TX, 8-fluoro-N-[(1S)-1-[(3-fluorophenyl)methyl]-1,3-dimethyl-butyl]quinoline-3-carboxamide+TX, N-[(1R)-1-benzyl-1,3-dimethyl-butyl]-8-fluoro-quinoline-3-carboxamide+TX, N-[(1S)-1-benzyl-1,3-dimethyl-butyl]-8-fluoro-quinoline-3-carboxamide+TX, N-((1R)-1-benzyl-3-chloro-1-methyl-but-3-enyl)-8-fluoro-quinoline-3-carboxamide+TX, N-((1S)-1-benzyl-3-chloro-1-methyl-but-3-enyl)-8-fluoro-quinoline-3-carboxamide+TX (these compounds may be prepared from the methods described in WO2017/153380); 1-(6,7-dimethylpyrazolo[1,5-a]pyridin-3-yl)-4,4,5-trifluoro-3,3-dimethyl-isoquinoline+TX, 1-(6,7-dimethylpyrazolo[1,5-a]pyridin-3-yl)-4,4,6-trifluoro-3,3-dimethyl-isoquinoline+TX, 4,4-difluoro-3,3-dimethyl-1-(6-methylpyrazolo[1,5-a]pyridin-3-yl)isoquinoline+TX, 4,4-difluoro-3,3-dimethyl-1-(7-methylpyrazolo[1,5-a]pyridin-3-yl)isoquinoline+TX, 1-(6-chloro-7-methyl-pyrazolo[1,5-a]pyridin-3-yl)-4,4-difluoro-3,3-dimethyl-isoquinoline+TX (these compounds may be prepared from the methods described in WO2017/025510); 1-(4,5-dimethylbenzimidazol-1-yl)-4,4,5-trifluoro-3,3-dimethyl-isoquinoline+TX, 1-(4,5-dimethylbenzimidazol-1-yl)-4,4-difluoro-3,3-dimethyl-isoquinoline+TX, 6-chloro-4,4-difluoro-3,3-dimethyl-1-(4-methylbenzimidazol-1-yl)isoquinoline+TX, 4,4-difluoro-1-(5-fluoro-4-methyl-benzimidazol-1-yl)-3,3-dimethyl-isoquinoline+TX, 3-(4,4-difluoro-3,3-dimethyl-1-isoquinolyl)-7,8-dihydro-6H-cyclopenta[e]benzimidazole+TX (these compounds may be prepared from the methods described in WO2016/156085); N-methoxy-N-[[4-[5-(trifluoromethyl)-1,2,4-oxadiazol-3-yl]phenyl]methyl]cyclopropanecarboxamide+TX, N,2-dimethoxy-N-[[4-[5-(trifluoromethyl)-1,2,4-oxadiazol-3-yl]phenyl]methyl]propanamide+TX, N-ethyl-2-methyl-N-[[4-[5-(trifluoromethyl)-1,2,4-oxadiazol-3-yl]phenyl]methyl]propanamide+TX, 1-methoxy-3-methyl-1-[[4-[5-(trifluoromethyl)-1,2,4-oxadiazol-3-yl]phenyl]methyl]urea+TX, 1,3-dimethoxy-1-[[4-[5-(trifluoromethyl)-1,2,4-oxadiazol-3-yl]phenyl]methyl]urea+TX, 3-ethyl-1-methoxy-1-[[4-[5-(trifluoromethyl)-1,2,4-oxadiazol-3-yl]phenyl]methyl]urea+TX, N-[[4-[5-(trifluoromethyl)-1,2,4-oxadiazol-3-yl]phenyl]methyl]propanamide+TX, 4,4-dimethyl-2-[[4-[5-(trifluoromethyl)-1,2,4-oxadiazol-3-yl]phenyl]methyl]isoxazolidin-3-one+TX, 5,5-dimethyl-2-[[4-[5-(trifluoromethyl)-1,2,4-oxadiazol-3-yl]phenyl]methyl]isoxazolidin-3-one+TX, ethyl 1-[[4-[5-(trifluoromethyl)-1,2,4-oxadiazol-3-yl]phenyl]methyl]pyrazole-4-carboxylate+TX, N,N-dimethyl-1-[[4-[5-(trifluoromethyl)-1,2,4-oxadiazol-3-yl]phenyl]methyl]-1,2,4-triazol-3-amine+TX. The compounds in this paragraph may be prepared from the methods described in WO 2017/055473, WO 2017/055469, WO 2017/093348 and WO 2017/118689; 2-[6-(4-chlorophenoxy)-2-(trifluoromethyl)-3-pyridyl]-1-(1,2,4-triazol-1-yl)propan-2-ol+TX (this compound may be prepared from the methods described in WO 2017/029179); 2-[6-(4-bromophenoxy)-2-(trifluoromethyl)-3-pyridyl]-1-(1,2,4-triazol-1-yl)propan-2-ol+TX (this compound may be prepared from the methods described in WO 2017/029179); 3-[2-(1-chlorocyclopropyl)-3-(2-fluorophenyl)-2-hydroxy-propyl]imidazole-4-carbonitrile+TX (this compound may be prepared from the methods described in WO 2016/156290); 3-[2-(1-chlorocyclopropyl)-3-(3-chloro-2-fluoro-phenyl)-2-hydroxy-propyl]imidazole-4-carbonitrile+TX (this compound may be prepared from the methods described in WO 2016/156290); (4-phenoxyphenyl)methyl 2-amino-6-methyl-pyridine-3-carboxylate+TX (this compound may be prepared from the methods described in WO 2014/006945); 2,6-Dimethyl-1H,5H-[1,4]dithiino[2,3-c:5,6-c']dipyrrole-1,3,5,7(2H,6H)-tetrone+TX (this compound may be prepared from the methods described in WO 2011/138281); N-methyl-4-[5-(trifluoromethyl)-1,2,4-oxadiazol-3-yl]benzenecarbothioamide+TX; N-methyl-4-[5-(trifluoromethyl)-1,2,4-oxadiazol-3-yl]benzamide+TX; (Z,2E)-5-[1-(2,4-dichlorophenyl)pyrazol-3-yl]oxy-2-methoxyimino-N,3-dimethyl-pent-3-enamide+TX (this compound may be prepared from the methods described in WO 2018/153707); N'-(2-chloro-5-methyl-4-phenoxy-phenyl)-N-ethyl-N-methyl-formamidine+TX; N'-[2-chloro-4-(2-fluorophenoxy)-5-methyl-phenyl]-N-ethyl-N-methyl-formamidine+TX (this compound may be prepared from the methods described in WO 2016/202742); 2-(difluoromethyl)-N-[(3S)-3-ethyl-1,1-dimethyl-indan-4-yl]pyridine-3-carboxamide+TX (this compound may be prepared from the methods described in WO 2014/095675); (5-methyl-2-pyridyl)-[4-[5-(trifluoromethyl)-1,2,4-oxadiazol-3-yl]phenyl]methanone+TX, (3-methylisoxazol-5-yl)-[4-[5-(trifluoromethyl)-1,2,4-oxadiazol-3-yl]phenyl]methanone+TX (these compounds may be prepared from the methods described in WO 2017/220485); 2-oxo-N-propyl-2-[4-[5-(trifluoromethyl)-1,2,4-oxadiazol-3-yl]phenyl]acetamide+TX (this compound may be prepared from the methods described in WO 2018/065414); ethyl 1-[[5-[5-(trifluoromethyl)-1,2,4-oxadiazol-3-yl]-2-thienyl]methyl]pyrazole-4-carboxylate+TX (this compound may be prepared from the methods described in WO 2018/158365); 2,2-difluoro-N-methyl-2-[4-[5-(trifluoromethyl)-1,2,4-oxadiazol-3-yl]phenyl]acetamide+TX, N-[(E)-methoxyiminomethyl]-4-[5-(trifluoromethyl)-1,2,4-oxadiazol-3-yl]benzamide+TX, N—[(Z)-methoxyiminomethyl]-4-[5-(trifluoromethyl)-1,2,4-oxadiazol-3-yl]benzamide+TX, N—[N-methoxy-C-methyl-carbonimidoyl]-4-[5-(trifluoromethyl)-1,2,4-oxadiazol-3-yl]benzamide+TX (these compounds may be prepared from the methods described in WO 2018/202428);

microbials including: *Acinetobacter Iwoffii*+TX, *Acremonium alternatum*+TX+TX, *Acremonium cephalosporium*+TX+TX, *Acremonium diospyri*+TX, *Acremonium obclavatum*+TX, *Adoxophyes orana granulovirus* (AdoxGV) (Capex®)+TX, *Agrobacterium radiobacter* strain K84 (Galltrol-A®)+TX, *Alternaria alternate*+TX, *Alternaria cassia*+TX, *Alternaria destruens* (Smolder®)+TX, *Ampelomyces quisqualis* (AQ10®)+TX, *Aspergillus flavus* AF36 (AF36®)+TX, *Aspergillus flavus* NRRL 21882 (Aflaguard®)+TX, *Aspergillus* spp.+TX, *Aureobasidium pullulans*+TX, *Azospirillum*+TX, (MicroAZ®+TX, TAZO B®)+TX, *Azotobacter*+TX, *Azotobacter chroocuccum* (Azotomeal®)+TX, *Azotobacter* cysts (Bionatural Blooming Blossoms®)+TX, *Bacillus amyloliquefaciens*+TX, *Bacillus cereus*+TX, *Bacillus chitinosporus* strain CM-1+TX, *Bacillus chitinosporus* strain AQ746+TX, *Bacillus licheniformis* strain HB-2 (Biostart™ Rhizoboost®)+TX, *Bacillus licheniformis* strain 3086 (EcoGuard®+TX, Green Releaf®)+TX, *Bacillus circulans*+TX, *Bacillus firmus* (BioSafe®+TX, BioNem-WP®+TX, VOTiVO®)+TX, *Bacillus firmus* strain 1-1582+TX, *Bacillus macerans*+TX, *Bacillus marismortui*+TX, *Bacillus megaterium*+TX, *Bacillus mycoides* strain AQ726+TX, *Bacillus papillae* (Milky Spore Powder®)+TX, *Bacillus pumilus* spp.+TX, *Bacillus pumilus* strain GB34 (Yield Shield®)+TX, *Bacillus pumilus* strain AQ717+TX, *Bacillus pumilus* strain QST 2808 (Sonata®+TX, Ballad Plus®)+TX, *Bacillus spahericus* (VectoLex®)+TX, *Bacillus* spp.+TX, *Bacillus* spp. strain AQ175+TX, *Bacillus* spp. strain AQ177+TX, *Bacillus* spp. strain AQ178+TX, *Bacillus subtilis* strain QST 713 (CEASE®+TX, Serenade®+TX, Rhapsody®)+TX, *Bacillus subtilis* strain QST 714 (JAZZ®)+TX, *Bacillus subtilis* strain AQ153+TX, *Bacillus subtilis* strain AQ743+TX, *Bacillus subtilis* strain QST3002+TX, *Bacillus subtilis* strain QST3004+TX, *Bacillus subtilis* var. *amyloliquefaciens* strain FZB24 (Taegro®+TX, Rhizopro®)+TX, *Bacillus thuringiensis* Cry 2Ae+TX, *Bacillus thuringiensis* Cry1 Ab+TX, *Bacillus thuringiensis aizawai* GC 91 (Agree®)+TX, *Bacillus thuringiensis israelensis* (BMP123®+TX, Aquabac®+TX, VectoBac®)+TX, *Bacillus thuringiensis kurstaki* (Javelin®+TX, Deliver®+TX, CryMax®+TX, Bonide®+TX, Scutella WP®+TX, Turilav WP®+TX, Astuto®+TX, Dipel WP®+TX, Biobit®+TX, Foray®)+TX, *Bacillus thuringiensis kurstaki* BMP 123 (Baritone®)+TX, *Bacillus thuringiensis kurstaki* HD-1 (Bioprotec-CAF/3P®)+TX, *Bacillus thuringiensis* strain BD #32+TX, *Bacillus thuringiensis* strain AQ52+TX, *Bacillus thuringiensis* var. *aizawai* (XenTari®+TX, DiPel®)+TX, bacteria spp. (GROWMEND@+TX, GROWSWEET®+TX, Shootup®)+TX, bacteriophage of Clavipacter *michiganensis* (AgriPhage®)+TX, Bakflor®+TX, *Beauveria bassiana* (Beaugenic®+TX, Brocaril WP®)+TX, *Beauveria bassiana* GHA (Mycotrol ES®+TX, Mycotrol O®+TX, BotaniGuard®)+TX, *Beauveria brongniartii* (Engerlingspilz®+TX, Schweizer *Beauveria*®+TX, Melocont®)+TX, *Beauveria* spp.+TX, *Botrytis cineria*+TX, *Bradyrhizobium japonicum* (TerraMax®)+TX, *Brevibacillus brevis*+TX, *Bacillus thuringiensis tenebrionis* (Novodor®)+TX, BtBooster+TX, *Burkholderia cepacia* (Deny®+TX, Intercept®+TX, Blue Circle®)+TX, *Burkholderia gladii*+TX, *Burkholderia gladioli*+TX, *Burkholderia* spp.+TX, Canadian thistle fungus (CBH Canadian Bioherbicide®)+TX, *Candida* butyri+TX, *Candida famata*+TX, *Candida fructus*+TX, *Candida glabrata*+TX, *Candida guilliermondii*+TX, *Candida melibiosica*+TX, *Candida oleophila* strain O+TX, *Candida parapsilosis*+TX, *Candida pelliculosa*+TX, *Candida pulcherrima*+TX, *Candida reukaufii*+TX, *Candida saitoana* (Bio-Coat®+TX, Biocure®)+TX, *Candida sake*+TX, *Candida* spp.+TX, *Candida tenius*+TX, *Cedecea dravisae*+TX, *Cellulomonas flavigena*+TX, *Chaetomium cochliodes* (Nova-Cide®)+TX, *Chaetomium globosum* (Nova-Cide®)+TX, *Chromobacterium subtsugae* strain PRAA4-1T (Grandevo®)+TX, *Cladosporium cladosporioides*+TX, *Cladosporium oxysporum*+TX, *Cladosporium chlorocephalum*+TX, *Cladosporium* spp.+TX, *Cladosporium tenuissimum*+TX, *Clonostachys rosea* (EndoFine®)+TX, *Colletotrichum acutatum*+TX, *Coniothyrium minitans* (Cotans WG®)+TX, *Coniothyrium* spp.+TX, *Cryptococcus albidus* (YIELDPLUS®)+TX, *Cryptococcus humicola*+TX, *Cryptococcus infirmominiatus*+TX, *Cryptococcus laurentii*+TX, *Cryptophlebia leucotreta granulovirus* (Cryptex®)+TX, *Cupriavidus campinensis*+TX, *Cydia pomonella granulovirus* (CYD-X®)+TX, *Cydia pomonella granulovirus* (Madex®+TX, Madex Plus®+TX, Madex Max/Carpovirusine®)+TX, *Cylindrobasidium laeve* (Stumpout®)+TX, Cylindrocladium+TX, *Debaryomyces hansenii*+TX, *Drechslera hawaiinensis*+TX, *Enterobacter cloacae*+TX, *Enterobacteriaceae*+TX, *Entomophtora virulenta* (Vektor®)+TX, *Epicoccum nigrum*+TX, *Epicoccum purpurascens*+TX, *Epicoccum* spp.+TX, *Filobasidium floriforme*+TX, *Fusarium acuminatum*+TX, *Fusarium chlamydosporum*+TX, *Fusarium oxysporum* (Fusaclean®/Biofox C®)+TX, *Fusarium proliferatum*+TX, *Fusarium* spp.+TX, *Galactomyces geotrichum*+TX, *Gliocladium catenulatum* (Primastop®+TX, Prestop®)+TX, *Gliocladium roseum*+TX, *Gliocladium* spp. (SoilGard®)+TX, *Gliocladium virens* (Soilgard®)+TX, *Granulovirus* (Granupom®)+TX, *Halobacillus halophilus*+TX, *Halobacillus litoralis*+TX, *Halobacillus trueperi*+TX, *Halomonas* spp.+TX, *Halomonas subglaciescola*+TX, *Halovibrio variabilis*+TX, *Hanseniaspora uvarum*+TX, *Helicoverpa armigera* nucleopolyhedrovirus (Helicovex®)+TX, *Helicoverpa zea* nuclear polyhedrosis virus (Gemstar®)+TX, Isoflavone-*formononetin* (Myconate®)+TX, *Kloeckera apiculata*+TX, *Kloeckera* spp.+TX, *Lagenidium giganteum* (Laginex®)+TX, *Lecanicillium*

*longisporum* (Vertiblast®)+TX, *Lecanicillium muscarium* (Vertikil®)+TX, *Lymantria dispar* nucleopolyhedrosis virus (Disparvirus®)+TX, *Marinococcus halophilus*+TX, *Meira geulakonigii*+TX, *Metarhizium anisopliae* (Met52®)+TX, *Metarhizium anisopliae* (Destruxin WP®)+TX, *Metschnikowia fruticola* (Shemer®)+TX, *Metschnikowia pulcherrima*+TX, *Microdochium dimerum* (Antibot®)+TX, *Micromonospora coerulea*+TX, *Microsphaeropsis ochracea*+TX, *Muscodor albus* 620 (Muscudor®)+TX, *Muscodor roseus* strain A3-5+TX, *Mycorrhizae* spp. (AMykor®+TX, Root Maximizer®)+TX, *Myrothecium verrucaria* strain AARC-0255 (DiTera®)+TX, BROS PLUS®+TX, *Ophiostoma piliferum* strain D97 (Sylvanex®)+TX, *Paecilomyces farinosus*+TX, *Paecilomyces fumosoroseus* (PFR-97®+TX, PreFeRal®)+TX, *Paecilomyces linacinus* (Biostat WP®)+TX, *Paecilomyces lilacinus* strain 251 (MeloCon WG®)+TX, *Paenibacillus polymyxa*+TX, *Pantoea agglomerans* (BlightBan $C_9$-1®)+TX, *Pantoea* spp.+TX, *Pasteuria* spp. (Econem®)+TX, *Pasteuria nishizawae*+TX, *Penicillium aurantiogriseum*+TX, *Penicillium billai* (Jumpstart®+TX, TagTeam®)+TX, *Penicillium brevicompactum*+TX, *Penicillium frequentans*+TX, *Penicillium griseofulvum*+TX, *Penicillium purpurogenum*+TX, *Penicillium* spp.+TX, *Penicillium viridicatum*+TX, *Phlebiopsis gigantean* (Rotstop®)+TX, phosphate solubilizing bacteria (Phosphomeal®)+TX, *Phytophthora cryptogea*+TX, *Phytophthora palmivora* (Devine®)+TX, *Pichia anomala*+TX, *Pichia guilermondii*+TX, *Pichia membranaefaciens*+TX, *Pichia onychis*+TX, *Pichia stipites*+TX, *Pseudomonas aeruginosa*+TX, *Pseudomonas aureofasciens* (Spot-Less Biofungicide®)+TX, *Pseudomonas cepacia*+TX, *Pseudomonas chlororaphis* (AtEze®)+TX, *Pseudomonas corrugate*+TX, *Pseudomonas fluorescens* strain A506 (BlightBan A506®)+TX, *Pseudomonas putida*+TX, *Pseudomonas reactans*+TX, *Pseudomonas* spp.+TX, *Pseudomonas syringae* (Bio-Save®)+TX, *Pseudomonas viridiflava*+TX, *Pseudomons fluorescens* (Zequanox®)+TX, *Pseudozyma flocculosa* strain PF-A22 UL (Sporodex L®)+TX, *Puccinia canaliculata*+TX, *Puccinia thlaspeos* (Wood Warrior®)+TX, *Pythium paroecandrum*+TX, *Pythium oligandrum* (Polygandron®+TX, Polyversum®)+TX, *Pythium periplocum*+TX, *Rhanella aquatilis*+TX, *Rhanella* spp.+TX, *Rhizobia* (Dormal®+TX, Vault®)+TX, *Rhizoctonia*+TX, *Rhodococcus globerulus* strain AQ719+TX, *Rhodosporidium diobovatum*+TX, *Rhodosporidium toruloides*+TX, *Rhodotorula* spp.+TX, *Rhodotorula glutinis*+TX, *Rhodotorula graminis*+TX, *Rhodotorula mucilagnosa*+TX, *Rhodotorula rubra*+TX, *Saccharomyces cerevisiae*+TX, *Salinococcus roseus*+TX, *Sclerotinia minor*+TX, *Sclerotinia minor* (SARRITOR®)+TX, *Scytalidium* spp.+TX, *Scytalidium uredinicola*+TX, *Spodoptera exigua* nuclear polyhedrosis virus (Spod-X®+TX, Spexit®)+TX, *Serratia marcescens*+TX, *Serratia plymuthica*+TX, *Serratia* spp.+TX, *Sordaria fimicola*+TX, *Spodoptera littoralis* nucleopolyhedrovirus (Littovir®)+TX, *Sporobolomyces roseus*+TX, *Stenotrophomonas maltophilia*+TX, *Streptomyces ahygroscopicus*+TX, *Streptomyces albaduncus*+TX, *Streptomyces exfoliates*+TX, *Streptomyces galbus*+TX, *Streptomyces griseoplanus*+TX, *Streptomyces griseoviridis* (Mycostop®)+TX, *Streptomyces lydicus* (Actinovate®)+TX, *Streptomyces lydicus* WYEC-108 (ActinoGrow®)+TX, *Streptomyces violaceus*+TX, *Tilletiopsis minor*+TX, *Tilletiopsis* spp.+TX, *Trichoderma asperellum* (T34 Biocontrol®)+TX, *Trichoderma gamsii* (Tenet®)+TX, *Trichoderma atroviride* (Plantmate®)+TX, *Trichoderma hamatum* TH 382+TX, *Trichoderma harzianum rifai* (Mycostar®)+TX, *Trichoderma harzianum* T-22 (Trianum-P®+TX, PlantShield HCO+TX, RootShield®+TX, Trianum-G®)+TX, *Trichoderma harzianum* T-39 (Trichodex®)+TX, *Trichoderma inhamatum*+TX, *Trichoderma koningii*+TX, *Trichoderma* spp. LC 52 (Sentinel®)+TX, *Trichoderma lignorum*+TX, *Trichoderma longibrachiatum*+TX, *Trichoderma polysporum* (Binab T®)+TX, *Trichoderma taxi*+TX, *Trichoderma virens*+TX, *Trichoderma virens* (formerly *Gliocladium virens* GL-21) (SoilGuard®)+TX, *Trichoderma viride*+TX, *Trichoderma viride* strain ICC 080 (Remedier®)+TX, *Trichosporon pullulans*+TX, *Trichosporon* spp.+TX, *Trichothecium* spp.+TX, *Trichothecium roseum*+TX, *Typhula phacorrhiza* strain 94670+TX, *Typhula phacorrhiza* strain 94671+TX, *Ulocladium atrum*+TX, *Ulocladium oudemansii* (Botry-Zen®)+TX, *Ustilago maydis*+TX, various bacteria and supplementary micronutrients (Natural II®)+TX, various fungi (Millennium Microbes®)+TX, *Verticillium chlamydosporium*+TX, *Verticillium lecanii* (Mycotal®+TX, Vertalec®)+TX, Vip3Aa20 (VIPtera®)+TX, *Virgibaclillus marismortui*+TX, *Xanthomonas campestris* pv. *Poae* (Camperico®)+TX, *Xenorhabdus bovienii*+TX, *Xenorhabdus nematophilus;*

Plant extracts including: pine oil (Retenol®)+TX, azadirachtin (Plasma Neem Oil®+TX, AzaGuard®+TX, MeemAzal®+TX, Molt-X®+TX, Botanical IGR (Neemazad®+TX, Neemix®)+TX, canola oil (Lilly Miller Vegol®)+TX, *Chenopodium ambrosioides* near *ambrosioides* (Requiem®)+TX, *Chrysanthemum* extract (Crisant®)+TX, extract of neem oil (Trilogy®)+TX, essentials oils of *Labiatae* (Botania®)+TX, extracts of clove rosemary peppermint and thyme oil (Garden insect killer®)+TX, Glycinebetaine (Greenstim®)+TX, garlic+TX, lemongrass oil (GreenMatch®)+TX, neem oil+TX, *Nepeta cataria* (Catnip oil)+TX, *Nepeta catarina*+TX, nicotine+TX, oregano oil (MossBuster®)+TX, *Pedaliaceae* oil (Nematon®)+TX, *pyrethrum*+TX, *Quillaja saponaria* (NemaQ®)+TX, *Reynoutria sachalinensis* (Regalia®+TX, Sakalia®)+TX, rotenone (Eco Roten®)+TX, Rutaceae plant extract (Soleo®)+TX, soybean oil (Ortho ecosense®)+TX, tea tree oil (Timorex Gold®)+TX, thymus oil+TX, AGNIQUE® MMF+TX, BugOil®+TX, mixture of rosemary sesame pepermint thyme and cinnamon extracts (EF 300®)+TX, mixture of clove rosemary and peppermint extract (EF 400®)+TX, mixture of clove peppermint garlic oil and mint (Soil Shot®)+TX, kaolin (Screen®)+TX, storage glucam of brown algae (Laminarin®);

pheromones including: blackheaded fireworm pheromone (3M Sprayable Blackheaded Fireworm Pheromone®)+TX, Codling Moth Pheromone (Paramount dispenser-(CM)/Isomate C-Plus®)+TX, Grape Berry Moth Pheromone (3M MEC-GBM Sprayable Pheromone®)+TX, Leafroller pheromone (3M MEC—LR Sprayable Pheromone®)+TX, Muscamone (Snip7 Fly Bait®+TX, Starbar Premium Fly Bait®)+TX, Oriental Fruit Moth Pheromone (3M oriental fruit moth sprayable Pheromone®)+TX, Peachtree Borer Pheromone (Isomate-P®)+TX, Tomato Pinworm Pheromone (3M Sprayable pheromone®)+TX, Entostat powder (extract from palm tree) (Exosex CM®)+TX, (E+TX,Z+TX,Z)-3+TX,8+TX,11 Tetradecatrienyl acetate+TX, (Z+TX,Z+TX,E)-7+TX,11+TX,13-Hexadecatrienal+TX, (E+TX,Z)-7+TX,9-Dodecadien-1-yl acetate+TX, 2-Methyl-1-butanol+TX, Calcium acetate+TX, Scenturion®+TX, Biolure®+TX, Check-Mate®+TX, Lavandulyl senecioate; Macrobials including: *Aphelinus abdominalis*+TX, *Aphidius ervi* (*Aphelinus*-System®)+TX, *Acerophagus papaya*+TX, *Adalia bipunctata* (Adalia-System®)+TX, *Adalia bipunctata* (Adaline®)+TX, *Adalia bipunctata* (Aphidalia®)+TX, *Ageniaspis citricola*+TX, *Ageniaspis fuscicollis*+TX, *Amblyseius andersoni* (Anderline®+TX *andersoni*-System®)+TX, *Amblyseius californicus* (Amblyline®+TX, Spical®)+TX, *Amblyseius cucumeris* (Thripex®+TX, Bugline *cucumeris*®)+TX, *Amblyseius fallacis* (Fallacis®)+TX, *Amblyseius swirskii* (Bugline swirskii®+TX, Swirskii-Mite®)+TX, *Amblyseius womersleyi* (WomerMite®)+TX, *Amitus hesperidum*+TX, *Anagrus atomus*+TX, *Anagyrus fusciventris*+TX, *Anagyrus kamali*+TX, *Anagyrus loecki*+TX, *Anagyrus pseudococci* (Citripar®)+TX, *Anicetus benefices*+TX, *Anisopteromalus calandrae*+TX, *Anthocoris nemoralis* (Anthocoris-System®)+TX, *Aphelinus abdominalis* (Apheline®+TX, Aphiline®)+TX, *Aphelinus asychis*+TX, *Aphidius colemani* (Aphipar®)+TX, *Aphidius ervi* (Ervipar®)+TX, *Aphidius gifuensis*+TX, *Aphidius matricariae* (Aphipar-M®)+TX, *Aphidoletes aphidimyza* (Aphidend®)+TX, *Aphidoletes aphidimyza* (Aphidoline®)+TX, *Aphytis lingnanensis*+TX, *Aphytis melinus*+TX, *Aprostocetus hagenowii*+TX, *Atheta coriaria* (Staphyline®)+TX, *Bombus* spp.+TX, *Bombus terrestris* (Natupol Beehive®)+TX, *Bombus terrestris* (Beeline®+TX, Tripol®)+TX, *Cephalonomia stephanoderis*+TX, *Chilocorus nigritus*+TX, *Chrysoperla carnea* (Chrysoline®)+TX, *Chrysoperla carnea* (Chrysopa®)+TX, *Chrysoperla rufilabris*+TX, *Cirrospilus ingenuus*+TX, *Cirrospilus quadristriatus*+TX, *Citrostichus phyllocnistoides*+TX, *Closterocerus chamaeleon*+TX, *Closterocerus* spp.+TX, *Coccidoxenoides perminutus* (Planopar®)+TX, *Coccophagus cowperi*+TX, *Coccophagus lycimnia*+TX, *Cotesia flavipes*+TX, *Cotesia plutellae*+TX, *Cryptolaemus montrouzieri* (Cryptobug®+TX, Cryptoline®)+TX, *Cybocephalus nipponicus*+TX, *Dacnusa sibirica*+TX, *Dacnusa sibirica* (Minusa®)+TX, *Diglyphus isaea* (Diminex®)+TX, *Delphastus catalinae* (Delphastus®)+TX, *Delphastus pusillus*+TX, *Diachasmimorpha krausii*+TX, *Diachasmimorpha longicaudata*+TX, *Diaparsis jucunda*+TX, *Diaphorencyrtus aligarhensis*+TX, *Diglyphus isaea*+TX, *Diglyphus isaea* (Miglyphus®+TX, Digline®)+TX, *Dacnusa sibirica* (DacDigline®+TX, Minex®)+TX, *Diversinervus* spp.+TX, *Encarsia citrina*+TX, *Encarsia formosa* (*Encarsia* max®+TX, Encarline®+TX, En-Strip®)+TX, *Eretmocerus eremicus* (Enermix®)+TX, *Encarsia guadeloupae*+TX, *Encarsia haitiensis*+TX, *Episyrphus balteatus* (Syrphidend®)+TX, *Eretmoceris siphonini*+TX, *Eretmocerus californicus*+TX, *Eretmocerus eremicus* (Ercal®+TX, Eretline e®)+TX, *Eretmocerus eremicus* (Bemimix®)+TX, *Eretmocerus hayati*+TX, *Eretmocerus mundus* (Bemipar®+TX, Eretline m®)+TX, *Eretmocerus siphonini*+TX, *Exochomus quadripustulatus*+TX, *Feltiella acarisuga* (Spidend®)+TX, *Feltiella acarisuga* (Feltiline®)+TX, *Fopius arisanus*+TX, *Fopius ceratitivorus*+TX, *Formononetin* (Wirless Beehome®)+TX, *Franklinothrips vespiformis* (Vespop®)+TX, *Galendromus occidentalis*+TX, *Goniozus legneri*+TX, *Habrobracon hebetor*+TX, *Harmonia axyridis* (HarmoBeetle®)+TX, *Heterorhabditis* spp. (Lawn Patrol®)+TX, *Heterorhabditis bacteriophora* (NemaShield HB®+TX, Nemaseek®+TX, Terranem-Nam®+TX, Terranem®+TX, Larvanem®+TX, B-Green®+TX, NemAttack®+TX, Nematop®)+TX, *Heterorhabditis megidis* (Nemasys H®+TX, BioNem H®+TX, Exhibitline hm®+TX, Larvanem-M®)+TX, *Hippodamia convergens*+TX, *Hypoaspis aculeifer* (Aculeifer-System®+TX, Entomite-A®)+TX, *Hypoaspis miles* (Hypoline m®+TX, Entomite-M®)+TX, *Lbalia leucospoides*+TX, *Lecanoideus floccissimus*+TX, *Lemophagus errabundus*+TX, *Leptomastidea abnormis*+TX, *Leptomastix dactylopii* (Leptopar®)+TX, *Leptomastix epona*+TX, *Lindorus lophanthae*+TX, *Lipolexis oregmae*+TX, *Lucilia caesar* (Natufly®)+TX, *Lysiphlebus testaceipes*+TX, *Macrolophus caliginosus* (Mirical-N®+TX, Macroline c®+TX, Mirical®)+TX, *Mesoseiulus longipes*+TX, *Metaphycus flavus*+TX, *Metaphycus lounsburyi*+TX, *Micromus angulatus* (Milacewing®)+TX, *Microterys flavus*+TX, *Muscidifurax raptorellus* and *Spalangia cameroni* (Biopar®)+TX, *Neodryinus typhlocybae*+TX, *Neoseiulus californicus*+TX, *Neoseiulus cucumeris* (THRYPEX®)+TX, *Neoseiulus fallacis*+TX, *Nesideocoris tenuis* (NesidioBug®+TX, Nesibug®)+TX, *Ophyra aenescens* (Biofly®)+TX, *Orius insidiosus* (Thripor-I@+TX, Oriline i®)+TX, *Orius laevigatus* (Thripor-L®+TX, Oriline I®)+TX, *Orius majusculus* (Oriline m®)+TX, *Orius strigicollis* (Thripor-S®)+TX, *Pauesia juniperorum*+TX, *Pediobius foveolatus*+TX, *Phasmarhabditis hermaphrodita* (Nemaslug®)+TX, *Phymastichus coffea*+TX, *Phytoseiulus macropilus*+TX, *Phytoseiulus persimilis* (Spidex®+TX, Phytoline p®)+TX, *Podisus maculiventris* (Podisus®)+TX, *Pseudacteon curvatus*+TX, *Pseudacteon obtusus*+TX, *Pseudacteon tricuspis*+TX, *Pseudaphycus maculipennis*+TX, *Pseudleptomastix mexicana*+TX, *Psyllaephagus pilosus*+TX, *Psyttalia concolor* (complex)+TX, *Quadrastichus* spp.+TX, *Rhyzobius lophanthae*+TX, *Rodolia cardinalis*+TX, *Rumina decollate*+TX, *Semielacher petiolatus*+TX, *Sitobion avenae* (Ervibank®)+TX, *Steinernema carpocapsae* (Nematac C®+TX, Millenium®+TX, BioNem C®+TX, NemAttack@+TX, Nemastar®+TX, Capsanem®)+TX, *Steinernema feltiae* (NemaShield®+TX, Nemasys F®+TX, BioNem F®+TX, *Steinernema*-System®+TX, NemAttack®+TX, Nemaplus®+TX, Exhibitline sf®+TX, Scia-rid®+TX, Entonem®)+TX, *Steinernema kraussei* (Nemasys L®+TX, BioNem L®+TX, Exhibitline srb®)+TX, *Steinernema riobrave* (BioVector®+TX, BioVektor®)+TX, *Steinernema scapterisci* (Nematac S®)+TX, *Steinernema* spp.+TX, *Steinernematid* spp. (Guardian Nematodes®)+TX, *Stethorus punctillum* (Stethorus®)+TX, *Tamarixia radiate*+TX, *Tetrastichus setifer*+TX, *Thripobius semiluteus*+TX, *Torymus sinensis*+TX, *Trichogramma brassicae* (Tricholine b®)+TX, *Trichogramma brassicae* (Tricho-Strip®)+TX, *Trichogramma evanescens*+TX, *Trichogramma minutum*+TX, *Trichogramma ostriniae*+TX, *Trichogramma platneri*+TX, *Trichogramma pretiosum*+TX, *Xanthopimpla stemmator;* other biologicals including: abscisic acid+TX, bioSea®+TX, *Chondrostereum purpureum* (Chontrol Paste®)+TX, *Colletotrichum gloeosporioides* (Collego®)+TX,

*Copper Octanoate* (Cueva®)+TX, Delta traps (Trapline d®)+TX, *Erwinia amylovora* (Harpin) (ProAct®+TX, Ni-HIBIT Gold CST®)+TX, Ferri-phosphate (Ferramol®)+TX, Funnel traps (Trapline y®)+TX, Gallex®+TX, Grower's Secret®+TX, Homo-brassonolide+TX, Iron Phosphate (Lilly Miller Worry Free Ferramol Slug & Snail Bait®)+TX, MCP hail trap (Trapline f®)+TX, *Microctonus hyperodae*+TX, *Mycoleptodiscus terrestris* (Des-X®)+TX, BioGain®+TX, Aminomite®+TX, Zenox®+TX, Pheromone trap (Thripline ams®)+TX, potassium bicarbonate (MilStop®)+TX, potassium salts of fatty acids (Sanova®)+TX, potassium silicate solution (Sil-Matrix®)+TX, potassium iodide+potassiumthiocyanate (Enzicur®)+TX, SuffOil-X®+TX, Spider venom+TX, *Nosema locustae* (Semaspore Organic Grasshopper Control®)+TX, Sticky traps (Trapline YF®+TX, Rebell Amarillo®)+TX and Traps (Takitrapline y+b®)+TX; and a safener, such as benoxacor+TX, cloquintocet (including cloquintocet-mexyl)+TX, cyprosulfamide+TX, dichlormid+TX, fenchlorazole (including fenchlorazole-ethyl)+TX, fenclorim+TX, fluxofenim+TX, furilazole+TX, isoxadifen (including isoxadifen-ethyl)+TX, mefenpyr (including mefenpyr-diethyl)+TX, metcamifen+TX and oxabetrinil+TX.

The references in brackets behind the active ingredients, e.g. [3878-19-1]refer to the Chemical Abstracts Registry number. The above described mixing partners are known. Where the active ingredients are included in "The Pesticide Manual" [The Pesticide Manual—A World Compendium; Thirteenth Edition; Editor: C. D. S. TomLin; The British Crop Protection Council], they are described therein under the entry number given in round brackets hereinabove for the particular compound; for example, the compound "abamectin" is described under entry number (1). Where "[CCN]" is added hereinabove to the particular compound, the compound in question is included in the "Compendium of Pesticide Common Names", which is accessible on the internet [A. Wood; Compendium of Pesticide Common Names, Copyright © 1995-2004]; for example, the compound "acetoprole" is described under the internet address http://www.alanwood.net/pesticides/acetoprole.html.

Most of the active ingredients described above are referred to hereinabove by a so-called "common name", the relevant "ISO common name" or another "common name" being used in individual cases. If the designation is not a "common name", the nature of the designation used instead is given in round brackets for the particular compound; in that case, the IUPAC name, the IUPAC/Chemical Abstracts name, a "chemical name", a "traditional name", a "compound name" or a "development code" is used or, if neither one of those designations nor a "common name" is used, an "alternative name" is employed. "CAS Reg. No" means the Chemical Abstracts Registry Number.

The active ingredient mixture of the compounds of formula (I) selected from the compounds defined in the Tables 1 to 35 and Table P1 to P8 with active ingredients described above comprises a compound selected from one compound defined in the Tables 1 to 35 and Table P1 to P8 and an active ingredient as described above preferably in a mixing ratio of from 100:1 to 1:6000, especially from 50:1 to 1:50, more especially in a ratio of from 20:1 to 1:20, even more especially from 10:1 to 1:10, very especially from 5:1 and 1:5, special preference being given to a ratio of from 2:1 to 1:2, and a ratio of from 4:1 to 2:1 being likewise preferred, above all in a ratio of 1:1, or 5:1, or 5:2, or 5:3, or 5:4, or 4:1, or 4:2, or 4:3, or 3:1, or 3:2, or 2:1, or 1:5, or 2:5, or 3:5, or 4:5, or 1:4, or 2:4, or 3:4, or 1:3, or 2:3, or 1:2, or 1:600, or 1:300, or 1:150, or 1:35, or 2:35, or 4:35, or 1:75, or 2:75, or 4:75, or 1:6000, or 1:3000, or 1:1500, or 1:350, or 2:350, or 4:350, or 1:750, or 2:750, or 4:750. Those mixing ratios are by weight.

The mixtures as described above can be used in a method for controlling pests, which comprises applying a composition comprising a mixture as described above to the pests or their environment, with the exception of a method for treatment of the human or animal body by surgery or therapy and diagnostic methods practised on the human or animal body.

The mixtures comprising a compound of formula (I) selected from the compounds defined in the Tables 1 to 35 and Table P1 to P8 and one or more active ingredients as described above can be applied, for example, in a single "ready-mix" form, in a combined spray mixture composed from separate formulations of the single active ingredient components, such as a "tank-mix", and in a combined use of the single active ingredients when applied in a sequential manner, i.e. one after the other with a reasonably short period, such as a few hours or days. The order of applying the compounds of formula (I) and the active ingredients as described above is not essential for working the present invention.

The compositions according to the invention can also comprise further solid or liquid auxiliaries, such as stabilizers, for example unepoxidized or epoxidized vegetable oils (for example epoxidized coconut oil, rapeseed oil or soya oil), antifoams, for example silicone oil, preservatives, viscosity regulators, binders and/or tackifiers, fertilizers or other active ingredients for achieving specific effects, for example bactericides, fungicides, nematocides, plant activators, molluscicides or herbicides.

The compositions according to the invention are prepared in a manner known per se, in the absence of auxiliaries for example by grinding, screening and/or compressing a solid active ingredient and in the presence of at least one auxiliary for example by intimately mixing and/or grinding the active ingredient with the auxiliary (auxiliaries). These processes for the preparation of the compositions and the use of the compounds I for the preparation of these compositions are also a subject of the invention.

The application methods for the compositions, that is the methods of controlling pests of the abovementioned type, such as spraying, atomizing, dusting, brushing on, dressing, scattering or pouring—which are to be selected to suit the intended aims of the prevailing circumstances—and the use of the compositions for controlling pests of the abovementioned type are other subjects of the invention. Typical rates of concentration are between 0.1 and 1000 ppm, preferably between 0.1 and 500 ppm, of active ingredient. The rate of application per hectare is generally 1 to 2000 g of active ingredient per hectare, in particular 10 to 1000 g/ha, preferably 10 to 600 g/ha.

A preferred method of application in the field of crop protection is application to the foliage of the plants (foliar application), it being possible to select frequency and rate of application to match the danger of infestation with the pest in question. Alternatively, the active ingredient can reach the plants via the root system (systemic action), by drenching the locus of the plants with a liquid composition or by incorporating the active ingredient in solid form into the locus of the plants, for example into the soil, for example in the form of granules (soil application). In the case of paddy rice crops, such granules can be metered into the flooded paddy-field.

The compounds of formula (I) of the invention and compositions thereof are also be suitable for the protection of plant propagation material, for example seeds, such as fruit, tubers or kernels, or nursery plants, against pests of the abovementioned type. The propagation material can be treated with the compound prior to planting, for example seed can be treated prior to sowing. Alternatively, the compound can be applied to seed kernels (coating), either by soaking the kernels in a liquid composition or by applying a layer of a solid composition. It is also possible to apply the compositions when the propagation material is planted to the site of application, for example into the seed furrow during drilling. These treatment methods for plant propagation material and the plant propagation material thus treated are further subjects of the invention. Typical treatment rates would depend on the plant and pest/fungi to be controlled and are generally between 1 to 200 grams per 100 kg of seeds, preferably between 5 to 150 grams per 100 kg of seeds, such as between 10 to 100 grams per 100 kg of seeds.

The term seed embraces seeds and plant propagules of all kinds including but not limited to true seeds, seed pieces, suckers, corns, bulbs, fruit, tubers, grains, rhizomes, cuttings, cut shoots and the like and means in a preferred embodiment true seeds.

The present invention also comprises seeds coated or treated with or containing a compound of formula I. The term “coated or treated with and/or containing” generally signifies that the active ingredient is for the most part on the surface of the seed at the time of application, although a greater or lesser part of the ingredient may penetrate into the seed material, depending on the method of application. When the said seed product is (re)planted, it may absorb the active ingredient. In an embodiment, the present invention makes available a plant propagation material adhered thereto with a compound of formula I. Further, it is hereby made available, a composition comprising a plant propagation material treated with a compound of formula I.

Seed treatment comprises all suitable seed treatment techniques known in the art, such as seed dressing, seed coating, seed dusting, seed soaking and seed pelleting. The seed treatment application of the compound formula (I) can be carried out by any known methods, such as spraying or by dusting the seeds before sowing or during the sowing/planting of the seeds.

The compounds of the invention can be distinguished from other similar compounds by virtue of greater efficacy at low application rates and/or different pest control, which can be verified by the person skilled in the art using the experimental procedures, using lower concentrations if necessary, for example 10 ppm, 5 ppm, 2 ppm, 1 ppm or 0.2 ppm; or lower application rates, such as 300, 200 or 100, mg of Al per $m^2$. The greater efficacy can be observed by an increased safety profile (against non-target organisms above and below ground (such as fish, birds and bees), improved physico-chemical properties, or increased biodegradability).

In each aspect and embodiment of the invention, “consisting essentially” and inflections thereof are a preferred embodiment of “comprising” and its inflections, and “consisting of” and inflections thereof are a preferred embodiment of “consisting essentially of” and its inflections.

The disclosure in the present application makes available each and every combination of embodiments disclosed herein.

It should be noted that the disclosure herein in respect of a compound of formula I applies equally in respect of a compound of each of formulae Ia, Ib, and Tables 1 to 35.

BIOLOGICAL EXAMPLES

The Examples which follow serve to illustrate the invention. Certain compounds of the invention can be distinguished from known compounds by virtue of greater efficacy at low application rates, which can be verified by the person skilled in the art using the experimental procedures outlined in the Examples, using lower application rates if necessary, for example 50 ppm, 24 ppm, 12.5 ppm, 6 ppm, 3 ppm, 1.5 ppm, 0.8 ppm or 0.2 ppm.

Example B1: *Diabrotica balteata* (Corn Root Worm)

Maize sprouts placed onto an agar layer in 24-well microtiter plates were treated with aqueous test solutions prepared from 10'000 ppm DMSO stock solutions by spraying. After drying, the plates were infested with L2 larvae (6 to 10 per well). The samples were assessed for mortality and growth inhibition in comparison to untreated samples 4 days after infestation.

The following compounds gave an effect of at least 80% control in at least one of the two categories (mortality or growth inhibition) at an application rate of 200 ppm: P1.2, P2.1, P2.2, P2.5, P2-17, P3.4, P7.1, P8.1

Example B2: *Euschistus heros* (Neotropical Brown Stink Bug)

Soybean leaves on agar in 24-well microtiter plates were sprayed with aqueous test solutions prepared from 10'000 ppm DMSO stock solutions. After drying the leaves were infested with N2 nymphs. The samples were assessed for mortality and growth inhibition in comparison to untreated samples 5 days after infestation.

The following compounds gave an effect of at least 80% control in at least one of the two categories (mortality or growth inhibition) at an application rate of 200 ppm: P2.1., P8.1

Example B3: *Plutella xylostella* (Diamond Back Moth)

24-well microtiter plates with artificial diet were treated with aqueous test solutions prepared from 10'000 ppm DMSO stock solutions by pipetting. After drying, *Plutella* eggs were pipetted through a plastic stencil onto a gel blotting paper and the plate was closed with it. The samples were assessed for mortality and growth inhibition in comparison to untreated samples 8 days after infestation. The following compounds gave an effect of at least 80% control in at least one of the two categories (mortality or growth inhibition) at an application rate of 200 ppm: P1.2, P1.15, P1.51, P2.1, P2.2, P2.5, P2.10, P2.15, P2.16, P5.1, P5.2, P5.3, P7.1, P8.1

Example B4: *Myzus persicae* (Green Peach Aphid). Intrinsic Activity

Test compounds prepared from 10'000 ppm DMSO stock solutions were applied by pipette into 24-well microtiter plates and mixed with sucrose solution. The plates were closed with a stretched Parafilm. A plastic stencil with 24 holes was placed onto the plate and infested pea seedlings were placed directly on the Parafilm. The infested plate was closed with a gel blotting paper and another plastic stencil and then turned upside down. The samples were assessed for mortality 5 days after infestation.

The following compounds resulted in at least 80% mortality at a test rate of 12 ppm: P1.3, P1.4, P1.22, P1.26

Example B5: *Tetranychus urticae* (Two-Spotted Spider Mite): Feeding/Contact Activity Bean leaf discs on agar in 24-well microtiter plates were sprayed with aqueous test solutions prepared from 10'000 ppm DMSO stock solutions. After drying the leaf discs were infested with a mite population of mixed ages. The samples were assessed for mortality on mixed population (mobile stages) 8 days after infestation.

The following compounds resulted in at least 80% mortality at an application rate of 200 ppm: P1.1, P1.2, P1.3, P1.4, P1.5, P1.6, P1.7, P1.8, P1.10, P1.11, P1.12, P1.13, P1.14, P1.15, P1.16, P1.17, P1.18, P1.19, P1.20, P1.21, P1.22, P1.23, P1.24, P1.25, P1.26, P1.27, P1.28, P1.29, P1.30, P1.31, P1.33, P1.34, P1.35, P1.36, P1.37, P1.39, P1.40, P1.41, P1.42, P1.43, P1.44, P1.45, P1.46, P1.49, P1.50, P1.52, P2.1, P2.2, P2.3, P2.4, P2.5, P2.6, P2.7, P2.8, P2.9, P2.10, P2.11, P2.12, P2.13, P2.17, P3.1, P3.2, P3.3, P3.4, P3.5, P3.6, P3.7, P3.8, P3.9, P4.1, P4.2, P5.2, P6.1, P7.1., P8.1

The invention claimed is:

1. A compound of formula (I)

(I)

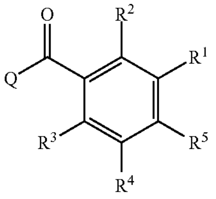

wherein $R^1$ is CN, C(=S)$NH_2$ or $C_1$-$C_6$-haloalkyl;

$R^2$ is H, OH, halogen, $C_1$-$C_6$-alkoxy or $C_1$-$C_6$-haloalkoxy;

$R^3$ is H, halogen, cyano, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_6$-cycloalkyl, $C_3$-$C_6$-halocycloalkyl, $C_1$-$C_6$-alkoxy, or $C_1$-$C_6$-haloalkyoxy;

$R^4$ is H, halogen, cyano, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_6$-cycloalkyl, $C_3$-$C_6$-halocycloalkyl, $C_1$-$C_6$-alkoxy, or $C_1$-$C_6$-haloalkyoxy;

$R^5$ is phenyl or phenyl substituted with 1 to 3 substituents $R^6$;

Q is a cyclic amine represented by formula IIa or a cyclic amine represented by formula IIb, (IIa)

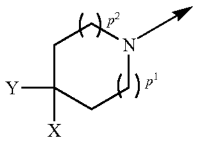

(IIb)

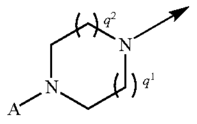

wherein the arrow indicates the connection to the carbonyl group;

$p^1$ and $p^2$ are each 0, or $p^1$ and $p^2$ are each 1;

$q^1$ is 1 or 2 and indicates the number of methylene groups;

$q^2$ is 1 or 2 and indicates the number of methylene groups;

X is hydrogen, hydroxyl, $C_1$-$C_6$-alkoxy, cyano or halogen;

Y is cyano, $C_1$-$C_6$-alkyl, $C_1$-$C_6$-alkoxy-$C_1$-$C_6$-alkyl, $C_1$-$C_6$-alkylsulfanyl-$C_1$-$C_6$-alkyl, $C_1$-$C_6$-alkylsulfinyl-$C_1$-$C_6$-alkyl, $C_1$-$C_6$-alkylsulfonyl-$C_1$-$C_6$-alkyl, $C_3$-$C_6$-alkenylsulfanyl-$C_1$-$C_6$-alkyl, $C_3$-$C_6$-alkenylsulfinyl-$C_1$-$C_6$-alkyl, $C_3$-$C_6$-alkenylsulfonyl-$C_1$-$C_6$-alkyl, $C_3$-$C_6$-alkynylsulfanyl-$C_1$-$C_6$-alkyl, $C_3$-$C_6$-alkynylsulfinyl-$C_1$-$C_6$-alkyl, $C_3$-$C_6$-alkynylsulfonyl-$C_1$-$C_6$-alkyl, $C_1$-$C_6$-alkoxycarbonyl, $C_1$-$C_6$-alkoxycarbonylamino, $R^aR^b$NC(O), $R^c$C(O) $NR^d$, $R^eSO_2NR^f$, $R^g$O—N=$CR^h$, 4 to 6 membered non-aromatic heterocyclic ring system in which one or two carbons are replaced independently by nitrogen, oxygen, sulfur, or sulfonyl, phenyl, phenyl substituted with 1 to 3 substituents $R^8$, 5 or 6 membered monocyclic heteroaryl, or 5 or 6 membered monocyclic heteroaryl substituted with 1 to 3 substituents $R^9$; or X and Y together form a double bond to a nitrogen which is substituted with a group $R^m$O;

A is cyano, $C_1$-$C_6$-cyanoalkyl, $C_2$-$C_6$-cyanoalkenyl, $C_3$-$C_6$-cyanocycloalkyl, $C_1$-$C_6$-haloalkyl, $C_2$-$C_6$-haloalkenyl, $C_3$-$C_6$-halocycloalkyl, $C_1$-$C_6$-alkoxy-$C_1$-$C_6$-alkyl, $C_1$-$C_6$-alkoxycarbonyl, $C_2$-$C_6$-alkenyloxycarbonyl, $C_2$-$C_6$-alkynyloxycarbonyl, $C_1$-$C_6$-alkylsulfanyl-$C_1$-$C_6$-alkyl, $C_1$-$C_6$-alkylsulfinyl-$C_1$-$C_6$-alkyl, $C_1$-$C_6$-alkylsulfonyl-$C_1$-$C_6$-alkyl, $R^iSO_2$, $R^jR^kNSO_2$, phenyl, phenyl substituted with 1 to 3 substituents $R^{10}$, heteroaryl (which is either a 5 or 6 membered monocyclic or a 9 or 10 membered bicyclic), or heteroaryl (which is either a 5 or 6 membered monocyclic or a 9 or 10 membered bicyclic) substituted with 1 to 3 substituents $R^{11}$;

$R^a$ and $R^b$ are independently selected from hydrogen, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_6$-cycloalkyl and $C_3$-$C_6$-halocycloalkyl and $C_1$-$C_6$-alkylsulfonyl;

$R^c$ and $R^d$ are independently selected from hydrogen, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_6$-cycloalkyl and $C_3$-$C_6$-halocycloalkyl;

$R^f$ is hydrogen, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_6$-cycloalkyl or $C_3$-$C_6$-halocycloalkyl;

$R^e$ and $R^i$ are independently selected from $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_6$-cycloalkyl and $C_3$-$C_6$-halocycloalkyl;

$R^g$ and $R^h$ are independently selected from hydrogen, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_6$-cycloalkyl and $C_3$-$C_6$-halocycloalkyl;

$R^j$ and $R^k$ are independently selected from hydrogen, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_6$-cycloalkyl and $C_3$-$C_6$-halocycloalkyl;

$R^m$ is hydrogen, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_6$-cycloalkyl or $C_3$-$C_6$-halocycloalkyl; and $R^6$, $R^8$, $R^9$, $R^{10}$, $R^{11}$ are independently selected from halogen, cyano, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_6$-cycloalkyl, $C_3$-$C_6$-halocycloalkyl, $C_1$-$C_6$-alkoxy, $C_1$-$C_6$-haloalkoxy, $C_1$-$C_6$-alkylsulfonyl and $C_1$-$C_6$-haloalkylsulfanyl;

or an agrochemically acceptable salt, stereoisomer, enantiomer, tautomer and N-oxide of the compound of formula I.

2. The compound according to claim 1, wherein $R^3$ is methyl, methoxy, ethoxy, difluoromethyl or trifluoromethyl.

3. The compound according to claim 1, wherein $R^1$ is CN or C(=S) $NH_2$.

4. The compound according to claim 1, wherein $R^2$ is hydrogen and $R^4$ is hydrogen or cyano.

5. The compound according to claim 1, wherein $R^6$ is independently selected from halogen, cyano, $C_1$-$C_3$-alkyl, $C_1$-$C_3$-haloalkyl, $C_1$-$C_3$-alkoxy; $C_1$-$C_3$-haloalkoxy, $C_1$-$C_3$-alkylsulfonyl and $C_1$-$C_3$-haloalkylsulfanyl.

6. The compound according to claim 1, wherein Q is formula IIa, wherein X is hydrogen or, hydroxyl; Y is $C_1$-$C_3$-alkylsulfanyl-methyl, $C_1$-$C_3$-alkylsulfinyl-methyl, $C_1$-$C_3$-alkylsulfonyl-methyl, $C_3$-$C_4$-alkenylsulfanyl-methyl, $C_3$-$C_4$-alkenylsulfinyl-methyl, $C_3$-$C_4$-alkenylsulfonyl-methyl, $C_3$-$C_4$-alkynylsulfanyl-methyl, $C_3$-$C_4$-alkynylsulfinyl-methyl, $C_3$-$C_4$-alkynylsulfonyl-methyl, methanesulfonylamido, ethanesulfonylamido, 1,1-dioxo-1,2-thiazolidin-2-yl, 1,2,4-oxadiazole-3-yl, 2-pyridyl, substituted 2-pyridyl or, substituted 1,2,4-oxadiazole-3-yl, where the substituents for each are 1 to 3 substituents independently selected from chlorine and methyl; or X and Y together form a double bond to a nitrogen which is substituted with methoxy or ethoxy.

7. The compound according to claim 1, wherein $q^1$ and $q^2$ are each 1.

8. The compound according to claim 1, wherein Q is formula IIb, wherein A is cyano, $C_1$-$C_3$-cyanoalkyl, $C_1$-$C_3$-haloalkyl, $C_2$-$C_3$-haloalkenyl, $C_1$-$C_3$-alkoxy-$C_1$-$C_3$-alkyl, $C_1$-$C_3$-alkoxycarbonyl, $C_1$-$C_3$-alkylsulfanyl-$C_1$-$C_3$-alkyl, $C_1$-$C_3$-alkylsulfinyl-$C_1$-$C_3$-alkyl, $R^fSO_2$, or 6 membered monocyclic heteroaryl substituted with 1 to 3 substituents independently selected from fluorine and chlorine.

9. A composition comprising a compound as defined in claim 1, one or more auxiliaries and diluent, and optionally one or more additional agrochemical ingredients.

10. A method (i) of combating and controlling insects, acarines, nematodes or molluscs which comprises applying to a pest, to a locus of a pest, or to a plant susceptible to attack by a pest an insecticidally, acaricidally, nematicidally or molluscicidally effective amount of a compound as defined as defined in claim 1; or (ii) for the protection of plant propagation material from the attack by insects, acarines, nematodes or molluscs, which comprises treating the propagation material or the site, where the propagation material is planted, with an effective amount of a compound as defined in claim 1; or (iii) of controlling parasites in or on an animal in need thereof comprising administering to the animal an effective amount of a compound as defined in claim 1.

11. A plant propagation material, comprising, or treated with or adhered thereto, a compound as defined in claim 1.

12. A method (i) of combating and controlling insects, acarines, nematodes or molluscs which comprises applying to a pest, to a locus of a pest, or to a plant susceptible to attack by a pest an insecticidally, acaricidally, nematicidally or molluscicidally effective amount of a a composition as defined claim 9; or (ii) for the protection of plant propagation material from the attack by insects, acarines, nematodes or molluscs, which comprises treating the propagation material or the site, where the propagation material is planted, with an effective amount of a composition as defined claim 9; or (iii) of controlling parasites in or on an animal in need thereof comprising administering to the animal an effective amount of a composition as defined claim 9.

13. A plant propagation material, comprising, or treated with or adhered thereto, a composition as defined claim 9.

14. A compound selected from any one in Tables P1-P8:

TABLE P1

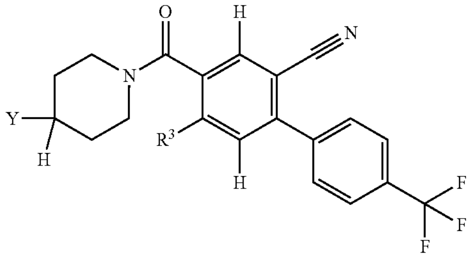

| Comp. No | Y | $R^3$ |
|---|---|---|
| P1.1 | 5-methyl-1,2,4-oxadiazole-3-yl | $CF_3$ |
| P1.2 | $CH_2SCH_2CH_3$ | $CF_3$ |
| P1.3 | $CH_2S(=O)CH_2CH_3$ | $CF_3$ |
| P1.4 | $CH_2SO_2CH_2CH_3$ | $CF_3$ |
| P1.5 | 1,1-dioxo-1,2-thiazolidin-2-yl | $CF_3$ |
| P1.6 | 5-methyl-1,2,4-oxadiazole-3-yl | $CH_3$ |
| P1.7 | $CH_2SCH_2CH_3$ | $CH_3$ |
| P1.8 | 1,1-dioxo-1,2-thiazolidin-2-yl | $CH_3$ |
| P1.9 | 5-methyl-1,2,4-oxadiazole-3-yl | H |
| P1.10 | $CH_2SCH_2CH_3$ | H |
| P1.11 | 1,1-dioxo-1,2-thiazolidin-2-yl | H |
| P1.12 | $CH_2SCH_3$ | $CF_3$ |
| P1.13 | $CH_2S(=O)CH_3$ | $CF_3$ |
| P1.14 | $CH_2SO_2CH_3$ | $CF_3$ |
| P1.15 | $CH_2SCH_2CH=CH_2$ | $CF_3$ |
| P1.16 | $CH_2S(=O)CH_2CH=CH_2$ | $CF_3$ |
| P1.17 | $CH_2SO_2CH_2CH=CH_2$ | $CF_3$ |
| P1.18 | $CH_2SCH_2CHCH$ | $CF_3$ |
| P1.19 | $CH_2S(=O)CH_2CHCH$ | $CF_3$ |
| P1.20 | $CH_2SO_2CH_2CHCH$ | $CF_3$ |
| P1.21 | $CH_2SCH_2CH_2CH_3$ | $CF_3$ |
| P1.22 | $CH_2S(=O)CH_2CH_2CH_3$ | $CF_3$ |
| P1.23 | $CH_2SO_2CH_2CH_2CH_3$ | $CF_3$ |
| P1.24 | $CH_2SCH_3$ | $CH_3$ |
| P1.25 | $CH_2S(=O)CH_3$ | $CH_3$ |
| P1.26 | $CH_2SO_2CH_3$ | $CH_3$ |
| P1.27 | $CH_2SCH_2CH=CH_2$ | $CH_3$ |
| P1.28 | $CH_2S(=O)CH_2CH=CH_2$ | $CH_3$ |
| P1.29 | $CH_2SO_2CH_2CH=CH_2$ | $CH_3$ |
| P1.30 | $CH_2SCH_2CHCH$ | $CH_3$ |
| P1.31 | $CH_2S(=O)CH_2CHCH$ | $CH_3$ |
| P1.32 | $CH_2SO_2CH_2CHCH$ | $CH_3$ |
| P1.33 | $CH_2SCH_2CH_2CH_3$ | $CH_3$ |
| P1.34 | $CH_2S(=O)CH_2CH_2CH_3$ | $CH_3$ |
| P1.35 | $CH_2SO_2CH_2CH_2CH_3$ | $CH_3$ |
| P1.36 | (E)-N-methoxy-imino-methyl | $CF_3$ |

TABLE P1-continued

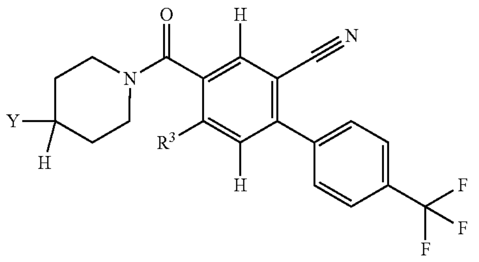

| Comp. No | Y | $R^3$ |
|---|---|---|
| P1.37 | (E)-N-ethoxy-imino-methyl | $CF_3$ |
| P1.38 | methylsulfonyl-carbamoyl | $CF_3$ |
| P1.39 | dimethylcarbamoyl | $CF_3$ |
| P1.40 | ethyl(methyl)carbamoyl | $CF_3$ |
| P1.41 | methanesulfonamido | $CF_3$ |
| P1.42 | ethanesulfonamido | $CF_3$ |
| P1.43 | 5-methyl-1,2,4-oxadiazole-3-yl | $OCH_3$ |
| P1.44 | $CH_2SCH_2CH_3$ | $OCH_3$ |
| P1.45 | 5-methyl-1,2,4-oxadiazole-3-yl | $OCH_2CH_3$ |
| P1.46 | $CH_2SCH_2CH_3$ | $OCH_2CH_3$ |
| P1.47 | ethoxycarbonyl | $CF_3$ |
| P1.48 | tert-butoxy-carbonylamino | $CF_3$ |
| P1.49 | trifluoromethyl-sulfonylamino | $CF_3$ |
| P1.50 | 1-methyl-1,2,4-triazol-3-yl | $CF_3$ |
| P1.51 | phenyl | $CF_3$ |
| P1.52 | ethoxymethyl | $CF_3$ |
| P1.53 | cyano | $CF_3$ |

TABLE P2

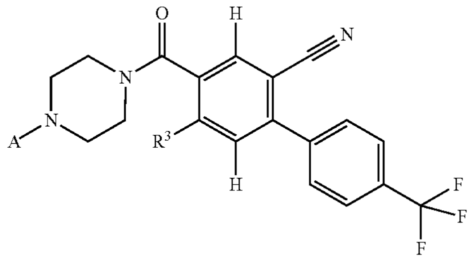

| Comp. No | A | $R^3$ |
|---|---|---|
| P2.1 | 3,5-dichloro-2-pyridyl | $CF_3$ |
| P2.2 | 3,5-dichloro-2-pyridyl | $CH_3$ |
| P2.3 | 3,5-dichloro-2-pyridyl | H |
| P2.4 | 3,5-dichloro-2-pyridyl | $OCH_3$ |
| P2.5 | 3,5-dichloro-2-pyridyl | $OCH_2CH_3$ |
| P2.6 | cyano | $CF_3$ |
| P2.7 | $CH_2CN$ | $CF_3$ |
| P2.8 | $CH_2CH_2CN$ | $CF_3$ |
| P2.9 | 2,2,2-trifluoroethyl | $CF_3$ |
| P2.10 | 3,3-dichloroallyl | $CF_3$ |
| P2.11 | $CH_2CH_2SCH_3$ | $CF_3$ |
| P2.12 | $CH_2CH_2S(=O)CH_3$ | $CF_3$ |
| P2.13 | methylsulfonyl | $CF_3$ |
| P2.14 | trifluoromethyl-sulfonyl | $CF_3$ |

TABLE P2-continued

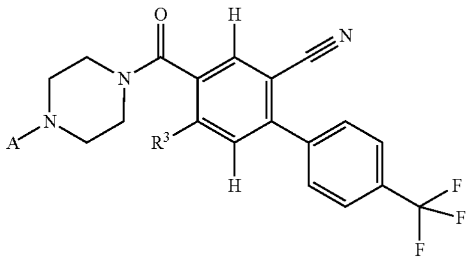

| Comp. No | A | $R^3$ |
|---|---|---|
| P2.15 | tert-butoxy-carbonyl | $CF_3$ |
| P2.16 | trifluoromethyl-carbonyl | $CF_3$ |
| P2.17 | methoxyethyl | $CF_3$ |

TABLE P3

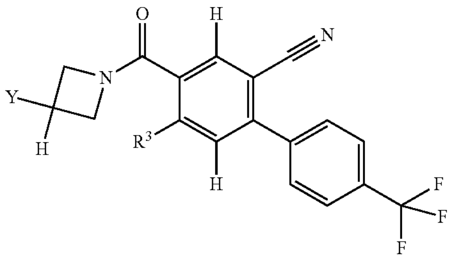

| Comp. No | Y | $R^3$ |
|---|---|---|
| P3.1 | $CH_2SCH_3$ | $CF_3$ |
| P3.2 | $CH_2S(=O)CH_3$ | $CF_3$ |
| P3.3 | $CH_2SO_2CH_3$ | $CF_3$ |
| P3.4 | $CH_2SCH_2CH_3$ | $CF_3$ |
| P3.5 | $CH_2S(=O)CH_2CH_3$ | $CF_3$ |
| P3.6 | $CH_2SO_2CH_2CH_3$ | $CF_3$ |
| P3.7 | $CH_2S(=O)CH_2CH_2CH_3$ | $CF_3$ |
| P3.8 | $CH_2SO_2CH_2CH_2CH_3$ | $CF_3$ |
| P3.9 | $CH_2SCH_2CH_2CH_3$ | $CF_3$ |

Table P4:

(I-e)

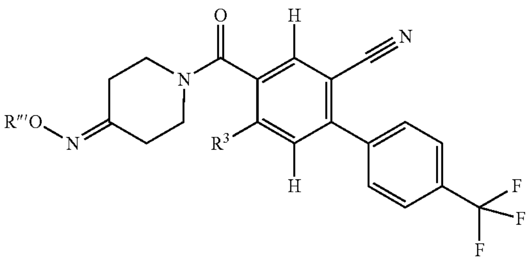

TABLE P4

| Comp. No | R''' | $R^3$ |
|---|---|---|
| P4.1 | methyl | $CF_3$ |
| P4.2 | ethyl | $CF_3$ |

TABLE P4-continued

| Comp. No | R''' | $R^3$ |
|---|---|---|

;

Table P5:

(I-g)

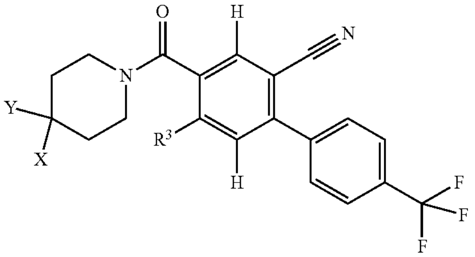

TABLE P5

| Comp. No | Y | X | $R^3$ |
|---|---|---|---|
| P5.1 | phenyl | OH | $CF_3$ |
| P5.2 | 4-Cl-phenyl | OH | $CF_3$ |
| P5.3 | 4-Cl-phenyl | $OCH_3$ | $CF_3$ |

;

Table P6:

(I-h)

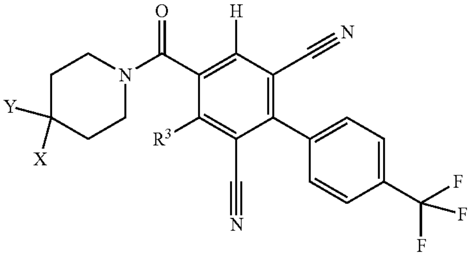

TABLE P6

| Comp. No | Y | $R^3$ |
|---|---|---|
| P6.1 | 5-methyl-1,2,4-oxadiazole-3-yl | $CH_3$ |

;

Table P7:

(I-i)

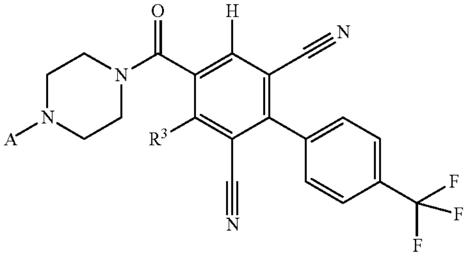

TABLE P7

| Comp. No | A | $R^3$ |
|---|---|---|
| P7.1 | 3,5-dichloro-2-pyridyl | $CH_3$ |

;

and

Table P8:

(I-j)

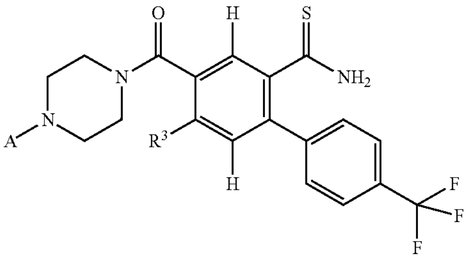

TABLE P8

| Comp. No | A | $R^3$ |
|---|---|---|
| P8.1 | 3,5-dichloro-2-pyridyl | $CH_3$ |

.

15. The compound of claim 14, selected from

5-[4-(5-methyl-1,2,4-oxadiazol-3-yl) Piperidine-1-carbonyl]-4-(trifluoromethyl)-2-[4-(trifluoromethyl) phenyl] benzonitrile (Compound P1.1);

5-[4-(3,5-Dichloro-2-pyridyl) piperazine-1-carbonyl]-4-(trifluoromethyl)-2-[4-(trifluoromethyl) phenyl]benzonitrile (Compound P2.1);

5-[4-(3,5-Dichloro-2-pyridyl) piperazine-1-carbonyl]-4-(trifluoromethyl)-2-[4-(trifluoromethyl) phenyl]benzenecarbothioamide (Compound P8.1);

5-[4-(3,5-Dichloro-2-pyridyl) piperazine-1-carbonyl]-4-ethoxy-2-[4-(trifluoromethyl)-phenyl]-benzonitrile (Compound P2.5);

4-Ethoxy-5-[4-(ethylsulfanylmethyl) piperidine-1-carbonyl]-2-[4-(trifluoromethyl) phenyl]-benzonitrile (Compound P1.46);

4-Ethoxy-5-[4-(ethylsulfanylmethyl) piperidine-1-carbonyl]-2-[4-(trifluoromethyl) phenyl]-benzonitrile (Compound P3.7); and 4-Methyl-5-[4-(5-methyl-1,2,4-oxadiazol-3-yl) piperazine-1-carbonyl]-2-[4-(trifluoromethyl)phenyl]benzene-1,3-dicarbonitrile (Compound P6.1).

16. A composition comprising a compound of claim 14, one or more auxiliaries and diluents, and optionally one or more additional agrochemically active ingredients.

17. A composition comprising a compound of claim 15, one or more auxiliaries and diluents, and optionally one or more additional agrochemically active ingredients.

* * * * *